US008609644B2

(12) United States Patent
Cerri et al.

(10) Patent No.: US 8,609,644 B2
(45) Date of Patent: Dec. 17, 2013

(54) AMINO DERIVATIVES OF ANDROSTANES AND ANDROSTENES AS MEDICAMENTS FOR CARDIOVASCULAR DISORDERS

(75) Inventors: Alberto Cerri, Milan (IT); Marco Torri, Rho (IT); Silvia Armaroli, Gallo Poggio Renatico (IT); Leonardo Banfi, Novate Milanese (IT); Giuseppe Bianchi, Milan (IT); Giulio Carzana, Milan (IT); Patrizia Ferrari, Varese (IT); Rosamaria Michaeletti, Milan (IT); Simona Sputore, Meda (IT); Maria Pia Zappavigna, Magenta (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 574 days.

(21) Appl. No.: 12/295,497

(22) PCT Filed: Apr. 11, 2007

(86) PCT No.: PCT/EP2007/053524
§ 371 (c)(1),
(2), (4) Date: Nov. 2, 2010

(87) PCT Pub. No.: WO2007/118832
PCT Pub. Date: Oct. 25, 2007

(65) Prior Publication Data
US 2011/0053902 A1    Mar. 3, 2011

(30) Foreign Application Priority Data

Apr. 13, 2006   (EP) .................................... 06112598

(51) Int. Cl.
*A61K 31/566* (2006.01)
*C07J 41/00* (2006.01)

(52) U.S. Cl.
USPC .......................................... 514/169; 552/502

(58) Field of Classification Search
USPC ................... 514/173, 169; 552/502
See application file for complete search history.

(56) References Cited

U.S. PATENT DOCUMENTS

| 3,013,009 A | 12/1961 | Marshall |
| 3,120,515 A | 2/1964 | Christiansen |
| 3,210,386 A | 10/1965 | Birkenmeyer et al. |
| 5,144,017 A | 9/1992 | LaBella et al. |

FOREIGN PATENT DOCUMENTS

| EP | 0825197 A2 | 2/1998 |
| GB | 868303 A | 5/1961 |
| GB | 948879 | 2/1964 |
| GB | 1042292 A | 9/1966 |

OTHER PUBLICATIONS

Jindal, "Synthesis and antineoplastic activity of 2-alkylaminoethyl derivatives of various steroidal oximes", European Journal of Medicinal Chemistry, 2003, 38(11-12), pp. 1025-1034.*
Office Action issued on Oct. 26, 2012, in corresponding JP Application No. 2009-504741 (English Translation).
De Munari, et al., Structure-based design and synthesis of novel potent Na+,K+-ATPase inhibitors derived from a 5α,14α-androstane scaffold as positive inotropic compounds, Journal of Medical Chemistry, vol. 46(17), 2003, pp. 3644-3654.
Temma, et al., Effects of progesterone derivatives on sodium pump activity and force of myocardial contraction in isolated guinea pig heart, Research Communications in Chemical Pathology and Pharmacology, vol. 41(1), 1983, pp. 51-63.
Ulubelen, et al., Cardioactive terpenoids and a new rearranged diterpene from *Salvia syriaca*, Plant Medica, Thieme, Stuttgart, vol. 66(7), 2000, pp. 627-629.
Le Men, et al., Chemistry and pharmacology of hemi synthetic compounds for cardio vascular activity derivatives of paravallarine a naturally occurring steroid, Chimica Therapeutica, vol. 5(1), 1970, pp. 41-54.
Kamernitskii, et al., A new class of cardiotonic steroids, Database CA Chemical Abstracts Service, vol. 17(1), 141-143, 1991.

* cited by examiner

*Primary Examiner* — Sreeni Padmanabhan
*Assistant Examiner* — Sahar Javanmard
(74) *Attorney, Agent, or Firm* — Lucas & Mercanti, LLP

(57) ABSTRACT

Compounds of formula (I) wherein: the groups are as defined in the description, are useful for the preparation of medicaments for the treatment of cardiovascular disorders, in particular heart failure and hypertension. The compounds are inhibitors of the enzymatic activity of the Na+, K+-ATPase. Said compounds are used for the preparation of a medicament for the treatment of a disease caused by the hypertensive effects of endogenous ouabain, such as renal failure progression in autosomal dominant polycystic renal disease (ADPKD), preeclamptic hypertension and proteinuria and renal failure progression in patients with adducin polymorphisms.

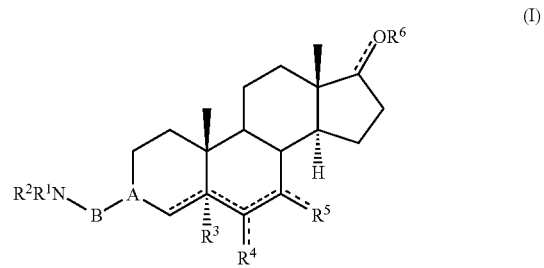

12 Claims, No Drawings

AMINO DERIVATIVES OF ANDROSTANES AND ANDROSTENES AS MEDICAMENTS FOR CARDIOVASCULAR DISORDERS

The present invention relates to new amino derivatives at position 3 of 5- and/or 6- and/or 7-substituted androstanes and androstenes, processes for their preparation, and to pharmaceutical compositions containing them for the treatment of cardiovascular disorders, such as heart failure and hypertension.

BACKGROUND OF THE INVENTION

Cardiovascular diseases are still the first cause of morbidity and mortality in the western world; among these, hypertension and heart failure are two frequent diseases. Hypertension is one of the most important cardiovascular risk factor and more than one third of population over 60 suffer from this disease. Congestive heart failure affects 1-2% of the population and even 10% of the very elderly; the percentage is expected to rise (Sharpe N., et al., *The Lancet*, 1998, 352, (suppl. 1), 3-17). Beside, hypertension may be one of more important causes of heart failure in the elderly (*Eur. Heart J.*, 2001, 22, 1527-1560). Although a number of effective drugs are available for the treatment of both hypertension and heart failure, further research is in progress to find more effective and safe compounds. Several drugs are used in combination for the treatment of heart failure, and among positive inotropic agents, digoxin is the most prescribed digitalis cardiac glycoside that can improve the myocardial performance. A very well-known drawback of digitalis drugs is their arrhythmogenic side-effect. Evidence of digitalis toxicity emerges at two- to three-fold higher serum concentration than the therapeutic dose, such as disturbances of conduction and cardiac arrhythmias which are characteristics of digitalis toxicity (Hoffman, B. F.; Bigger, J. T., *Digitalis and Allied Cardiac Glycosides. In The Pharmacological Basis of Therapeutics*, 8th ed.; Goodman Gilman, A.; Nies, A. S.; Rall, T. W; Taylor, P., Eds.; Pergamon Press, New York, 1990, pp 814-839).

The capability of the natural digitalis compounds to increase the myocardial force of contraction is strictly related to their cardenolide structure having a 17β-lactone on a 14-hydroxy-5β,14β-androstane skeleton.

DESCRIPTION OF THE PRIOR ART

In the field of steroidal derivatives some groups of compounds are reported to possess positive inotropic properties or other activities related to the cardiovascular system.

Particularly, within pregnane derivatives the following papers are interesting.

GB 868,303 discloses pregnane-20-one derivatives possessing progestational and antifibrillatory action.

Other aminoalkylesters of 3β-hydroxypregn-5-en-20-one derivatives are disclosed by GB 966,060, with anorectic, antiarrhythmic and antiatherogenic activities, and U.S. Pat. No. 3,013,009, with eurithmic, anticonvulsant, and antihypertensive activities.

U.S. Pat. No. 5,144,017 discloses "compounds that bind to the digitalis receptor" including androstane and pregnane derivatives. According to the inventors, the binding to the digitalis receptor parallels the ability to elicit characteristic cellular response. The inventors focus on the capability of the different classes of steroids of yielding glycosides derivatives with typical digoxin-like actions on the heart as well as on other tissues, which seems to be important improve the toxicity of these compounds. Even though some androstane derivatives are reported, the more interesting compounds are 3-glycosides of pregnane derivatives.

Pregnane guanylhydrazones with positive inotropic cardiac effect are reported by S. Schütz, et al., *Arzneimittel-Forschung*, 1969, 19, 69-75.

Particularly relevant to the activity of these compounds is the guanylhydrazone substituent, since "replacement of the guanyl hydrazone groups by other related residues results in a loss of activity".

Other pregnene-20-one derivatives, such as clormadinone acetate and megestrol acetate are reported to inhibit the activity of $Na^+$, $K^+$-ATPase but they were not "capable of eliciting an inotropic action by themselves" (K. Temma, et al., *Research. Comm. Chem. in Pathology and Pharmacology*, 1983, 41, 51-63).

In the field of 5α,14α-androstane the following papers are interesting.

GB 1,175,219 and U.S. Pat. No. 3,580,905 disclose 3-(aminoalkoxycarbonylalkylene)steroid derivatives which possess digitalis like activities with "a ratio between the dose which produces toxic symptoms (onset of cardiac arrhythmias) and the effective dose comparable with such a ratio as measured for standard cardiac glycosides". Besides no clear advantage over digitalis glycosides, the compounds with the highest ratio produce the lowest increase in contractile force.

6-Hydroxy and 6-oxoandrostane derivatives are disclosed in EP 0 825 197 B1 as ligands and inhibitors of $Na^+$, $K^+$-ATPase, and positive inotropic agents possessing a lower toxicity when compared with digoxin, as evaluated on the basis of the acute toxicity in mice. The same compounds are also reported by S. De Munari, et al., *J. Med. Chem.* 2003, 64, 3644-3654.

The evidence that high levels of endogenous ouabain (EO), a closely related isomer of ouabain, are implicated in human hypertension and cardiac hypertrophy and failure stimulated the pharmacological research for developing novel anti-hypertensive agents active as ouabain antagonists. The pathogenetic mechanisms through which increased EO levels affect cardiovascular system involve the modulation of Na-K ATPase, the key enzyme responsible for renal tubular sodium reabsorption and the activation of signalling transduction pathways implicated in growth-related gene transcription. By studying both genetic and experimental rat models of hypertension and comparing them with humans, it has been demonstrated that elevated levels of circulating EO and the genetic polymorphism of the cytoskeletal protein adducin associate with hypertension and high renal Na-K pump activity. Ouabain itself induces hypertension and up-regulates renal Na-K pump when chronically infused at low doses into rats (OS). In renal cultured cells, either incubated for several days with nanomolar concentrations of ouabain or transfected with the hypertensive adducin genetic variant, the Na-K pump results enhanced. Moreover, both EO and adducin polymorphism affect cardiac complications associated to hypertension, the former through the activation of a signalling transduction pathway. As a consequence, a compound able to interact with the cellular and molecular alterations, sustained by EO or mutated adducin, may represent the suitable treatment for those patients in whom these mechanisms are at work (Ferrandi M., et al., Curr Pharm Des. 2005; 11(25): 3301-5).

As reported above, the crucial point of positive inotropic agents is the ability to discriminate between the potency in inducing an increase of myocardial force of contraction and the onset of cardiac arrhythmias.

There is still a constant need to make available drugs showing a better therapeutic ratio and/or a longer duration of action, both of them important factors for the compliance of patients. Preferably, the drugs can be administered by oral route.

Other substituted steroids are reported possessing completely different pharmacological activities.

Dehydroepiandrosterone 3β-aminoethers or aminoesters substituted in position 7 with a keto or eventually substituted alkoxy groups are disclosed in US 2003/0054021 and WO 03/035023 A1 as cosmetical or therapeutical treatments of cutaneous disorders related to keratinous afflictions.

3-Dialkylaminoethers and 3-dialkylaminothioethers of 3β-hydroxy-6α-methylandrostanes or of 3β-hydroxy-6-methyl-5-androstenes are disclosed in U.S. Pat. No. 3,210,386 as hypocholesterolemic and antiparasitic agents.

SUMMARY OF THE INVENTION

It has now been found that 3-amino derivatives of 5- and/or 6- and/or 7-substituted androstanes and androstenes meet the needs of to provide drugs with a better therapeutic ratio and/or longer duration of action. Some of these compounds come from the modification of the compounds disclosed in EP 0 825 197, leading to unexpected pharmacological properties.

The compounds of the present invention have the general formula (I):

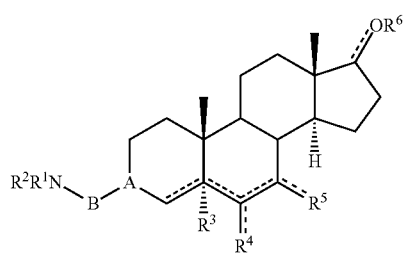

I wherein:
A is $CH\sim X$, $C=N\sim O$, $CR^7\sim CH=CH\sim$, $CR^7\sim CH_2$, $CR^8\sim XC=O$, $CR^8\sim XC(=O)X'$, wherein the left end carbon atom in any of these groups is at position 3 of the androstane skeleton;
X and X', which can be the same or different, are O, S(O)$_x$ or NR$^9$;
R$^7$ is hydrogen or hydroxy;
R$^8$ and R$^9$ are, independently, H, $C_1$-$C_6$ alkyl group;
x is an integer number comprised between 0 and 2;
B is a $C_1$-$C_6$ straight or branched alkylene or a $C_3$-$C_6$ cycloalkylene, optionally containing a phenyl ring;
R$^1$ and R$^2$, which can be the same or different, are H, $C_1$-$C_6$ alkyl, phenyl-$C_1$-$C_4$ alkyl or when R$^1$ is hydrogen, R$^2$ can also be $C(=NR^{10})NHR^{11}$ or R$^1$ and R$^2$ can be taken together with the nitrogen atom to form an unsubstituted or substituted saturated or unsaturated mono heterocyclic 4-, 5- or 6-membered ring optionally containing another heteroatom selected from the group consisting of oxygen, sulphur or nitrogen, and R$^1$ and R$^2$ can be optionally substituted by one or more hydroxy, methoxy, ethoxy groups;
R$^{10}$ and R$^{11}$, which can be the same or different, are H, $C_1$-$C_6$ alkyl, or R$^{10}$ and R$^{11}$ can be taken together with the nitrogen atoms and the guanidinic carbon atom to form an unsubstituted or substituted saturated or unsaturated mono heterocyclic 5- or 6-membered ring optionally containing another heteroatom selected from the group consisting of oxygen, sulphur or nitrogen;
R$^3$ is H, $C_1$-$C_6$ alkyl, ONO$_2$, OR$^{12}$;
R$^{12}$ is H, $C_1$-$C_6$ alkyl, optionally substituted by one or more hydroxy, methoxy, ethoxy; or R$^{12}$ is allyl or propargyl;
when the bond --- linking the carbon atom in position 6 of the androstane skeleton with R$^4$ is a double bond, R$^4$ is $N\sim OR^{13}$ or $CR^{14}R^{15}$;
when the bond --- linking the carbon atom in position 7 of the androstane skeleton with R$^5$ is a double bond, R$^5$ is O, with the meaning of a keto group, or $N\sim OR^{13}$ or $CR^{14}R^{15}$;
R$^{13}$ is H, $C_1$-$C_6$ alkyl, optionally substituted by one or more hydroxy, methoxy, ethoxy; or R$^{13}$ is allyl or propargyl;
R$^{14}$ and R$^{15}$, which can be the same or different, are H, $C_1$-$C_6$ alkyl group, optionally substituted by one or more hydroxy, methoxy, ethoxy; or R$^{14}$ and R$^{15}$, which can be the same or different, are allyl, propargyl, F, COOR$^{16}$, CN, CONR$^{17}$R$^{18}$, or R$^{14}$ and R$^{15}$ taken together form a cycloalkylene substituent;
R$^{16}$ is H, $C_1$-$C_6$ alkyl group optionally substituted by one or more hydroxy, methoxy, ethoxy;
R$^{17}$ and R$^{18}$, which can be the same or different, are H, $C_1$-$C_6$ alkyl groups or R$^{17}$ and R$^{18}$ can optionally be taken together with the nitrogen atom to form a heterocyclic group,
when the bond --- linking the carbon atom in position 6 of the androstane skeleton with R$^4$ is a single bond, R$^4$ is H, $C_1$-$C_6$ alkyl group, vinyl, ethynyl, COOR$^{16}$, CN, CONR$^{17}$R$^{18}$, ONO$_2$, NHCHO, NHCOCH$_3$, CH=N$\sim$OH, spirocyclopropane, spirooxirane, where the alkyl group can be optionally substituted by one or more hydroxy, methoxy, ethoxy;
when the bond --- linking the carbon atom in position 7 of the androstane skeleton with R$^5$ is a single bond, R$^5$ is H, $C_1$-$C_6$ alkyl group, vinyl, ethynyl, COOR$^{16}$, CN, CONR$^{17}$R$^{18}$, OR$^{19}$, ONO$_2$, NHCHO, NHCOCH$_3$, CH=N$\sim$OH, spirocyclopropane, spirooxirane, where the alkyl group can be optionally substituted by one or more hydroxy, methoxy, ethoxy;
R$^{16}$, R$^{17}$, and R$^{18}$ are as above defined;
R$^{19}$ is H, $C_1$-$C_6$ alkyl group optionally substituted by one or more hydroxy, methoxy, ethoxy;
R$^6$ is H, $C_1$-$C_6$ alkyl group or $C_2$-$C_6$ acyl group, when the bond --- in position 17 of the androstane skeleton is a single bond and, as a consequence, the remaining substituent in position 17 is H, and R$^6$ is not present when the bond --- in position 17 is a double bond with the meaning of a keto group;
R$^{16}$, R$^{17}$, and R$^{18}$, when present in the same compound in different positions, can be the same or different;
the symbol $\sim$ represents an α or β single bond or an E or Z diastereoisomer when it is linked to a double bond;
the symbol --- in positions 4, 5, 6, 7, and 17 represents, independently, a single or double bond, and when it is a single exocyclic bond in positions 6, 7, or 17, it can be an α or β single bond;
with the following provisos:
when the symbol --- in position 5-6 only is a double bond while the others in position 4-5 and 6-7 are single bonds and R$^4$ is methyl with A meaning CH$\sim$X wherein X is oxygen or sulphur, R$^2$R$^1$N is not dimethylamino or diethylamino or morpholino,
when A is CR$^8\sim$XC=O or CR$^8\sim$XC=OX', wherein R$^8$ is hydrogen, X is oxygen and X' is O or NH, and when A is CH$\sim$X, wherein X is oxygen, when the symbol --- in position 5-6 is a double bond R$^5$ is not oxygen, with the symbol --- in position 7, linking R$^5$, meaning a double bond, or R$^5$ is not OR$^{19}$, with the symbol --- in position 7, linking R$^5$, meaning a single bond,
that at least one of R$^3$, R$^4$ and R$^5$ are not hydrogen at the same time.

Where the compounds of formula (I) can exhibit tautomerism, the formula is intended to cover all tautomers; the invention includes within its scope all the possible stereoisomers, Z and E isomers, optical isomers and their mixtures, the metabolites and the metabolic precursors of compound of formula (I).

Also the pharmaceutical acceptable salts are included in the scope of the invention. Pharmaceutical acceptable salts are salts which retain the biological activity of the base and are derived from such known pharmacologically acceptable acids such as, e.g., hydrochloric, hydrobromic, sulfuric, phosphoric, nitric, fumaric, succinic, oxalic, malic, tartaric, maleic, citric, methanesulfonic or benzoic acid and others commonly used in the art.

The $C_1$-$C_6$ alkyl group may be branched or straight chains or cyclic groups, e.g. methyl, ethyl, n-propyl, i-propyl, n-butyl, t-butyl, cyclopentyl or cyclohexyl.

The $C_1$-$C_6$ alkylenic group may be branched or straight chains or cyclic groups, e.g. ethylene, trimethylene, propylene, tetramethylene, dimethylethylene, cyclopropylene, cyclobutylene, cyclopentylene, cyclohexylene.

The $C_2$-$C_6$ acyl groups may have branched, straight or cyclic chains and preferably are acetyl, propionyl, butyryl, pivaloyl, cyclopentanecarbonyl.

In the context of the present invention metabolite and metabolic precursor means active metabolite and metabolic precursor, namely a compound of formula (I) which has been transformed by a metabolic reaction, but substantially maintains or increases the pharmacological activity.

Examples of metabolites or metabolic precursors are hydroxylated, carboxylated, sulphonated, glycosylated, glycuronated, methylated or demethylated oxidated or reduced derivatives of the compounds of formula (I).

Some compounds of formula (I) can also be prodrugs of the active forms.

Further object of the present invention is the use of said compounds of general formula (I) in the preparation of a medicament useful in the treatment of cardiovascular diseases such as heart failure and hypertension.

DETAILED DESCRIPTION OF THE INVENTION

According to a first preferred embodiment of the present invention, the compounds of formula (I) are those in which the symbols $R^3$ and $R^5$ represent H, the symbol $R^4$ represents methylene, difluoromethylene, hydroxyimino, methoxyimino, when the symbols --- in position 6 linking $R^4$ and in position 17 represent double bonds, while the other symbols --- represent single bonds, $R^1R^2N$ and B are as defined above, and the symbol A is C=N$\sim\sim\sim$O, in particular 2-amino-ethoxyimino, 3-aminopropoxyimino, 2-(N-methylamino)ethoxyimino, 3-(N-methylamino)propoxyimino, (R)-2-aminopropoxyimino, (S)-2-aminopropoxyimino, 3-amino-2-methyl-2-propoxyimino, or the symbol A is $CR^8\sim\sim\sim$XC=O, where $R^8$ and X are as defined above, in particular 3β-(3-aminopropionyloxy), 3β-(3-aminobutiroyloxy), 3β-(3-amino-2-methylpropionyloxy), or the symbol A is $CR^7\sim\sim\sim$CH=CH$\sim\sim\sim$ where $R^7$ is as defined above, in particular 3α-(5-aminopent-1Z-enyl), 3α-(4-aminobut-1Z-enyl) or A is CH$\sim\sim\sim$X where X is S, in particular 3α-(3-aminopropylthio), 3α-(3-aminopropylsulfinyl).

In a second preferred embodiment of the present invention, the compounds of formula (I) are those in which the symbols $R^3$ and $R^5$ represent H, the symbol $R^4$ represents α-methyl, α-carbamoyl, α-methoxycarbonyl, α-hydroxymethyl, α-(2-hydroxyethyl), α-methoxymethyl, α-nitroxy, α-formylamino, α-ethynyl when the symbol --- in position 17 represents a double bond while the other symbols --- represent single bonds, $R^1R^2N$ and B are as defined above, and the symbol A is C=N$\sim\sim\sim$O, in particular 2-amino-ethoxyimino, 3-aminopropoxyimino, 2-(N-methylamino)ethoxyimino, 3-(N-methylamino)propoxyimino, (R)-2-aminopropoxyimino, (S)-2-aminopropoxyimino, 3-amino-2-methyl-2-propoxyimino, or the symbol A is $CR^8\sim\sim\sim$XC=O, where $R^8$ and X are as defined above, in particular 3β-(3-aminopropionyloxy), 3β-(3-aminobutiroyloxy), 3β-(3-amino-2-methylpropionyloxy), or the symbol A is $CR^7\sim\sim\sim$CH=CH$\sim\sim\sim$ where $R^7$ is as defined above, in particular 3α-(5-aminopent-1Z-enyl), 3α-(4-aminobut-1Z-enyl) or A is CH$\sim\sim\sim$X where X is S, in particular 3α-(3-aminopropylthio), 3α-(3-aminopropylsulfinyl).

In a third preferred embodiment of the present invention, the compounds of formula (I) are those in which the symbol $R^3$ represents hydroxy, the symbol $R^5$ represents H, the symbol $R^4$ represents methylene, difluoromethylene, hydroxyimino, methoxyimino, when the symbols --- in position 6 linking $R^4$ and in position 17 represent double bonds, while the other symbols --- represent single bonds, $R^1R^2N$ and B are as defined above, and the symbol A is C=N$\sim\sim\sim$O, in particular 2-amino-ethoxyimino, 3-aminopropoxyimino, 2-(N-methylamino)ethoxyimino, 3-(N-methylamino)propoxyimino, (R)-2-aminopropoxyimino, (S)-2-aminopropoxyimino, 3-amino-2-methyl-2-propoxyimino, or the symbol A is $CR^8\sim\sim\sim$XC=O, where $R^8$ and X are as defined above, in particular 3β-(3-aminopropionyloxy), 3β-(3-aminobutiroyloxy), 3β-(3-amino-2-methylpropionyloxy), or the symbol A is $CR^7\sim\sim\sim$CH=CH$\sim\sim\sim$ where $R^7$ is as defined above, in particular 3α-(5-aminopent-1Z-enyl), 3α-(4-aminobut-1Z-enyl) or A is CH$\sim\sim\sim$X where X is S, in particular 3α-(3-aminopropylthio), 3α-(3-aminopropylsulfinyl).

In a fourth preferred embodiment of the present invention, the compounds of formula (I) are those in which the symbol $R^3$ represents hydroxy, the symbol $R^5$ represents H, the symbol $R^4$ represents α-methyl, α-carbamoyl, α-methoxycarbonyl, α-hydroxymethyl, α-methoxymethyl, α-nitroxy, α-formylamino, α-ethynyl, when the symbol --- in position 17 represents a double bond while the other symbols --- represent single bonds, $R^1R^2N$ and B are as defined above, and the symbol A is C=N$\sim\sim\sim$O, in particular 2-amino-ethoxyimino, 3-aminopropoxyimino, 2-(N-methylamino)ethoxyimino, 3-(N-methylamino)propoxyimino, (R)-2-aminopropoxyimino, (S)-2-aminopropoxyimino, 3-amino-2-methyl-2-propoxyimino, or the symbol A is $CR^8\sim\sim\sim$XC=O, where $R^8$ and X are as defined above, in particular 3β-(3-aminopropionyloxy), 3β-(3-aminobutiroyloxy), 3β-(3-amino-2-methylpropionyloxy), or the symbol A is $CR^7\sim\sim\sim$CH=CH$\sim\sim\sim$ where $R^7$ is as defined above, in particular 3α-(5-aminopent-1Z-enyl), 3α-(4-aminobut-1Z-enyl) or A is CH$\sim\sim\sim$X where X is S, in particular 3α-(3-aminopropylthio), 3α-(3-aminopropylsulfinyl).

In a fifth preferred embodiment of the present invention, the compounds of formula (I) are those in which the symbols $R^3$ and $R^4$ represent H, the symbol $R^5$ represents methylene, difluoromethylene, hydroxyimino, methoxyimino, when the symbols --- in position 7 linking $R^4$ and in position 17 represent double bonds, while the other symbols --- represent single bonds, $R^1R^2N$ and B are as defined above, and the symbol A is C=N$\sim\sim\sim$O, in particular 2-aminoethoxyimino, 3-aminopropoxyimino, 2-(N-methylamino)ethoxyimino, 3-(N-methylamino)propoxyimino, (R)-2-aminopropoxyimino, (S)-2-aminopropoxyimino, 3-amino-2-methyl-2-propoxyimino, or the symbol A is $CR^8\sim\sim\sim$XC=O, where $R^8$ and X are as defined above, in particular 3β-(3-aminopropionyloxy), 3β-(3-aminobutiroyloxy), 3β-(3-amino-2-methylpropionyloxy), or the symbol A is CR$^7$~~~CH═CH~~~ where R$^7$ is as defined above, in particular 3α-(5-aminopent-1Z-enyl), 3α-(4-aminobut-1Z-enyl) or A is CH~~~X where X is S, in particular 3α-(3-aminopropylthio), 3α-(3-aminopropylsulfinyl).

In a sixth preferred embodiment of the present invention, the compounds of formula (I) are those in which the symbols R$^3$ and R$^4$ represent H, the symbol R$^5$ represents α-hydroxy, α-methyl, α-carbamoyl, α-methoxycarbonyl, α-hydroxymethyl, α-methoxymethyl, α-nitroxy, α-formylamino, α-ethynyl, β-hydroxy, β-methyl, β-carbamoyl, β-methoxycarbonyl, β-hydroxymethyl, β-methoxymethyl, β-nitroxy, β-formylamino, β-ethynyl, when the symbol --- in position 17 represents a double bond while the other symbols --- represent single bonds, R$^1$R$^2$N and B are as defined above, and the symbol A is C═N~~~O, in particular 2-amino-ethoxyimino, 3-aminopropoxyimino, 2-(N-methylamino)ethoxyimino, 3-(N-methylamino)propoxyimino, (R)-2-aminopropoxyimino, (S)-2-aminopropoxyimino, 3-amino-2-methyl-2-propoxyimino, or the symbol A is CR$^8$~~~XC═O, where R$^8$ and X are as defined above, in particular 3β-(3-aminopropionyloxy), 3β-(3-aminobutiroyloxy), 3β-(3-amino-2-methylpropionyloxy), or the symbol A is CR$^7$~~~CH═CH~~~ where R$^7$ is as defined above, in particular 3α-(5-aminopent-1Z-enyl), 3α-(4-aminobut-1Z-enyl) or A is CH~~~X where X is S, in particular 3α-(3-aminopropylthio), 3α-(3-aminopropylsulfinyl).

In a seventh preferred embodiment of the present invention, the compounds of formula (I) are those in which the symbol R$^3$ represents hydroxy, the symbol R$^4$ represents H, the symbol R$^5$ represents methylene, hydroxyimino, methoxyimino, when the symbols --- in position 7 linking R$^5$ and in position 17 represent double bonds, while the other symbols --- represent single bonds, R$^1$R$^2$N and B are as defined above, and the symbol A is C═N~~~O, in particular 2-aminoethoxyimino, 3-aminopropoxyimino, 2-(N-methylamino)ethoxyimino, 3-(N-methylamino)propoxyimino, (R)-2-aminopropoxyimino, (S)-2-aminopropoxyimino, 3-amino-2-methyl-2-propoxyimino, or the symbol A is CR$^8$~~~XC═O, where R$^8$ and X are as defined above, in particular 3β-(3-aminopropionyloxy), 3β-(3-aminobutiroyloxy), 3β-(3-amino-2-methylpropionyloxy), or the symbol A is CR$^7$~~~CH═CH~~~ where R$^7$ is as defined above, in particular 3α-(5-aminopent-1Z-enyl), 3α-(4-aminobut-1Z-enyl) or A is CH~~~X where X is S, in particular 3α-(3-aminopropylthio), 3α-(3-aminopropylsulfinyl).

In an eighth preferred embodiment of the present invention, the compounds of formula (I) are those in which the symbol R$^3$ represents hydroxy, the symbol R$^4$ represents H, the symbol R$^5$ represents α-methyl, α-carbamoyl, α-methoxycarbonyl, α-hydroxymethyl, α-methoxymethyl, α-nitroxy, α-formylamino, α-ethynyl, β-methyl, β-carbamoyl, β-methoxycarbonyl, β-hydroxymethyl, β-methoxymethyl, β-nitroxy, β-formylamino, β-ethynyl, when the symbol --- in position 17 represents a double bond while the other symbols --- represent single bonds, R$^1$R$^2$N and B are as defined above, and the symbol A is C═N~~~O, in particular 2-amino-ethoxyimino, 3-aminopropoxyimino, 2-(N-methylamino)ethoxyimino, 3-(N-methylamino)propoxyimino, (R)-2-aminopropoxyimino, (S)-2-aminopropoxyimino, 3-amino-2-methyl-2-propoxyimino, or the symbol A is CR$^8$~~~XC═O, where R$^8$ and X are as defined above, in particular 3β-(3-aminopropionyloxy), 3β-(3-aminobutiroyloxy), 3β-(3-amino-2-methylpropionyloxy), or the symbol A is CR$^7$~~~CH═CH~~~ where R$^7$ is as defined above, in particular 3α-(5-aminopent-1Z-enyl), 3α-(4-aminobut-1Z-enyl) or A is CH~~~X where X is S, in particular 3α-(3-aminopropylthio), 3α-(3-aminopropylsulfinyl).

In a ninth preferred embodiment of the present invention, the compounds of formula (I) are those in which the symbol R$^3$ represents hydroxy, the symbols R$^4$ and R$^5$ represent H, when the symbol --- in position 17 represents a double bond while the other symbols --- represent single bonds, R$^1$R$^2$N and B are as defined above, and the symbol A is C═N~~~O, in particular 2-amino-ethoxyimino, 3-aminopropoxyimino, 2-(N-methylamino)ethoxyimino, 3-(N-methylamino)propoxyimino, (R)-2-aminopropoxyimino, (S)-2-aminopropoxyimino, 3-amino-2-methyl-2-propoxyimino, or the symbol A is CR$^8$~~~XC═O, where R$^8$ and X are as defined above, in particular 3β-(3-aminopropionyloxy), 3β-(3-aminobutiroyloxy), 3β-(3-amino-2-methylpropionyloxy), or the symbol A is CR$^7$~~~CH═CH~~~ where R$^7$ is as defined above, in particular 3α-(5-aminopent-1Z-enyl), 3α-(4-aminobut-1Z-enyl) or A is CH~~~X where X is S, in particular 3α-(3-aminopropylthio), 3α-(3-aminopropylsulfinyl).

In a tenth preferred embodiment of the present invention, the compounds of formula (I) are those in which the symbol R$^3$ represents H, the symbols R$^4$ represents α-hydroxymethyl, and R$^5$ represents α-hydroxy, keto, when the symbol --- in position 17 represents a double bond while the other symbols --- represent single bonds, R$^1$R$^2$N and B are as defined above, and the symbol A is C═N~~~O, in particular 2-amino-ethoxyimino, 3-aminopropoxyimino, 2-(N-methylamino)ethoxyimino, 3-(N-methylamino)propoxyimino, (R)-2-aminopropoxyimino, (S)-2-aminopropoxyimino, 3-amino-2-methyl-2-propoxyimino, or the symbol A is CR$^8$~~~XC═O, where R$^8$ and X are as defined above, in particular 3β-(3-aminopropionyloxy), 3β-(3-aminobutiroyloxy), 3β-(3-amino-2-methylpropionyloxy), or the symbol A is CR$^7$~~~CH═CH~~~ where R$^7$ is as defined above, in particular 3α-(5-aminopent-1Z-enyl), 3α-(4-aminobut-1Z-enyl) or A is CH~~~X where X is S, in particular 3α-(3-aminopropylthio), 3α-(3-aminopropylsulfinyl).

Preferred examples of specific compounds (I) of the present invention are:

EZ 3-(2-aminoethoxyimino)-6-methyleneandrostan-17-one,
EZ 3-(3-aminopropoxyimino)-6-methyleneandrostan-17-one,
EZ 3-(2-(N-methylamino)ethoxyimino)-6-methyleneandrostan-17-one,
EZ 3-(3-(N-methylamino)propoxyimino)-6-methyleneandrostan-17-one,
EZ (R)-3-(2-aminopropoxyimino)-6-methyleneandrostan-17-one,
EZ (S)-3-(2-aminopropoxyimino)-6-methyleneandrostan-17-one,
EZ 3-(3-amino-2-methyl-2-propoxyimino)-6-methyleneandrostan-17-one,
3β-(3-aminopropionyloxy)-6-methyleneandrostan-17-one,
3β-(3-aminobutirroyloxy)-6-methyleneandrostan-17-one,
3β-(3-amino-2-methylpropionyloxy)-6-methyleneandrostan-17-one,
3α-(5-aminopent-1Z-enyl)-6-methyleneandrostan-17-one,
3α-(4-aminobut-1Z-enyl)-6-methyleneandrostan-17-one,
3α-(3-aminopropylthio)-6-methyleneandrostan-17-one,
3α-(3-aminopropylsulfinyl)-6-methyleneandrostan-17-one,
and the corresponding 6-difluoromethylene, 6-hydroxyimino and 6-methoxyimino derivatives;
EZ 3-(2-aminoethoxyimino)-6α-methylandrostan-17-one,
EZ 3-(3-aminopropoxyimino)-6α-methylandrostan-17-one,
EZ 3-(2-(N-methylamino)ethoxyimino)-6α-methylandrostan-17-one, EZ 3-(3-(N-methylamino)propoxyimino)-6α-methylandrostan-17-one,
EZ (R)-3-(2-aminopropoxyimino)-6α-methylandrostan-17-one,
EZ (S)-3-(2-aminopropoxyimino)-6α-methylandrostan-17-one,
EZ 3-(3-amino-2-methyl-2-propoxyimino)-6α-methylandrostan-17-one,
3β-(3-aminopropionyloxy)-6α-methylandrostan-17-one,
3β-(3-aminobutirroyloxy)-6α-methylandrostan-17-one,
3β-(3-amino-2-methylpropionyloxy)-6α-methylandrostan-17-one,
3α-(5-aminopent-1Z-enyl)-6α-methylandrostan-17-one,
3α-(4-aminobut-1Z-enyl)-6α-methylandrostan-17-one,
3α-(3-aminopropylthio)-6α-methylandrostan-17-one,
3α-(3-aminopropylsulfinyl)-6α-methylandrostan-17-one,
and the corresponding 6α-carbamoyl, 6α-methoxycarbonyl, 6α-hydroxymethyl, 6α-(2-hydroxyethyl), 6α-methoxymethyl, 6α-nitroxy, 6α-formylamino, 6α-ethynyl derivatives;
EZ 3-(2-aminoethoxyimino)-5α-hydroxy-6α-methylandrostan-17-one,
EZ 3-(3-aminopropoxyimino)-5α-hydroxy-6α-methylandrostan-17-one,
EZ 3-(2-(N-methylamino)ethoxyimino)-5α-hydroxy-6α-methylandrostan-17-one,
EZ 3-(3-(N-methylamino)propoxyimino)-5α-hydroxy-6α-methylandrostan-17-one,
EZ (R)-3-(2-aminopropoxyimino)-5α-hydroxy-6α-methylandrostan-17-one,
EZ (S)-3-(2-aminopropoxyimino)-5α-hydroxy-6α-methylandrostan-17-one,
EZ 3-(3-amino-2-methyl-2-propoxyimino)-5α-hydroxy-6α-methylandrostan-17-one,
3β-(3-aminopropionyloxy)-5α-hydroxy-6α-methylandrostan-17-one,
3β-(3-aminobutirroyloxy)-5α-hydroxy-6α-methylandrostan-17-one,
3β-(3-amino-2-methylpropionyloxy)-5α-hydroxy-6α-methylandrostan-17-one,
3α-(5-aminopent-1Z-enyl)-5α-hydroxy-6α-methylandrostan-17-one,
3α-(4-aminobut-1Z-enyl)-5α-hydroxy-6α-methylandrostan-17-one,
3α-(3-aminopropylthio)-5α-hydroxy-6α-methylandrostan-17-one,
3α-(3-aminopropylsulfinyl)-5α-hydroxy-6α-methylandrostan-17-one,
and the corresponding 6α-carbamoyl, 6α-methoxycarbonyl, 6α-hydroxymethyl, 6α-methoxymethyl, 6α-nitroxy, 6α-formylamino, α-ethynyl derivatives;
EZ 3-(2-aminoethoxyimino)-7-methyleneandrostan-17-one,
EZ 3-(3-aminopropoxyimino)-7-methyleneandrostan-17-one,
EZ 3-(2-(N-methylamino)ethoxyimino)-7-methyleneandrostan-17-one,
EZ 3-(3-(N-methylamino)propoxyimino)-7-methyleneandrostan-17-one,
EZ (R)-3-(2-aminopropoxyimino)-7-methyleneandrostan-17-one,
EZ (S)-3-(2-aminopropoxyimino)-7-methyleneandrostan-17-one,
EZ 3-(3-amino-2-methyl-2-propoxyimino)-7-methyleneandrostan-17-one,
3β-(3-aminopropionyloxy)-7-methyleneandrostan-17-one,
3β-(3-aminobutirroyloxy)-7-methyleneandrostan-17-one,
3β-(3-amino-2-methylpropionyloxy)-7-methyleneandrostan-17-one,
3α-(5-aminopent-1Z-enyl)-7-methyleneandrostan-17-one,
3α-(4-aminobut-1Z-enyl)-7-methyleneandrostan-17-one,
3α-(3-aminopropylthio)-7-methyleneandrostan-17-one,
3α-(3-aminopropylsulfinyl)-7-methyleneandrostan-17-one,
and the corresponding 7-difluoromethylene, 7-oxo, 7-hydroxyimino and 7-methoxyimino derivatives;
EZ 3-(2-aminoethoxyimino)-7α-methylandrostan-17-one,
EZ 3-(3-aminopropoxyimino)-7α-methylandrostan-17-one,
EZ 3-(2-(N-methylamino)ethoxyimino)-7α-methylandrostan-17-one,
EZ 3-(3-(N-methylamino)propoxyimino)-7α-methylandrostan-17-one,
EZ (R)-3-(2-aminopropoxyimino)-7α-methylandrostan-17-one,
EZ (S)-3-(2-aminopropoxyimino)-7α-methylandrostan-17-one,
EZ 3-(3-amino-2-methyl-2-propoxyimino)-7α-methylandrostan-17-one,
3β-(3-aminopropionyloxy)-7α-methylandrostan-17-one,
3β-(3-aminobutirroyloxy)-7α-methylandrostan-17-one,
3β-(3-amino-2-methylpropionyloxy)-7α-methylandrostan-17-one,
3α-(5-aminopent-1Z-enyl)-7α-methylandrostan-17-one,
3α-(4-aminobut-1Z-enyl)-7α-methylandrostan-17-one,
3α-(3-aminopropylthio)-7α-methylandrostan-17-one,
3α-(3-aminopropylsulfinyl)-7α-methylandrostan-17-one,
and the corresponding 7α-hydroxy, 7α-carbamoyl, 7α-methoxycarbonyl, 7α-hydroxymethyl, 7α-methoxymethyl, 7α-nitroxy, 7α-formylamino, 7α-ethynyl derivatives and the corresponding 7β-methyl, 7β-hydroxy, 7β-carbamoyl, 7β-methoxycarbonyl, 7β-hydroxymethyl, 7β-methoxymethyl, 7β-nitroxy, 7β-formylamino, 7β-ethynyl derivatives;
EZ 3-(2-aminoethoxyimino)-5α-hydroxy-6-methyleneandrostan-17-one,
EZ 3-(3-aminopropoxyimino)-5α-hydroxy-6-methyleneandrostan-17-one,
EZ 3-(2-(N-methylamino)ethoxyimino)-5α-hydroxy-6-methyleneandrostan-17-one,
EZ 3-(3-(N-methylamino)propoxyimino)-5α-hydroxy-6-methyleneandrostan-17-one,
EZ (R)-3-(2-aminopropoxyimino)-5α-hydroxy-6-methyleneandrostan-17-one,
EZ (S)-3-(2-aminopropoxyimino)-5α-hydroxy-6-methyleneandrostan-17-one,
EZ 3-(3-amino-2-methyl-2-propoxyimino)-5α-hydroxy-6-methyleneandrostan-17-one,
3β-(3-aminopropionyloxy)-5α-hydroxy-6-methyleneandrostan-17-one,
3β-(3-aminobutirroyloxy)-5α-hydroxy-6-methyleneandrostan-17-one,
3β-(3-amino-2-methylpropionyloxy)-5α-hydroxy-6-methyleneandrostan-17-one,
3α-(5-aminopent-1Z-enyl)-5α-hydroxy-6-methyleneandrostan-17-one,
3α-(4-aminobut-1Z-enyl)-5α-hydroxy-6-methyleneandrostan-17-one,
3α-(3-aminopropylthio)-5α-hydroxy-6-methyleneandrostan-17-one,
3α-(3-aminopropylsulfinyl)-5α-hydroxy-6-methyleneandrostan-17-one,
and the corresponding 6-difluoromethylene, 6-hydroxyimino and 6-methoxyimino derivatives;
EZ 3-(2-aminoethoxyimino)-5α-hydroxy-7-methyleneandrostan-17-one,
EZ 3-(3-aminopropoxyimino)-5α-hydroxy-7-methyleneandrostan-17-one, EZ 3-(2-(N-methylamino)ethoxyimino)-5α-hydroxy-7-methyleneandrostan-17-one,
EZ 3-(3-(N-methylamino)propoxyimino)-5α-hydroxy-7-methyleneandrostan-17-one,
EZ (R)-3-(2-aminopropoxyimino)-5α-hydroxy-7-methyleneandrostan-17-one,
EZ (S)-3-(2-aminopropoxyimino)-5α-hydroxy-7-methyleneandrostan-17-one,
EZ 3-(3-amino-2-methyl-2-propoxyimino)-5α-hydroxy-7-methyleneandrostan-17-one,
3β-(3-aminopropionyloxy)-5α-hydroxy-7-methyleneandrostan-17-one,
3β-(3-aminobutirroyloxy)-5α-hydroxy-7-methyleneandrostan-17-one,
3β-(3-amino-2-methylpropionyloxy)-5α-hydroxy-7-methyleneandrostan-17-one,
3α-(5-aminopent-1Z-enyl)-5α-hydroxy-7-methyleneandrostan-17-one,
3α-(4-aminobut-1Z-enyl)-5α-hydroxy-7-methyleneandrostan-17-one,
3α-(3-aminopropylthio)-5α-hydroxy-7-methyleneandrostan-17-one,
3α-(3-aminopropylsulfinyl)-5α-hydroxy-7-methyleneandrostan-17-one,
and the corresponding 7-hydroxyimino and 7-methoxyimino derivatives;
EZ 3-(2-aminoethoxyimino)-5α-hydroxy-7α-methylandrostan-17-one,
EZ 3-(3-aminopropoxyimino)-5α-hydroxy-7α-methylandrostan-17-one,
EZ 3-(2-(N-methylamino)ethoxyimino)-5α-hydroxy-7α-methylandrostan-17-one,
EZ 3-(3-(N-methylamino)propoxyimino)-5α-hydroxy-7α-methylandrostan-17-one,
EZ (R)-3-(2-aminopropoxyimino)-5α-hydroxy-7α-methylandrostan-17-one,
EZ (S)-3-(2-aminopropoxyimino)-5α-hydroxy-7α-methylandrostan-17-one,
EZ 3-(3-amino-2-methyl-2-propoxyimino)-5α-hydroxy-7α-methylandrostan-17-one,
3β-(3-aminopropionyloxy)-5α-hydroxy-7α-methylandrostan-17-one,
3β-(3-aminobutirroyloxy)-5α-hydroxy-7α-methylandrostan-17-one,
3β-(3-amino-2-methylpropionyloxy)-5α-hydroxy-7α-methylandrostan-17-one,
3α-(5-aminopent-1Z-enyl)-5α-hydroxy-7α-methylandrostan-17-one,
3α-(4-aminobut-1Z-enyl)-5α-hydroxy-7α-methylandrostan-17-one,
3α-(3-aminopropylthio)-5α-hydroxy-7α-methylandrostan-17-one,
3α-(3-aminopropylsulfinyl)-5α-hydroxy-7α-methylandrostan-17-one,
and the corresponding 7α-carbamoyl, 7α-methoxycarbonyl, 7α-hydroxymethyl, 7α-methoxymethyl, 7α-nitroxy, 7α-formylamino, 7α-ethynyl derivatives and the corresponding 7β-methyl, 7β-carbamoyl, 7β-methoxycarbonyl, 7β-hydroxymethyl, 7β-methoxymethyl, 7β-nitroxy, 7β-formylamino, 7β-ethynyl derivatives;
EZ 3-(2-aminoethoxyimino)-5α-hydroxyandrostan-17-one,
EZ 3-(3-aminopropoxyimino)-5α-hydroxyandrostan-17-one,
EZ 3-(2-(N-methylamino)ethoxyimino)-5α-hydroxyandrostan-17-one,
EZ 3-(3-(N-methylamino)propoxyimino)-5α-hydroxyandrostan-17-one,
EZ (R)-3-(2-aminopropoxyimino)-5α-hydroxyandrostan-17-one,
EZ (S)-3-(2-aminopropoxyimino)-5α-hydroxyandrostan-17-one,
EZ 3-(3-amino-2-methyl-2-propoxyimino)-5α-hydroxyandrostan-17-one,
3β-(3-aminopropionyloxy)-5α-hydroxyandrostan-17-one,
3β-(3-aminobutirroyloxy)-5α-hydroxyandrostan-17-one,
3β-(3-amino-2-methylpropionyloxy)-5α-hydroxyandrostan-17-one,
3α-(5-aminopent-1Z-enyl)-5α-hydroxyandrostan-17-one,
3α-(4-aminobut-1Z-enyl)-5α-hydroxyandrostan-17-one,
3α-(3-aminopropylthio)-5α-hydroxyandrostan-17-one,
3α-(3-aminopropylsulfinyl)-5α-hydroxyandrostan-17-one;
EZ 3-(2-aminoethoxyimino)-6α-hydroxymethylandrostane-7,17-dione,
EZ 3-(3-aminopropoxyimino)-6α-hydroxymethylandrostan-7,17-dione,
EZ 3-(2-(N-methylamino)ethoxyimino)-6α-hydroxymethylandrostane-7,17-dione,
EZ 3-(3-(N-methylamino)propoxyimino)-6α-hydroxymethylandrostane-7,17-dione,
EZ (R)-3-(2-aminopropoxyimino)-6α-hydroxymethylandrostane-7,17-dione,
EZ (S)-3-(2-aminopropoxyimino)-6α-hydroxymethylandrostane-7,17-dione,
EZ 3-(3-amino-2-methyl-2-propoxyimino)-6α-hydroxymethylandrostane-7,17-dione,
3β-(3-aminopropionyloxy)-6α-hydroxymethylandrostane-7,17-dione,
3β-(3-aminobutirroyloxy)-6α-hydroxymethylandrostane-7,17-dione,
3β-(3-amino-2-methylpropionyloxy)-6α-hydroxymethylandrostane-7,17-dione,
3α-(5-aminopent-1Z-enyl)-6α-hydroxymethylandrostane-7,17-dione,
3α-(4-aminobut-1Z-enyl)-6α-hydroxymethylandrostane-7,17-dione,
3α-(3-aminopropylthio)-6α-hydroxymethylandrostane-7,17-dione,
3α-(3-aminopropylsulfinyl)-6α-hydroxymethylandrostane-7,17-dione,
EZ 3-(2-aminoethoxyimino)-6α-hydroxymethyl-7α-hydroxyandrostane-17-one,
EZ 3-(3-aminopropoxyimino)-6α-hydroxymethyl-7α-hydroxyandrostane-17-one,
EZ 3-(2-(N-methylamino)ethoxyimino)-6α-hydroxymethyl-6α-hydroxyandrostane-17-one,
EZ 3-(3-(N-methylamino)propoxyimino)-6α-hydroxymethyl-6α-hydroxyandrostane-17-one,
EZ (R)-3-(2-aminopropoxyimino)-6α-hydroxymethylandrostane-7,17-dione,
EZ (S)-3-(2-aminopropoxyimino)-6α-hydroxymethyl-7α-hydroxyandrostane-17-one,
EZ 3-(3-amino-2-methyl-2-propoxyimino)-6α-hydroxymethyl-7α-hydroxyandrostane-17-one,
3β-(3-aminopropionyloxy)-6α-hydroxymethyl-7α-hydroxyandrostane-17-one,
3β-(3-aminobutirroyloxy)-6α-hydroxymethyl-7α-hydroxyandrostane-17-one,
3β-(3-amino-2-methylpropionyloxy)-6α-hydroxymethyl-7α-hydroxyandrostane-17-one,
3α-(5-aminopent-1Z-enyl)-6α-hydroxymethyl-7α-hydroxyandrostane-17-one,
3α-(4-aminobut-1Z-enyl)-6α-hydroxymethyl-7α-hydroxyandrostane-17-one, 3α-(3-aminopropylthio)-6α-hydroxymethyl-7α-hydroxyandrostane-17-one, 3α-(3-aminopropylsulfinyl)-6α-hydroxymethyl-7α-hydroxyandrostane-17-one, and the corresponding pure E and Z isomers of the EZ mixtures reported above.

The invention furthermore provides a process for the preparation of compounds of general formula (I) starting from compounds of general formula (II)

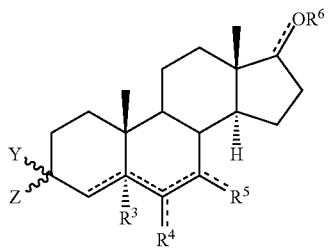

where the symbols $R^3$, $R^4$, $R^5$, $R^6$, and --- have the meanings defined above and $R^4$ is also O when the bond --- linking the carbon atom of the androstane skeleton with $R^4$ is double bond and $OR^{19}$ when the bond --- linking the carbon atom of the androstane skeleton with $R^4$ is single bond and Y and Z represent together a keto group (=O) or =N∼OBNR$^1$R$^2$ when the symbols ∼ are taken together with the meaning of double bond or, when the symbols ∼ are single bonds, Y is hydroxy, mercapto, NHR$^9$, CHO, XBNR$^1$R$^2$ or a leaving group when Z is hydrogen, or Y is hydroxy, mercapto, NHR$^9$ when Z is $C_1$-$C_6$ alkyl group or Y is CH=CH∼BNR$^1$R$^2$, CH$_2$BNR$^1$R$^2$ when Z is R$^7$ or Y is XC(=O)BNR$^1$R$^2$, XC(=O)X'BNR$^1$R$^2$ when Z is R$^8$ and R$^7$ and R$^8$ are as above defined.

Compounds of general formula (I) where the symbols $R^1$, $R^2$, $R^3$, $R^4$, $R^5$, $R^6$, B and --- have the meanings defined above and A is C=N∼O can be obtained from compounds of formula (II) where Y and Z represent together a keto group (=O), when the symbols ∼ are taken together with the meaning of double bond, by reaction with compounds of general formula (III), $$R^2R^1N-B-ONH_2 \quad (III)$$

where $R^2$, $R^1$, and B have the meanings defined above, in the form of the free base or of a salt, such as, for example, dihydrochloride, in a solvent such as dioxane, tetrahydrofuran, 1,2-dimethoxyethane, methanol, ethanol, N,N-dimethylformamide, water or their mixtures, at a temperature ranging from 0° C. and the reflux temperature. The reaction may be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate.

Compounds of general formula (I) where the symbols $R^1$, $R^2$, $R^3$, $R^4$, $R^5$, $R^6$, B and --- have the meanings defined above and A is CR$^7$∼CH=CH∼CR$^7$∼CH$_2$, where $R^7$ is hydroxy, can be obtained from compounds of formula (II) where Y and Z represent together a keto group (=O), when the symbols ∼ are taken together with the meaning of double bond, by reaction with compounds of general formula (IV) and (V)

$$W-B-CH=CHMetT \quad (IV)$$

$$W-B-CH_2MetT \quad (V)$$

where B have the meanings defined above, Met is a metal atom and T is nothing, halogen or a different metal atom depending on the oxidation state of the Met metal atom, such as, for example, Li, MgCl, MgBr, MgI, and CuLi and W is $R^2R^1N$, $R^1PGN$, $PG_2N$, $N_3$, where $R^1$ and $R^2$ are alkyl or phenylalkyl, and PG is a protective group, such as, for example, benzyl, Boc, Cbz, acetyl, to give compounds of general formula (I) directly or after transformation of the groups $R^1PGN$, $PG_2N$, $N_3$. The organometallic reaction can be carried out in a solvent such as dioxane, tetrahydrofuran, 1,2-dimethoxyethane, diethyl ether, hexane, toluene or their mixtures, at a temperature ranging from −70° C. and the reflux temperature. The reaction can be carried out in the presence of transition metal salts, such as, for example, Li$_2$CuCl$_4$, CeCl$_3$.

When W is $R^1PGN$ or $PG_2N$, the protective group can be removed after the organometallic reaction according to well established procedures described in organic chemistry, to give compounds of general formula (I).

When W is $N_3$, the azido group can be transformed after the organometallic reaction according to well established procedures described in organic chemistry, to give compounds of general formula (I), such as, for example, catalytic hydrogenation, reduction with sodium borohydride and a transition metal salt, treatment with triphenylphosphine followed by aqueous hydrolysis.

Compounds of general formula (I) where the symbols $R^1$, $R^2$, $R^3$, $R^4$, $R^5$, $R^6$, B and --- have the meanings defined above and A is CH∼X, where X is NR$^9$, can be obtained from compounds of formula (II) where Y and Z represent together a keto group (=O) when the symbols ∼ are taken together with the meaning of double bond by reaction with compounds of general formula (VI), $$W-B-NHR^9 \quad (VI)$$

where W, R$^9$, and B have the meanings defined above, in the form of the free base or of a salt, in a solvent such as dioxane, tetrahydrofuran, 1,2-dimethoxyethane, methanol, ethanol, N,N-dimethylformamide, water or their mixtures, at a temperature ranging from 0° C. and the reflux temperature, in the presence of a reducing agent, such as, for example, sodium borohydride or sodium cyanoborohydride. The reaction may be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate, until the desired pH is reached.

Compounds of general formula (I) where the symbols $R^1$, $R^2$, $R^3$, $R^4$, $R^5$, $R^6$, B and --- have the meanings defined above and A is CH∼X, where X is O, S or NR$^9$, can be obtained from compounds of formula (II) where Y is hydroxy, mercapto, NHR$^9$, when Z is hydrogen by reaction with compounds of general formula (VII), $$W-B-LG \quad (VII)$$

where W is $R^2R^1N$, $R^1PGN$, $PG_2N$, $N_3$, where $R^1$, $R^2$, and B are as defined above, PG is a protective group, such as, for example, benzyl, Boc, Cbz, acetyl, to give compounds of general formula (I) directly or after transformation of the groups $R^1PGN$, $PG_2N$, $N_3$, and LG is a leaving group, such as, for example, chloro, bromo, iodo, mesyloxy, p-toluensulfonyloxy, trifluoromethanesulfonyloxy. The reaction can be carried out in a solvent such as diethyl ether, dioxane, tetrahydrofuran, 1,2-dimethyethane, N,N-dimethylformamide, dimethylsulfoxide, toluene, or their mixtures, at a temperature ranging from 0° C. and the reflux temperature. The reaction can be carried out in the presence of a base, such as, for example, sodium or potassium hydroxide, sodium or potassium carbonate, sodium or potassium hydrogencarbonate, sodium or potassium hydride, sodium or potassium methoxide, sodium or potassium tert-butoxide, and, optionally, of a salt, such as, for example, sodium or potassium iodide. The reaction can be carried out also in a mixture of organic solvent, such as, for example, dichloromethane, chlorobenzene, toluene, hexane, and water, in the presence of sodium or potassium hydroxide and a quaternary ammonium salt, such as, for example, tetrabutylammonium chloride or bromide or iodide or hydrogensulfate, at a temperature ranging from 0° C. and the reflux temperature of the mixture.

Compounds of general formula (I) where the symbols $R^1$, $R^2$, $R^3$, $R^4$, $R^5$, $R^6$, B and ___ have the meanings defined above and A is CHX, where X is O, S or $NR^9$, can be obtained from compounds of formula (II) where Y is a leaving group such as, for example, chloro, bromo, iodo, mesyloxy, p-toluensulfonyloxy, trifluoromethanesulfonyloxy, and Z is hydrogen, by reaction with compounds of general formula (VIII),

W—B—X—H           (VIII)

where W is $R^2R^1N$, $R^1PGN$, $PG_2N$, $N_3$, where $R^1$, $R^2$, and B are as defined above, PG is a protective group, such as, for example, benzyl, Boc, Cbz, acetyl, and X is O, S or $NR^9$, where $R^9$ is as defined above, to give compounds of general formula (I) directly or after transformation of the groups $R^1PGN$, $PG_2N$, $N_3$. The reaction can be carried out in the same conditions reported above for the reaction of compounds of general formula (II) with compounds of general formula (VII).

Compounds of general formula (I) where the symbols $R^1$, $R^2$, $R^3$, $R^4$, $R^5$, $R^6$, B and ___ have the meanings defined above and A is $CR^7$CH═CH where $R^7$ is hydrogen, can be obtained from compounds of general formula (II) where Y is CHO and Z is hydrogen, by reaction with compounds of general formula (IX), W—B—P$^+$R$^{20}$Hal$^-$           (IX)

where W is $R^2R^1N$, $R^1PGN$, $PG_2N$, $N_3$, where $R^1$, $R^2$, and B are as defined above, PG is a protective group, such as, for example, benzyl, Boc, Cbz, acetyl, $R^{20}$ is a $C_1$-$C_6$ alkyl or aryl, such as, for example, methyl, n-butyl, phenyl, o-tolyl, and Hal is a halogen, such as, for example, chloro, bromo, iodo. The reaction can be carried out in a solvent such as diethyl ether, dioxane, tetrahydrofuran, 1,2-dimethoxyethane, toluene, or their mixtures, at a temperature ranging from -78° C. and the reflux temperature. The reaction is carried out in the presence of a base, such as, for example, sodium or potassium hydride, sodium or potassium methoxide, sodium or potassium tert-butoxide. The reaction can be carried out also in a mixture of organic solvent, such as, for example, dichloromethane, chlorobenzene, toluene, hexane, and water, in the presence of sodium or potassium hydroxide and a quaternary ammonium salt, such as, for example, tetrabutylammonium chloride or bromide or iodide or hydrogensulfate, at a temperature ranging from 0° C. and the reflux temperature of the mixture.

Compounds of general formula (I) where the symbols $R^1$, $R^2$, $R^3$, $R^4$, $R^5$, $R^6$, B and ___ have the meanings defined above and A is $CR^8$XC═O, where $R^8$ is hydrogen or $C_1$-$C_6$ alkyl group, X is O, S, or $NR^9$ can be obtained from compounds of formula (II) where Y is hydroxy, mercapto, $NHR^9$ and Z is hydrogen or $C_1$-$C_6$ alkyl group by reaction with compounds of general formula (X),

W—B—COOH           (X)

where W is $R^2R^1N$, $R^1PGN$, $PG_2N$, $N_3$, where $R^1$, $R^2$, and B are as defined above, PG is a protective group, such as, for example, benzyl, Boc, Cbz, acetyl, to give compounds of general formula (I) directly or after transformation of the groups $R^1PGN$, $PG_2N$, $N_3$. The reaction can be carried out in a solvent such as diethyl ether, dioxane, tetrahydrofuran, 1,2-dimethoxyethane, toluene, acetone, ethyl acetate, dichloromethane, chloroform, N,N-dimethylformamide, dimethylsulfoxide, water or their mixtures, at a temperature ranging from -30° C. and the reflux temperature, in the presence of a condensing reagent such as, N,N'-dicyclohexylcarbodiimide, N-ethyl-N'-(3-dimethylaminopropyl)carbodiimide hydrochloride, $SOCl_2POCl_3$, or $PCl_5$, or compounds of formula (X) can be treated previously with $SOCl_2$, $POCl_3$, $PCl_5$, optionally in the presence of a base, such as, for example, sodium or potassium hydroxide, sodium or potassium carbonate, sodium or potassium hydrogencarbonate, triethylamine, pyridine, or 4-dimethylaminopyridine.

Compounds of general formula (I) where the symbols $R^1$, $R^2$, $R^3$, $R^4$, $R^5$, $R^6$, B and ___ have the meanings defined above and A is $CR^8$X(C═O)X', where $R^8$ is hydrogen or $C_1$-$C_6$ alkyl group, X is O, S, or $NR^9$, and X' is NH can be obtained from compounds of formula (II) where Y is hydroxy, mercapto, $NHR^9$ and Z is hydrogen or $C_1$-$C_6$ alkyl group by reaction with compounds of general formula (XI),

W—B—NCO           (XI)

where W is $R^2R^1N$, $R^1PGN$, $PG_2N$, $N_3$, where $R^1$, $R^2$, and B are as defined above, PG is a protective group, such as, for example, benzyl, Boc, Cbz, acetyl, to give compounds of general formula (I) directly or after transformation of the groups $R^1PGN$, $PG_2N$, $N_3$. The reaction can be carried out in a solvent such as diethyl ether, dioxane, tetrahydrofuran, 1,2-dimethoxyethane, toluene, acetone, ethyl acetate, dichloromethane, chloroform, N,N-dimethylformamide, dimethylsulfoxide, ethanol, methanol, water or their mixtures, at a temperature ranging from -30° C. and the reflux temperature.

Compounds of general formula (I) where the symbols $R^1$, $R^2$, $R^3$, $R^4$, $R^5$, $R^6$, B and ___ have the meanings defined above and A is $CR^8$X(C═O)X', where $R^8$ is hydrogen or $C_1$-$C_6$ alkyl group, X is O, S, or $NR^9$, and X' is O, S, $NR^9$ can be obtained from compounds of formula (II) where Y is hydroxy, mercapto, $NHR^9$ and Z is hydrogen or $C_1$-$C_6$ alkyl group by reaction with compounds of general formula (XII),

W—B—X'—H           (XII)

where W is $R^2R^1N$, $R^1PGN$, $PG_2N$, $N_3$, where $R^1$, $R^2$, B and X' are as defined above, PG is a protective group, such as, for example, benzyl, Boc, Cbz, acetyl, to give compounds of general formula (I) directly or after transformation of the groups $R^1PGN$, $PG_2N$, $N_3$. The reaction can be carried out in a solvent such as diethyl ether, dioxane, tetrahydrofuran, 1,2-dimethoxyethane, toluene, acetone, ethyl acetate, dichloromethane, chloroform, N,N-dimethylformamide, dimethylsulfoxide, or their mixtures, at a temperature ranging from -60° C. and the reflux temperature using a carbonyl donating group, such as, for example, carbonyldiimidazole, phosgene, triphosgene, in the presence of a base, such as, for example, sodium or potassium hydroxide, sodium or potassium carbonate, sodium or potassium hydrogencarbonate, triethylamine, pyridine, or 4-dimethylaminopyridine.

Compounds of general formula (I) where the symbols $R^1$, $R^2$, $R^3$, $R^4$, $R^5$, $R^6$, B and --- have the meanings defined above and A is $CH\sim X$, $CR^8\sim XC=O$, $CR^8\sim XC(=O)X'$, where X and X' are $NR^9$, and $R^9$ is $C_1$-$C_6$ alkyl group, can be obtained from compounds of formula (I) where A is $CH\sim X$, $CR^8\sim XC=O$, $CR^8\sim XC(=O)X'$, where X and X' are NH, by alkylation with a $C_1$-$C_6$ alkyl-LG, where LG is a leaving group, such as, for example, chloro, bromo, iodo, mesyloxy, p-toluensulfonyloxy, trifluoromethanesulfonyloxy. The reaction can be carried out in a solvent such as diethyl ether, dioxane, tetrahydrofuran, 1,2-dimethoxyethane, N,N-dimethylformamide, dimethylsulfoxide, toluene, or their mixtures, at a temperature ranging from 0° C. and the reflux temperature, optionally in the presence of a base, such as, for example, sodium or potassium hydroxide, sodium or potassium carbonate, sodium or potassium hydrogencarbonate, sodium or potassium hydride, sodium or potassium methoxide, sodium or potassium tert-butoxide, and, optionally, of a salt, such as, for example, sodium or potassium iodide. The reaction can be carried out also in a mixture of organic solvent, such as, for example, dichloromethane, chlorobenzene, toluene, hexane, and water, in the presence of sodium or potassium hydroxide and a quaternary ammonium salt, such as, for example, tetrabutylammonium chloride or bromide or iodide or hydrogensulfate, at a temperature ranging from 0° C. and the reflux temperature of the mixture.

Compounds of general formula (I) where the symbols $R^1$, $R^2$, $R^3$, $R^4$, $R^5$, $R^6$, B have the meanings defined above, --- is a single bond and A is $CH\sim X$, where X is $NR^9$, and $R^9$ is $C_1$-$C_6$ alkyl group, can be obtained from compounds of formula (I) where A is $CH\sim X$, and X is NH, by reaction with $CH_2O$, or $C_1$-$C_5$ alkyl-CHO in a solvent such as dioxane, tetrahydrofuran, 1,2-dimethoxyethane, methanol, ethanol, N,N-dimethylformamide, water or their mixtures, at a temperature ranging from 0° C. and the reflux temperature, in the presence of a reducing agent, such as, for example, sodium borohydride or sodium cyanoborohydride. The reaction can be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate, until the desired pH is reached.

Compounds of general formula (I) where the symbols $R^1$, $R^2$, $R^3$, $R^4$, $R^5$, $R^6$, B and --- have the meanings defined above and A is $CH\sim X$, where X is $S(O)_x$ and x is 1 or 2, can be obtained from compounds of formula (I) where A is $CH\sim X$, where X is $S(O)_x$ and x is 0, by one of the reagents reported in the literature for such a kind of oxidation, such as, for example, hydrogen peroxide, sodium metaperiodate, tert-butyl hypochlorite, sodium chlorite, sodium hypochlorite, sodium perborate, N-methylmorpholine-N-oxide and tetrapropylammonium periodate, potassium hydrogen persulfate, and peracids; according to the reaction conditions, that is temperature and equivalents of oxidant, the oxidation can give the compounds of general formula (I) above described where x is 1 or 2.

Compounds of general formula (I) where the symbols A, B, $R^1$, $R^2$, $R^3$, $R^4$, $R^5$, $R^6$, and --- have the meanings defined above, can be obtained by reduction of the corresponding compounds of general formula (I) where the symbol --- is double bond, by catalytic hydrogenation, either with hydrogen gas or in hydrogen transfer conditions, in the presence of a metal catalyst, such as, Pd/C, $PtO_2$, Pt, Pt/C, Raney Nickel. As a hydrogen transfer reagent, ammonium formate, sodium hypophosphite or cyclohexadiene can be used. The reaction can be carried out in a solvent, such as, for example, ethanol, methanol, ethyl acetate, dioxane, tetrahydrofuran, acetic acid, N,N-dimethylformamide, water or their mixtures, at a temperature ranging from 0° C. and the reflux temperature, at a pressure ranging from atmospheric pressure to 10 atm. According to the substrate and the conditions used, the hydrogenation can selectively affect one or more double bonds.

Compounds of general formula (I) where the symbols B, $R^1$, $R^2$, $R^3$, $R^4$, $R^5$, $R^6$, and --- have the meanings defined above, and A is $CR^7\sim CH=CH\sim CR^7\sim CH_2$, where $R^7$ is hydrogen, can be obtained from the corresponding compounds of general formula (I) where $R^7$ is hydroxy by deoxygenation with one of the methods reported in literature for such a kind of reaction, such as, for example, reaction with thiocarbonyldiimidazole and tri-n-butylstannane, carbon disulfide in the presence of a base followed by methyl iodide and treatment with tri-n-butylstannane, $NaBH_3CN$ and $ZnI_2$, $NaBH_4$ in acetic acid.

Compounds of general formula (I) where the symbols A, B, $R^3$, $R^4$, $R^5$, $R^6$, and --- have the meanings defined above, $R^1$ is hydrogen and $R^2$ is $C(=NR^{10})NHR^{11}$, where $R^{10}$ and $R^{11}$ have the meanings reported above, can be obtained from the corresponding compounds of general formula (I) where $R^1$ and $R^2$ are hydrogen, by reaction with compounds of general formula (XIII)

$$TC(=NR^{10})NHR^{11} \qquad (XIII)$$

where $R^9$ and $R^{10}$ have the meanings reported above and T is a leaving group, such as, for example, methylthio, 1-pyrazolyl. The reaction can be carried out in a solvent such as dioxane, tetrahydro-furan, 1,2-dimethoxyethane, methanol, ethanol, N,N-dimethyl-formamide, water or their mixtures, at a temperature ranging from 0° C. and the reflux temperature, optionally in the presence of a base, such as sodium or potassium hydroxide, triethylamine, diethyliso-propylamine.

Compounds of general formula (I) where the symbols A, B, $R^1$, $R^2$, $R^3$, $R^6$, and --- have the meanings defined above, $R^4$ is not $N\sim OR^{13}$ and $R^5$ is $N\sim OR^{13}$ when the bond --- linking the carbon atom in position 6 with $R^4$ can be single or double and the carbon atom in position 7 of the androstane skeleton with $R^5$ is double bond, can be obtained from the corresponding compounds of general formula (I) where $R^4$ is not $N\sim OR^{13}$ and $R^5$ is O, with the meaning of a keto group, with one of the methods reported in literature for such reactions, such as, for example, by reaction with compounds of general formula $H_2NOR^{13}$ where $R^{13}$ has the meanings defined above, in the form of the free base or of a salt, such as, for example, hydrochloride, in a solvent such as dioxane, tetrahydrofuran, 1,2-dimethoxyethane, methanol, ethanol, N,N-dimethylformamide, pyridine, water or their mixtures, at a temperature ranging from 0° C. and the reflux temperature. The reaction may be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate.

Compounds of general formula (I) where the symbols A, B, $R^1$, $R^2$, $R^3$, $R^6$, and --- have the meanings defined above, $R^4$ is $N\sim OR^{13}$ and $R^5$ is not $N\sim OR^{13}$ when the bond $\sim$ linking the carbon atom in position 6 with $R^4$ is double bond and the carbon atom in position 7 of the androstane skeleton with $R^5$ can be single or double bond, can be obtained from the corresponding compounds of general formula (II) where $R^4$ is O, with the meaning of a keto group and $R^5$ is not $N\sim OR^{13}$, with one of the methods reported in literature for such reactions, such as, for example, by reaction with compounds of general formula $H_2NOR^{13}$.

Compounds of general formula (I) where the symbols A, B, $R^1$, $R^2$, $R^3$, $R^6$, and ___ have the meanings defined above, $R^4$ and $R^5$ are $N\sim OR^{13}$ when the bonds ___ linking the carbon atoms in position 6 and 7 with $R^4$ and $R^5$, respectively, are double, can be obtained from the corresponding compounds of general formula (II) where $R^4$ and $R^5$ are O, with the meaning of a keto group, with one of the methods reported in literature for such reactions, such as, for example, by reaction with compounds of general formula $H_2NOR^{13}$.

Compounds of general formula (I) where the symbols A, B, $R^1$, $R^2$, $R^3$, $R^6$, and ___ have the meanings defined above, and $R^4$ is not $CR^{14}R^{15}$ and $R^5$ is $CR^{14}R^{15}$ when the bond ___ linking the carbon atom in position 6 with $R^4$ and the carbon atom in position 7 of the androstane skeleton with $R^5$ is double bond, can be obtained from the corresponding compounds of general formula (I) where $R^4$ is not $CR^{14}R^{15}$ and $R^5$ is O, with the meaning of a keto group, with one of the methods reported in literature for such reactions, such as, for example, by reaction with compounds of general formula (XIV) or (XV),

  (XIV)

  (XV)

where $R^{14}$, $R^{15}$, and $R^{20}$ are as defined above and Hal is a halogen, such as, for example, chloro, bromo, iodo. The reaction with compounds of general formula (XIV) or (XV) can be carried out in a solvent such as diethyl ether, dioxane, tetrahydrofuran, 1,2-dimethoxyethane, toluene, N,N-dimethylformamide, dimethylsulfoxide, n-pentane or their mixtures, at a temperature ranging from −78° C. and the reflux temperature. The reaction is carried out in the presence of a base, such as, for example, sodium or potassium hydride, sodium or potassium methoxide, sodium or potassium tert-butoxide. The reaction can be carried out also in a mixture of organic solvent, such as, for example, dichloromethane, chlorobenzene, toluene, hexane, and water, in the presence of sodium or potassium hydroxide and a quaternary ammonium salt, such as, for example, tetrabutylammonium chloride or bromide or iodide or hydrogensulfate, at a temperature ranging from 0° C. and the reflux temperature of the mixture. The reaction with compounds of general formula (XV) can be carried out also in water or in a mixture of the above mentioned solvents with water, at a temperature ranging from 0° C. and the reflux temperature. These reactions can be carried out in the presence of a base, such as, for example, sodium or potassium hydroxide, sodium or potassium hydrogencarbonate, sodium or potassium carbonate, triethylamine, diisopropylethylamine, optionally in the presence of a salt, such as lithium chloride.

Compounds of general formula (I) where the symbols A, B, $R^1$, $R^2$, $R^3$, $R^6$, and ___ have the meanings defined above, and $R^4$ is $CR^{14}R^{15}$ and $R^5$ is not $CR^{14}R^{15}$ when the bond ___ linking the carbon atom in position 6 with $R^4$ is double and the carbon atom in position 7 of the androstane skeleton with $R^5$ can be single or double bond, can be obtained from the corresponding compounds of general formula (II) where $R^4$ is O, with the meaning of a keto group, and $R^5$ is not $CR^{14}R^{15}$, with one of the methods reported in literature for such reactions, such as, for example, by reaction with compounds of general formula (XIV) or (XV),

  (XIV)

  (XV)

where $R^{14}$, $R^{15}$, and $R^{20}$ are as defined above and Hal is a halogen.

Compounds of general formula (I) where the symbols A, B, $R^1$, $R^2$, $R^3$, $R^6$, and ___ have the meanings defined above, and $R^4$ and $R^5$ are $CR^{14}R^{15}$ when the bonds ___ linking the carbon atoms in position 6 and the carbon atom in position 7 with $R^4$ and $R^5$, respectively, are double bond, can be obtained from the corresponding compounds of general formula (II) where $R^4$ and $R^5$ are both O, with the meaning of a keto group, with one of the methods reported in literature for such reactions, such as, for example, by reaction with compounds of general formula (XIV) or (XV),

  (XIV)

  (XV)

where $R^{14}$, $R^{15}$, and $R^{20}$ are as defined above and Hal is a halogen.

Compounds of general formula (I) where the symbols A, B, $R^1$, $R^2$, $R^3$, $R^6$, and ___ have the meanings defined above, and $R^4$ and $R^5$, independently, are $C_1$-$C_6$ alkyl groups substituted with a hydroxy group, in particular are hydroxymethyl, when the bonds ___ linking the carbon atom in position 6 of the androstane skeleton with $R^4$ and the carbon atom in position 7 with $R^5$ are single bonds, can be obtained from the corresponding compounds of general formula (I) where $R^4$ and $R^5$, being $R^4$ and $R^5$ the same or different, are $CR^{14}R^{15}$, where $R^{14}$ and $R^{15}$ are hydrogens, when the bonds ___ linking the carbon atom in position 6 of the androstane skeleton with $R^4$ and the carbon atom in position 7 with $R^5$ are double bonds, with one of the methods reported in literature for such reactions, such as, for example, by reaction with a borane, such as, for example, borane, or its complexes with dimethylamine or dimethylsulfide, 9-borabicyclononane, diisopinocanphenylborane, diisoamylborane, in an ethereal solvent, such as, for example, diethyl ether, tetrahydrofuran, dioxane, 1,2-dimethoxyethane, followed by treatment with an alkaline aqueous hydrogen peroxide solution or sodium perborate.

With the same methods, also compounds of general formula (I) where the symbols A, B, $R^1$, $R^2$, $R^3$, $R^6$, and ___ have the meanings defined above, and $R^4$ and $R^5$, independently, are $C_1$-$C_6$ alkyl groups substituted with a hydroxy group, in particular are hydroxyethyl, when the bonds ___ linking the carbon atom in position 6 of the androstane skeleton with $R^4$ and the carbon atom in position 7 with $R^5$ are single bonds, can be obtained from the corresponding compounds of general formula (I) where $R^4$ and $R^5$, being $R^4$ and $R^5$ the same or different, are vinyl, when the bonds ___ linking the carbon atom in position 6 of the androstane skeleton with $R^4$ and the carbon atom in position 7 with $R^5$ are single bonds. Compounds of general formula (I) where the substituents $R^4$ and $R^5$, independently, are vinyl, when the bonds ___ linking the carbon atom in position 6 of the androstane skeleton with $R^4$ and the carbon atom in position 7 with $R^5$ are single bonds, can be obtained by reaction of compounds of general formula (I) where $R^4$ and $R^5$, independently, are CHO, with methyltriphenyl-phosphonium chloride or bromide or iodide by using the same reaction conditions above described involving compounds of general formula (XIV) or (XV).

Compounds of general formula (I) where the symbols A, B, $R^1$, $R^2$, $R^3$, $R^4$, $R^6$, and ___ have the meanings defined above, and $R^5$, is O, with the meaning of a keto group, when the bond ___ linking the carbon atom in position 7 of the androstane skeleton with $R^5$ is double bond, can be obtained from the corresponding compounds of general formula (I) where $R^5$ is hydroxy, when the bond --- linking the carbon atom in position 7 of the androstane skeleton with $R^5$ is single bond, with one of the reagents reported in literature for such oxidations, such as, for example, iodoxybenzoic acid, Dess-Martin periodinane, oxalyl chloride and triethylamine, $CrO_3$ in pyridine or in sulfuric acid and acetone, pyridinium chlorochromate, pyridinium dichromate.

Compounds of general formula (II), as defined above, can be prepared starting from known compounds with proper functionality in the different positions, already reported in the literature or from commercially available compounds, such as, for example, 3β-hydroxyandrost-5-en-17-one, 3β-hydroxyandrost-5-ene-7,17-dione, following the general procedures listed below. The following list of compounds is an example, not limiting the scope of the invention, of reported methods of preparation of compounds (II): androstane-3,6,17-trione, androstane-3α,6β,17β-triol, 6α-hydroxyandrostane-3,17-dione, 3β,17β-dihydroxyandrost-4-en-6-one, 3,3:17,17-bis(ethylendioxy)androstane-6α-ol, 3,3:17,17-bis(ethylendioxy)androstane-6β-ol, 3,3:17,17-bis(ethylenedioxy)androstane-6-one and 6α,17β-dihydroxyandrostan-3-one reported in S. De Munari et al, *J. Med. Chem.*, 2003, 3644; 3β-acetoxyandrost-5-ene-7,17-dione in E. S. Arsenou et al., *Steroids* 68 (2003) 407-4143; 3,3:17,17-bis(ethylendioxy)androst-5-en-7-one in Pui-Kai Li and R. W. Brueggemeier, *J. Med. Chem.* 1990, 33, 101-105.

Compounds of general formula (II) where the symbols $R^3$, $R^4$, $R^5$, $R^6$, and --- have the meanings defined above and Y and Z represent together =NOBNR$^1$R$^2$, when the symbols  are taken together with the meaning of double bond, where the symbols $R^1$, $R^2$, B and  have the meanings defined above, can be obtained from compounds of formula (II) where Y and Z represent together a keto group (=O), when the symbols  are taken together with the meaning of double bond, by reaction with compounds of general formula (III), $$R^2R^1N\text{---}B\text{---}ONH_2 \qquad (III)$$

where $R^2$, $R^1$, and B have the meanings defined above, in the form of the free base or of a salt, by using the same conditions described above for the reaction of compounds (III) with compounds of general formula (II) in order to obtain compounds of formula (I).

Compounds of general formula (II) where the symbols $R^3$, $R^4$, $R^5$, $R^6$, and --- have the meanings defined above and Y is CH=CH BNR$^1$R$^2$, CH$_2$BNR$^1$R$^2$ when Z is $R^7$, where $R^7$ is hydroxy or hydrogen and the symbols $R^1$, $R^2$, B and  have the meanings defined above, can be obtained from compounds of formula (II) where Y and Z represent together a keto group (=O), when the symbols  are taken together with the meaning of double bond, by reaction with compounds of general formula (IV) and (V)

$$W\text{---}B\text{---}CH=CHMetT \qquad (IV)$$

$$W\text{---}B\text{---}CH_2MetT \qquad (V)$$

where B have the meanings defined above, Met is a metal atom and T is nothing, halogen or a different metal atom depending on the oxidation state of the Met metal atom, such as, for example, Li, MgCl, MgBr, MgI, and CuLi and W is $R^2R^1N$, $R^1PGN$, $PG_2N$, $N_3$, where $R^1$ and $R^2$ are alkyl or phenylalkyl, and PG is a protective group, such as, for example, benzyl, Boc, Cbz, acetyl, to give compounds of general formula (I) directly or after transformation of the groups $R^1PGN$, $PG_2N$, $N_3$. The organometallic reaction can be carried out in the same conditions described above for the reaction of compounds (IV) and (V) with compounds of general formula (II) in order to obtain compounds of formula (I) and the transformation of the protective groups or of the azido can be carried out as described above.

Compounds of general formula (II) where the symbols $R^3$, $R^4$, $R^5$, $R^6$, and --- have the meanings defined above and Y is $XBN^1R^2$ when Z is hydrogen, where X is O, S or $NR^9$ and $R^1$, $R^2$ and B have the meanings defined above, can be obtained from compounds of formula (II) where Y is hydroxy, mercapto, $NHR^9$, when Z is hydrogen by reaction with compounds of general formula (VII), $$W\text{---}B\text{---}LG \qquad (VII)$$

where W is $R^2R^1N$, $R^1PGN$, $PG_2N$, $N_3$, where $R^1$, $R^2$, and B are as defined above, PG is a protective group, such as, for example, benzyl, Boc, Cbz, acetyl, to give compounds of general formula (I) directly or after transformation of the groups $R^1PGN$, $PG_2N$, $N_3$, and LG is a leaving group, such as, for example, chloro, bromo, iodo, mesyloxy, p-toluensulfonyloxy, trifluoromethanesulfonyloxy. The reaction can be reaction can be carried out in the same conditions described above for the reaction of compounds (VII) with compounds of general formula (II) in order to obtain compounds of formula (I) and the transformation of the protective groups or of the azido can be carried out as described above.

Compounds of general formula (II) where the symbols $R^3$, $R^4$, $R^5$, $R^6$, and --- have the meanings defined above and Y is $CR^7$CH=CH when $R^7$ is hydrogen, can be obtained from compounds of general formula (II) where Y is CHO and Z is hydrogen, by reaction with compounds of general formula (IX), $$W\text{---}B\text{---}P^+R^{20}Hal^- \qquad (IX)$$

where W is $R^2R^1N$, $R^1PGN$, $PG_2N$, $N_3$, where $R^1$, $R^2$, and B are as defined above, PG is a protective group, such as, for example, benzyl, Boc, Cbz, acetyl, $R^{20}$ is a $C_1$-$C_6$ alkyl or aryl, such as, for example, methyl, n-butyl, phenyl, o-tolyl, and Hal is a halogen, such as, for example, chloro, bromo, iodo. The reaction can be carried out in the same conditions described above for the reaction of compounds (IX) with compounds of general formula (II) in order to obtain compounds of formula (I) and the transformation of the protective groups or of the azido can be carried out as described above.

Compounds of general formula (II) where the symbols $R^3$, $R^4$, $R^5$, $R^6$, and --- have the meanings defined above and Y is $X(C=O)BNR^1R^2$, when Z is hydrogen or $C_1$-$C_6$ alkyl group, X is O, S, or $NR^9$, and $R^1$, $R^2$, and B are as defined above, can be obtained from compounds of formula (II) where Y is hydroxy, mercapto, $NHR^9$ and Z is hydrogen or $C_1$-$C_6$ alkyl group by reaction with compounds of general formula (X), $$W\text{---}B\text{---}COOH \qquad (X)$$

where W is $R^2R^1N$, $R^1PGN$, $PG_2N$, $N_3$, where $R^1$, $R^2$, and B are as defined above, PG is a protective group, such as, for example, benzyl, Boc, Cbz, acetyl, to give compounds of general formula (I) directly or after transformation of the groups $R^1PGN$, $PG_2N$, $N_3$. The reaction can be carried out in the same conditions described above for the reaction of compounds (X) with compounds of general formula (II) in order to obtain compounds of formula (I) and the transformation of the protective groups or of the azido can be carried out as described above.

Compounds of general formula (I) where the symbols $R^3$, $R^4$, $R^5$, $R^6$, and --- have the meanings defined above and Y is  $X(C=O)X'BNR^1R^2$, where Z is hydrogen or $C_1$-$C_6$ alkyl group, X is O, S, or $NR^9$, and $R^1$, $R^2$, and B are as defined above, and X' is NH can be obtained from compounds of formula (II) where Y is hydroxy, mercapto, NHR$^9$ and Z is hydrogen or C$_1$-C$_6$ alkyl group by reaction with compounds of general formula (XI),

W—B—NCO (XI)

where W is R$^2$R$^1$N, R$^1$PGN, PG$_2$N, N$_3$, where R$^1$, R$^2$, and B are as defined above, PG is a protective group, such as, for example, benzyl, Boc, Cbz, acetyl, to give compounds of general formula (I) directly or after transformation of the groups R$^1$PGN, PG$_2$N, N$_3$. The reaction can be carried out in the same conditions described above for the reaction of compounds (XI) with compounds of general formula (II) in order to obtain compounds of formula (I) and the transformation of the protective groups or of the azido can be carried out as described above.

Compounds of general formula (II) where the symbols R$^3$, R$^4$, R$^5$, R$^6$, B and --- have the meanings defined above and Y is X(C=O)X'BNR$^1$R$^2$, when Z is hydrogen or C$_1$-C$_6$ alkyl group, X is O, S, or NR$^9$, and X' is O, S, NR$^9$ and R$^1$, R$^2$, and B are as defined above, can be obtained from compounds of formula (II) where Y is hydroxy, mercapto, NHR$^9$ and Z is hydrogen or C$_1$-C$_6$ alkyl group by reaction with compounds of general formula (XII),

W—B—X'—H (XII)

where W is R$^2$R$^1$N, R$^1$PGN, PG$_2$N, N$_3$, where R$^1$, R$^2$, B and X' are as defined above, PG is a protective group, such as, for example, benzyl, Boc, Cbz, acetyl, to give compounds of general formula (I) directly or after transformation of the groups R$^1$PGN, PG$_2$N, N$_3$. The reaction can be carried out in the same conditions described above for the reaction of compounds (XII) with compounds of general formula (II) in order to obtain compounds of formula (I) and the transformation of the protective groups or of the azido can be carried out as described above.

Compounds of general formula (II), where R$^3$ and R$^5$ are, independently, C$_1$-C$_6$ alkyl, can be prepared from compounds of general formula (II), where R$^3$ and R$^5$ are hydrogen and R$^4$ is oxygen, when the symbol --- linking R$^4$ to the androstane skeleton is double bond, the symbol --- linking R$^5$ to the androstane skeleton is single bond and the symbols --- in positions 4-5, 5-6, and 6-7 are single bonds, by treatment with a base, such as, for example, sodium or potassium hydride, sodium or potassium methoxide, sodium or potassium tert-butoxide, lithium diisopropylamide in a solvent such as diethyl ether, dioxane, tetrahydrofuran, 1,2-dimethoxyethane, toluene, N,N-dimethylformamide, dimethylsulfoxide or their mixtures, at a temperature ranging from –78° C. and the reflux temperature, followed by quenching with a C$_1$-C$_6$ alkyl-LG, where LG is a leaving group, such as, for example, chloro, bromo, iodo, mesyloxy, p-toluensulfonyloxy, trifluoromethanesulfonyloxy, at a temperature ranging from –78° C. and the reflux temperature. The reaction can be carried out also in a mixture of organic solvent, such as, for example, dichloromethane, chlorobenzene, toluene, hexane, and water, in the presence of sodium or potassium hydroxide and a quaternary ammonium salt, such as, for example, tetrabutylammonium chloride or bromide or iodide or hydrogensulfate, at a temperature ranging from 0° C. and the reflux temperature of the mixture.

By using the same reactions reported above, compounds of general formula (II), where R$^4$ is C$_1$-C$_6$ alkyl, can be prepared by treatment of the corresponding compounds of general formula (II), where R$^4$ is hydrogen and R$^5$ is oxygen, when the symbol --- linking R$^4$ to the androstane skeleton is single bond, the symbol --- linking R$^5$ to the androstane skeleton is double bond and the symbols --- in positions 4-5, 5-6, and 6-7 are single bonds.

Compounds of general formula (II) where R$^3$ is OR$^{12}$, can be obtained by treatment of compounds of general formula (II), where R$^3$ is hydroxy, when the symbols --- in positions 4-5 and 5-6, are single bonds, with compounds of general formula R$^{12}$-LG, where LG is a leaving group, such as, for example, chloro, bromo, iodo, mesyloxy, p-toluensulfonyloxy, trifluoromethanesulfonyloxy. The reaction can be carried out in a solvent such as diethyl ether, dioxane, tetrahydrofuran, 1,2-dimethoxyethane, N,N-dimethylformamide, dimethylsulfoxide, toluene, or their mixtures, at a temperature ranging from 0° C. and the reflux temperature, optionally in the presence of a base, such as, for example, sodium or potassium hydroxide, sodium or potassium carbonate, sodium or potassium hydrogencarbonate, sodium or potassium hydride, sodium or potassium methoxide, sodium or potassium tert-butoxide, and, optionally, of a salt, such as, for example, sodium or potassium iodide. The reaction can be carried out also in a mixture of organic solvent, such as, for example, dichloromethane, chlorobenzene, toluene, hexane, and water, in the presence of sodium or potassium hydroxide and a quaternary ammonium salt, such as, for example, tetrabutylammonium chloride or bromide or iodide or hydrogensulfate, at a temperature ranging from 0° C. and the reflux temperature of the mixture.

By using the same reactions reported above, compounds of general formula (II) where R$^5$ is OR$^{19}$, can be obtained by treatment of compounds of general formula (II), where R$^5$ is hydroxy, when the symbols --- in positions 4-5, 5-6, and 6-7, are single bonds, with compounds of general formula R$^{19}$-LG.

By using the same reactions reported above, compounds of general formula (II) where R$^6$ is C$_1$-C$_6$ alkyl group, can be obtained by treatment of compounds of general formula (II) where R$^6$ is H, when the symbol --- in positions 17 is single bond, with compounds of general formula C$_1$-C$_6$ alkyl-LG.

Compounds of general formula (II) where R$^3$, R$^4$, and R$^5$ are, independently, ONO$_2$ can be obtained by treatment of compounds of general formula (II), where R$^3$, R$^4$, and R$^5$ are, independently, hydroxy, when the symbols --- in positions 4-5, 5-6, and 6-7 are single bonds, with nitric acid in acetic anhydride or acetic acid, nitric acid and sulfuric acid in dichloromethane, nitrosyl fluoride or tetrafluoborate in acetonitrile.

Compounds of general formula (II), where the substituents R$^4$ and R$^5$, independently, are N~~~ OR$^{13}$, where the bonds --- linking the carbon atom in position 6 of the androstane skeleton with R$^4$ and the carbon atom in position 7 with R$^5$ are double bonds, and the symbols --- in positions 4-5, 5-6, and 6-7 are single bonds, can be obtained by treatment of compounds of general formula (II), where R$^4$ and R$^5$ are, independently, oxygen, with the meaning of keto groups, being R$^4$ and R$^5$ the same or different, by reaction with compounds of general formula H$_2$NOR$^{13}$, where R$^{13}$ has the meanings defined above, in the form of the free base or of a salt, such as, for example, hydrochloride, in a solvent such as dioxane, tetrahydrofuran, 1,2-dimethoxyethane, methanol, ethanol, N,N-dimethylformamide, water or their mixtures, at a temperature ranging from 0° C. and the reflux temperature. The reaction may be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate.

Compounds of general formula (II), where the substituents $R^4$ and $R^5$, independently, are $CR^{14}R^{15}$, and the bonds --- linking the carbon atom in position 6 of the androstane skeleton with $R^4$ and the carbon atom in position 7 with $R^5$ are double bonds, and the symbols --- in positions 4-5, 5-6, and 6-7 are single bonds, can be obtained by reaction of compounds of general formula (II) where $R^4$ and $R^5$ are, independently, oxygen, with the meaning of keto groups, being $R^4$ and $R^5$ the same or different, with compounds of general formula (XIV) or (XV),

(XIV)

(XV)

where $R^{14}$, $R^{15}$, and $R^{20}$ are as defined above and Hal is a halogen, such as, for example, chloro, bromo, iodo, in the same reaction conditions above described involving compounds of general formula (XIV) or (XV).

Compounds of general formula (II) where the substituents $R^4$ and $R^5$, independently, are $C_1$-$C_6$ alkyl groups substituted with a hydroxy group, in particular are hydroxymethyl, when the bonds --- linking the carbon atom in position 6 of the androstane skeleton with $R^4$ and the carbon atom in position 7 with $R^5$ are single bonds, can be obtained from compounds of general formula (II) where $R^4$ and $R^5$, being $R^4$ and $R^5$ the same or different, are $CR^{14}R^{15}$, where $R^{14}$ and $R^{15}$ are hydrogens, when the bonds --- linking the carbon atom in position 6 of the androstane skeleton with $R^4$ and the carbon atom in position 7 with $R^5$ are double bonds, with one of the methods reported in literature for such reactions, such as, for example, with a borane, such as, for example, borane, or its complexes with dimethylamine or dimethylsulfide, 9-borabicyclononane, diisopinocanphenylborane, diisoamylborane, in an ethereal solvent, such as, for example, diethyl ether, tetrahydrofuran, dioxane, 1,2-dimethoxyethane, followed by treatment with an alkaline aqueous hydrogen peroxide solution or sodium perborate.

With the same methods, also compounds of general formula (II) in which the substituents $R^4$ and $R^5$, independently, are $C_1$-$C_6$ alkyl groups substituted with a hydroxy group, in particular are hydroxyethyl, when the bonds --- linking the carbon atom in position 6 of the androstane skeleton with $R^4$ and the carbon atom in position 7 with $R^5$ are single bonds, can be obtained from compounds of general formula (II) where $R^4$ and $R^5$, being $R^4$ and $R^5$ the same or different, are vinyl, when the bonds --- linking the carbon atom in position 6 of the androstane skeleton with $R^4$ and the carbon atom in position 7 with $R^5$ are single bonds.

Compounds of general formula (II) where the substituents $R^4$ and $R^5$, independently, are vinyl, when the bonds --- linking the carbon atom in position 6 of the androstane skeleton with $R^4$ and the carbon atom in position 7 with $R^5$ are single bonds, can be obtained by reaction of compounds of general formula (II) where $R^4$ and $R^5$, independently, are CHO, with methyltriphenylphosphonium chloride or bromide or iodide by using the same reaction conditions above described involving compounds of general formula (XIV) or (XV).

Compounds of general formula (II) where the substituents $R^4$ and $R^5$, independently, are ethynyl, when the bonds --- linking the carbon atom in position 6 of the androstane skeleton with $R^4$ and the carbon atom in position 7 with $R^5$ are single bonds, can be obtained by reaction of compounds of general formula (II) where $R^4$ and $R^5$, independently, are CHO, with chloromethyltriphenylphosphonium chloride or bromide or iodide and n-butyllithium from $-78°$ C. to room temperature followed by further treatment with n-butyllithium.

Compounds of general formula (II) where the substituents $R^4$ and $R^5$, independently, are $C_1$-$C_6$ alkyl groups, when the bonds --- linking the carbon atom in position 6 of the androstane skeleton with $R^4$ and the carbon atom in position 7 with $R^5$ are single bonds, can be obtained from compounds of general formula (II) where $R^4$ and $R^5$, being $R^4$ and $R^5$ the same or different, are $CR^{14}R^{15}$, where $R^{14}$ and $R^{15}$ are hydrogen or $C_1$-$C_5$ alkyl groups, when the bonds --- linking the carbon atom in position 6 of the androstane skeleton with $R^4$ and the carbon atom in position 7 with $R^5$ are double bonds, with one of the methods reported in literature for such reactions, such as by catalytic hydrogenation, in the reaction conditions described above for a similar transformation of compounds of general formula (I).

Compounds of general formula (II), where $R^4$ and $R^5$, independently, are $C_1$-$C_6$ alkyl groups, in particular methyl and ethyl, when the bonds --- linking the carbon atom in position 6 of the androstane skeleton with $R^4$ and the carbon atom in position 7 with $R^5$ are single bonds, can be obtained from compounds of general formula (II) where $R^4$ and $R^5$, being $R^4$ and $R^5$ the same or different, are hydroxymethyl and 2-hydroxyethyl with one of the methods reported in literature for such reactions, such as treatment with mesyl or tosylchloride, in the presence of a base, followed by reduction with a hydride, such as, for example, sodium borohydride or lithium aluminumhydride, or by deoxygenation with one of the methods reported in literature for such a kind of reaction, such as, for example, reaction with thiocarbonyldiimidazole and tri-n-butylstannane, carbon disulfide in the presence of a base followed by methyl iodide and treatment with tri-n-butylstannane, $NaBH_3CN$ and $ZnI_2$, $NaBH_4$ in acetic acid.

Compounds of general formula (II), where $R^4$ and $R^5$, independently, are $COOR^{16}$, where $R^{16}$ is hydrogen, when the bonds --- linking the carbon atom in position 6 of the androstane skeleton with $R^4$ and the carbon atom in position 7 with $R^5$ are single bonds, can be obtained from compounds of general formula (II) where $R^4$ and $R^5$, being $R^4$ and $R^5$ the same or different, are hydroxymethyl, by oxidation with one of the reagents reported in literature for such oxidations, such as, for example, iodoxybenzoic acid, Dess-Martin periodinane, oxalyl chloride and triethylamine and dimethylsulfoxide in methylene chloride, $CrO_3$ in pyridine or in sulfuric acid and acetone, pyridinium chlorochromate, pyridinium dichromate, to give the intermediate aldehyde where $R^4$ and $R^5$, independently, are CHO, followed by further oxidation to the carboxylic acid with one of the reagents reported in literature for such oxidations, such as, for example, potassium permanganate, chromic anhydride in sulfuric acid/acetone, pyridinium dichromate in N,N-dimethylformamide.

Compounds of general formula (II), where $R^4$ and $R^5$, independently, are $COOR^{16}$ or $CONR^{17}R^{18}$, where $R^{16}$ is a $C_1$-$C_6$ alkyl group and $R^{17}$ and $R^{18}$ are as above defined, when the bonds --- linking the carbon atom in position 6 of the androstane skeleton with $R^4$ and the carbon atom in position 7 with $R^5$ are single bonds, can be obtained from compounds of general formula (II) where $R^4$ and $R^5$, being $R^4$ and $R^5$ the same or different, are COOH, by treatment with diazomethane, trimethylsilyldiazomethane or a compound of general formula $R^{16}OH$ or $HNR^{17}R^{18}$ with one of the methods reported in literature for such transformations, such as, for example, condensation in the presence of a condensing reagent such as, N,N'-dicyclohexylcarbodiimide, N-ethyl-N'-(3-dimethylaminopropyl)carbodiimide hydrochloride, $SOCl_2$, $POCl_3$, or $PCl_5$, or compounds of formula (II) can be treated previously with $SOCl_2$, $POCl_3$, $PCl_5$, optionally in the presence of a base, such as, for example, sodium or potassium hydroxide, sodium or potassium carbonate, sodium or potassium hydrogencarbonate, triethylamine, pyridine, or 4-dimethylaminopyridine.

Compounds of general formula (II), where $R^4$ and $R^5$, independently, are $CONR^{17}R^{18}$, where and $R^{17}$ and $R^{18}$ are as above defined, when the bonds --- linking the carbon atom in position 6 of the androstane skeleton with $R^4$ and the carbon atom in position 7 with $R^5$ are single bonds, can be obtained from compounds of general formula (II) where $R^4$ and $R^5$, being $R^4$ and $R^5$ the same or different, are $COOR^{16}$, where $R^{16}$ is a $C_1$-$C_6$ alkyl group, by treatment with a compound of general formula $HNR^{17}R^{18}$ with one of the methods reported in literature for such transformations, such as, for example, in water, methanol or ethanol, eventually in the presence of a catalytic amount of sodium methoxide at a temperature ranging from 0° C. to the reflux temperature also in a sealed bomb.

Compounds of general formula (II), where $R^4$ and $R^5$, independently, are $CH=N_{\sim\sim\sim}OH$, when the bonds --- linking the carbon atom in position 6 of the androstane skeleton with $R^4$ and the carbon atom in position 7 with $R^5$ are single bonds, can be obtained from compounds of general formula (II) where $R^4$ and $R^5$, being $R^4$ and $R^5$ the same or different, are CHO, by treatment with hydroxylamine as the free base or in the form of a salt, such as hydrochloride, sulfate, phosphate, in a solvent such as dioxane, tetrahydrofuran, 1,2-dimethoxyethane, methanol, ethanol, N,N-dimethylformamide, water or their mixtures, at a temperature ranging from 0° C. and the reflux temperature. The reaction can be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate.

Compounds of general formula (II), where $R^4$ and $R^5$, independently, are CN, when the bonds --- linking the carbon atom in position 6 of the androstane skeleton with $R^4$ and the carbon atom in position 7 with $R^5$ are single bonds, can be obtained from compounds of general formula (II) where $R^4$ and $R^5$ are oxygen, with the meaning of keto groups, being $R^4$ and $R^5$ the same or different, where the bonds --- linking the carbon atom in position 6 of the androstane skeleton with $R^4$ and the carbon atom in position 7 with $R^5$ are double bonds, and the symbols --- in positions 4-5, 5-6, and 6-7 are single bonds, with one of the methods reported in literature for such transformations, such as, for example, treatment with tosylmethyl isocyanide in the presence of a base.

Compounds of general formula (II), where $R^4$ and $R^5$, independently, are $NHCHO$ and $NHCOCH_3$, when the bonds --- linking the carbon atom in position 6 of the androstane skeleton with $R^4$ and the carbon atom in position 7 with $R^5$ are single bonds, can be obtained from compounds of general formula (II) where $R^4$ and $R^5$ are $N_{\sim\sim\sim}OR^{13}$, where $R^{13}$ is hydrogen, being $R^4$ and $R^5$ the same or different, where the bonds --- linking the carbon atom in position 6 of the androstane skeleton with $R^4$ and the carbon atom in position 7 with $R^5$ are double bonds, and the symbols --- in positions 4-5, 5-6, and 6-7 are single bonds, with one of the methods reported in literature for such reductions, such as, for example, treatment with lithium aluminumhydride, catalytic hydrogenation, or sodium or lithium or magnesium in an alcohol to give the corresponding amine where $R^4$ and $R^5$ are $NH_2$, followed by formylation with formic acid or acetylation with acetic acid in the presence of a condensing agent, such as, for example, N,N'-dicyclohexylcarbodiimide, N-ethyl-N'-(3-dimethylaminopropyl)carbodiimide hydrochloride, or acetylation with acetic anhydride, optionally in the presence of a base, such as, for example, triethylamine, pyridine or 4-dimethylaminopyridine.

Compounds of general formula (II), where $R^4$ and $R^5$, independently, are spiroxirane, when the bonds --- linking the carbon atom in position 6 of the androstane skeleton with $R^4$ and the carbon atom in position 7 with $R^5$ are single bonds, can be obtained from compounds of general formula (II) where $R^4$ and $R^5$ are $CR^{14}R^{15}$, where $R^{14}$ and $R^{15}$ are hydrogen, being $R^4$ and $R^5$ the same or different, where the bonds --- linking the carbon atom in position 6 of the androstane skeleton with $R^4$ and the carbon atom in position 7 with $R^5$ are double bonds, and the symbols --- in positions 4-5, 5-6, and 6-7 are single bonds, with one of the reagents reported in literature for such reactions, such as, for example perbenzoic acid, m-chloroperbenzoic acid, magnesium perphthalate, perphthalic acid, peracetic acid or hydrogen peroxide and sodium hydroxide in acetonitrile.

Compounds of general formula (II), where $R^4$ and $R^5$, independently, are spirooxirane, when the bonds --- linking the carbon atom in position 6 of the androstane skeleton with $R^4$ and the carbon atom in position 7 with $R^5$ are single bonds, can be obtained from compounds of general formula (II) where $R^4$ and $R^5$, independently, are O, with the meaning of keto groups, where the bonds --- linking the carbon atom in position 6 the androstane skeleton with $R^4$ and the carbon atom in position 7 with $R^5$ are double bonds, being $R^4$ and $R^5$ the same or different, and the symbols --- in positions 4-5, 5-6, and 6-7 are single bonds, with one of the reagents reported in literature for such reactions, such as, for example trimethylsulfonium iodide or trimethylsulfoxonium iodide in the presence of a base, such as sodium hydride, sodium methoxide, potassium tert-butoxide.

Compounds of general formula (II), where $R^4$ and $R^5$, independently, are spirocyclopropane, when the bonds --- linking the carbon atom in position 6 of the androstane skeleton with $R^4$ and the carbon atom in position 7 with $R^5$ are single bonds, can be obtained from compounds of general formula (II) where $R^4$ and $R^5$ are $CR^{14}R^{15}$, where $R^{14}$ and $R^{15}$ are hydrogen, being $R^4$ and $R^5$ the same or different, where the bonds --- linking the carbon atom in position 6 of the androstane skeleton with $R^4$ and the carbon atom in position 7 with $R^5$ are double bonds, and the symbols --- in positions 4-5, 5-6, and 6-7 are single bonds, with one of the reagents reported in literature for such reactions, such as, for example, diiodomethane and diethyltin or tin-copper alloy.

Compounds of general formula (II) where $R^6$ is $C_2$-$C_6$ acyl group, when the bond --- in position 17 of the androstane skeleton is a single bond, can be obtained from compounds of general formula (II) where $R^6$ is hydrogen, with one of the methods reported in literature for such reactions, such as, for example, by reaction with compounds of general formula $C_1$-$C_5$ alkyl-COOH in the presence of a condensing reagent such as, N,N'-dicyclohexylcarbodiimide, N-ethyl-N'-(3-dimethylaminopropyl)carbodiimide hydrochloride, $SOCl_2$ $POCl_3$, or $PCl_5$, or compounds of formula $C_1$-$C_5$ alkyl-COOH can be treated previously with $SOCl_2$, $POCl_3$, $PCl_5$, optionally in the presence of a base, such as, for example, sodium or potassium hydroxide, sodium or potassium carbonate, sodium or potassium hydrogencarbonate, triethylamine, pyridine, or 4-dimethylaminopyridine.

Compounds of general formula (II) where Y is mercapto, where the symbols $R^3$, $R^4$, $R^5$, $R^6$, and --- have the meanings defined above and Z is hydrogen or $C_1$-$C_6$ alkyl group, can be obtained from compounds of general formula (II) where Y is hydroxy, with one of the methods reported in literature for such reactions, such as, for example, by reaction with thiocarboxylic acids, such as thioacetic acid, in the presence of diethyl or diisopropyl azodicarboxylate and tributylphosphine or triphenylphosphine, followed by cleavage of the thioester group with ammonia, sodium methanethiolate or propanethiolate.

Compounds of general formula (II) where Y is $NHR^9$, where the symbols $R^3$, $R^4$, $R^5$, $R^6$, $R^9$, and ___ have the meanings defined above and Z is hydrogen, can be obtained from compounds of general formula (II) where Y and Z represent together a keto group (=O), when the symbols ∼∼∼ are taken together with the meaning of double bond, with one of the methods reported in literature for such reactions, such as, for example, by reaction with compounds of general formula $NH_2R^9$ in the presence of a reducing agent, such as, for example, sodium borohydride or sodium cyanoborohydride at the appropriate pH.

Compounds of general formula (II) where Y is $NHR^9$, where the symbols $R^3$, $R^4$, $R^5$, $R^6$, and ___ have the meanings defined above, $R^9$ is hydrogen and Z is hydrogen, can be obtained from compounds of general formula (II) where Y and Z represent together a keto group (=O), when the symbols ∼∼∼ are taken together with the meaning of double bond, with one of the methods reported in literature for such reactions, such as, for example, by reaction with compounds of general formula $HONH_2$ to give the oxime followed by reduction with a reducing agent, such as, for example, sodium in an alcohol, lithium aluminumhydride, or by hydrogenation over a metal catalyst, such as, for example, Pt, Pd or Raney Nickel.

Compounds of general formula (II) where Y is CHO, where the symbols $R^3$, $R^4$, $R^5$, $R^6$, and ___ have the meanings defined above and Z is hydrogen, can be obtained from compounds of general formula (II) where Y and Z represent together a keto group (=O), when the symbols ∼∼∼ are taken together with the meaning of double bond, with one of the methods reported in literature for such reactions, such as, for example, by reaction with methoxymethyl triphenylphosphonium chloride in the presence of a strong base, such as, for example, sodium hydride or potassium tert-butoxide, followed by acidic hydrolysis of the intermediate methyl enolether; by reaction with trimethylsulfonium iodide or trimethylsulfoxonium iodide in the presence of a base, such as sodium hydride, sodium methoxide, potassium tert-butoxide followed by treatment with boron trifluoride etherate; by reaction with methyltriphenylphosphonium iodide in the presence of a base, such as sodium hydride, sodium methoxide, potassium tert-butoxide, to give the methylene derivative, which on treatment with borane and sodium perborate or alkaline hydrogen peroxide gives the hydroxymethyl derivative, which can be oxidized to the desired carboxaldehyde with one of the reagents reported in literature for such oxidations, such as, for example, iodoxybenzoic acid, Dess-Martin periodinane, oxalyl chloride and triethylamine, $CrO_3$ in pyridine or in sulfuric acid and acetone, pyridinium chlorochromate, pyridinium dichromate.

Compounds of general formula (II) where Y is hydroxy, where the symbols $R^3$, $R^4$, $R^5$, $R^6$, and ___ have the meanings defined above and Z is $C_1$-$C_6$ alkyl group can be obtained from compounds of general formula (II) where Y and Z represent together a keto group (=O), when the symbols ∼∼∼ are taken together with the meaning of double bond, with one of the methods reported in literature for such reactions, such as, for example, by reaction with a compound of general formula $C_1$-$C_6$ alkylMetT, where Met is a metal atom and T is nothing, halogen or a different metal atom depending on the oxidation state of the Met metal atom, such as, for example, Li, MgCl, MgBr, MgI, and CuLi.

Compounds of general formula (II) where Y is $NHR^9$, where the symbols $R^3$, $R^4$, $R^5$, $R^6$, and ___ have the meanings defined above, $R^9$ is hydrogen and Z is $C_1$-$C_6$ alkyl group can be obtained from compounds of general formula (II) where Y is hydroxy with one of the methods reported in literature for such reactions, such as, for example, by reaction with hydrocyanic acid in the presence of a strong acid such as, for example, sulfuric acid, followed by hydrolysis of the intermediate formamide.

Compounds of general formula (III)-(XV) are commercially available or can be prepared from commercially available compounds by standard procedures.

In all said transformations, any interfering reactive group can be protected and then deprotected according to well established procedures described in organic chemistry (see for example: T. W. Greene and P. G. M. Wuts "Protective Groups in Organic Synthesis", J. Wiley & Sons, Inc., 3$^{rd}$ Ed., 1999) and well known to those skilled in the art.

All said transformations are only examples of well established procedures described in organic chemistry (see for example: J. March "Advanced Organic Chemistry", J. Wiley & Sons, Inc., 4$^{th}$ Ed., 1992) and well known to those skilled in the art.

We have found that the derivatives (I), prepared according to the invention, and their pharmaceutically acceptable salts are useful agents for the treatment of cardiovascular disorders, such as heart failure and hypertension. Moreover said compounds show affinity and inhibit the enzymatic activity of the $Na^+$, $K^+$-ATPase.

Since the compounds of the present invention are shown to be able to antagonize the molecular effects induced by nanomolar ouabain concentrations on the Na-KATPase, they will be effective the treatment of the diseases caused by the hypertensive effects of endogenous ouabain.

According to a preferred embodiment of the invention the diseases caused by the hypertensive effects of endogenous ouabain include: renal failure progression in autosomal dominant polycystic renal disease (ADPKD), preeclamptic hypertension and proteinuria and renal failure progression in patients with adducin polymorphisms.

In autosomal dominant polycystic renal disease (ADPKD), cyst formation and enlargement are due to cell proliferation and transepithelial secretion of fluids, causing progressive impairment renal function and kidney failure. 1 over 1000 subjects are affected by ADPKD which represents the first genetic cause of renal failure. Renal Na-K ATPase is essential for ion and fluid transport in ADPKD cells and its mislocation and function alteration have been described in this pathology (Wilson P D et al. Am J Pathol 2000; 156:253-268). Ouabain, the inhibitor of the Na-KATPase, inhibits fluid secretion in ADPKD cysts (Grantham J J et al. I Clin. Invest. 1995; 95:195-202) at micromolar concentrations, conversely, at nanomolar concentrations, which are similar to the circulating endogenous ouabain ones, ouabain stimulates ADPKD cell proliferation but does not affect normal human kidney cell growth (Nguyen A N et al. 2007; 18:46-57). It has been demonstrated that ouabain stimulates ADPKD proliferation by binding to the Na-KATPase with high affinity and triggering the activation of the MEK-ERK pathway (Nguyen A N et al. 2007; 18:46-57).

Preeclampsia is a potential devastating disorder of hypertension in pregnancy for which an effective treatment is still lacking. Elevated circulating levels of cardenolides and bufodienolides have been reported in preeclamptic patients and in rat models of the disease (Lopatin D A et al J. Hypertens.

1999; 17:1179-1187; Graves S V et al. Am J Hypertens. 1995; 8:5-11; Adair C D et al. Am J Nephrol. 1996; 16:529-531). The data available suggest that in preeclampsia elevated plasma concentrations of Na-K ATPase inhibitors lead to vasoconstriction and malignant hypertension (Vu H V et al. Am J Nephrol. 2005; 25:520-528). Recently, Digoxin-specific Fab (Digibind) have been proved to reduce blood pressure and increase natriuresis in preeclamptic patients (Pullen M A al. JPET 2004; 310:319-325).

Glomerulosclerosis-associated proteinuria is due to an impairment of the slit-pore structure formed by the podocyte foot-processes in the glomerulus. In particular, slit diaphragm proteins such as nephrin, ZO1, podocyn, synaptopodin and others, in addition to their structural functions participate in common signaling pathways regulated by Fyn a tyrosin kinase of the Src family kinases (Benzing T. J Am Soc Nephrol 2004; 15:1382-1391). Recently, a key role in the structure of the slit pore has been ascribed to beta adducin, a cytoskeletal protein under the control of Fyn (Gotoh H BBRC 2006; 346:600-605; Shima T et al. JBC 2001; 276: 42233-42240). Adducin polymorphisms joint to that of ACE have been found associated to impaired renal function in European and Chinese populations (Wang J G et al. J Mol Med 2004; 82:715-722; Wang J G et al. Am J Kidney Dis. 2001; 38: 1158-1168). Rostafuroxin and analogues, as endogenous ouabain antagonists, have been described to be able to antagonize the molecular effect of adducin polymorphism on tyrosine kinase signaling (Ferrandi M. et al. JBC, 2004; 279:33306-14; Ferrari et al. Am J Physiol Regul 2006; 290:R529-535; Ferrari P. et al. Med Hypothes. 2007; 68:1307-1314).

The pharmaceutical compositions will contain at least one compound of Formula (I) as an active ingredient, in an amount such as to produce a significant therapeutic effect. The compositions covered by the present invention are entirely conventional and are obtained with methods which are common practice in the pharmaceutical industry, such as, for example, those illustrated in *Remington's Pharmaceutical Science Handbook*, Mack Pub. N.Y.—last edition. According to the administration route chosen, the compositions will be in solid or liquid form, suitable for oral, parenteral or intravenous administration. The compositions according to the present invention contain, along with the active ingredient, at least one pharmaceutically acceptable vehicle or excipient. These may be particularly useful formulation coadjuvants, e.g. solubilising agents, dispersing agents, suspension agents, and emulsifying agents.

Moreover the compounds of the present invention possess positive inotropic features, as shown by slow intravenous infusion in anesthetized guinea pig according to Cerri (Cerri A. et al., J. Med. Chem. 2000, 43, 2332) and have a low toxicity when compared with standard cardiotonic steroids, e.g. digoxin.

The following examples illustrate the invention without limiting it.

Example 1

(E,Z) 3-(2-Aminoethoxyimino)-17-oxoandrostane-6α-yl nitrate fumarate (I-aa)

To a stirred solution of 3,17-dioxoandrostane-6α-yl nitrate (II-aa, Prepn. 1, 1.14 g) in THF (30 mL), a solution of 2-aminoethoxyamine dihydrochloride (223 mg), Na$_2$HPO$_4$.12H$_2$O (2.30 g) in H$_2$O (11.6 mL) was rapidly added dropwise. After 1.5 h, NaCl (1.8 g) was added and the mixture stirred for 10 min. The phases were separated and the aqueous phase was extracted with THF (2×). The combined organic extracts were dried over Na$_2$SO$_4$, filtered and evaporated to dryness. The crude product was purified by flash chromatography (SiO$_2$, CHCl$_3$/MeOH/26% NH$_4$OH 90/10/1). To the concentrated fractions a stoichiometric amount of fumaric acid in MeOH was added. After addition of a 1/1 mixture of EtOAc/Et$_2$O, the precipitate was filtered to give the title compound I-aa as a white solid (0.57 g, 33%). $^1$H-NMR (300 MHz, DMSO-d$_6$, ppm from TMS): δ 8.76 (bb, 4H), 6.41 (s, 1H), 4.98 (m, 1H), 4.04 (m, 2H), 3.16 (m, 0.5H), 3.06 (m, 0.5H), 2.98 (m, 2H), 2.45-0.75 (m, 19H), 0.98 (s, 1.5H), 0.97 (s, 1.5H), 0.80 (s, 3H).

Example 2

(E,Z) 3-(2-Aminoethoxyimino)-17-oxoandrostane-6β-yl nitrate fumarate (I-ab)

Prepared in 60% yield as described in Example 1 starting from 3,17-dioxoandrostane-6β-yl nitrate (II-ab, Prepn. 2) and 2-aminoethoxyamine dihydrochloride. $^1$H-NMR (300 MHz, DMSO-d$_6$, ppm from TMS): δ 8.41 (bb, 4H), 6.40 (s, 2H), 5.23 (m, 0.5H), 5.19 (m, 0.5H), 4.03 (m, 2H), 3.05 (m, 1H), 2.96 (m, 2H), 2.45-0.70 (m, 19H), 1.00 (s, 1.5H), 0.99 (s, 1.5H), 0.80 (s, 3H).

Example 3

(E,Z) 3-(2-Aminoethoxyimino)-6α-cyanoandrostan-17-one fumarate (I-ac)

Prepared in 65% yield as described in Example 1 starting from 6α-cyanoandrostane-3,17-dione (II-ac, Prepn. 3) and 2-aminoethoxyamine dihydrochloride. $^1$H-NMR (300 MHz, DMSO-d$_6$, ppm from TMS): δ 9.07 (bb, 4H), 6.40 (s, 2H), 4.07 (m, 2H), 3.24 (m, 0.5H), 3.06 (m, 0.5H), 2.99 (m, 2H), 2.77 (m, 1H), 2.45-0.70 (m, 19H), 0.88 (s, 1.5H), 0.87 (s, 1.5H), 0.77 (s, 3H).

Example 4

(E,Z) 3-(2-Aminoethoxyimino)-5α-hydroxyandrostan-17-one fumarate (I-ad)

To a stirred solution of 5α-hydroxyandrostane-3,17-dione (II-ad, Prepn. 4, 447 mg) in THF (10 mL), a solution of 2-aminoethoxyamine dihydrochloride (223 mg) in H$_2$O (5 mL) was rapidly added dropwise. After 1.5 h, NaCl (556 mg) was added and the mixture stirred for 10 min. The phases were separated and the aqueous phase was extracted with THF (2×). The combined organic extracts were dried over Na$_2$SO$_4$, filtered and evaporated to give an oily residue. The crude product was dissolved in CH$_2$Cl$_2$ (10 mL) and washed with a saturated aqueous solution of NaCl (3×). The organic layer was dried over Na$_2$SO$_4$ and evaporated to dryness. The crude product was purified by flash chromatography (SiO$_2$, CHCl$_3$/MeOH/26% NH$_4$OH 90/10/1). To the concentrated fractions a stoichiometric amount of fumaric acid in MeOH was added. After addition of a 1/1 mixture of EtOAc/Et$_2$O, the precipitate was filtered to give the title compound I-ad (420 mg, 60%). $^1$H-NMR (300 MHz, DMSO-d$_6$, ppm from TMS): δ 9.10 (bb, 4H), 6.40 (s, 2H), 4.32 (bb, 1H), 4.03 (m, 2H), 2.96 (m, 3H), 2.45-1.00 (m, 20H), 0.97 (s, 3H), 0.76 (s, 3H).

Example 5

(E,Z) 3-(2-Aminoethoxyimino)-5α-hydroxy-6β-cyanoandrostane-17-one fumarate (I-ae)

Prepared in 50% yield as described in Example 1 starting from 5α-hydroxy-6β-cyanoandrostane-3,17-dione (II-ae, Prepn. 5) and 2-aminoethoxyamine dihydrochloride. $^1$H-NMR (300 MHz, DMSO-d$_6$, ppm from TMS): δ 7.50 (bb, 5H), 6.35 (s, 2H), 4.03 (m, 2H), 3.30-0.95 (m, 22H), 1.22 (s, 3H), 0.81 (s, 3H).

Example 6

(E,Z)-3-(2-Aminoethoxyimino)-7α-methylandrostane-6-(E)-hydroxy-imino-17-one hydrochloride (I-af)

Prepared in 64% yield as described in Example 4 starting from 6-(E)-hydroxyimino-7α-methylandrostane-3,17-dione (II-af, Prepn. 6) and 2-aminoethoxyamine dihydrochloride. The crude product was triturated with Et$_2$O. $^1$H-NMR (300 MHz, DMSO-d$_6$, ppm from TMS): δ 10.30 (s, 1H), 7.62 (bb, 3H), 4.07 (m, 2H), 3.08 (m, 0.5H), 2.99 (m, 2H), 2.95 (m, 0.5H), 2.73 (m, 0.5H), 2.68 (m, 0.5H), 2.45-1.00 (m, 17H), 1.08 (s, 3H), 0.78 (s, 3H).

Example 7

(E,Z) 3-(2-Aminoethoxyimino)-6-(2-spiro-1,3-dioxolane)androstane-17-one fumarate (I-ag)

Prepared in 53% yield as described in Example 1 starting from 6,6-ethylendioxyandrostane-3,17-dione (II-ag, Prepn. 7) and 2-aminoethoxyamine dihydrochloride. The crude product was purified by flash chromatography (SiO$_2$, CHCl$_3$/MeOH/26% NH$_4$OH 90/10/1). To the concentrated fractions a stoichiometric amount of fumaric acid in MeOH was added. After addition of a 1/1 mixture of EtOAc/Et$_2$O, the precipitate was filtered to give the title compound I-ag. $^1$H-NMR (300 MHz, DMSO-d$_6$, ppm from TMS): δ 8.00 (bb, 4H), 6.40 (s, 2H), 4.05-3.65 (m, 6H), 3.12 (m, 0.5H) 3.04 (m, 0.5H) 2.97 (m, 2H) 2.45-0.70 (m, 19H), 0.97 (s, 1.5H), 0.95 (s, 1.5H), 0.78 (s, 3H).

Example 8

(E,Z) 3-(2-Aminoethoxyimino)-6-methyleneandrostan-17-one hydrochloride (I-ah)

Prepared in 90% yield as described in Example 4 starting from 6-methyleneandrostane-3,17-dione (II-ah, Prepn. 8) and 2-aminoethoxyamine dihydrochloride. The crude product was triturated with Et$_2$O. $^1$H-NMR (300 MHz, DMSO-d$_6$, ppm from TMS): δ 8.08 (bb, 3H), 4.83 (bs, 0.5H), 4.80 (bs, 0.5H), 4.53 (bs, 0.5H), 4.49 (bs, 0.5H), 4.09 (m, 2H), 3.15-2.95 (m, 3H), 2.45-0.90 (m, 19H), 0.77 (s, 3H), 0.75 (s, 3H).

Example 9

(E) 3-(2-Aminoethoxyimino)-6-methyleneandrostan-17-one hydrochloride (I-ai)

Prepared in 40% yield as described in Example 1 starting from 6-methyleneandrostane-3,17-dione (II-ah, Prepn. 8) and 2-aminoethoxyamine dihydrochloride. The crude product (1.65 g) was crystallized twice from EtOAc to give the title compound I-ai. H-NMR (300 MHz, DMSO-d$_6$, ppm from TMS): δ 7.97 (bb, 3H), 4.81 (bs, 1H), 4.49 (bs, 1H), 4.08 (t, 2H), 3.10 (m, 1H), 3.02 (t, 2H), 2.45-0.85 (m, 19H), 0.77 (s, 3H), 0.75 (s, 3H).

Example 10

(E,Z) 3-(2-Aminoethoxyimino)-6β-hydroxymethylandrostan-17-one hydrochloride (I-aj)

Prepared in 85% yield as described in Example 4 starting from 6β-hydroxymethylandrostane-3,17-dione (II-ai, Prepn. 9) and 2-aminoethoxyamine dihydrochloride. $^1$H-NMR (300 MHz, DMSO-d$_6$, ppm from TMS): δ 8.14 (bb, 3H), 4.42 (t, 0.5H), 4.40 (t, 0.5H), 4.08 (m, 2H), 3.50-3.25 (m, 2H), 3.05 (m, 0.5H), 3.00 (m, 2H), 2.91 (m, 0.5H), 2.50-0.60 (m, 20H), 0.84 (s, 1.5H), 0.82 (s, 1.5H), 0.80 (s, 3H).

Example 11

(E,Z) 3-(2-Aminoethoxyimino)-6β-methoxymethylandrostan-17-one hydrochloride (I-ak)

Prepared in 60% yield as described in Example 4 starting from 6β-methoxymethylandrostane-3,17-dione (II-aj, Prepn. 10) and 2-aminoethoxyamine dihydrochloride. $^1$H-NMR (300 MHz, DMSO-d$_6$, ppm from TMS): δ 8.06 (bb, 3H), 4.07 (m, 2H), 3.35 (m, 2H), 3.32 (s, 3H),), 3.07 (m, 0.5H), 3.02 (m, 2H), 2.92 (m, 0.5H), 2.45-0.62 (m, 20H), 0.86 (s, 1.5H), 0.85 (s, 1.5H), 0.81 (s, 3H).

Example 12

(E,Z) 3-(2-Aminoethoxyimino)-6α-vinylandrostan-17-one hydrochloride (I-al)

Prepared in 90% yield as described in Example 4 starting from 6α-vinylandrostane-3,17-dione (II-ak, Prepn. 11) and 2-aminoethoxyamine dihydrochloride. 1H-NMR (300 MHz, DMSO-d6, ppm from TMS): δ 7.95 (bb, 3H), 5.51 (m, 1H), 4.98 (m, 2H), 4.05 (m, 2H), 3.06 (m, 0.5H), 3.01 (m, 2H), 2.97 (m, 0.5H), 2.44-0.67 (m, 20H), 0.91 (s, 1.5H), 0.90 (s, 1.5H), 0.78 (s, 3H).

Example 13

(E,Z) 3-(2-Aminoethoxyimino)-6α-(2-hydroxyethyl)androstan-17-one hydrochloride (I-am)

Prepared in 85% yield as described in Example 4 starting from 6α-(2-hydroxyethyl)androstane-3,17-dione (II-al, Prepn. 12) and 2-aminoethoxyamine dihydrochloride. 1H-NMR (300 MHz, DMSO-d$_6$, ppm from TMS): δ 7.95 (bb, 3H), 4.37 (br, 1H), 4.08 (m, 2H), 3.42 (m, 2H), 3.22 (m, 0.5H), 3.06 (m, 0.5H), 3.02 (m, 2H), 2.44-0.90 (m, 22H), 0.88 (s, 1.5H), 0.87 (s, 1.5H), 0.78 (s, 3H).

Example 14

3-(E,Z)-(2-Aminoethoxyimino)-17-oxoandrostane-6α-carbaldehyde (E,Z)-oxime fumarate (I-an)

Prepared in 52% yield as described in Example 1 starting from 3,17-dioxoandrostane-6α-carbaldehyde (E,Z)-oxime (II-am, Prepn. 13) and 2-aminoethoxyamine dihydrochloride. $^1$H-NMR (300 MHz, DMSO-d$_6$, ppm from TMS): δ 10.72 (bb, 0.5H), 10.46 (bb, 0.5H), 8.00 (bb, 4H), 7.10 (d, 0.25H), 7.07 (d, 0.25H) 6.42 (d, 0.25H), 6.40 (s, 2H), 6.38 (d, 0.25H), 4.05 (m, 2H), 3.02 (m, 2H), 3.05 (m, 1H), 2.88 (m, 0.5H), 2.45-0.67 (m, 19.5H), 0.91 (s, 1.5H), 0.90 (s, 1.5H), 0.77 (s, 3H).

Example 15

(E,Z) 3-(2-Aminoethoxyimino)-6α-hydroxymethylandrostan-17-one hydrochloride (I-ao)

Prepared in 60% yield as described in Example 4 starting from 6α-hydroxymethylandrostane-3,17-dione (II-an, Prepn. 14) and 2-aminoethoxyamine dihydrochloride. $^1$H-NMR (300 MHz, DMSO-$d_6$, ppm from TMS): δ 7.73 (bb, 3H), 4.37 (t, 1H), 4.06 (m, 2H), 3.37 (m, 2H), 3.16 (m, 0.5H), 3.06 (m, 0.5H), 3.02 (m, 2H), 2.45-0.60 (m, 20H), 0.89 (s, 1.5H), 0.87 (s, 1.5H), 0.78 (s, 3H).

Example 16

(E,Z) 3-(2-Aminoethoxyimino)-6α-acetoxymethylandrostan-17-one fumarate (I-ap)

Prepared in 30% yield as described in Example 1 starting from 6α-acetoxymethylandrostane-3,17-dione (II-ao, Prepn. 15) and 2-aminoethoxyamine dihydrochloride. The crude product was purified by flash chromatography (SiO$_2$, CHCl$_3$/MeOH/26% NH$_4$OH 95/5/0.5). To the concentrated fractions a stoichiometric amount of fumaric acid in MeOH was added. After addition of a 1/1 mixture of EtOAc/Et$_2$O, the precipitate was filtered to give the title compound I-ap. $^1$H-NMR (300 MHz, DMSO-$d_6$, ppm from TMS): δ 8.00 (bb, 4H), 6.40 (s, 2H), 4.05-3.80 (m, 4H), 3.05 (m, 1H), 2.95 (m, 2H), 2.45-0.58 (m, 20H), 2.00 (s, 3H), 0.89 (s, 3H), 0.78 (s, 3H).

Example 17

(E) 3-(2-Aminoethoxyimino)-6α-methoxymethylandrostan-17-one hydrochloride (I-aq)

Prepared in 33% yield as described in Example 1 starting from 6α-methoxymethylandrostane-3,17-dione (II-ap, Prepn. 16) and 2-aminoethoxyamine dihydrochloride. The crude product was crystallized from Et$_2$O/EtOAc. $^1$H-NMR (300 MHz, DMSO-$d_6$, ppm from TMS): δ 7.82 (bb, 3H), 4.06 (m, 2H), 3.22 (m, 2H), 3.20 (s, 3H), 3.05 (m, 1H), 3.02 (m, 2H), 2.45-0.60 (m, 20H), 0.89 (s, 3H), 0.78 (s, 3H).

Example 18

(E,Z) 3-(2-Aminoethoxyimino)-6α-carboxyandrostan-17-one hydrochloride (I-ar)

To a stirred solution of 6α-carboxyandrostane-3,17-dione (II-aq, Prepn. 17, 50 mg) in dioxane (1 mL) and a solution of 2-aminoethoxyamine dihydrochloride (22 mg) in H$_2$O (0.5 mL) was added dropwise. After 2 h the mixture was freeze-dried and the residue was triturated with Et$_2$O to give the title compound I-ar (52 mg, 80%). $^1$H-NMR (300 MHz, DMSO-$d_6$, ppm from TMS): δ 8.24 (bb, 4H), 4.07 (m, 2H), 3.01 (m, 3H), 2.45-0.70 (m, 20H), 0.90 (s, 1.5H), 0.89 (s, 1.5H), 0.78 (s, 3H).

Example 19

(Z) 3-(2-Aminoethoxyimino)-6α-carbamoylandrostan-17-one hydrochloride (I-as)

Following the procedure described in Example 1 and starting from 6α-carbamoylandrostane-6,17-dione (II-ar, Prepn. 18, 90 mg), the title compound I-as was obtained as a white solid precipitated from THF (46 mg, 40%). $^1$H-NMR (300 MHz, DMSO-$d_6$, ppm from TMS): 7.78 (3H, bb), 7.37 (1H, s), 6.79 (1H, s), 4.05 (2H, m), 2.99 (2H, m), 2.91 (1H, m), 2.45-0.65 (20H, m), 0.89 (3H, s), 0.78 (3H, s).

Example 20

(E,Z) 3-(2-Aminoethoxyimino)-6α-carbamoylandrostan-17-one fumarate (I-at)

The residue of the mother liquor of reaction of Example 19 was evaporated and purified by flash chromatography (SiO$_2$, CH$_2$Cl$_2$:MeOH:NH$_3$ 9:1:0.1). The residue of the pure fractions was dissolved in methanol and treated with fumaric acid to give the title compound I-at (61 mg, 40%), as a white solid. $^1$H-NMR (300 MHz, DMSO-$d_6$, ppm from TMS): 8.00 (4H, bb), 7.38 (0.5H, s), 7.32 (0.5H, s), 6.80 (0.5H, s), 6.78 (0.5H, s), 6.40 (2H, s), 4.05 (2H, m), 3.06 (0.5H, m), 2.99 (2H, m), 2.91 (0.5H, m), 2.45-0.65 (20H, m), 0.89 (3H, s), 0.78 (3H, s).

Example 21

(E,Z) 3-(2-Aminoethoxyimino)-6α-methoxycarbonylandrostan-17-one hydrochloride (I-au)

Prepared in 62% yield as described in Example 1 starting from 6α-methoxycarbonylandrostane-3,17-dione (II-as, Prepn. 19, 100 mg) and 2-aminoethoxyamine dihydrochloride (43 mg), after washing the crude with Et$_2$O/EtOAc and centrifugation. $^1$H-NMR (300 MHz, DMSO-$d_6$, ppm from TMS): 7.75 (3H, bb), 4.06 (2H, m), 3.60 (3H, s), 3.07 (0.5H, m, E isomer), 3.01 (2H, m), 2.79 (0.5H, m, Z isomer), 2.55-0.92 (20H, m), 0.91 (1.5H, s, E isomer), 0.90 (1.5H, s, Z isomer), 0.78 (3H, s).

Example 22

(E,Z) 3-(2-Aminoethoxyimino)-6-(E)-hydroxyiminoandrostan-17-one hydrochloride (I-av)

Prepared as described in Example 1 starting from 6-(E)-hydroxyiminoandrostane-3,17-dione (II-at, Prepn. 20, 400 mg) and 2-aminoethoxyamine dihydrochloride (188 mg). The crude product was crystallized from MeOH/EtOAc to give the title compound as a white solid (367 mg, 70%). $^1$H-NMR (300 MHz, DMSO-$d_6$, ppm from TMS): δ 10.58 (s, 0.5H), 10.51 (s, 0.5H), 7.98 (m, 3H), 4.08 (m, 2H), 3.29 (m, 1H), 3.13 (m, 0.5H), 3.10 (m, 0.5H), 3.02 (m, 2H), 2.45-0.95 (m, 18H), 0.79 (s, 6H).

Example 23

(E,Z)-3-(2-Aminoethoxyimino)-6-(E)-methoxyiminoandrostan-17-one hydrochloride (I-aw)

Prepared in 60% yield as described in Example 1 starting from 6-(E)-methoxyiminoandrostane-3,17-dione (II-au, Prepn. 21) and 2-aminoethoxyamine dihydrochloride. $^1$H-NMR (300 MHz, DMSO-$d_6$, ppm from TMS): δ 8.03 (bb, 3H), 4.09 (m, 2H), 3.75 (s, 1.5H), 3.73 (s, 1.5H), 3.24-3.05 (m, 2H), 3.02 (m, 2H), 2.45-0.95 (m, 18H), 0.78 (s, 3H), 0.77 (s, 3H).

Example 24

(E,Z)-3-(2-Aminoethoxyimino)-6-(E)-ethoxyiminoandrostan-17-one hydrochloride (I-ax)

Following the procedure described in Example 1 and starting from 6-(E)-ethoxyiminoandrostane-3,17-dione (II-av, Prepn. 22, 80 mg) and 2-aminoethoxyamine dihydrochloride (34 mg), the title compound I-ax was obtained (81 mg, 80%) after flash chromatography (SiO$_2$, CH$_2$Cl$_2$:MeOH:NH$_3$ 9:1: 0.1). $^1$H-NMR (300 MHz, DMSO, ppm from TMS): δ 7.85 (3H, bb), 4.07 (2H, m), 4.00 (1H, q), 3.98 (1H, q), 3.20 (1H, m), 3.10 (1H, m), 3.03 (2H, m), 2.46-0.98 (18H, m), 1.17 (1.5H, t), 1.16 (1.5H, t), 0.78 (6H, s).

Example 25

(E,Z)-3-(2-Aminoethoxyimino)-6-(E)-allyloxyiminoandrostan-17-one fumarate (I-ay)

Following the procedure described in Example 1 and starting from 6-(E)-allyloxyiminoandrostane-3,17-dione (II-aw, Prepn. 23, 121 mg) and 2-aminoethoxyamine dihydrochloride (50 mg), the title compound I-ay was obtained (134 mg, 75%) after flash chromatography (SiO$_2$, CH$_2$Cl$_2$:MeOH:NH$_3$ 9:1:0.1). $^1$H-NMR (300 MHz, DMSO, ppm from TMS): δ 9.01 (4H, bb), 6.40 (2H, s), 5.93 (1H, m), 5.18 (2H, m), 4.49 (2H, m), 4.05 (2H, m), 3.22 (1H, m), 3.09 (1H, m), 2.98 (2H, m), 2.44-0.98 (18H, m), 0.78 (6H, s).

Example 26

(E,Z) 3-(2-Aminoethoxyimino)-6β-methylandrostan-17-one hydrochloride (I-az)

Prepared in 64% yield as described in Example 1 starting from 6β-methylandrostane-3,17-dione (II-ax, Prepn. 24) and 2-aminoethoxyamine dihydrochloride. The crude product was triturated with EtOAc. $^1$H-NMR (300 MHz, DMSO-d$_6$, ppm from TMS): δ 7.89 (bb, 3H), 4.06 (m, 2H), 3.07 (m, 0.5H), 3.02 (m, 2H), 2.81 (m, 0.5H), 2.45-0.60 (m, 20H), 0.96 (s, 1.5H), 0.95 (s, 1.5H), 0.91 (d, 1.5H), 0.90 (d, 1.5H), 0.81 (s, 3H).

Example 27

(E,Z) 3-(2-Aminoethoxyimino)-6α-methylandrostan-17-one hydrochloride (I-ba)

Prepared in 83% yield as described in Example 1 starting from 6α-methylandrostane-3,17-dione (II-ay, Prepn. 25) and 2-aminoethoxyamine dihydrochloride. The crude product was crystallized from MeOH/EtOAc to give the title compound I-ba as a white solid. $^1$H-NMR (300 MHz, DMSO-d$_6$, ppm from TMS): δ 7.83 (bb, 3H), 4.07 (m, 2H), 3.16 (m, 0.5H), 3.06 (m, 0.5H), 3.03 (m, 2H), 2.45-0.55 (m, 20H), 0.89 (s, 1.5H), 0.87 (s, 1.5H), 0.84 (s, 1.5H), 0.81 (s, 1.5H), 0.78 (s, 3H).

Example 28

(E,Z)-3-(2-Aminoethoxyimino)androstane-6(S)-(spiro-2'-oxirane)-17-one hydrochloride (I-bb)

Prepared in 40% yield as described in Example 1 starting from 6(S)-(spiro-2'-oxirane)androstane-3,17-dione (II-az, Prepn. 26) and 2-aminoethoxyamine dihydrochloride. $^1$H-NMR (300 MHz, DMSO-d$_6$, ppm from TMS): δ 7.80 (bb, 3H), 4.06 (m, 2H), 3.07 (m, 0.5H), 3.01 (m, 2H), 2.90 (m, 0.5H), 2.76 (d, 1H), 2.57 (d, 1H), 2.45-0.75 (m, 19H), 0.92 (s, 3H), 0.78 (s, 3H).

Example 29

(E,Z)-3-(2-Aminoethoxyimino)androstane-6(R)-(spiro-2'-oxirane)-17-one hydrochloride (I-bc)

Prepared in 50% yield as described in Example 1 starting from 6(R)-(spiro-2'-oxirane)androstane-3,17-dione (II-ba, Prepn. 26) and 2-aminoethoxyamine dihydrochloride. The crude product was dissolved in H$_2$O and freeze-dried to give the title compound II-bc. $^1$H-NMR (300 MHz, DMSO-d$_6$, ppm from TMS): δ 7.75 (bb, 3H), 4.06 (m, 2H), 3.05 (m, 0.5H), 2.99 (m, 2H), 2.83 (m, 0.5H), 2.75 (d, 0.5H), 2.72 (d, 0.5H), 2.30 (d, 0.5H), 2.27 (d, 0.5H), 2.45-0.90 (m, 19H), 0.96 (s, 1.5H), 0.94 (s, 1.5H), 0.80 (s, 3H).

Example 30

(E,Z) 3-(2-Aminoethoxyimino)-6α-ethynylandrostan-17-one hydrochloride (I-bd)

Prepared in 76% yield as described in Example 1 starting from 6α-ethynylandrostane-3,17-dione (II-bb, Prepn. 27) and 2-aminoethoxyamine dihydrochloride. $^1$H-NMR (300 MHz, DMSO-d$_6$, ppm from TMS): δ 7.90 (bb, 3H), 4.06 (m, 2H), 3.05 (m, 3H), 2.98 (d, 0.5H), 2.97 (d, 0.5H), 2.61-0.66 (m, 20H), 0.88 (s, 1.5H), 0.87 (s, 1.5H), 0.77 (s, 3H).

Example 31

(E,Z) 3-(2-Aminoethoxyimino)-6α-formamidoandrostan-17-one fumarate (I-be)

Prepared in 59% yield as described in Example 1 starting from 6α-formamidoandrostane-3,17-dione (II-bc, Prepn. 28) and 2-aminoethoxyamine dihydrochloride. The crude product was purified by flash chromatography (SiO$_2$, CHCl$_3$/MeOH/26% NH$_4$OH 90/10/1). To the concentrated fractions a stoichiometric amount of fumaric acid in MeOH was added. After addition of a 1/1 mixture of EtOAc/Et$_2$O, the precipitate was filtered to give the title compound I-be. $^1$H-NMR (300 MHz, DMSO-d$_6$, ppm from TMS): δ 8.20 (m, 4H), 8.10 (bd, 0.5H), 8.03 (bd, 0.5H), 8.01 (bd, 0.5H), 7.90 (bd, 0.5H), 6.44 (s, 2H), 4.05 (m, 2H), 3.72 (m, 1H), 3.16 (m, 0.5H) 3.06 (m, 0.5H) 3.00 (m, 2H), 2.45-0.65 (m, 19H), 0.93 (s, 1.5H), 0.92 (s, 1.5H), 0.78 (s, 3H).

Example 32

(E,Z) 3-(2-Aminoethoxyimino)-6α-acetamidoandrostan-17-one hydrochloride (I-bf)

Prepared in 84% yield as described in Example 1 starting from 6α-acetamidoaminoandrostane-3,17-dione (II-bd, Prepn. 29) and 2-aminoethoxyamine dihydrochloride. The crude product was triturated with EtOAc. $^1$H-NMR (300 MHz, DMSO-d$_6$, ppm from TMS): δ 7.87 (bb, 3H), 7.83 (d, 0.5H), 7.67 (d, 0.5H), 4.07 (m, 2H), 3.65 (m, 1H), 3.15 (m, 0.5H), 3.07 (m, 0.5H), 3.03 (m, 2H), 2.45-0.65 (m, 19H), 1.81 (s, 1.5H), 1.79 (s, 1.5H), 0.93 (s, 1.5H), 0.91 (s, 1.5H), 0.78 (s, 3H).

Example 33

(E,Z) 3-(2-Aminoethoxyimino)-6-(E)-ethylidenandrostan-17-one hydrochloride (I-bg)

Prepared in 71% yield as described in Example 1 starting from 6(E)-ethylidenandrostane-3,17-dione (II-be, Prepn. 30)

and 2-aminoethoxyamine dihydrochloride. $^1$H-NMR (300 MHz, DMSO-d$_6$, ppm from TMS): δ 8.01 (bb, 3H), 5.01 (q, 0.5H), 4.97 (q, 0.5H), 4.08 (m, 2H), 3.03 (m, 3H), 2.69 (m, 1H), 2.45-0.85 (m, 21H), 0.77 (s, 3H), 0.72 (s, 3H).

Example 34

(E,Z) 3-(2-Aminoethoxyimino)-6-difluoromethyl-eneandrostan-17-one hydrochloride (I-bh)

Prepared in 61% yield as described in Example 1 starting from 6-difluoromethyleneandrostane-3,17-dione (II-bf, Prepn. 31) and 2-aminoethoxyamine dihydrochloride. The crude product was dissolved in H$_2$O and freeze-dried. $^1$H-NMR (300 MHz, DMSO-d$_6$, ppm from TMS): δ 7.62 (bb, 3H), 4.07 (m, 2H), 3.27 (m, 0.5H), 3.07 (m, 0.5H), 3.01 (m, 2H), 2.45-0.80 (m, 19H), 0.89 (s, 3H), 0.78 (s, 3H).

Example 35

(E) 3-(2-Aminoethoxyimino)-17-oxoandrostane-6-(E)-ylideneacetonitrile hydrochloride (I-bi)

Prepared in 61% yield as described in Example 1 starting from 3,17-dioxoandrostane-6-(E)-ylideneacetonitrile (II-bg, Prepn. 32) and 2-aminoethoxyamine dihydrochloride. The crude product was dissolved in H$_2$O and freeze-dried. $^1$H-NMR (300 MHz, DMSO-d$_6$, ppm from TMS): δ 7.95 (bb, 3H), 5.26 (bs, 1H), 4.08 (m, 2H), 3.04 (m, 3H), 2.82 (m, 1H), 2.45-1.00 (m, 18H), 0.79 (s, 3H), 0.75 (s, 3H).

Example 36

(E,Z) 3-(2-Aminoethoxyimino)-6-(E)-[2-hydroxy-ethylidene]androstan-17-one hydrochloride (I-bj)

Prepared in 70% yield as described in Example 1 starting from 6(E)-[2-hydroxyethylidene]androstane-3,17-dione (II-bh, Prepn. 33) and 2-aminoethoxyamine dihydrochloride. 1H-NMR (300 MHz, DMSO-d$_6$, ppm from TMS): δ 7.75 (bb, 3H), 5.08 (bt, 0.5H), 5.05 (bt, 0.5H), 4.56 (t, 0.5H), 4.53 (t, 0.5H), 4.12-3.92 (m, 4H), 3.05 (m, 3H), 2.65 (m, 1H), 2.45-0.85 (m, 18H), 0.77 (s, 3H), 0.75 (s, 3H).

Example 37

Methyl [3-(E,Z)-(2-aminoethoxyimino)-17-oxoan-drostane-6-(E)-ylidene]-acetate hydrochloride (I-bk)

Prepared in 87% yield as described in Example 1 starting from (E)-(3,17-dioxoandrostane-6-ylidene)acetic acid methyl ester (II-bi, Prepn. 34) and 2-aminoethoxyamine dihydrochloride. The crude product was triturated with EtOAc. $^1$H-NMR (300 MHz, DMSO-d$_6$, ppm from TMS): δ 8.09 (bb, 3H), 5.45 (s, 0.5H), 5.41 (s, 0.5H), 4.10 (m, 2H), 3.94 (m, 1H), 3.62 (s, 3H), 3.05 (s, 3H), 2.50-1.00 (m, 18H), 0.77 (s, 3H), 0.75 (s, 3H).

Example 38

E,Z) 3-(2-Aminoethoxyimino)-6-(spirocyclopro-pane)androstane-17-one hydrochloride (I-bl)

Prepared in 92% yield as described in Example 1 starting from 6-(spirocyclopropane)androstane-3,17-dione (II-bj, Prepn. 35) and 2-aminoethoxyamine dihydrochloride. 1H-NMR (300 MHz, DMSO-d$_6$, ppm from TMS): δ 7.88 (bb, 3H) 4.06 (m, 2H), 3.06 (m, 0.5H), 3.00 (m, 2H), 2.70 (m, 0.5H), 2.43-0.89 (m, 19H), 0.95 (s, 3H), 0.79 (s, 3H), 0.57-0.16 (m, 4H).

Example 39

(E,Z) 3-(2-Aminoethoxyimino)-6α-acetamidomethy-landrostan-17-one hydrochloride (I-bm)

Prepared by using the same reaction conditions described in Example 1 and starting from 6α-acetamidomethylandros-tane-6,17-dione (II-bk, Prepn. 36, 155 mg) and 2-aminoet-hoxyamine dihydrochloride (49 mg), after 2 hrs the reaction mixture was quenched with brine and extracted with THF. The combined organic layers were washed with brine then dried over Na$_2$SO$_4$ and the solvent evaporated to dryness. The solid obtained was washed with EtOAc and Et$_2$O. After drying under vacuum overnight the title compound I-bm (120 mg, 61%) was obtained, as a white solid. $^1$H-NMR (300 MHz, DMSO-d$_6$, ppm from TMS): δ 7.92 (0.5H, t), 7.82 (3H, bb), 7.71 (0.5H, t), 4.07 (2H, m), 3.40 (0.5H, m), 3.25-2.69 (4.5H, m), 2.46-0.57 (20H, m), 1.84 (1.5H, s), 1.80 (1.5H, s), 0.87 (3H, s), 0.78 (3H, s).

Example 40

(E,Z) 3-(2-Aminoethoxyimino)-6α-formamidom-ethylandrostane-17-one hydrochloride (I-bn)

Following reaction conditions described in Example 4 and starting from 6α-formamidomethylandrostane-3,17-dione (II-bl, Prepn. 37, 65 mg) and 2-aminoethoxyamine dihydro-chloride (21 mg), the title compound was obtained (50 mg, 60%) after flash chromatography (SiO$_2$, CH$_2$Cl$_2$:MeOH:NH$_3$ 9:1:0.1). $^1$H-NMR (300 MHz, DMSO-d$_6$, ppm from TMS): δ 8.17-7.95 (2H, m), 7.85 (3H, bb), 4.07 (2H, m), 3.20-2.80 (5H, m), 2.45-0.59 (20H, m), 0.88 (1.5H, s), 0.87 (1.5H, s), 0.78 (3H, s).

Example 41

(E,Z)-3-(2-Aminoethoxyimino)-5α-hydroxy-6-(E)-hydroxyiminoandrostane-17-one fumarate (I-bo)

Prepared in 77% yield as described in Example 1 starting from 5α-hydroxy-6-(E)-hydroxyiminoandrostane-3,17-di-one (II-bm, Prepn. 38) and 2-aminoethoxyamine dihydro-chloride. The crude product was purified by flash chromatography (SiO$_2$, CHCl$_3$/MeOH/26% NH4OH 90/10/1). To the concentrated fractions a stoichiometric amount of fumaric acid in MeOH was added. After addition of a 1/1 mixture of EtOAc/Et2O, the precipitate was filtered to give the title compound I-bo. 1H-NMR (300 MHz, DMSO-d$_6$, ppm from TMS): δ 10.68 (bb, 1H), 9.01 (bb, 4H), 6.41 (s, 2H), 5.11 (bb, 1H), 4.05 (m, 2H), 3.26 (d, 0.5H), 3.11 (m, 1H), 3.01 (m, 0.5H), 2.98 (m, 2H), 2.63-1.13 (m, 17H), 0.82 (s, 3H), 0.76 (s, 3H).

Example 42

(E,Z)-3-(2-Aminoethoxyimino)-5α-hydroxy-6-(E)-methoxyiminoandrostane-17-one fumarate (I-bp)

Prepared in 50% yield as described in Example 41 starting from 5α-hydroxy-6-(E)-methoxyiminoandrostane-3,17-di-one (II-bn, Prepn. 39) and 2-aminoethoxyamine dihydrochlo-ride. 1H-NMR (300 MHz, DMSO-d$_6$, ppm from TMS): δ

8.00 (bb, 4H), 6.40 (s, 2H), 5.21 (s, 1H), 4.05 (m, 2H), 3.75 (s, 3H), 3.25 (d, 0.5H), 3.10-2.90 (m, 3.5H), 2.62-1.04 (m, 17H), 0.83 (s, 3H), 0.76 (s, 3H).

Example 43

(E,Z) 3-(2-Aminoethoxyimino)-5α-hydroxy-6-methylenandrostane-17-one hydrochloride (I-bq)

Prepared by following the reaction conditions described in Example 1 and starting from 5α-hydroxy-6-methylenandrostane-3,17-dione (II-bo, Prepn. 40, 500 mg) and 2-aminoethoxyamine dihydrochloride (236 mg). The combined organic layers were washed with brine, dried over $Na_2SO_4$ and the solvent evaporated to dryness. The solid obtained was washed with $EtOAc/Et_2O$. After drying under vacuum overnight the title compound I-bq was obtained (483 mg, 74%). $^1$H-NMR (300 MHz, DMSO-$d_6$, ppm from TMS): δ 7.88 (bb, 3H), 4.87 (m, 0.5H), 4.83 (m, 0.5H), 4.71 (m, 0.5H), 4.66 (m, 0.5H), 4.64 (s, 0.5H), 4.55 (s, 0.5H), 4.08 (m, 2H), 3.20 (d, 0.5H), 3.07 (m, 0.5H), 3.03 (m, 2H) 2.61-1.11 (m, 18H), 0.84 (s, 1.5H), 0.83 (s, 1.5H), 0.76 (s, 3H).

Example 44

(E,Z) 3-(2-Aminoethoxyimino)androstane-7,17-dione fumarate (I-br)

Prepared in 50% yield as described in Example 1 starting from androstane-3,7,17-trione (II-bp, Prepn. 41) and 2-aminoethoxyamine dihydrochloride. $^1$H-NMR (300 MHz, DMSO-$d_6$, ppm from TMS): δ 8.86 (bb, 4H), 6.40 (s, 2H), 4.03 (m, 2H), 3.09 (m, 0.5H), 2.97 (m, 2H), 2.93 (m, 0.5H) 2.66 (m, 1H), 2.55-0.95 (m, 18H), 1.13 (s, 3H), 0.78 (s, 3H).

Example 45

(E,Z)-3-(2-Aminoethoxyimino)-7-(E)-hydroxyiminoandrostane-17-one fumarate-(I-bs)

Prepared in 50% yield as described in Example 1 starting from 7-(E)-hydroxyiminoandrostane-17-one (II-bq, Prepn. 42) and 2-aminoethoxyamine dihydrochloride. 1H-NMR (300 MHz, DMSO-$d_6$, ppm from TMS): δ 10.37 (bb, 1H), 8.85 (bb, 4H), 6.40 (s, 2H), 4.04 (m, 1H), 3.02 (m, 4H), 2.97-0.84 (m, 18H), 1.01 (s, 3H), 0.80 (s, 3H).

Example 46

(E,Z)-3-(2-Aminoethoxyimino)-7-(E)-methoxyiminoandrostan-17-one fumarate (I-bt)

Prepared in 55% yield as described in Example 1 starting from 7-(E)-methoxyiminoandrostane-17-one (II-br, Prepn. 43) and 2-aminoethoxyamine dihydrochloride. $^1$H-NMR (300 MHz, DMSO-$d_6$, ppm from TMS): δ 8.00 (bb, 3H), 6.40 (s, 2H), 4.02 (m, 2H), 3.72 (s, 3H), 2.97 (m, 4H), 2.60-0.87 (m, 18H) 1.01 (s, 3H), 0.80 (s, 3H).

Example 47

(E,Z)-3-(2-Aminoethoxyimino)-7-(E)-allyloxyiminoandrostan-17-one fumarate (I-bu)

Prepared in 75% yield as described in Example 1 starting from 7-(E)-allyloxyiminoandrostane-3,17-dione (II-bs, Prepn. 44) and 2-aminoethoxyamine dihydrochloride. $^1$H-NMR (300 MHz, DMSO-$d_6$, ppm from TMS): δ 8.70 (m, 4H), 6.39 (s, 2H), 5.93 (m, 1H), 5.23 (m, 1H), 5.16 (m, 1H), 4.46 (m, 2H) 4.02 (m, 2H), 3.10-2.85 (m, 4H), 2.60-0.89 (m, 18H), 1.01 (s, 3H), 0.80 (s, 3H).

Example 48

(E,Z) 3-(2-Aminoethoxyimino)-7α-hydroxyandrostane-17-one fumarate (I-bv)

Prepared in 55% yield as described in Example 1 starting from 7α-hydroxyandrostane-3,17-dione (II-bt, Prepn. 45) and 2-aminoethoxyamine dihydrochloride. $^1$H-NMR (300 MHz, DMSO-$d_6$, ppm from TMS): δ 8.70 (m, 4H), 6.40 (s, 2H), 4.30 (bb, 1H), 4.03 (m, 2H), 3.74 (m, 1H), 3.07 (m, 0.5H), 2.98 (m, 2H) 2.77 (m, 0.5H), 2.44-0.91 (m, 19H), 0.85 (s, 3H), 0.76 (s, 3H).

Example 49

(E,Z)-3-(2-Aminoethoxyimino)-7α-formamidoandrostane-3,17-dione hydrochloride (I-bw)

Prepared in 70% yield as described in Example 1 starting from 7α-formamidoandrostane-3,17-dione (II-bu, Prepn. 46) and 2-aminoethoxyamine dihydrochloride. The crude product was triturated with $Et_2O$. $^1$H-NMR (300 MHz, DMSO-$d_6$, ppm from TMS): δ 8.30-7.70 (m, 5H), 4.07 (m, 3H), 3.09 (m, 0.5H), 3.03 (m, 2H), 2.80 (m, 0.5H), 2.43-0.95 (m, 19H), 0.89 (s, 3H), 0.78 (s, 3H).

Example 50

(E,Z) 3-(2-Aminoethoxyimino)-7-methyleneandrostane-17-one hydrochloride (I-bx)

Prepared in 50% yield as described in Example 1 starting from 7-methyleneandrostane-3,17-dione (II-bv, Prepn. 47) and 2-aminoethoxyamine dihydrochloride. The crude product was triturated with EtOAc. $^1$H-NMR (300 MHz, DMSO-$d_6$, ppm from TMS): δ 7.85 (bb, 3H), 4.73 (m, 1H), 4.68 (m, 1H), 4.07 (m, 2H), 3.07 (m, 0.5H), 3.04 (m, 2H), 2.93 (m, 0.5H), 2.45-0.73 (m, 19H), 1.00 (s, 3H), 0.81 (s, 3H).

Example 51

(E,Z) 3-(2-Aminoethoxyimino)-7β-methylandrostane-17-dione hydrochloride (I-by)

Prepared in 78% yield as described in Example 1 starting from 7-methylandrostane-3,17-dione (II-bw, Prepn. 48) and 2-aminoethoxyamine dihydrochloride. The crude product was triturated with $Et_2O$ and then was dissolved in $H_2O$ and freeze-dried to give the title compound I-by. $^1$H-NMR (300 MHz, DMSO-$d_6$, ppm from TMS): δ 7.87 (bb, 3H), 4.06 (m, 2H), 3.07 (m, 0.5H), 3.02 (m, 2H), 2.86 (m, 0.5H), 2.44-0.66 (m, 20H), 0.98 (d, 3H), 0.84 (s, 3H), 0.79 (s, 3H).

Example 52

(E,Z) 3-(2-Aminoethoxyimino)-7α-hydroxymethylandrostane-17-one hydrochloride (I-bz)

Prepared in 85% yield as described in Example 1 starting from 7α-hydroxymethylandrostane-3,17-dione (II-bx, Prepn. 49) and 2-aminoethoxyamine dihydrochloride. The crude product was crystallized from EtOAc to give the title compound I-bz. $^1$H-NMR (300 MHz, DMSO-d$_6$, ppm from TMS): δ 7.90 (bb, 3H), 4.33 (t, 0.5H), 4.32 (t, 0.5H), 4.07 (m, 2H), 3.45 (m, 2H), 3.07 (m, 0.5H), 3.03 (m, 2H), 2.82 (m, 0.5H), 2.43-0.91 (m, 20H), 0.89 (s, 1.5H), 0.88 (s, 1.5H), 0.76 (s, 3H).

Example 53

(E,Z) 3-(2-Aminoethoxyimino)-7β-hydroxymethylandrostane-17-one hydrochloride (I-ca)

Prepared in 55% yield as described in Example 1 starting from 7β-hydroxymethylandrostane-3,17-dione (II-by, Prepn. 49) and 2-aminoethoxyamine dihydrochloride. The crude product was crystallized from EtOAc to give the title compound I-ca. $^1$H-NMR (300 MHz, DMSO-d$_6$, ppm from TMS): δ 7.91 (bb, 3H), 4.38 (bb, 1H), 4.07 (m, 2H), 3.39 (m, 2H), 3.08 (m, 0.5H), 3.12 (m, 2H), 2.41-0.67 (m, 20H), 0.83 (s, 3H), 0.78 (s, 3H).

Example 54

(E,Z) 3-(2-Aminoethoxyimino)-7-(spirocyclopropane)androstan-17-one hydrochloride (I-cb)

Prepared in 85% yield as described in Example 1 starting from 7-(spirocyclopropane)-androstane-3,17-dione (II-bz, Prepn. 50) and 2-aminoethoxyamine dihydrochloride. The combined organic extracts were dried over Na$_2$SO$_4$, filtered and evaporated to dryness. The crude product was triturated with Et$_2$O and then was dissolved in H$_2$O and freeze-dried to give the title compound I-cb. 1H-NMR (300 MHz, DMSO-d$_6$, ppm from TMS): δ 7.67 (bb, 3H) 4.04 (m, 2H), 3.08 (m, 0.5H), 3.01 (m, 2H), 2.79 (m, 0.5H), 2.38-0.10 (m, 23H), 0.93 (s, 1.5H), 0.92 (s, 1.5H), 0.78 (s, 3H).

Example 55

3-(E,Z)-(2-Aminoethoxyimino)-6-(Z)-hydroxyimino-7α-hydroxyandrostane-17-one hydrochloride (I-cc)

Prepared in 65% yield as described in Example 1 starting from 6-(Z)-hydroxyimino-7α-hydroxyandrostane-3,17-dione (II-ca, Prepn. 51) and 2-aminoethoxyamine dihydrochloride. The combined organic extracts were dried over Na$_2$SO$_4$, filtered and evaporated to dryness. The crude product was triturated with Et$_2$O. $^1$H-NMR (300 MHz, DMSO-d$_6$, ppm from TMS): δ 10.72 (s, 0.5H), 10.64 (s, 0.5H), 7.84 (bb, 3H), 5.15 (d, 0.5H), 5.13 (d, 0.5H), 5.02 (m, 1H), 4.08 (m, 2H), 3.09 (m, 0.5H), 3.04 (m, 2H), 2.99 (m, 0.5H), 2.65-1.02 (m, 17H), 0.77 (s, 3H), 0.75 (s, 1.5H), 0.74 (s, 1.5H).

Example 56

(E,Z) 3-(2-Aminoethoxyimino)-6α-hydroxymethylandrostane-7,17-dione hydrochloride (I-cd)

Prepared in 65% yield as described in Example 1 starting from 6α-hydroxymethylandrostane-3,7,17-trione (II-cb, Prepn. 52) and 2-aminoethoxyamine dihydrochloride. The combined organic extracts were dried over Na$_2$SO$_4$, filtered and evaporated to dryness. The crude product was triturated with Et$_2$O. $^1$H-NMR (300 MHz, DMSO-d$_6$, ppm from TMS): δ 7.81 (bb, 3H), 4.22 (t, 0.5H), 4.20 (t, 0.5H), 4.07 (m, 2H), 3.53 (m, 2H), 3.23-2.97 (m, 3H), 2.75-0.97 (m, 18H), 1.18 (s, 1.5H), 1.17 (s, 1.5H), 0.78 (s, 3H).

Example 57

(E,Z) 3-(2-N-Methylaminoethoxyimino)-6-(E)-methoxyiminoandrostan-17-one hydrochloride (I-ce)

Prepared in 60% yield as described in Example 1 starting from 6-(E)-methoxyiminoandrostane-3,17-dione (II-au, Prepn. 21) and 2-N-methylaminoethoxyamine dihydrochloride (III-a, Prepn. 53). $^1$H-NMR (300 MHz, DMSO-d$_6$, ppm from TMS): δ 8.77 (bb, 2H), 4.15 (m, 2H), 3.75 (s, 1.5H), 3.73 (s, 1.5H), 3.25-3.05 (m, 4H), 2.55 (s, 3H), 2.45-1.00 (m, 18H), 0.78 (s, 3H), 0.77 (s, 3H).

Example 58

(E,Z) 3-(2-N-Methylaminoethoxyimino)-5α-hydroxy-6-(E)-hydroxyiminoandrostan-17-one hydrochloride (I-cf)

Prepared in 75% yield as described in Example 1 starting from 5α-hydroxy-6-(E)-hydroxyiminoandrostane-3,17-dione (II-bm, Prepn. 38) and 2-N-methylaminoethoxyamine dihydrochloride (III-a, Prepn. 53). 1H-NMR (300 MHz, DMSO-d$_6$, ppm from TMS): δ 10.68 (s, 0.5H), 10.65 (s, 0.5H), 8.53 (bb, 2H), 5.09 (s, 0.5H), 4.97 (s, 0.5H), 4.14 (m, 2H), 3.24 (d, 0.5H), 3.14 (m, 3H), 3.05 (m, 0.5H), 2.55 (s, 3H), 2.44-1.13 (m, 17H), 0.82 (s, 3H), 0.76 (s, 3H).

Example 59

(E,Z) 3-(2-N-Methylaminoethoxyimino)-5α-hydroxy-6-methylenandrostan-17-one hydrochloride (I-cg)

Prepared in 70% yield as described in Example 1 starting from 5α-hydroxy-6-methylenandrostan-3,17-dione (II-bo, Prepn. 40) and 2-N-methylaminoethoxyamine dihydrochloride (III-a, Prepn. 53). The crude product was triturated with Et$_2$O. $^1$H-NMR (300 MHz, DMSO-d$_6$, ppm from TMS): δ 8.63 (bb, 2H), 4.86 (m, 0.5H), 4.84 (m, 0.5H), 4.70 (m, 0.5H), 4.66 (m, 0.5H), 4.65 (s, 0.5H), 4.59 (s, 0.5H), 4.14 (m, 2H), 3.19 (d, 0.5H), 3.14 (m, 2H), 3.04 (m, 0.5H), 2.61-1.09 (m, 18H), 2.96 (s, 3H), 0.84 (s, 1.5H), 0.83 (s, 1.5H) 0.76 (s, 3H).

Example 60

(E,Z) 3-(3-N-Methylaminopropoxyimino)-6-(E)-hydroxyiminoandrostan-17-one hydrochloride (I-ch)

Prepared as described in Example 1 starting from 6-(E)-hydroxyiminoandrostane-3,17-dione (II-at, Prepn. 20, 400 mg) and 3-N-methylaminopropoxyamine dihydrochloride (III-b, Prepn. 54, 225 mg). The crude product was crystallized from MeOH/EtOAc to give the title compound as a white solid (388 mg, 70%). $^1$H-NMR (300 MHz, DMSO-d$_6$, ppm from TMS): δ 10.57 (s, 0.5H), 10.53 (s, 0.5H), 8.70 (bb, 2H), 3.96 (m, 2H), 3.35-2.85 (m, 4H), 2.51 (s, 1.5H), 2.50 (s, 1.5H), 2.45-0.97 (m, 20H), 0.77 (s, 6H).

Example 61

(E,Z) 3-(3-N-Methylaminopropoxyimino)-6-(E)-methoxyiminoandrostan-17-one hydrochloride (I-ci)

Prepared in 60% yield as described in Example 1 starting from 6-(E)-methoxyiminoandrostane-3,17-dione (II-au, Prepn. 21) and 3-N-methylaminopropoxyamine dihydrochloride (III-b, Prepn. 54). $^1$H-NMR (300 MHz, DMSO-$d_6$, ppm from TMS): δ 8.60 (bb, 2H), 3.97 (m, 2H), 3.75 (s, 1.5H), 3.73 (s, 1.5H), 3.19 (dd, 1H), 3.05 (m, 0.5H), 2.99 (m, 0.5H), 2.90 (m, 2H), 2.52 (s, 3H), 2.45-0.99 (m, 20H), 0.78 (s, 1.5H), 0.78 (s, 1.5H), 0.77 (s, 3H).

Example 62

(E) 3-(3-N-Methylaminopropoxyimino)-6-methyleneandrostan-17-one fumarate (I-cj)

Following the procedure described in Example 4 and starting from 6-methyleneandrostane-3,17-dione (II-ah, Prepn. 8, 345 mg) and 3-N-methylaminopropoxyamine dihydrochloride (III-b, Prepn. 54, 245 mg), the title compound I-cj was obtained as a white solid after flash chromatography (SiO$_2$, CH$_2$Cl$_2$:MeOH:NH$_3$ 9:1:0.1), concentration of the fractions, addition of fumaric acid and filtration (310 mg, 70%). $^1$H-NMR (300 MHz, DMSO-$d_6$, ppm from TMS): δ 6.41 (2H, s), 4.80 (1H, m), 4.49 (1H, m), 3.96 (2H, t), 3.01 (1H, m), 2.80 (2H, m), 2.46 (3H, s), 2.45-0.90 (21H, m), 0.77 (3H, s), 0.75 (3H, s).

Example 63

(E,Z) 3-(3-N-Methylaminopropoxyimino)-6-methyleneandrostane-17-one fumarate (I-ck)

Following the procedure described in Example 62 the title compound I-ck was obtained as an off white solid after evaporation of the mother liquor and filtration (90 mg, 20%). $^1$H-NMR (300 MHz, DMSO-$d_6$, ppm from TMS): δ 6.41 (2H, s), 4.82 (0.5H, m), 4.80 (0.5H, m), 4.52 (0.5H, m), 4.49 (0.5H, m), 3.96 (2H, t), 3.01 (0.5H, m), 2.96 (0.5H, m), 2.80 (2H, m), 2.46 (1.5H, s), 2.45 (1.5H, s), 2.45-0.90 (21H, m), 0.77 (3H, s), 0.75 (3H, s).

Example 64

(E,Z) 3-(3-N-Methylaminopropoxyimino)-6α-hydroxymethylandrostan-17-one hydrochloride (I-cl)

Prepared in 67% yield as described in Example 1 starting from 6α-hydroxymethylandrostane-3,17-dione (II-an, Prepn. 14) and 3-N-methylaminopropoxyamine dihydrochloride (III-b, Prepn. 54). $^1$H-NMR (300 MHz, DMSO-$d_6$, ppm from TMS): δ 8.64 (bb, 2H), 4.36 (t, 1H), 3.96 (m, 2H), 3.33 (m, 2H), 3.16 (m, 0.5H), 2.97 (m, 0.5H), 2.89 (m, 2H), 2.51 (s, 3H), 2.45-0.60 (m, 22H), 0.88 (s, 1.5H), 0.87 (s, 1.5H), 0.78 (s, 3H).

Example 65

(Z,E) 3-(3-N-Methylaminopropoxyimino)-6α-methoxycarbonylandrostan-17-one hydrochloride (I-cm)

Prepared following the same reaction conditions described in Example 1 and starting from 6α-methoxycarbonylandrostane-3,17-dione (II-as, Prepn. 19, 325 mg) and 3-N-methylaminopropoxyamine dihydrochloride (III-b, Prepn. 54, 171 mg). After 1.5 hrs the reaction mixture was extracted with THF, the organic layer washed with brine and the solvent dried over Na$_2$SO$_4$, and evaporated to dryness. The resulting solid was washed with Et$_2$O and centrifuged to give, after drying, the title compound I-cm (290 mg, 65%) as a white powder. $^1$H-NMR (300 MHz, DMSO-$d_6$, ppm from TMS): δ 8.36 (2H, bb), 3.95 (2H, m), 3.61 (1.5H, s), 3.60 (1.5H, s), 2.98 (0.5H, m), 2.87 (2H, m), 2.77 (0.5H, m), 2.53 (1.5H, s), 2.52 (1.5H, s), 2.44-0.72 (22H, m), 0.91 (3H, s), 0.78 (3H, s).

Example 66

(Z,E) 3-(3-N-Methylaminopropoxyimino)-6α-carbamoylandrostan-17-one hydrochloride (I-cn)

Prepared following the same reaction conditions described in Example 1 and starting from 6α-carbamoylandrostane-6,17-dione (II-ar, Prepn. 18, 500 mg) and 3-N-methylaminopropoxyamine dihydrochloride (III-b, Prepn. 54, 265 mg). After 2 hrs the reaction mixture was extracted with THF, the organic layer washed with brine, the solvent dried over Na$_2$SO$_4$ and evaporated to dryness. The resulting solid was washed with EtOAc, filtrated to give, after drying, the title compound I-cn (570 mg, 84%) as a white powder. $^1$H-NMR (300 MHz, DMSO-$d_6$, ppm from TMS): 8.53 (2H, bb), 7.36 (0.5H, bb), 7.32 (0.5H, bb), 6.79 (1H, bb), 3.95 (2H, m), 2.89 (3H, m), 2.54 (1.5H, s), 2.51 (1.5H, s), 2.45-0.65 (22H, m), 0.89 (3H, s), 0.78 (3H, s).

Example 67

(E,Z) 3-(3-N-Methylaminopropoxyimino)-6α-formamidoandrostan-17-one hydrochloride (I-co)

Prepared in 76% yield as described in Example 4 starting from 6α-formamidoandrostane-3,17-dione (II-bc, Prepn. 28) and 3-N-methylaminopropoxyamine dihydrochloride (III-b, Prepn. 54). The crude product was dissolved in H$_2$O and freeze-dried to give the title compound I-co. $^1$H-NMR (300 MHz, DMSO-$d_6$, ppm from TMS): δ 8.57 (bb, 2H), 8.06-7.57 (m, 2H), 3.96 (m, 2H), 3.72 (m, 1H), 3.07 (m, 0.5H), 2.97 (m, 0.5H), 2.88 (m, 2H), 2.52 (s, 3H), 2.46-0.65 (m, 21H), 0.93 (s, 1.5H), 0.92 (s, 1.5H), 0.78 (s, 3H).

Example 68

(E,Z) 3-(3-N-Methylaminopropoxyimino)-6-(spirocyclopropane)androstan-17-one hydrochloride (I-cp)

Prepared in 93% yield as described in Example 4 starting from 6-(spirocyclopropane)androstane-3,17-dione (II-bj, Prepn. 35) and 3-N-methylaminopropoxyamine dihydrochloride (III-b, Prepn. 54). The combined organic extracts were dried over Na$_2$SO$_4$, filtered and evaporated to dryness to give the title compound I-cp. 1H-NMR (300 MHz, DMSO-$d_6$, ppm from TMS): δ 8.55 (bb, 2H), 3.95 (m, 2H), 2.96 (m, 0.5H), 2.88 (m, 2H), 2.62 (m, 0.5H), 2.52 (s, 3H), 2.43-0.70 (m, 21H), 0.96 (s, 1.5H), 0.95 (s, 1.5H), 0.79 (s, 3H), 0.52 (m, 1H), 0.40 (m, 1H), 0.25 (m, 1H), 0.10 (m, 1H).

Example 69

(E,Z) 3-(3-N-Methylaminopropoxyimino)-6α-ethynylandrostan-17-one hydrochloride (I-cq)

Prepared in 70% yield as described in Example 1 starting from 6α-ethynylandrostane-3,17-dione (II-bb, Prepn. 27) and 3-N-methylaminopropoxyamine dihydrochloride (III-b, Prepn. 54). $^1$H-NMR (300 MHz, DMSO-$d_6$, ppm from TMS): δ 8.90 (bb, 2H), 3.98 (m, 2H), 3.44 (m, 0.5H), 3.00 (m, 0.5H), 3.01 (d, 0.5H), 2.97 (d, 0.5H), 2.86 (m, 2H), 2.75-0.70 (m, 22H), 2.49 (s, 1.5H), 2.48 (s, 1.5H), 0.87 (s, 3H), 0.77 (s, 3H).

Example 70

(E,Z) 3-(3-N-Methylaminopropoxyimino)-5α-hydroxy-6-(E)-hydroxyiminoandrostan-17-one hydrochloride (I-cr)

Prepared in 57% yield as described in Example 4 starting 5α-hydroxy-6-(E)-hydroxyiminoandrostane-3,17-dione (II-bm, Prepn. 38) and 3-N-methylaminopropoxyamine dihydrochloride (III-b, Prepn. 54). The combined organic extracts were dried over $Na_2SO_4$, filtered and evaporated to dryness to give the title compound I-cr. $^1$H-NMR (300 MHz, DMSO-$d_6$, ppm from TMS): δ 10.68 (s, 0.5H), 10.66 (s, 0.5H), 8.63 (bb, 2H), 5.07 (s, 0.5H), 5.04 (s, 0.5H), 3.98 (m, 2H), 3.15 (d, 0.5H), 3.11 (m, 1H), 2.97 (m, 0.5H), 2.88 (m, 2H), 2.60-1.10 (m, 19H), 2.49 (s, 3H), 0.82 (s, 1.5H), 0.81 (s, 1.5H), 0.76 (s, 3H).

Example 71

(E,Z) 3-(3-N-Methylaminopropoxyimino)-5α-hydroxy-6-(E)-methoxyimino-androstan-17-one fumarate (I-cs)

Prepared in 57% yield as described in Example 1 starting 5α-hydroxy-6-(E)-methoxyiminoandrostane-3,17-dione (II-bn, Prepn. 39) and 3-N-methylaminopropoxyamine dihydrochloride (III-b, Prepn. 54). $^1$H-NMR (300 MHz, DMSO-$d_6$, ppm from TMS): δ 8.00 (bb, 3H), 6.40 (s, 2H), 5.20 (s, 1H), 3.96 (m, 2H), 3.77 (s, 1.5H), 3.75 (s, 1.5H), 3.12 (d, 0.5H), 3.02 (m, 1H), 2.95 (m, 0.5H) 2.80 (m, 2H), 2.44 (s, 1.5H), 2.43 (s, 1.5H), 2.60-1.09 (m, 19H), 0.82 (s, 3H), 0.76 (s, 3H).

Example 72

(E,Z) 3-(3-N-Methylaminopropoxyimino)-5α-hydroxy-6-methylenandrostan-17-one hydrochloride (I-ct)

Prepared in 70% yield as described in Example 1 starting from 5α-hydroxy-6-methylenandrostan-3,17-dione (II-bo, Prepn. 40) and 3-N-methylaminopropoxyamine dihydrochloride (III-b, Prepn. 54). The crude product was triturated with $Et_2O$. $^1$H-NMR (300 MHz, DMSO-$d_6$, ppm from TMS): δ 8.70 (bb, 2H), 4.85 (m, 0.5H), 4.83 (m, 0.5H), 4.70 (m, 0.5H), 4.65 (m, 0.5H), 4.63 (s, 1H), 3.97 (m, 2H), 3.09 (d, 0.5H), 2.97 (m, 0.5H), 2.91 (m, 2H), 2.60-1.08 (m, 20H), 2.91 (s, 1.5H), 2.90 (s, 1.5H), 0.82 (s, 1.5H) 0.75 (s, 3H).

Example 73

(E,Z) 3-(3-N-Methylaminopropoxyimino)androstane-7,17-dione fumarate (I-cu)

Prepared in 50% yield as described in Example 1 starting from androstane-3,7,17-trione (II-bp, Prepn. 41) and 3-N-methylaminopropoxyamine dihydrochloride (III-b, Prepn. 54). $^1$H-NMR (300 MHz, DMSO-$d_6$, ppm from TMS): δ 9.00 (bb, 3H), 6.40 (s, 2H), 3.96 (m, 2H), 3.01 (m, 0.5H), 2.84 (m, 0.5H), 2.80 (m, 2H) 2.46 (m, 3H), 2.74-0.98 (m, 21H), 1.13 (s, 3H), 0.78 (s, 3H).

Example 74

(E,Z) 3-(3-N-Methylaminopropoxyimino)-7-(spirocyclopropane)androstan-17-one hydrochloride (I-cv)

Prepared in 65% yield as described in Example 1 starting from 7-(spirocyclopropane)androstane-3,17-dione (II-bz, Prepn. 50) and 3-N-methylaminopropoxyamine dihydrochloride (III-b, Prepn. 54). The combined organic extracts were dried over $Na_2SO_4$, filtered and evaporated to dryness. The crude product was triturated with $Et_2O$ and then was dissolved in $H_2O$ and freeze-dried to give the title compound I-cv. 1H-NMR (300 MHz, DMSO-$d_6$, ppm from TMS): δ 8.44 (bb, 2H), 3.95 (m, 2H), 2.98 (m, 0.5H), 2.89 (m, 2H), 2.68 (m, 0.5H), 2.53 (s, 3H) 2.37-0.10 (m, 25H), 0.93 (s, 1.5H), 0.92 (s, 1.5H), 0.78 (s, 3H).

Example 75

(E,Z) 3-(3-N-Methylaminopropoxyimino)-7β-hydroxymethylandrostane-17-one hydrochloride (I-cw)

Prepared in 80% yield as described in Example 1 starting from 7β-hydroxymethylandrostane-3,17-dione (II-by, Prepn. 49) and 3-N-methylaminopropoxyamine dihydrochloride (III-b, Prepn. 54). The crude product was crystallized from EtOAc to give the title compound I-cw. $^1$H-NMR (300 MHz, DMSO-$d_6$, ppm from TMS): δ 8.43 (bb, 2H), 4.37 (t, 1H), 3.96 (s, 2H), 3.41 (m, 2H), 2.99 (m, 0.5H), 2.90 (m, 2H), 2.55 (s, 3H) 2.41-0.67 (m, 22H), 0.83 (s, 3H), 0.78 (s, 3H).

Example 76

(E,Z) 3-(3-N-Methylaminopropoxyimino)-7-(E)-hydroxyiminoandrostan-17-one fumarate (I-cx)

Prepared in 55% yield as described in Example 1 starting from 7(E)-hydroxyiminoandrostan-17-one (II-bq, Prepn. 42) and 3-N-methylaminopropoxyamine dihydrochloride (III-b, Prepn. 54). $^1$H-NMR (300 MHz, DMSO-$d_6$, ppm from TMS): δ 10.38 (bb, 1H), 8.80 (bb, 3H), 6.40 (s, 2H), 3.96 (m, 2H), 3.00 (m, 4H), 2.50-0.70 (m, 20H), 2.49 (s, 3H), 1.02 (s, 3H), 0.80 (s, 3H).

Example 77

(E,Z) 3-(cis-4-Aminocyclohexyloxyimino)-6-(E)-hydroxyiminoandrostan-17-one hydrochloride (I-cy)

Prepared as described in Example 1 starting from 6-(E)-hydroxyiminoandrostane-3,17-dione (II-at, Prepn. 20, 615 mg) and cis-4-aminocyclohexyloxyamine dihydrochloride (III-c, Prepn. 55, 406 mg). The crude was purified by flash chromatography ($SiO_2$, $CH_2Cl_2$:MeOH:$NH_3$ 9:1:0.1). To the concentrated fractions 5M HCl in EtOAc was added. After dilution with $Et_2O$, the solid was collected by filtration to give the title compound I-cy (540 mg, 60%). $^1$H-NMR (300 MHz, DMSO-$d_6$, ppm from TMS): δ 10.50 (bb, 1H), 7.84 (3H, bb), 4.10 (1H, m), 3.15 (0.5H, m, E isomer), 3.03 (0.5H, m, Z isomer), 3.01 (1H, m), 2.55-1.20 (14H, m), 0.79 (4.5H, s), 0.78 (1.5H, s, Z isomer).

Example 78

(E,Z) 3-(cis-2-Aminocyclopentyloxyimino)-6-(E)-hydroxyiminoandrostan-17-one hydrochloride (I-cz)

Prepared as a white solid (470 mg, 71%) from cis-2-aminocyclopentyloxyamine dihydrochloride (III-d, Prepn. 56, 250 mg) and 6-(E)-hydroxyiminoandrostane-3,17-dione (II-at, Prepn. 20, 515 mg) by the procedure described in Example 1. $^1$H-NMR (300 MHz, DMSO-$d_6$, ppm from TMS): δ 10.40

(bb, 1H), 9.10 (3H, bb), 4.49 (1H, m), 3.47 (1H, m), 3.19 (1H, m), 2.60-1.20 (25H, m), 0.79 (6H, s).

Example 79

(E,Z) 3-(trans-2-Aminocyclopentyloxyimino)-6-(E)-hydroxyiminoandrostan-17-one hydrochloride (I-da)

Following the procedure described in Example 1 and starting from 6-(E)-hydroxyiminoandrostane-3,17-dione (II-at, Prepn. 20, 280 mg) and trans-2-aminocyclopentyloxyamine dihydrochloride (III-e, Prepn. 57, 137 mg), the title compound I-da was obtained after precipitation from THF as a white solid (220 mg, 56%). $^1$H-NMR (300 MHz, DMSO, ppm from TMS): δ 7.98 (3H, bb), 4.42 (1H, m), 3.42 (1H, m), 2.99 (0.5H, m, E isomer), 2.94 (0.5H, m, Z isomer), 2.60-1.20 (25H, m), 0.78 (6H, s).

Example 80

3β-(5-Aminopentyl)-6-(E)-hydroxyiminoandrostan-17-one fumarate (I-db)

Prepared as described in Example 1 starting from 3β-(5-aminopentyl)androstane-6,17-dione (Prepn. 58, 0.39 g) and NH$_2$OH.HCl. The crude residue was purified by flash chromatography (SiO$_2$; CH$_2$Cl$_2$:MeOH 9:1 then CH$_2$Cl$_2$:MeOH:NH$_3$ 90:10:1). To the concentrated fractions the stoichiometric amount of fumaric acid in MeOH was added. After addition of EtOAc, the precipitate was filtered to give 0.18 g (47%) of the title compound I-db as a white solid. $^1$H-NMR (300 MHz, DMSO-d$_6$, ppm from TMS): δ 10.40 (1H, s), 7.98 (3H, bb), 6.35 (2H, s), 3.28 (1H, m), 2.73 (2H, m), 2.50-0.85 (29H, m), 0.77 (3H, s), 0.63 (3H, s).

Example 81

3β-(5-Aminopent-1-(Z)-enyl)-6-(E)-hydroxyiminoandrostan-17-one fumarate-(I-dc)

Prepared in 40% yield as described in Example 1 starting from (Z) 3β-(5-aminopent-1-enyl)androstane-6,17-dione (Prepn. 59, 385 mg) as a white solid. $^1$H-NMR (300 MHz, DMSO-d$_6$, ppm from TMS): δ 10.36 (1H, s), 7.80 (3H, bb), 6.35 (2H, s), 5.25 (2H, m), 3.28 (1H, m), 2.73 (2H, m), 2.55-1.05 (25H, m), 0.78 (3H, s), 0.67 (3H, s).

Example 82

3β-(4-Aminobutyl)-6-(E)-hydroxyiminoandrostan-17-one fumarate (I-dd)

Prepared in 44% yield as described in Example 1 starting from 3β-(4-aminobutyl)androstane-6,17-dione (Prepn. 60, 290 mg), as a white solid. $^1$H-NMR (300 MHz, DMSO-d$_6$, ppm from TMS): δ 10.30 (1H, s), 7.80 (3H, bb), 6.35 (2H, s), 3.28 (1H, m), 2.74 (2H, m), 2.50-0.85 (27H, m), 0.77 (3H, s), 0.63 (3H, s).

Example 83

3β-(4-Aminobut-1-(Z)-enyl)-6-(E)-hydroxyiminoandrostane-17-one fumarate (I-de)

Prepared in 44% yield as described in Example 1 starting from (Z) 3β-(4-aminobut-1-enyl)androstane-6,17-dione (Prepn. 61, 415 mg) as a white solid. $^1$H-NMR (300 MHz, DMSO-d$_6$, ppm from TMS): 10.25 (1H, s), 7.80 (3H, bb), 6.35 (2H, s), 5.38 (1H, m), 5.23 (1H, m), 3.29 (1H, m), 2.75 (2H, m), 2.55-1.10 (23H, m), 0.78 (3H, s), 0.67 (3H, s).

Example 84

3α-(5-Aminopentyl)-6-(E)-hydroxyiminoandrostan-17-one fumarate (I-df)

Prepared in 59% yield as described in Example 1 starting from 3α-(5-aminopentyl)androstane-6,17-dione (Prepn. 62, 60 mg) as a white solid. $^1$H-NMR (300 MHz, DMSO-d$_6$, ppm from TMS): δ 10.20 (1H, s), 7.70 (3H, bb), 6.35 (2H, s), 3.29 (1H, m), 2.73 (2H, m), 2.50-1.10 (29H, m), 0.77 (3H, s), 0.67 (3H, s).

Example 85

3α-(5-Aminopent-1-(Z)-enyl)-6-(E)-hydroxyiminoandrostan-17-one fumarate (I-dg)

Prepared in 34% yield as described in Example 1 starting from (Z) 3α-(5-aminopent-1-enyl)androstane-6,17-dione (Prepn. 63, 250 mg), as a white solid. $^1$H-NMR (300 MHz, DMSO-d$_6$, ppm from TMS): δ 10.36 (1H, s), 8.00 (3H, bb), 6.35 (2H, s), 5.77 (1H, m), 5.27 (1H, m), 3.29 (1H, m), 2.74 (3H, m), 2.54-1.09 (24H, m), 0.77 (3H, s), 0.69 (3H, s).

Example 86

3α-(4-Aminobutyl)-6-(E)-hydroxyiminoandrostane-17-one fumarate (I-dh)

Prepared in 60% yield as described in Example 4 starting from 3α-(4-aminobutyl)androstane-6,17-dione (Prepn. 64, 55 mg), as a white solid. $^1$H-NMR (300 MHz, DMSO-d$_6$, ppm from TMS): δ 10.35 (1H, s), 7.79 (3H, bb), 6.35 (1H, s), 3.28 (1H, m), 2.74 (2H, m), 2.50-1.15 (27H, m), 0.77 (3H, s), 0.67 (3H, s).

Example 87

3α-(4-Aminobut-1-(Z)-enyl)-6-(E)-hydroxyiminoandrostan-17-one fumarate (I-di)

Prepared in 53% yield as described in Example 1 starting from (Z) 3α-(4-aminobut-1-enyl)androstane-6,17-dione (Prepn. 65, 60 mg), as a white solid. $^1$H-NMR (300 MHz, DMSO-d$_6$, ppm from TMS): δ 10.30 (1H, s), 7.80 (3H, bb), 6.35 (2H, s), 5.84 (1H, m), 5.28 (1H, m), 3.29 (1H, m), 2.74 (3H, m), 2.55-1.10 (22H, m), 0.78 (3H, s), 0.70 (3H, s).

Example 88

3α-(6-Aminohex-1-(Z)-enyl)-6-(E)-hydroxyiminoandrostan-17-one fumarate (I-dj)

Prepared in 40% yield as described in Example 4 starting from (Z) 3α-(6-aminohex-1-enyl)androstane-6,17-dione (Prepn. 66, 133 mg), as a white powder. $^1$H-NMR (300 MHz, DMSO-d$_6$, ppm from TMS): δ 10.25 (1H, s), 7.73 (3H, bb), 6.35 (1H, s), 5.71 (1H, m), 5.26 (1H, m), 3.29 (1H, m), 2.74 (3H, m), 2.56-1.12 (26H, m), 0.78 (3H, s), 0.69 (3H, s).

Example 89

3α-(5-Aminopent-1-(Z)-enyl)-5α-hydroxyandrostane-17-one fumarate (I-dk)

The title compound I-dk was prepared in 95% yield from 5-(5α-hydroxy-17-keto-androstane-3α-yl)pent-4-(Z)-en-1-yl carbamic acid 9H-fluoren-9-yl methyl ester (Prepn. 67) by the procedure described for the preparation of 3,3:17,17-bis(ethylendioxy)-7α-aminoandrostane (Prepn. 46). The crude product was purified by flash chromatography (SiO$_2$, CH$_2$Cl$_2$/MeOH 90/10/NH$_3$). To the concentrated fractions a stoichiometric amount of fumaric acid in MeOH was added. After addition of a 1/1 mixture of EtOAc/Et$_2$O, the precipitate was filtered to give the title compound I-dk. $^1$H-NMR (300 MHz, DMSO-d$_6$, ppm from TMS): δ 8.00 (m, 4H), 6.40 (s, 2H), 6.10 (m, 1H), 5.05 (m, 1H), 3.55 (s, 1H), 2.73 (m, 2H), 2.66 (m, 1H), 2.42-0.99 (m, 25H), 0.90 (s, 3H), 0.76 (s, 3H).

Example 90

3β-(2-Aminoacetoxy)-6-(E)-hydroxyiminoandrostane-17-one hydrochloride (I-dl)

Following the procedure described in Example 4 and starting from 3β-(2-aminoacetoxy)androstane-6,17-dione fumarate (Prepn. 68, 290 mg) the title compound I-dl was obtained in 75% yield after purification by flash chromatography (SiO$_2$; CH$_2$Cl$_2$:MeOH 9:1) and formation of the hydrochloride salt. $^1$H-NMR (300 MHz, DMSO-d$_6$, ppm from TMS): δ 10.40 (1H, s), 8.00 (3H, bb), 4.67 (1H, m), 3.49 (2H, s), 3.27 (1H, m), 2.55-1.15 (19H, m), 0.78 (3H, s), 0.69 (3H, s).

Example 91

3β-(3-Aminopropionyloxy)-6-(E)-hydroxyiminoandrostan-17-one hydrochloride (I-dm)

Following the procedure described in Example 1 and starting from 3β-(3-aminopropionyloxy)androstane-6,17-dione fumarate (Prepn. 69, 260 mg) and hydroxylamine hydrochloride (41 mg), the title compound I-dm was obtained (168 mg, 75%), after purification by flash chromatography (SiO$_2$; CH$_2$Cl$_2$:MeOH 9:1). $^1$H-NMR (300 MHz, DMSO-d$_6$, ppm from TMS): δ 10.42 (1H, s), 8.13 (3H, bb), 4.63 (1H, m), 3.27 (1H, m), 2.98 (2H, t), 2.64 (2H, t), 2.45-0.95 (19H, m), 0.77 (3H, s), 0.69 (3H, s).

Example 92

3β-(4-Aminobutyryloxy)-6-(E)-hydroxyiminoandrostan-17-one hydrochloride (I-dn)

Following the procedure described in Example 4 and starting from 3β-(4-aminobutyryloxy)androstane-6,17-dione fumarate (Prepn. 70, 290 mg) the title compound I-dn was obtained in 75% yield after purification by flash chromatography (SiO$_2$; CH$_2$Cl$_2$:MeOH 9:1) and formation of the hydrochloride salt. $^1$H-NMR (300 MHz, DMSO-d$_6$, ppm from TMS): δ 10.35 (1H, s), 7.93 (3H, bb), 4.89 (1H, m), 3.28 (1H, m), 2.78 (2H, t), 2.50-1.15 (23H, m), 0.78 (3H, s), 0.69 (3H, s).

Example 93

3β-[3(R,S)-Aminobutyryloxy]-6-(E)-hydroxyiminoandrostan-17-one hydrochloride (I-do)

Following the procedure described in Example 4 and starting from 3β-(3R,S-aminobutyryloxy)androstane-6,17-dione fumarate (Prepn. 71, 200 mg) the title compound I-do was obtained in 75% yield after purification by flash chromatography (SiO$_2$; CH$_2$Cl$_2$:MeOH 9:1) and formation of the hydrochloride salt. $^1$H-NMR (300 MHz, DMSO-d$_6$, ppm from TMS): δ 10.30 (1H, s), 8.00 (bb, 3H) 4.63 (m, 1H), 3.47 (m, 1H), 3.28 (1H, m), 2.78-1.12 (m, 21H), 1.21 (d, 3H), 0.78 (s, 3H), 0.70 (s, 3H).

Example 94

3β-[2(R,S)-Methyl-3-aminopropionyloxy]-6-(E)-hydroxyimino-androstan-17-one hydrochloride (I-dp)

Following the procedure described in Example 4 and starting from 3β-(3R,S-aminobutyryloxy)androstane-6,17-dione fumarate (Prepn. 72, 240 mg) the title compound I-dp was obtained in 55% yield after purification by flash chromatography (SiO$_2$; CH$_2$Cl$_2$:MeOH 9:1) and formation of the hydrochloride salt. $^1$H-NMR (300 MHz, DMSO-d$_6$, ppm from TMS): δ 10.30 (1H, s), 7.98 (bb, 3H) 4.61 (m, 1H), 3.26-1.03 (m, 23H), 1.15 (d, 1.5H), 1.14 (d, 1.5H), 0.78 (s, 3H), 0.70 (s, 3H).

Example 95

3β-[N-(2-Aminoethyl)carbamoyloxy]-6-(E)-hydroxyiminoandrostan-17-one hydrochloride (I-dq)

Following the procedure described in Example 4 and starting from 3β-[N-(2-aminoethyl)carbamoyloxy]androstane-6,17-dione fumarate (Prepn. 73, 190 mg) the title compound I-dq was obtained in 45% yield after purification by flash chromatography (SiO$_2$; CH$_2$Cl$_2$:MeOH 9:1) and formation of the hydrochloride salt. $^1$H-NMR (300 MHz, DMSO-d$_6$, ppm from TMS): δ 10.30 (1H, s), 7.57 (3H, bb), 7.20 (1H, t), 4.42 (1H, m), 3.27 (1H, m), 3.17 (2H, m), 2.78 (2H, t), 2.50-1.15 (19H, m), 0.78 (3H, s), 0.68 (3H, s).

Example 96

3β-(4-Aminobutyramido)-6-(E)-hydroxyiminoandrostan-17-one hydrochloride (I-dr)

Following the procedure described in Example 4 and starting from 3β-(4-aminobutyramido)androstane-6,17-dione fumarate (Prepn. 74, 220 mg) the title compound I-dr was obtained in 57% yield after purification by flash chromatography (SiO$_2$; CH$_2$Cl$_2$:MeOH 9:1) and formation of the hydrochloride salt. $^1$H-NMR (300 MHz, DMSO-d$_6$, ppm from TMS): δ 10.25 (1H, s), 7.85 (1H, d), 7.76 (3H, bb), 3.45 (1H, m), 3.26 (1H, m), 2.76 (2H, m), 2.45-1.15 (23H, m), 0.78 (3H, s), 0.66 (3H, s).

Example 97

3β-(3-Aminopropionamido)-6-(E)-hydroxyiminoandrostan-17-one hydrochloride (I-ds)

Following the procedure described in Example 4 and starting from 3β-(3-aminopropionamido)androstane-6,17-dione fumarate (Prepn. 75, 190 mg) the title compound I-ds was obtained in 62% yield after purification by flash chromatography (SiO$_2$; CH$_2$Cl$_2$:MeOH 9:1) and formation of the hydrochloride salt. $^1$H-NMR (300 MHz, DMSO-d$_6$, ppm from TMS): δ 10.30 (1H, s), 8.01 (1H, d), 7.76 (3H, bb), 3.48 (1H, m), 3.28 (1H, m), 2.96 (2H, m), 2.45-1.15 (21H, m), 0.78 (3H, s), 0.67 (3H, s).

Example 98

3β-(3-N-Methylaminopropoxy]-6-(E)-hydroxyiminoandrostan-17-one fumarate (I-dt)

A solution of 3β-[3-(N-tert-butoxycarbonyl-N-methyl) aminopropoxy]-6-hydroxyiminoandrostane-17-(2-spiro-1, 3-dioxolane) (Prepn. 76, 105 mg) in THF (5 mL) was treated with a solution of 5M HCl in EtOAc (0.2 mL) and stirred at 0° C. for 1.5 hrs. After evaporation, purification by flash chromatography (SiO$_2$; CH$_2$Cl$_2$:MeOH:NH$_3$ 9:1:0.1), and addition of fumaric acid to the concentrated fractions, the title compound I-dt (61 mg, 62%) was obtained as a white solid. $^1$H-NMR (300 MHz, DMSO-d$_6$, ppm from TMS): δ 10.43 (1H, bb), 9.00 (3H, bb), 6.45 (2H, s), 3.55-2.80 (6H, m), 2.49 (3H, s), 2.45-0.89 (21H, m), 0.76 (3H, s), 0.65 (3H, s).

Example 99

3β-(3-N-Methylaminopropoxy)-6α-hydroxymethylandrostane-17-one fumarate (I-du)

A solution of 3β-[3-(N-tert-butoxycarbonyl-N-methyl) aminopropoxy]-6α-hydroxymethylandrostane-17-(2-spiro-1,3-dioxolane) (Prepn. 77, 100 mg) in THF (5 mL) was treated with a solution of 5M HCl in EtOAc (0.15 mL) and stirred at 0° C. for 1.5 hrs. The mixture was evaporated and the residue purified by flash chromatography (SiO$_2$; CH$_2$Cl$_2$: MeOH:NH$_3$ 9:1:0.1). After addition of fumaric acid to the concentrated fractions the title compound I-du was obtained (100 mg, 85%) as a white solid. $^1$H-NMR (300 MHz, DMSO-d$_6$, ppm from TMS): δ 10.00 (3H, bb), 6.41 (2H, s), 4.33 (1H, bb), 3.50-2.80 (7H, m), 2.49 (3H, s), 2.45-0.55 (23H, m), 0.77 (6H, s).

Example 100

3α-(2-Aminoethylthio)-6-(E)-hydroxyiminoandrostane-17-one fumarate (I-dv)

To a stirred solution of 3α-(2-trifluoroacetamidoethylthio)-6-(E)-hydroxyiminoandrostan-17-one (Prepn. 78, 115 mg) in MeOH/H$_2$O 95/5 (7 mL), K$_2$CO$_3$ (159 mg) was added. The mixture was refluxed for 1.5 hrs and then concentrated, washed with water, extracted with CH$_2$Cl$_2$ and dried with Na$_2$SO$_4$. Fumaric acid (27 mg) was added and the resulting solution evaporated to dryness. The residue was purified by flash chromatography (SiO$_2$, CH$_2$Cl$_2$/MeOH/NH$_3$ 9/1/0.1). To the concentrated fractions a stoichiometric amount of fumaric acid in MeOH was added. The solution was concentrated and the resulting mixture centrifugated. The solid was washed with Et$_2$O/EtOH 9/1 (0.8 mL) to give, after centrifugation, the title compound I-dv (53 mg, 50%). $^1$H-NMR (300 MHz, DMSO-d$_6$, ppm from TMS): δ 10.45 (1H, s), 8.10 (3H, m), 6.35 (2H, s), 3.29 (1H, dd), 3.22 (1H, m), 2.86 (2H, t), 2.67 (1H, m), 2.60 (2H, t), 2.50-0.80 (20H, m), 0.76 (3H, s), 0.67 (3H, s).

Example 101

3α-(3-Aminopropylthio)-6-(E)-hydroxyiminoandrostane-17-one hemifumarate (I-dw)

The title compound was prepared in 50% yield as described in Example 100 starting from 3α-(3-trifluoroacetamidopropylthio)-6-(E)-hydroxyiminoandrostan-17-one (Prepn. 79, 53 mg). $^1$H-NMR (300 MHz, DMSO-d$_6$, ppm from TMS): δ 10.39 (1H, s), 8.00 (4H, bb), 6.35 (2H, s), 3.29 (1H, dd), 3.21 (1H, m), 2.70 (2H, m), 2.50-0.90 (23H, m), 0.76 (3H, s), 0.68 (3H, s).

Example 102

3α-(4-Aminobutylthio)-6-(E)-hydroxyiminoandrostane-17-one fumarate (I-dx)

The title compound was prepared in 53% yield as described in Example 100 starting from 3α-(4-trifluoroacetamidobutylthio)-6-(E)-hydroxyiminoandrostan-17-one (Prepn. 80, 120 mg). $^1$H-NMR (300 MHz, DMSO-d$_6$, ppm from TMS): δ 10.43 (1H, s), 8.00 (3H, m), 6.35 (2H, s), 3.28 (1H, dd), 2.73 (2H, m), 2.64 (1H, m), 2.50-1.15 (25H, m), 0.78 (3H, s), 0.68 (3H, s).

Example 103

3α-(3-N-Methylaminopropylthio)-6-(E)-hydroxyiminoandrostane-17-one hemifumarate (I-dy)

The title compound was prepared in 50% yield as described in Example 100 starting from 3α-(3-N-methyltrifluoroacetamidopropylthio)-6-(E)-hydroxyiminoandrostan-17-one (Prepn. 81, 115 mg). $^1$H-NMR (300 MHz, DMSO-d$_6$, ppm from TMS): δ 10.43 (1H, s), 8.00 (3H, m), 6.35 (1H, s), 3.28 (1H, dd), 3.22 (1H, m), 2.67 (2H, m), 2.35 (3H, s), 2.50-0.80 (23H, m), 0.76 (3H, s), 0.67 (3H, s).

Example 104

3α-(3-Aminopropylthio)-6-methyleneandrostane-17-one fumarate (I-dz)

To a solution of 3α-(3-N-trifluoroacetamidopropylthio)-6-methyleneandrostane-17-one (Prepn. 82, 85 mg) in MeOH/H$_2$O 8/2 (5 mL), Ambersep 900 OH (1.4 g) was added and the resulting mixture was stirred overnight at room temperature. The resin was filtered and the solvent evaporated to small volume. Fumaric acid (20 mg) was added and the solution evaporated to dryness. The resulting solid was washed with Et$_2$O, filtered and dessiccated to give the title compound I-dz (80 mg, 90% yield) as a white powder. $^1$H-NMR (300 MHz, DMSO-d$_6$, ppm from TMS): δ 9.50 (4H, bb), 6.38 (2H, s), 4.73 (1H, m), 4.41 (1H, m), 3.24 (1H, m), 2.81 (2H, m), 2.56-0.84 (24H, m), 0.75 (3H, s), 0.65 (3H, s).

Example 105

3α-(3-N-Methylaminopropylthio)-6-methyleneandrostane-17-one fumarate (I-ea)

The title compound was prepared in 60% yield as described in Example 80 starting from 3α-(3-N-methyltrifluoroacetamidopropylthio)-6-methyleneandrostan-17-one (Prepn. 83, 75 mg). $^1$H-NMR (300 MHz, DMSO-d$_6$, ppm from TMS): δ

8.00 (3H, bb), 6.40 (2H, s), 4.73 (1H, m), 4.41 (1H, m), 3.25 (1H, m), 2.80 (2H, m), 2.50-0.89 (24H, m), 2.45 (3H, s), 0.75 (3H, s), 0.65 (3H, s).

Example 106

3α-[(S)-3-Aminopropylsulfinyl]-6-methyleneandrostane-17-one fumarate (I-eb)

The title compound was prepared in 90% yield as described in Example 104 starting from 3α-[(S)-3-trifluoroacetamidopropylsulfonyl]-6-methyleneandrostane-17-one (Prepn. 84, 100 mg). $^1$H-NMR (300 MHz, DMSO-$d_6$, ppm from TMS): δ 7.98 (3H, bb), 6.42 (2H, s), 4.72 (1H, m), 4.41 (1H, m), 3.24 (3H, m), 2.50-0.86 (24H, m), 0.75 (3H, s), 0.65 (3H, s).

Example 107

3α-[(R)-3-Aminopropylsulfinyl]-6-methyleneandrostane-17-one fumarate (I-ec)

The title compound was prepared in 90% yield as described in Example 104 starting from 3α-[(R)-3-trifluoroacetamidopropylsulfonyl]-6-methyleneandrostane-17-one (Prepn. 85, 70 mg). $^1$H-NMR (300 MHz, DMSO-$d_6$, ppm from TMS): δ 7.98 (3H, bb), 6.42 (2H, s), 4.70 (1H, m), 4.41 (1H, m), 3.24 (3H, m), 2.50-0.86 (24H, m), 0.75 (3H, s), 0.65 (3H, s).

Example 108

(E,Z) 3-(2-Aminoethoxyimino)-7α-methoxymethylandrostane-17-one hydrochloride (I-ed)

Prepared in 80% yield as described in Example 1 and starting from 7α-methoxymethylandrostane-3,17-dione (Prepn. 86) and 2-aminoethoxyamine dihydrochloride as a white powder. $^1$H-NMR (300 MHz, DMSO-$d_6$, ppm from TMS): δ 7.95 (3H, bb), 3.35 (3H, s), 3.15 (2H, m), 2.53-0.75 (25H, m), 0.85 (3H, s), 0.78 (3H, s).

Example 109

(E,Z) 3-(2-Aminoethoxyimino)-7α-methoxyandrostane-17-one hemifumarate (I-ee)

Prepared as described in Example 1 and starting from 7α-methoxyandrostane-3,17-dione (Prepn. 87) and 2-aminoethoxyamine dihydrochloride. After flash chromatography (SiO$_2$, CH$_2$Cl$_2$:MeOH:NH$_3$ 9:1:0.1), concentration of the fractions, addition of fumaric acid and filtration the title compound was obtained in 75% yield as a white powder. $^1$H-NMR (300 MHz, DMSO-$d_6$, ppm from TMS): δ 7.98 (3H, bb), 6.42 (1H, s), 3.35 (3H, s), 2.58-1.00 (25H, m), 0.86 (3H, s), 0.78 (3H, s).

Example 110

3β-(2-Aminoethylthio)-6-(E)-hydroxyiminoandrostane-17-one fumarate (I-ef)

To a stirred solution of 3β-(2-trifluoroacetamidoethylthio)-6-(E)-hydroxyiminoandrostan-17-one (Prepn. 88, 120 mg) in MeOH/H$_2$O 95/5 (7 mL), K$_2$CO$_3$ (170 mg) was added. The mixture was refluxed for 1.5 hrs and then concentrated, washed with water, extracted with CH$_2$Cl$_2$ and dried with Na$_2$SO$_4$. Fumaric acid (30 mg) was added and the resulting solution evaporated to dryness. The residue was purified by flash chromatography (SiO$_2$, CH$_2$Cl$_2$/MeOH/NH$_3$ 9/1/0.1). To the concentrated fractions a stoichiometric amount of fumaric acid in MeOH was added. The solution was concentrated and the resulting mixture centrifugated. The solid was washed with Et$_2$O/EtOH 9/1 (1 mL) to give, after centrifugation, the title compound (55 mg, 50%). $^1$H-NMR (300 MHz, DMSO-$d_6$, ppm from TMS): δ 10.45 (1H, s), 8.10 (3H, m), 6.35 (2H, s), 3.30 (1H, dd), 3.22 (1H, m), 2.86 (2H, t), 2.67 (1H, m), 2.60 (2H, t), 2.50-0.80 (20H, m), 0.76 (3H, s), 0.67 (3H, s).

Example 111

3β-(3-Aminopropylthio)-6-(E)-hydroxyiminoandrostane-17-one fumarate (I-eg)

The title compound was prepared in 50% yield as described in Example 110 starting from 3β-(3-trifluoroacetamidopropylthio)-6-(E)-hydroxyiminoandrostane-17-one (Prepn. 89, 53 mg). $^1$H-NMR (300 MHz, DMSO-$d_6$, ppm from TMS): δ 10.39 (1H, s), 8.00 (4H, bb), 6.35 (2H, s), 3.31 (1H, dd), 3.22 (1H, m), 2.70 (2H, m), 2.50-0.90 (23H, m), 0.76 (3H, s), 0.68 (3H, s).

Example 112

3β-(4-Aminobutylthio)-6-(E)-hydroxyiminoandrostane-17-one fumarate (I-eh)

The title compound was prepared in 53% yield as described in Example 110 starting from 3β-(4-trifluoroacetamidobutylthio)-6-(E)-hydroxyiminoandrostane-17-one (Prepn. 90, 120 mg). $^1$H-NMR (300 MHz, DMSO-$d_6$, ppm from TMS): δ 10.43 (1H, s), 8.00 (3H, m), 6.35 (2H, s), 3.31 (1H, dd), 2.73 (2H, m), 2.66 (1H, m), 2.50-1.15 (25H, m), 0.78 (3H, s), 0.68 (3H, s).

Example 113

(E,Z) 3-(3-N-Methylaminopropoxyimino)-6α-hydroxymethylandrostane-7,17-dione fumarate (I-ei)

Prepared in 80% yield as described in Example 1 and starting from 6α-hydroxymethylandrostane-3,7,17-trione (II-cb, Prepn. 52) and 3-N-methylaminopropoxyamine dihydrochloride (III-b, Prepn. 54). The crude product was purified by flash chromatography (SiO$_2$, CH$_2$Cl$_2$/MeOH/26% NH$_4$OH 90/10/1). To the concentrated fractions the stoichiometric amount of fumaric acid in MeOH was added. The precipitate was filtered to give the title compound. $^1$H-NMR (300 MHz, DMSO-$d_6$, ppm from TMS): δ 8.44 (2H, bb), 6.40 (2H, s), 4.37 (1H, t), 3.96 (2H, m), 3.41 (2H, m), 2.80 (2H m), 2.50 (3H, s), 2.40-1.10 (21H, m), 0.98 (3H, s), 0.82 (3H, s).

Example 114

(E,Z) 3-(2-Aminoethoxyimino)-6α-hydroxymethyl-7α-hydroxyandrostane-17-one hydrochloride (I-ej)

Prepared in 85% yield as described in Example 1 starting from 6α-hydroxymethyl-7α-hydroxyandrostane-3,17-dione (Prepn. 91) and 2-aminoethoxyamine dihydrochloride. The combined organic extracts were dried over Na$_2$SO$_4$, filtered and evaporated to dryness. The crude product was triturated with Et$_2$O and then was dissolved in H$_2$O and freeze-dried to give the title compound. $^1$H-NMR (300 MHz, DMSO-d$_6$, ppm from TMS): δ 8.02 (3H, bb), 4.35 (1H, t), 4.26 (1H, d), 3.96 (2H, m), 3.86 (1H, m), 3.40 (2H, t), 2.97 (2H, m), 2.40-1.10 (19H, m), 0.99 (3H, s), 0.82 (3H, s).

Example 115

(E,Z) 3-(3-N-Methylaminopropoxyimino)-6α-hydroxymethyl-7α-hydroxyandrostane-17-one hydrochloride (I-ek)

Prepared in 80% yield as described in Example 1 starting from 6α-hydroxymethyl-7α-hydroxyandrostane-3,17-dione (Prepn. 91) and 3-N-methylaminopropoxyamine dihydrochloride (III-b, Prepn. 54). The combined organic extracts were dried over Na$_2$SO$_4$, filtered and evaporated to dryness. The crude product was triturated with Et$_2$O and then was dissolved in H$_2$O and freeze-dried to give the title compound. $^1$H-NMR (300 MHz, DMSO-d$_6$, ppm from TMS): δ 8.44 (2H, bb), 4.35 (1H, t), 4.26 (1H, d), 3.96 (2H, m), 3.86 (1H, m), 3.40 (2H, m), 2.80 (2H, m), 2.50 (2H, m), 2.40-1.10 (21H, m), 0.99 (3H, s), 0.85 (3H, s).

Example 116

E,Z)-3-[(S)-2-Aminopropoxyimino]androstane-6-(E)-hydroxyiminoandrostane-17-one hydrochloride (I-el)

Prepared as described in Example 1 starting from 6-(E)-hydroxyiminoandrostane-3,17-dione (II-at, Prepn. 20, 500 mg) and (S)-2-aminopropoxyamine dihydrochloride (Prepn. 92, 257 mg). The crude product was crystallized from MeOH/EtOAc to give the title compound as a white solid (503 mg, 75%). NMR (300 MHz, DMSO-d$_6$, ppm from TMS): δ 10.50 (1H, s), 7.98 (3H, m), 3.97 (2H, m), 3.40 (1H, m), 3.11 (0.5H, m), 3.05 (0.5H, m), 2.54-1.15 (22H, m), 0.79 (3H, s), 0.78 (3H, s)

Example 117

E,Z)-3-[(R)-2-Aminopropoxyimino]androstane-6-(E)-hydroxyiminoandrostane-17-one hydrochloride (I-em)

Prepared as described in Example 1 starting from 6-(E)-hydroxyiminoandrostane-3,17-dione (II-at, Prepn. 20, 500 mg) and (R)-2-aminopropoxyamine dihydrochloride (Prepn. 93, 257 mg). The crude product was crystallized from MeOH/EtOAc to give the title compound as a white solid (503 mg, 75%). $^1$H-NMR (300 MHz, DMSO-d$_6$, ppm from TMS): δ 10.50 (1H, s), 7.98 (3H, m), 3.97 (2H, m), 3.40 (1H, m), 3.11 (0.5H, m), 3.05 (0.5H, m), 2.54-1.15 (22H, m), 0.79 (3H, s), 0.78 (3H, s).

Example 118

(E,Z) 3-(2-Amino-2-methylpropoxyimino)-6-(E)-hydroxyiminoandrostane-17-one hydrochloride (I-en)

Prepared as described in Example 1 starting from 6-(E)-hydroxyiminoandrostane-3,17-dione (II-at, Prepn. 20, 500 mg) and 2-amino-2-methyl-1-propoxyamine dihydrochloride (Prepn. 94, 279 mg). The crude product was crystallized from MeOH/EtOAc to give the title compound as a white solid (485 mg, 70%). NMR (300 MHz, DMSO-d$_6$, ppm from TMS): δ 10.50 (1H, s), 7.84 (3H, m), 3.16 (0.5H, m), 3.08 (0.5H, m), 2.54-1.21 (21H, m), 1.20 (6H, s), 0.79 (3H, s), 0.77 (3H, s).

Example 119

(E,Z) 3-(3-Amino-2-methyl-2-propoxyimino)-6-(E)-hydroxyiminoandrostane-17-one hydrochloride (I-eo)

Prepared as described in Example 1 starting from 6-(E)-hydroxyiminoandrostane-3,17-dione (II-at, Prepn. 20, 500 mg) and 3-amino-2-methyl-2-propoxyamine dihydrochloride (Prepn. 95, 279 mg). The crude product was crystallized from MeOH/EtOAc to give the title compound as a white solid (519 mg, 75%). $^1$H-NMR (300 MHz, DMSO-d$_6$, ppm from TMS): δ 10.35 (1H, bb), 7.50 (3H, bb), 4.08 (m, 2H), 3.30-2.80 (5H, m), 1.22 (6H, s), 0.79 (6H, s).

Example 120

(E,Z) 3-(2-Aminoethoxyimino)-7-difluoromethyleneandrostane-17-one hydrochloride (I-ep)

Prepared as described in Example 1 starting from 7-difluoromethyleneandrostane-3,17-dione (Prepn. 96, 150 mg) and 2-aminoethoxyamine dihydrochloride (66 mg). The residue was triturated with THF/Et$_2$O 9/1. After filtration and drying under vacuum the title compound was obtained (88 mg, 50%) as a yellow solid. $^1$H-NMR (300 MHz, DMSO-d$_6$, ppm from TMS): δ 7.45 (3H, bs), 4.05 (2H, m), 3.10-0.95 (22H, m), 0.98 (3H, s), 0.80 (3H, s).

Example 121

3β-[3-(N-Methylamino)propionyloxy]-6-(E)-hydroxyiminoandrostane-17-one fumarate (I-eq)

A mixture of 3β-[3-(N-carbobenzyloxy-N-methylamino)propionyloxy]-6-(E)-hydroxyiminoandrostane-17-one (Prepn. 97, 160 mg) and 10% Pd/C (10 mg) in EtOH (7 mL) was stirred under H$_2$ at atm pressure for 1 h. The mixture was filtered through Celite. The filtrate treated with the theoretical amount of fumaric acid and evaporated to dryness. The residue was triturated with EtOAc/Et$_2$O 9/1 and filtered to give 3β-[3-(N-methylamino)propionyloxy]-6-(E)-hydroxyiminoandrostane-17-one fumarate (129 mg, 84%). $^1$H-NMR (300 MHz, DMSO-d$_6$, ppm from TMS): δ 10.30 (s, 1H), 7.83 (m, 3H), 6.40 (s, 2H), 4.60 (m, 1H), 3.00-1.10 (m, 24H), 2.42 (s, 3H), 0.78 (s, 3H), 0.71 (s, 3H).

Example 122

3β-[(2,2-Dimethyl)-3-aminopropionyloxy]-6-(E)-hydroxyiminoandrostane-17-one fumarate (I-er)

Prepared as described in Example 121 starting from 3β-[(2,2-dimethyl)-3-(N-carbobenzyloxy)aminopropionyloxy]-6-(E)-hydroxyiminoandrostane-17-one (Prepn. 98, 500 mg) as a white solid (397 mg, 80%). $^1$H-NMR (300 MHz, DMSO-d$_6$, ppm from TMS): δ 10.20 (1H, s), 7.98 (4H, bb), 6.40 (2H, s), 4.58 (1H, m), 3.00-1.10 (20H, m), 0.78 (3H, s), 0.72 (3H, s).

Preparation 1

3,17-Dioxoandrostane-6α-yl nitrate (II-aa)

To a solution of acetic anhydride (2.53 mL) and 65% HNO$_3$ (0.592 mL) cooled at 0° C., 3,3:17,17-bis(ethylendioxy)androstan-6α-ol (2.5 g) was added. After 2 h the mixture was quenched by careful addition of ice and 5% aqueous $NaHCO_3$ solution and was extracted with $CH_2Cl_2$ (3×). The combined organic extracts were washed with $H_2O$, dried over $Na_2SO_4$, and evaporated to dryness to give 3,3:17,17-bis(ethylendioxy)-androstane-6α-yl nitrate as a white solid (2.50 g, 89%). $^1$H-NMR (300 MHz, acetone-$d_6$, ppm from TMS): δ 4.94 (m, 1H), 3.94-3.75 (m, 8H), 2.24-0.74 (m, 20H), 0.98 (s, 3H), 0.85 (s, 3H).

A solution of 3,3:17,17-bis(ethylendioxy)androstane-6α-yl nitrate (2.50 g) and $pTSA.H_2O$ (6.05 g) in acetone (150 mL) was stirred at room temperature for 1.5 h. The solution was neutralized by addition of 5% aqueous $NaHCO_3$, and acetone was evaporated. The aqueous phase was extracted with $CH_2Cl_2$ (3×50 mL). The combined organic extracts were washed with $H_2O$, dried over $Na_2SO_4$ and evaporated to dryness. The residue was purified by flash chromatography ($SiO_2$, cyclohexane/acetone/$CH_2Cl_2$ 70/15/15) to give the title compound II-aa as a white solid (1.66 g, 75%). $^1$H-NMR (300 MHz, acetone-$d_6$, ppm from TMS): δ 5.09 (ddd, 1H), 2.60-0.95 (m, 17H), 1.25 (s, 3H), 0.90 (s, 3H).

Preparation 2

3,17-Dioxoandrostane-6-βyl nitrate (II-ab)

3,3:17,17-Bis(ethylendioxy)androstane-6β-yl nitrate was prepared in 50% yield from 3,3:17,17-bis(ethylendioxy)androstan-6β-ol following the procedure described above for the preparation of 3,3:17,17-bis(ethylendioxy)androstane-6α-yl nitrate (Prepn. 1). $^1$H-NMR (300 MHz, acetone-$d_6$, ppm from TMS): δ 5.16 (m, 1H), 3.93-3.76 (m, 8H), 2.20-0.77 (m, 20H), 1.00 (s, 3H), 0.85 (s, 3H).

Prepared in 75% yield from 3,3:17,17-bis(ethylendioxy) androstane-6α-yl nitrate following the procedure described above for the preparation of 3,17-dioxoandrostane-6α-yl nitrate (II-aa, Prepn 1). The crude product was purified by flash chromatography ($SiO_2$, cyclo-hexane/acetone/$CH_2Cl_2$ 70/15/15) to give II-ab. $^1$H-NMR (300 MHz, acetone-$d_6$, ppm from TMS): δ 5.24 (ddd, 1H), 2.72 (dd, 1H), 2.57-0.96 (m, 19H), 1.25 (s, 3H), 0.90 (s, 3H).

Preparation 3

6α-Cyanoandrostane-3,17-dione (II-ac)

To a solution of toluene-4-sulfonylmethyl isocyanide (2.23 g) in anhydrous DMSO (13 mL), stirred under $N_2$, potassium tert-butoxide (3.55 g) was added. After stirring for 5 min, anhydrous MeOH (0.40 mL) was added dropwise, followed after 10 min by 3,3:17,17-bis(ethylendioxy)androstane-6-one (3.27 g). After 72 h at room temperature, the reaction was quenched by addition of $H_2O$ and the mixture was neutralized by addition of 1N HCl and extracted with EtOAc (3×). The combined organic extracts were washed with $H_2O$, 5% $NaHCO_3$ solution, dried over $Na_2SO_4$, and evaporated to dryness. The residue was purified by flash chromatography ($SiO_2$, n-hexane/EtOAc 70/30) to give 6α-cyano-3,3:17,17-bis(ethylendioxy)androstane (1.05 g, 31%). $^1$H-NMR (300 MHz, acetone-$d_6$, ppm from TMS): δ 3.95-3.70 (m, 8H), 2.60 (m, 1H), 2.14-0.74 (m, 20H), 0.89 (s, 3H), 0.82 (s, 3H).

A solution of 6α-cyano-3,3:17,17-bis(ethylendioxy)androstane (1.05 g) and $pTSA.H_2O$ (2.46 g) in acetone (105 mL) was stirred at room temperature for 3 h. The solution was neutralized by addition of 5% aqueous $NaHCO_3$ and acetone was evaporated. The aqueous suspension was extracted with $CH_2Cl_2$ (3×). The combined organic extracts were washed with $H_2O$, dried over $Na_2SO_4$ and evaporated to dryness. The residue was purified by flash chromatography ($SiO_2$, n-hexane/EtOAc 70/30) to give the title compound II-ac (0.62 mg, 75%) as a white solid. $^1$H-NMR (300 MHz, acetone-$d_6$, ppm from TMS): δ 2.82 (ddd, 1H), 2.87-0.80 (m, 20H), 1.16 (s, 3H), 0.87 (s, 3H).

Preparation 4

5α-Hydroxyandrostane-3,17-dione (II-ad)

To a stirred solution of 3β-hydroxyandrost-5-en-17-one (0.81 g) in $CH_2Cl_2$ (7.4 mL) cooled at 0° C., a solution of mCPBA (0.77 mg) in $CH_2Cl_2$ (13.6 mL) was added dropwise. After 0.5 h at 0° C. and 0.5 h at room temperature, a 10% aqueous solution of $Na_2SO_3$ was added. The mixture was neutralized by addition of 5% $NaHCO_3$ solution and extracted with $CH_2Cl_2$ (3×100 mL). The combined organic extracts were washed with $H_2O$, dried over $Na_2SO_4$, and evaporated to dryness. The residue was purified by flash chromatography ($SiO_2$, n-hexane/$CH_2Cl_2$/acetone 60/20/20) to give 3β-hydroxy-5α,6α-epoxyandrostan-17-one (0.64 g, 75%). $^1$H-NMR (300 MHz, DMSO-$d_6$, ppm from TMS): δ 4.62 (d, 1H), 3.52 (m, 1H), 2.87 (d, 1H), 2.44-0.56 (m, 19H), 1.00 (s, 3H), 0.72 (s, 3H).

To a stirred suspension of $LiAlH_4$ (0.247 mg) in THF under N2 (10.5 mL), a solution of 3β-hydroxy-5α,6α-epoxyandrostan-17-one (0.64 g) in THF (20 mL) was added dropwise and the mixture was stirred at reflux for 8 h. The suspension was cooled with an ice bath and then quenched by careful addition of $H_2O$ (1 mL) and 4N NaOH (0.20 mL). The mixture was filtered through a Celite pad and the filter cake was washed with THF (3×10 mL). The filtrate was dried over $Na_2SO_4$, evaporated to dryness and the residue was purified by flash chromatography ($SiO_2$, n-hexane/$CH_2Cl_2$/acetone 40/30/30) to give androstane-3β,5α,17β-triol (0.48 g, 74%). $^1$H-NMR (300 MHz, DMSO-$d_6$, ppm from TMS): δ 4.37 (d, 1H), 4.19 (d, 1H), 3.78 (m, 1H), 3.62 (s, 1H), 3.39 (m, 1H), 1.87-0.80 (m, 21H), 0.86 (s, 3H), 0.59 (s, 3H).

A solution of androstane-3β,5α,17β-triol (0.48 g) and IBX (0.72 g) in DMSO (8 mL) was stirred at −15° C. overnight and then quenched at room temperature by addition of $H_2O$ (40 mL). After stirring for 15 min, the mixture was filtered and the cake was washed with EtOAc. The layers were separated, and the aqueous phase was extracted with EtOAc (3×40 mL). The combined organic extracts were dried over $Na_2SO_4$ and evaporated to dryness. The residue was purified by flash chromatography ($SiO_2$, n-hexane/$CH_2Cl_2$/acetone 60/20/20) to give the title compound II-ad (0.36 g, 75%). $^1$H-NMR (300 MHz, acetone-$d_6$, ppm from TMS): δ 3.48 (s, 1H), 2.72 (d, 1H), 2.60-1.18 (m, 20H), 1.23 (s, 3H), 0.86 (s, 3H).

Preparation 5

5α-Hydroxy-6β-cyanoandrostane-3,17-dione (II-ae)

A mixture of 3β-hydroxyandrost-5-en-17-one (13.0 g) and IBX (25.3 g) in THF (260 mL) was heated at reflux under stirring for 4 h. After cooling to room temperature, the mixture was filtered and the solid washed with EtOAc (3×50 mL). The filtrate was evaporated to dryness. The residue was taken up with $CH_2Cl_2$ and the suspension filtered. The filtrate was evaporated to dryness and the residue triturated with $Et_2O$/MeOH 9/1 (65 mL). After filtration and drying under vacuum, 5-androstene-3,17-dione (8.68 g, 67%) was obtained.

¹H-NMR (300 MHz, acetone-d₆, ppm from TMS): δ 5.40 (m, 1H), 3.41 (m, 1H), 2.76-1.06 (m, 18H), 1.29 (s, 3H), 0.91 (s, 3H).

A solution of 5-androstene-3,17-dione (4.72 g), ethylene glycol (37 mL) and pTSA (0.219 g) in toluene (530 mL) was stirred at reflux for 12 h with a Dean-Stark trap. After cooling to room temperature, the mixture was neutralized with 5% aqueous NaHCO₃ solution. The organic layer was separated, washed with H₂O (2×350 mL), dried over Na₂SO₄ and evaporated to dryness to give 3,3:17,17-bis(ethylendioxy)-5-androstene as a white solid (6.11 g, 99%). ¹H-NMR (300 MHz, acetone-d₆, ppm from TMS): δ 5.25 (m, 1H), 3.93-3.76 (m, 8H), 2.72 (d, 1H), 2.46 (m, 1H), 2.12-0.80 (m, 18H), 1.04 (s, 3H), 0.85 (s, 3H).

3,3:17,17-Bis(ethylendioxy)-5α,6α-epoxyandrostane was prepared in 45% yield from 3,3:17,17-bis(ethylendioxy)-5-androstene by the procedure described above for the preparation of 3β-hydroxy-5α,6α-epoxyandrostan-17-one (Prepn. 4). The crude product was purified by flash chromatography (SiO₂, n-hexane/EtOAc 80/20). ¹H-NMR (300 MHz, acetone-d₆, ppm from TMS): δ 3.92-3.75 (m, 8H), 2.68 (m, 1H), 2.56 (d, 1H), 1.99-1.06 (m, 18H), 1.09 (s, 3H), 0.78 (s, 3H).

To a stirred solution of 3,3:17,17-bis(ethylendioxy)-5α,6α-epoxyandrostane (2.26 g) in dry toluene (20 mL) under N₂, 1M Et₂AlCN in toluene (10.4 mL) was added dropwise. After 24 h at room temperature, EtOAc (20 mL), KF (23.5 g) and H₂O (1.4 mL) were added. The mixture was filtered and the cake washed with EtOAc. The organic layer was dried over Na₂SO₄ and evaporated to dryness. The residue was purified by flash chromatography (SiO₂, n-hexane/CH₂Cl₂/acetone 80/10/10) to give 3,3:17,17-bis(ethylendioxy)-5α-hydroxy-6β-cyanoandrostane (1.39 g, 57%). ¹H-NMR (300 MHz, acetone-d₆, ppm from TMS): δ 4.45 (s, 1H) 4.07-3.75 (m, 8H), 2.73 (dd, 1H), 2.31 (d, 1H), 2.00-2.21 (m, 18H), 1.24 (s, 3H), 0.98 (s, 3H).

The title compound II-ai was prepared in 82% yield from 3,3:17,17-bis(ethylendioxy)-5α-hydroxy-6β-cyanoandrostane by the procedure described above for the preparation of 6α-cyanoandrostane-3,17-dione (II-ac, Prepn. 3). The crude product was purified by flash chromatography (SiO₂, n-hexane/CH₂Cl₂/acetone 60/20/20) to give the title compound II-ae. ¹H-NMR (300 MHz, acetone-d₆, ppm from TMS): δ 4.27 (s, 1H), 3.21 (d, 1H), 2.92 (m, 1H), 2.62-1.24 (m, 18H), 1.50 (s, 3H), 0.93 (s, 3H).

Preparation 6

6-(E)-Hydroxyimino-7α-methylandrostane-3,17-dione (II-af)

To a stirred solution of 3,3:17,17-bis(ethylendioxy)androstane-6-one (0.20 g) in dry THF (3 mL) cooled at −78° C., a 1.5 M solution of LDA in THF (0.41 mL) was added dropwise. After 15 min CH₃I (0.13 mL) was added dropwise. The mixture was stirred at −20° C. for 3 h and then quenched by careful addition of 39% aqueous NH₄Cl solution and extracted with CH₂Cl₂ (2×50 mL). The combined organic extracts were washed with H₂O, dried over Na₂SO₄, and evaporated to dryness. The residue was purified by flash chromatography (SiO₂, n-hexane/CH₂Cl₂/acetone 90/5/5) to give 3,3:17,17-bis(ethylendioxy)-7α-methylandrostan-6-one (0.91 g, 44%). ¹H-NMR (300 MHz, acetone-d₆, ppm from TMS): δ 3.95-3.78 (m, 8H), 2.76 (dd, 1H), 2.30 (m, 1H), 2.08-1.17 (m, 17H), 1.09 (s, 3H), 0.84 (s, 3H), 0.76 (s, 3H).

To a stirred solution of 3,3:17,17-bis(ethylendioxy)-7α-methylandrostane-6-one (1.10 g) in THF (22 mL) a solution of NH₂OH.HCl (0.332 g), Na₂HPO₄.12H₂O (1.71 g) in H₂O (7.2 mL) was added. After stirring overnight at room temperature, NaCl was added and the mixture was extracted with EtOAc (2×). The combined organic extracts were washed with brine, dried over Na₂SO₄, filtered and evaporated to dryness to give 3,3:17,17-bis(ethylendioxy)-6(E)-hydroxyimino-7α-methylandrostane (1.08 g, 93%). ¹H-NMR (300 MHz, DMSO-d₆, ppm from TMS): δ 10.34 (s, 1H), 3.88-3.71 (m, 8H), 3.16 (dd, 1H), 2.22-0.86 (m, 21H), 0.74 (s, 3H), 0.64 (s, 3H).

The title compound II-af was prepared in 85% yield from 3,3:17,17-bis(ethylendioxy)-6-(E)-hydroxyimino-7α-methylandrostan-6-one by the procedure described above for the preparation of 6α-cyanoandrostane-3,17-dione (II-ac, Prepn. 3). The combined organic extracts were washed with H₂O, dried over Na₂SO₄ and evaporated to dryness. ¹H-NMR (300 MHz, acetone-d₆, ppm from TMS): δ 3.05 (dd, 1H), 2.64-1.09 (m, 21H), 1.01 (s, 3H), 0.89 (s, 3H).

Preparation 7

6,6-Ethylendioxyandrostane-3,17-dione (II-ag)

To a solution of androstane-3β,6α,17β-triol (3.00 g) in CH₂Cl₂/acetone/—H₂O (300/150/6 mL), activated MnO₂ (30.0 g, 345 mmol) was added in three portions over 8 h. The mixture was stirred at 45° C. overnight. After cooling to room temperature, the mixture was filtered through Celite. The filtrate was evaporated and the residue was purified by flash chromatography (SiO₂, CH₂Cl₂/n-n-hexane/i-PrOH 10/5/1) to give 3β,17β-dihydroxyandrostan-6-one (0.89 g, 30%). ¹H-NMR (300 MHz, DMSO-d₆, ppm from TMS): δ 4.54 (d, 1H), 4.48 (d, 1H), 3.45 (m, 1H), 3.30 (m, 1H), 2.27 (dd, 1H), 2.08-0.90 (m, 19H), 0.62 (s, 3H), 0.61 (s, 3H).

6,6-Ethylendioxyandrostane-3β,17β-diol was prepared in 70% yield from 3β,17β-dihydroxyandrostan-6-one by the procedure described above for the preparation of 3,3:17,17-bis(ethylendioxy)-5-androstene (Prepn. 5). The combined organic extracts were washed with H₂O, dried over Na₂SO₄ and evaporated to dryness to give 6,6-ethylendioxyandrostane-3β,17β-diol. ¹H-NMR (300 MHz, DMSO-d₆, ppm from TMS): δ 4.45 (d, 1H), 4.41 (d, 1H), 3.90-3.57 (m, 4H), 3.41 (m, 1H), 3.29 (m, 1H), 1.87-0.53 (m, 20H), 0.84 (s, 3H), 0.60 (s, 3H).

To a solution of 6,6-ethylendioxyandrostane-3β,17β-diol (0.216 g) in CH₂Cl₂ (8.7 mL) under N₂, NMNO (0.217 g), TPAP (10.8 mg) and 4 Å molecular sieves (0.30 g) were added. The mixture was stirred for 1 h and then SiO₂ was added. The mixture was purified by flash chromatography (SiO₂, n-hexane/EtOAc 50/50) to give the title compound II-ag (0.154 g, 72%). ¹H-NMR (300 MHz, acetone-d₆, ppm from TMS): δ 4.04-3.70 (m, 4H), 2.52-0.82 (m, 20H), 1.18 (s, 3H), 0.88 (s, 3H).

Preparation 8

6-Methyleneandrostane-3,17-dione (II-ah)

To a stirred suspension of methyltriphenylphosphonium bromide (9.50 g) in dry THF (77 mL) cooled at 0° C. under N₂, potassium tert-butoxide (2.91 g) was added. After stirring for 10 min, a solution of 3,3:17,17-bis(ethylendioxy)androstan-6-one (2.60 g) in dry THF (77 mL) was added dropwise at room temperature over 0.5 h. After 0.5 h at room temperature, the mixture was quenched by addition of 5% NaH₂PO₄ aqueous solution and extracted with Et₂O (2×60 mL). The combined organic extracts were washed with 5%

NaH$_2$PO$_4$ aqueous solution, brine, dried over Na$_2$SO$_4$ and evaporated to dryness. The residue was purified by flash chromatography (SiO$_2$, cyclohexane/EtOAc 85/15) to give 3,3:17,17-bis(ethylendioxy)-6-methyleneandrostane (2.66 g, 97%). $^1$H-NMR (300 MHz, acetone-d$_6$, ppm from TMS): δ 4.68 (m, 1H), 4.36 (m, 1H), 3.88-3.71 (m, 8H), 2.27-0.78 (m, 20H), 0.74 (s, 3H), 0.62 (s, 3H).

The title compound II-ah was prepared in 87% yield from 3,3:17,17-bis(ethylendioxy)-6-methyleneandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, acetone-d$_6$, ppm from TMS): δ 4.85 (m, 1H), 4.50 (m, 1H), 2.63-1.02 (m, 20H), 0.92 (s, 3H), 0.86 (s, 3H).

Preparation 9

6β-Hydroxymethylandrostane-3,17-dione (II-ai)

To a stirred solution of 3,3:17,17-bis(ethylendioxy)-6-methyleneandrostane (Prepn. 8, 2.89 g) in dry THF (29 mL) at 0° C. under N$_2$, 1M BH$_3$.THF complex in THF (5.21 mL) was added. After completing the addition, the mixture was stirred at 0° C. for 3 h. H$_2$O (2.3 mL) was cautiously added dropwise followed by 3N NaOH (3 mL) and 9.8 M H$_2$O$_2$ (0.91 mL). After stirring at room temperature overnight, H$_2$O (20 mL) was added. The mixture was extracted with EtOAc (2×20 mL). The combined organic extracts were washed with brine, dried over Na$_2$SO$_4$, filtered and evaporated to dryness. The residue was purified by flash chromatography (SiO$_2$, n-hexane/EtOAc 45/55) to give 3,3:17,17-bis(ethylendioxy)-6β-hydroxymethylandrostane (2.86 g, 95%). $^1$H-NMR (300 MHz, acetone-d$_6$, ppm from TMS): δ 3.94-3.75 (m, 8H), 3.52 (m, 2H), 3.36 (t, 1H), 2.05-0.65 (m, 21H), 0.84 (s, 3H), 0.81 (s, 3H).

The title compound (II-ai) was prepared in 85% yield from 3,3:17,17-bis(ethylendioxy)-6β-hydroxymethylandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, acetone-d$_6$, ppm from TMS): δ 3.71-3.47 (m, 3H), 2.82-0.79 (m, 21H), 1.08 (s, 3H), 0.89 (s, 3H).

Preparation 10

6β-Methoxymethylandrostane-3,17-dione (II-ai)

To a stirred solution of 3,3:17,17-bis(ethylendioxy)-6β-hydroxymethylandrostane (Prepn. 9, 0.80 g) in dry THF (11 mL) at 0° C., under N$_2$, NaH (60% dispersion, 96 mg) was added. After stirring the mixture at 0° C. for 1 h, CH$_3$I (144 µL) was added. After stirring overnight at room temperature, H$_2$O (10 mL) was added. The mixture extracted with EtOAc (2×20 mL). The combined organic extracts were dried over Na$_2$SO$_4$, filtered and evaporated to dryness. The residue was purified by flash chromatography (SiO$_2$, n-hexane/acetone 90/10) to give 3,3:17,17-bis(ethylendioxy)-6β-methoxymethylandrostane (0.70 g, 84%). $^1$H-NMR (300 MHz, acetone-d$_6$, ppm from TMS): δ 3.94-3.73 (m, 8H), 3.32 (m, 2H), 3.24 (s, 3H), 1.98-0.65 (m, 21H), 0.84 (s, 3H), 0.83 (s, 3H).

The title compound II-aj was prepared in 90% yield from 3,3:17,17-bis(ethylendioxy)-6β-methoxymethylandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. The residue was purified by flash chromatography (SiO$_2$, n-hexane/CH$_2$Cl$_2$/acetone 70/10/20). $^1$H-NMR (300 MHz, acetone-d$_6$, ppm from TMS): δ 3.45 (m, 2H), 3.27 (s, 3H), 2.80-0.80 (m, 21H), 1.10 (s, 3H), 0.89 (s, 3H).

Preparation 11

6α-Vinylandrostane-3,17-dione (II-ak)

To a solution of 3,3:17,17-bis(ethylendioxy)-6β-hydroxymethylandrostane (Prepn. 9, 0.63 g) in DMSO (6 mL), IBX (0.87 g) was added and stirred at room temperature for 1 h. The mixture was quenched by addition of H$_2$O (30 mL) and Et$_2$O (30 mL). After stirring for 15 min, the mixture was filtered and the cake was washed with Et$_2$O. The layers were separated and the aqueous phase was extracted with Et$_2$O (3×). The combined organic extracts were washed with brine, dried over Na$_2$SO$_4$ and evaporated to dryness. The residue was purified by flash chromatography (SiO$_2$, n-hexane/EtOAc 75/35) to give 3,3:17,17-bis(ethylendioxy)-6β-formylandrostane (0.52 g, 83%). $^1$H-NMR (300 MHz, acetone-d$_6$, ppm from TMS): δ 9.92 (d, 1H), 3.96-3.75 (m, 8H), 2.32-0.68 (m, 21H), 0.81 (s, 3H), 0.77 (s, 3H), A mixture of 3,3:17,17-bis(ethylendioxy)-6β-formylandrostane (0.61 g), K$_2$CO$_3$ (0.90 g) in MeOH (57 mL) was stirred overnight at room temperature. After evaporation, the residue was treated with H$_2$O (20 mL) and extracted with EtOAc (3×30 mL). The combined organic extracts were washed with brine (3×20 mL), dried over Na$_2$SO$_4$ and evaporated to dryness to give 3,3:17,17-bis(ethylendioxy)-6α-formylandrostane (0.57 g, 94%). $^1$H-NMR (300 MHz, acetone-d$_6$, ppm from TMS): δ 9.41 (d, 1H), 3.95-3.72 (m, 8H), 2.24-0.73 (m, 21H), 0.90 (s, 3H), 0.84 (s, 3H), 3,3:17,17-Bis(ethylendioxy)-6α-vinylandrostane was prepared in 70% yield from 3,3:17,17-bis(ethylendioxy)-6α-formylandrostane by the procedure described above for the preparation of 3,3:17,17-bis(ethylendioxy)-6-methyleneandrostane (Prepn. 8). The crude was purified by flash chromatography (SiO$_2$, n-hexane/EtOAc 88/12). $^1$H-NMR (300 MHz, acetone-d$_6$, ppm from TMS): δ 5.47 (m, 1H), 4.91 (m, 2H), 3.94-3.73 (m, 8H), 2.00-0.67 (m, 21H), 0.88 (s, 3H), 0.83 (s, 3H), The title compound II-ak was prepared in 92% yield from 3,3:17,17-bis(ethylendioxy)-6α-vinylandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, acetone-d$_6$, ppm from TMS): δ 5.51 (m, 1H), 4.97 (m, 2H), 2.53-0.82 (m, 21H), 1.14 (s, 3H), 0.98 (s, 3H), Preparation 12

6α-(2-Hydroxyethyl)androstane-3,17-dione (II-al)

3,3:17,17-Bis(ethylendioxy)-6α-(2-hydroxyethyl)androstane was prepared in 96% yield from 3,3:17,17-bis(ethylendioxy)-6α-vinylandrostane (Prepn. 11) by the procedure described above for the preparation of 3,3:17,17-bis(ethylendioxy)-6β-hydroxymethylandrostane (Prepn. 9). The crude was purified by flash chromatography (SiO$_2$, n-hexane/acetone 80/20). $^1$H-NMR (300 MHz, DMSO-d$_6$, ppm from TMS): δ 4.25 (t, 1H), 3.86-3.70 (m, 8H), 3.35 (m, 2H), 1.91-0.42 (m, 23H), 0.75 (s, 3H), 0.74 (s, 3H).

The title compound II-al was prepared in 100% yield from 3,3:17,17-bis(ethylendioxy)-6α-(2-hydroxyethyl)androstane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, dmso-d$_6$, ppm from TMS): δ 4.32 (t, 1H), 3.39 (m, 2H), 2.46-0.54 (m, 23H), 0.98 (s, 3H), 0.79 (s, 3H).

Preparation 13

3,17-Dioxoandrostane-6α-carbaldehyde (EZ)-oxime (II-am)

To a stirred solution of 3,3:17,17-bis(ethylendioxy)-6α-formylandrostane (Prepn. 11, 0.50 g) in pyridine (10 mL), NH$_2$OH.HCl (0.16 g) was added. After stirring overnight at room temperature, the solution was evaporated. The residue was treated with H$_2$O and extracted with CH$_2$Cl$_2$ (2×). The combined organic extracts were washed with brine, dried over Na$_2$SO$_4$, filtered and evaporated to dryness to give 3,3:17,17-bis(ethylendioxy)androstane-6α-carbaldehyde-(EZ)-oxime in 87% yield. $^1$H-NMR (300 MHz, DMSO-d$_6$, ppm from TMS): δ 10.58 (s, 0.15H), 10.35 (s, 0.85H), 6.98 (d, 0.85H), 6.28 (d, 0.15H), 3.90-3.68 (m, 8H), 2.89 (m, 0.15H), 2.04 (m, 0.85H), 1.93-0.55 (m, 20H), 0.79 (s, 3H), 0.76 (s, 3H).

The title compound II-am was prepared in 80% yield from 3,3:17,17-bis(ethylendioxy)androstane-6α-carbaldehyde-(E,Z)-oxime by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. The residue was purified by flash chromatography (SiO$_2$, n-hexane/CH$_2$Cl$_2$/acetone 40/20/20) to give the title compound II-am. $^1$H-NMR (300 MHz, DMSO-d$_6$, ppm from TMS): δ 10.72 (s, 0.1H), 10.44 (s, 0.9H), 7.05 (d, 0.9H), 6.35 (d, 0.1H), 2.50-0.72 (m, 21H), 1.03 (s, 3H), 0.80 (s, 3H).

Preparation 14

6α-Hydroxymethylandrostane-3,17-dione (II-an)

To a stirred suspension of 3,3:17,17-bis(ethylendioxy)-6α-formylandrostane (Prepn. 11, 0.52 g) in dioxane/H$_2$O 9/1 (25 mL), NaBH$_4$ (0.049 g) was added and the mixture was stirred overnight at room temperature. To the solution NaCl was added and the layers were separated. The aqueous phase was extracted with EtOAc (3×). The combined organic extracts were washed with brine, dried over Na$_2$SO$_4$ and evaporated to dryness to give 3,3:17,17-bis(ethylendioxy)-6α-hydroxymethylandrostane (0.45 g, 86%) $^1$H-NMR (300 MHz, acetone-d$_6$, ppm from TMS): δ 3.94-3.75 (m, 8H), 3.57-3.25 (m, 3H), 1.98-0.60 (m, 21H), 0.86 (s, 3H), 0.83 (s, 3H).

The title compound II-an was prepared in 85% yield from 3,3:17,17-bis(ethylendioxy)-6α-hydroxymethylandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, acetone-d$_6$, ppm from TMS): δ 3.50 (m, 3H), 2.52-0.74 (m, 21H), 1.11 (s, 3H), 0.88 (s, 3H).

Preparation 15

6α-Acetoxymethylandrostane-3,17-dione (II-ao)

To a stirred solution of 6α-hydroxymethylandrostane-3,17-dione (II-an, Prepn. 14, 42 mg) in pyridine (1.5 mL) at 0° C., DMAP (1 mg) and Ac$_2$O were added. After stirring overnight at room temperature, the solution was evaporated. The residue was treated with 1N HCl and extracted with EtOAc (2×). The combined organic extracts were washed with brine, dried over Na$_2$SO$_4$, filtered and evaporated to dryness to give the title compound II-ao (91%). $^1$H-NMR (300 MHz, acetone-d$_6$, ppm from TMS): δ 3.97 (m, 2H), 2.53-0.80 (m, 21H), 1.99 (m, 3H), 1.13 (s, 3H), 0.88 (s, 3H).

Preparation 16

6α-Methoxymethylandrostane-3,17-dione (II-ap)

3,3:17,17-Bis(ethylendioxy)-6α-methoxymethylandrostane was prepared in 84% yield from 3,3:17,17-bis(ethylendioxy)-6α-hydroxymethylandrostane (Prepn. 14) by the procedure described above for the preparation of 3,3:17,17-bis(ethylendioxy)-6β-methoxymethylandrostane (Prepn. 10). The combined organic extracts were washed with H$_2$O, dried over Na$_2$SO$_4$ and evaporated to dryness. The residue was purified by flash chromatography (SiO$_2$, cyclohexane/EtO$_2$ 80/20) to give 3,3:17,17-bis(ethylendioxy)-6α-methoxymethylandrostane. $^1$H-NMR (300 MHz, DMSO-d$_6$, ppm from TMS): δ 3.92-3.70 (m, 8H), 3.25 (dd, 1H), 3.23 (s, 3H), 3.14 (dd, 1H), 1.97-0.59 (m, 21H), 0.85 (s, 3H), 0.82 (s, 3H).

The title compound II-ap was prepared in 88% yield from 3,3:17,17-bis(ethylendioxy)-6α-methoxymethylandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, acetone-d$_6$, ppm from TMS): δ 3.25 (s, 3H), 3.24 (m, 2H), 2.53-0.75 (m, 21H), 1.11 (s, 3H), 0.87 (s, 3H).

Preparation 17

6α-Carboxyandrostane-3,17-dione (II-aq)

6α-Formylandrostane-3,17-dione was prepared in 85% yield from 3,3:17,17-bis(ethylendioxy)-6α-formylandrostane (Prepn. 11) by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness to give 6α-formylandrostane-3,17-dione. $^1$H-NMR (300 MHz, acetone-d$_6$, ppm from TMS): δ 9.50 (d, 1H), 2.56-0.82 (m, 21H), 1.16 (s, 3H), 0.88 (s, 3H).

To a stirred suspension of 6α-formylandrostane-3,17-dione (1.77 g) in t-ButOH (35 mL) and 5% aqueous Na$_2$HPO$_4$ solution (21.5 mL), 1N aqueous KMnO$_4$ (35 mL) was added. After 5 minutes at room temperature, the mixture was quenched by addition of 40% aqueous NaHSO$_3$ solution. The suspension was filtered, washed with H$_2$O and the filtrate was freeze-dried. The residue was taken up with H$_2$O (50 mL) and extracted with EtOAc (4×70 mL). The combined organic extracts were dried over Na$_2$SO$_4$ and evaporated to dryness to give the title compound II-aq (1.80 g, 96%). $^1$H-NMR (300 MHz, acetone-d$_6$, ppm from TMS): δ 11.99 (bb, 1H), 2.46-0.73 (m, 21H), 1.01 (s, 3H), 0.79 (s, 3H).

Preparation 18

6α-Carbamoylandrostane-3,17-dione (II-ar)

To a stirred suspension of 6α-carboxyandrostane-3,17-dione (II-aq, Prepn. 17, 600 mg) in dry toluene (12 mL), SOCl$_2$ (623 μL) was added. After stirring 5.5 h at 85° C. the solution was cooled at 0° C. and 2M NH₃ solution in MeOH (2.97 mL) was added. After stirring overnight at room temperature, the mixture was evaporated to dryness. The residue was treated with CH₂Cl₂ and H₂O and extracted with CH₂Cl₂. The combined organic extracts were washed with 10% K₂CO₃ solution, brine, dried over Na₂SO₄ and evaporated to dryness. The residue was purified by flash chromatography (SiO₂, n-hexane/acetone 50/50) to give the title compound II-ar (90 mg, 15%). ¹H-NMR (300 MHz, DMSO-d₆, ppm from TMS): δ 7.27 (bs, 1H), 6.78 (bs, 1H), 2.50-0.72 (m, 21H), 1.00 (s, 3H), 0.80 (s, 3H).

Preparation 19

6α-Methoxycarbonylandrostane-3,17-dione (II-as)

To a stirred solution of 6α-carboxyandrostane-3,17-dione (II-aq, Prepn. 17, 34 mg) in CH₂Cl₂ (1.5 mL) at 0° C., MeOH (8 μL), DMAP (1 mg) and EDAC (39.4 mg) were added. After stirring overnight at room temperature, H₂O was added and the mixture was extracted with CH₂Cl₂ (2×). The combined organic extracts were washed with H₂O, brine, dried over Na₂SO₄, filtered and evaporated to dryness. The residue was purified by flash chromatography (SiO₂, n-hexane/EtOAc 60/40) to give the title compound II-as (25 mg, 70%). ¹H-NMR (300 MHz, DMSO-d₆, ppm from TMS): δ 3.59 (s, 3H), 2.53-0.75 (m, 21H), 1.02 (s, 3H), 0.79 (s, 3H).

Preparation 20

6(E)-Hydroxyiminoandrostane-3,17-dione (II-at)

To a stirred solution of 3,3:17,17-bis(ethylendioxy)androstan-6-one (1.10 g) in THF (22 mL) a solution of NH₂OH.HCl (0.33 g), Na₂HPO₄.12H₂O (1.71 g) in H₂O (7.2 mL) was added. After stirring overnight at room temperature, NaCl was added and the mixture was extracted with EtOAc (2×). The combined organic extracts were washed with brine, dried over Na₂SO₄, filtered and evaporated to dryness to give 3,3:17,17-bis(ethylendioxy)-6(E)-hydroxyiminoandrostane (1.08 g, 93%). ¹H-NMR (300 MHz, DMSO-d₆, ppm from TMS): δ 10.34 (s, 1H), 3.88-3.71 (m, 8H), 3.16 (dd, 1H), 2.22-0.86 (m, 19H), 0.74 (s, 3H), 0.64 (s, 3H).

The title compound II-at was prepared in 70% yield from 3,3:17,17-bis(ethylendioxy)-6(E)-hydroxyiminoandrostane by the procedure described above for the preparation of 6α-cyanoandrostane-3,17-dione (II-ac, Prepn. 3). The combined organic extracts were washed with H₂O, dried over Na₂SO₄ and evaporated to dryness. The residue was purified by flash chromatography (SiO₂, n-hexane/acetone 70/30). ¹H-NMR (300 MHz, DMSO-d₆, ppm from TMS): δ 10.61 (s, 1H), 3.29 (dd, 1H), 2.61-1.03 (m, 19H), 0.88 (s, 3H), 0.79 (s, 3H).

Preparation 21

6(E)-Methoxyiminoandrostane-3,17-dione (II-au)

To a stirred solution of 3,3:17,17-bis(ethylendioxy)androstan-6-one (1.00 g) in pyridine (20 mL) NH₂OCH₃.HCl (0.39 g) was added. After stirring overnight at room temperature, the solution was evaporated and the residue was treated with H₂O and extracted with CH₂Cl₂ (2×). The combined organic extracts were washed with brine, dried over Na₂SO₄, filtered and evaporated to dryness to give 3,3:17,17-bis(ethylendioxy)-6(E)-methoxyiminoandrostane (1.04 g, 97%). ¹H-NMR (300 MHz, acetone-d₆, ppm from TMS): δ 3.94-3.76 (m, 8H), 3.73 (s, 3H), 3.22 (dd, 1H), 2.29-0.95 (m, 19H), 0.82 (s, 3H), 0.75 (s, 3H).

The title compound II-au was prepared in 70% yield from 3,3:17,17-bis(ethylendioxy)-6(E)-methoxyiminoandrostane by the procedure described above for the preparation of 6α-cyanoandrostane-3,17-dione (II-ac, Prepn. 3). The combined organic extracts were washed with H₂O, dried over Na₂SO₄ and evaporated to dryness. ¹H-NMR (300 MHz, acetone-d₆, ppm from TMS): δ 3.78 (s, 3H), 3.37 (dd, 1H), 2.68-1.14 (m, 19H), 1.01 (s, 3H), 0.98 (s, 3H).

Preparation 22

6(E)-Ethoxyiminoandrostane-3,17-dione (II-av)

3,3:17,17-Bis(ethylendioxy)-6(E)-ethoxyiminoandrostane was prepared in 90% yield starting from 3,3:17,17-bis(ethylendioxy)androstan-6-one and NH₂OCH₂CH₃.HCl by the procedure described above in Prepn. 21. ¹H-NMR (300 MHz, acetone-d₆, ppm from TMS): δ 3.99 (2H, q), 3.92-3.75 (8H, m), 3.25 (1H, dd), 2.25 (1H, m), 1.99-0.94 (18H, m), 1.17 (3H, t), 0.82 (3H, s), 0.75 (3H, s).

The title compound II-av was prepared in 100% yield from 3,3:17,17-bis(ethylendioxy)-6(E)-ethoxyiminoandrostane by the procedure described above for the preparation of 6α-cyanoandrostane-3,17-dione (II-ac, Prepn. 3). The combined organic extracts were washed with H₂O, dried over Na₂SO₄ and evaporated to dryness. ¹H-NMR (300 MHz, acetone-d₆, ppm from TMS): δ 4.03 (2H, q), 3.40 (1H, dd), 2.70-1.12 (19H, m), 1.20 (3H, t), 1.01 (3H, s), 0.87 (3H, s).

Preparation 23

6(E)-Allyloxyiminoandrostane-3,17-dione (II-aw)

Using the same reaction conditions described in Prepn. 21 and starting from 3,3:17,17-bis(ethylendioxy)androstan-6-one (250 mg) and O-allylhydroxylamine hydrochloride (140 mg), 3,3:17,17-bis(ethylendioxy)-6-(E)-allyloxyiminoandrostane was obtained (260 mg, 91%). ¹H-NMR (300 MHz, acetone-d₆, ppm from TMS): δ 5.97 (m, 1H), 5.22 (m, 1H), 5.11 (m, 1H), 4.47 (m, 2H,), 3.94-3.76 (m, 8H), 3.28 (dd, 1H), 2.26 (m, 1H), 2.03-0.95 (m, 18H), 0.82 (s, 3H), 0.75 (s, 3H).

The title compound II-aw was prepared in 70% yield from 3,3:17,17-bis(ethylendioxy)-6(E)-allyloxyiminoandrostane by the procedure described above for the preparation of 6α-cyanoandrostane-3,17-dione (II-ac, Prepn. 3). The combined organic extracts were washed with H₂O, dried over Na₂SO₄ and evaporated to dryness. ¹H-NMR (300 MHz, acetone-d₆, ppm from TMS): δ 5.99 (1H, m), 5.25 (1H, m), 5.14 (1H, m), 4.52 (2H, m), 4.42 (1H, dd), 2.68-1.15 (19H, m), 1.01 (3H, s), 0.88 (3H, s).

Preparation 24

6β-Methylandrostane-3,17-dione (II-ax)

To a stirred solution of 3,3:17,17-bis(ethylendioxy)-6β-hydroxymethylandrostane (Prepn. 9, 90 mg) and DMAP (5 mg) in CH₂Cl₂ (3 mL) under N₂, TCDI (78 mg) was added. After stirring 2 h at 40° C. H₂O was added and the mixture was extracted with CH₂Cl₂ (2×). The combined organic extracts were washed with brine, dried over Na₂SO₄, filtered and evaporated to dryness. The mixture was purified by flash chromatography (SiO₂, n-hexane/CH₂Cl₂/acetone 70/15/15) to give O-[3,3:17,17-bis(ethylendioxy)androstane-6β-ylmethyl]imidazole-1-carbothioate (95 mg, 83%). $^1$H-NMR (300 MHz, DMSO-d$_6$, ppm from TMS): δ 8.43 (dd, 1H), 7.76 (dd, 1H), 7.08 (dd, 1H), 4.82 (dd, 1H), 4.68 (dd, 1H), 3.90-3.70 (m, 8H), 2.17-0.89 (m, 21H), 0.84 (s, 3H), 0.79 (s, 3H).

To a stirred solution of Ph$_3$SnH (193 mg) in dry toluene (2 mL) under Ar, AIBN (5 mg) was added. After stirring 20 min at 90° C., a solution of O-[3,3:17,17-bis(ethylendioxy)androstane-6β-ylmethyl]imidazole-1-carbothioate (95 mg) in dry toluene (2 mL) was added dropwise. After stirring for 2 h at 110° C., the mixture was evaporated to dryness and the residue purified by flash chromatography (SiO$_2$, n-hexane/EtOAc 98/2) to give 3,3:17,17-bis(ethylendioxy)-6β-methylandrostane (30 mg, 42%). $^1$H-NMR (300 MHz, acetone-d$_6$, ppm from TMS): δ 3.92-3.78 (m, 8H), 2.10-0.62 (m, 21H), 0.92 (s, 3H), 0.88 (d, 3H), 0.85 (s, 3H).

The title compound II-ax was prepared in 94% yield from 3,3:17,17-bis(ethylendioxy)-6β-methylandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, acetone-d$_6$, ppm from TMS): δ 2.77-0.75 (m, 21H), 1.18 (s, 3H), 0.98 (d, 3H), 0.90 (s, 3H).

Preparation 25

6α-Methylandrostane-3,17-dione (II-ay)

To a stirred solution of DABCO (0.55 g) and 3,3:17,17-bis(ethylendioxy)-6α-hydroxymethylandrostane (Prepn. 14, 1.00 g) in dry CH$_2$Cl$_2$ (20 mL), under N$_2$ at 0° C., p-TSCl (0.703 g) was added. After stirring 2 h at room temperature, the mixture was filtered and the cake was washed with CH$_2$Cl$_2$. The organic layer was washed with brine, dried over Na$_2$SO$_4$, filtered and evaporated to dryness. The crude product was triturated with n-hexane/EtOAc (60/40) and filtered. After drying under vacuum at 40° C., 3,3:17,17-bis(ethylendioxy)-6α-[(4-methyl)benzenesulfonyloxymethyl]androstane (1.11 g, 80%) was obtained. $^1$H-NMR (300 MHz, acetone-d$_6$, ppm from TMS): δ 7.82 (m, 2H), 7.49 (m, 2H), 4.00-3.74 (m, 10H), 2.46 (s, 3H), 1.97-0.57 (m, 21H), 0.82 (s, 3H), 0.80 (s, 3H).

To a stirred solution of NaBH$_4$ (0.15 g) in dry DMSO (90 mL), under N$_2$, 3,3:17,17-bis(ethylendioxy)-6α-[(4-methyl)benzenesulfonyloxy-methyl]-androstane (1.11 g) was added in portions over 15 min. After stirring for 3 h at 80° C., the mixture was quenched at room temperature by careful addition of H$_2$O (200 mL). The suspension was extracted with Et$_2$O. The combined organic extracts were washed with brine, dried over Na$_2$SO$_4$ and evaporated to dryness. The mixture was purified by flash chromatography (SiO$_2$, n-hexane/EtOAc 90/10) to give 3,3:17,17-bis(ethylendioxy)-6α-methylandrostane (0.70 g, 90%). $^1$H-NMR (300 MHz, acetone-d$_6$, ppm from TMS): δ 3.94-3.72 (m, 8H), 1.98-0.53 (m, 21H), 0.85 (s, 3H), 0.83 (s, 3H), 0.79 (d, 3H).

The title compound II-ay was prepared in 94% yield from 3,3:17,17-bis(ethylendioxy)-6α-methylandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, acetone-d$_6$, ppm from TMS): δ 2.77-0.75 (m, 21H), 1.18 (s, 3H), 0.98 (d, 3H), 0.90 (s, 3H).

Preparation 26

6-(S)-Spiro-(2'-oxirane)androstane-3,17-one (II-az) and 6-(R)-spiro-(2'-oxirane)androstane-3,17-one (II-ba)

To a solution of 6-methyleneandrostane-3,17-dione (II-ah, Prepn. 8, 0.76 g) in CH$_2$Cl$_2$ (44 mL) stirred at 0° C., mCPBA (0.933 mg) was added in three portions over 0.5 h. After stirring at room temperature for 3 h the mixture was washed with 5% aqueous NaHCO$_3$ solution, 40% aqueous NaHSO$_3$ solution, 5% aqueous Na$_2$HPO$_4$ solution and brine. The organic layer was dried over Na$_2$SO$_4$ and evaporated to dryness. The residue was purified by flash chromatography (SiO$_2$, toluene/acetone 95/5) to give the title compounds II-az (30%) and II-ba (15%). $^1$H-NMR (300 MHz, acetone-d$_6$, ppm from TMS): II-az: δ 2.79 (dd, 1H), 2.59 (d, 1H), 2.53-0.94 (m, 20H), 1.16 (s, 3H), 0.88 (s, 3H); II-ba: δ 2.70-0.96 (m, 22H), 1.17 (s, 3H), 0.90 (s, 3H).

Preparation 27

6α-Ethynylandrostane-3,17-dione (II-bb)

To a stirred solution of (chloromethyl)triphenylphosphonium chloride (1.20 g) in dry THF (20 mL) at −78° C. under argon, 1.6 M n-butyllithium in n-hexane (1.5 mL) was added dropwise. After 30 min at room temperature, a solution of 3,3:17,17-bis(ethylendioxy)-6α-formylandrostane (Prepn. 11, 0.28 g) in dry THF (7 mL) was added dropwise. The mixture was heated at 70° C. for 1 h and then cooled to room temperature. The mixture was quenched by addition of brine and extracted with EtOAc (3×). The combined organic extracts were dried over Na$_2$SO$_4$, and evaporated to dryness. The crude product was dissolved in dry THF (20 mL) and stirred at −78° C. To the resulting solution 1.6 M n-butyllithium in n-hexane (2.24 mL) under argon was added dropwise. After 1 h at room temperature the mixture was quenched by addition of brine and extracted with Et$_2$O (3×). The combined organic extracts were dried over Na$_2$SO$_4$, and evaporated to dryness to give 3,3:17,17-bis(ethylendioxy)-6α-ethynylandrostane (160 mg, 46%), sufficiently pure to be used in the next step without further purification. $^1$H-NMR (300 MHz, acetone-d$_6$, ppm from TMS): δ 3.85 (m, 8H), 2.46 (d, 1H), 2.30-0.67 (m, 21H), 0.82 (s, 3H), 0.86 (s, 3H).

The title compound II-bb was prepared in 46% yield from 3,3:17,17-bis(ethylendioxy)-6α-ethynylandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. The residue was purified by flash chromatography (SiO$_2$, cyclohexane/CH$_2$Cl$_2$/acetone 80/10/10). $^1$H-NMR (300 MHz, acetone-d$_6$, ppm from TMS): δ 2.69-0.78 (m, 22H), 1.12 (s, 3H), 0.87 (s, 3H).

Preparation 28

6α-Formamidoandrostane-3,17-dione (II-bc)

To a stirred solution of 3,3:17,17-bis(ethylendioxy)-6(E)-hydroxyiminoandrostane (Prepn. 20, 0.88 g) in n-PrOH (26 mL), Na (2.0 g) was added in small pieces over 20 min. The mixture was stirred at reflux for 2 h. After cooling to room temperature, the mixture was quenched by careful addition of MeOH. To the solution H$_2$O was added carefully and the organic solvent was evaporated. The mixture was extracted with CH$_2$Cl$_2$ (3×). The combined organic extracts were washed with brine, dried over Na$_2$SO$_4$, filtered and evaporated to dryness. The mixture was purified by flash chromatography (SiO$_2$, CHCl$_3$/MeOH/26% NH$_4$OH 90/10/1) to give 3,3:17,17-bis(ethylendioxy)-6α-aminoandrostane (0.45 g, 53%). $^1$H-NMR (300 MHz, DMSO-d$_6$, ppm from TMS): δ 3.87-3.70 (m, 8H), 2.29 (m, 1H), 1.98-0.50 (m, 22H), 0.75 (s, 3H), 0.74 (s, 3H)

A 2 M solution of formic acid in CHCl$_3$ (0.67 mL) was added dropwise to a solution of DCC (106 mg) in CHCl$_3$ at 0° C. The mixture was stir-red for further 5 min and then added to an ice-cooled solution of 3,3:17,17-bis(ethylendioxy)-6α-aminoandrostane (100 mg) in pyridine (0.70 mL) over 30 min. The mixture was then stirred in an ice bath for 4 h. Evaporation of the solvent was followed by addition of Et$_2$O. The precipitate was removed by filtration and washed with Et$_2$O. The combined organic extracts were evaporated to dryness to give 3,3:17,17-bis(ethylendioxy)-6α-formamidoandrostane (100 mg, 95%). $^1$H-NMR (300 MHz, DMSO-d$_6$, ppm from TMS): δ 7.98-7.43 (m, 2H), 3.89-3.00 (m, 9H), 1.93-0.50 (m, 20H), 0.81 (s, 3H), 0.77 (s, 3H).

The title compound II-bc was prepared in 96% yield from 3,3:17,17-bis(ethylendioxy)-6α-formamidoandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, DMSO-d$_6$, ppm from TMS): δ 8.02-7.56 (m, 2H), 3.74 (m, 1H), 2.54-0.70 (m, 20H), 1.04 (s, 3H), 0.80 (s, 3H).

Preparation 29

6α-Acetamidoandrostane-3,17-dione (II-bd)

To a stirred solution of 3,3:17,17-bis(ethylendioxy)-6α-aminoandrostane (Prepn. 28, 100 mg) in dry pyridine (0.5 mL) at 0° C., under N$_2$, (CH$_3$CO)$_2$O (48 μL) was added dropwise. The mixture was stirred at room temperature for 1.5 h and the solution was evaporated to dryness. The residue was taken up with H$_2$O and extracted with EtOAc (2×). The combined organic extracts were washed with brine, dried over Na$_2$SO$_4$, filtered and evaporated to dryness to give 3,3:17,17-bis(ethylendioxy)-6α-acetamidoandrostane (103 mg, 94%). $^1$H-NMR (300 MHz, DMSO-d$_6$, ppm from TMS): δ 7.55 (d, 1H), 3.88-3.70 (m, 8H), 3.53 (m, 1H), 1.92-0.81 (m, 20H), 1.75 (s, 3H), 0.80 (s, 3H), 0.75 (s, 3H).

The title compound II-bd was prepared in 96% yield from 3,3:17,17-bis(ethylendioxy)-6α-acetamidoandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, DMSO-d$_6$, ppm from TMS): δ 7.61 (d, 1H), 3.67 (m, 1H), 2.51-0.68 (m, 20H), 1.78 (s, 3H), 1.04 (s, 3H), 0.80 (s, 3H).

Preparation 30

6(E)-Ethylidenandrostane-3,17-dione (II-be)

3,3:17,17-Bis(ethylendioxy)-6(E)-ethylidenandrostane was prepared in 96% yield from 3,3:17,17-bis(ethylendioxy)androstane-6-one and (ethyl)triphenylphosphonium bromide by the procedure described above for the preparation of 3,3:17,17-bis(ethylendioxy)-6-methyleneandrostane (Prepn. 8). The mixture was purified by flash chromatography (SiO$_2$, cyclohexane/EtOAc 85/15). $^1$H-NMR (300 MHz, acetone-d$_6$, ppm from TMS): δ 4.91 (m, 1H), 3.93-3.78 (m, 8H), 2.69 (m, 1H), 2.10-0.85 (m, 22H), 0.81 (s, 3H), 0.66 (s, 3H).

The title compound II-be was prepared in 96% yield from 3,3:17,17-bis(ethylendioxy)-6(E)-ethylidenandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, acetone-d$_6$, ppm from TMS): δ 4.99 (m, 1H), 2.86 (dd, 1H), 2.61-1.01 (m, 19H), 1.66 (m, 3H), 0.93 (s, 3H), 0.86 (s, 3H).

Preparation 31

6-Difluoromethyleneandrostane-3,17-dione (II-bf)

To a stirred solution of diethyl difluoromethylenephosphonate (0.67 μL) in DME (5.75 mL) in n-pentane (1.1 mL) at −78° C., 1.5 M pentane solution of tert-butyllithium (2.75 mL) was added dropwise under argon. After 15 min at the same temperature a solution of 3,3:17,17-bis(ethylendioxy)androstane-6-one (500 mg) in DME (4.5 mL) and n-pentane (1.25 mL) was added dropwise. The mixture was stirred at −78° C. for further 30 min and warmed up to room temperature. n-Pentane was distilled off and after heating at 80° C. for 4 h the mixture was quenched with H$_2$O and extracted with CH$_2$Cl$_2$ (3×). The combined organic extracts were dried over Na$_2$SO$_4$, and evaporated to dryness. The residue was purified by flash chromatography (SiO$_2$, cyclohexane/Et$_2$O 70/30) to give 3,3:17,17-bis(ethylendioxy)-6-difluoromethyleneandrostane (470 mg, 85%). $^1$H-NMR (300 MHz, acetone-d$_6$, ppm from TMS): δ 3.85 (m, 8H), 2.52-0.80 (m, 20H), 0.83 (s, 3H), 0.84 (s, 3H).

The title compound II-bf was prepared in 99% yield from 3,3:17,17-bis(ethylendioxy)-6-difluoromethyleneandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, acetone-d$_6$, ppm from TMS): δ 2.85-0.95 (m, 20H), 1.12 (s, 3H), 0.88 (s, 3H).

Preparation 32

3,17-Dioxoandrostane-6-(E)-ylideneacetonitrile (II-bg)

To a stirred suspension of NaH (60% dispersion in mineral oil, 204 mg) in THF (6 mL) at room temperature, diethyl cyanomethylphosphonate (895 μL) was added. After stirring for 0.5 h 3,3:17,17-bis(ethylendioxy)androstan-6-one (200 mg) was added to the yellow mixture. After stirring at reflux for 2 h the mixture was quenched by addition of brine and extracted with Et$_2$O (3×). The combined organic extracts were dried over Na$_2$SO$_4$, and evaporated to dryness. The residue was purified by flash chromatography (SiO$_2$, n-hexane/CH$_2$Cl$_2$/acetone 70/20/20) to give 3,3:17,17-bis(ethylendioxy)androstane-6-(E)-ylideneacetonitrile (150 mg, 71%). $^1$H-NMR (300 MHz, acetone-d$_6$, ppm from TMS): δ 5.03 (t, 1H), 3.95-3.78 (m, 8H), 2.90 (dd, 1H), 2.33 (m, 1H), 2.10-0.99 (m, 18H), 0.84 (s, 3H), 0.73 (s, 3H).

The title compound II-bg was prepared in 87% yield from 3,3:17,17-bis(ethylendioxy)androstane-6-(E)-ylideneacetonitrile by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, acetone-d$_6$, ppm from TMS): δ 5.15 (s, 1H), 3.04 (dd, 1H), 2.71-1.17 (m, 19H), 1.01 (s, 3H), 0.90 (s, 3H).

Preparation 33

6-[2-Hydroxy-(E)-ethylidene]androstane-3,17-dione (II-bh)

To a stirred solution of 3,3:17,17-bis(ethylendioxy)androstane-6-(E)-ylideneacetonitrile (Prepn. 35, 214 mg) in dry $CH_2Cl_2$ (10 mL) at −78° C. under $N_2$, 1M DIBAH in $CH_2Cl_2$ (1.56 mL) was added dropwise. The mixture was stirred at −78° C. for 1 h and then quenched by careful addition of a 2M solution of isopropyl alcohol in toluene (0.80 mL). After 1 h, $H_2O$ (70 µL) and THF (2.8 mL) were added and after an additional hour $SiO_2$ (0.76 g) and $Na_2SO_4$ (1.52 g) were added. The mixture was stirred for 1 h, filtered through a Celite pad and the filter cake washed with EtOAc. The filtrate was dried over $Na_2SO_4$, evaporated to give 3,3:17,17-bis(ethylendioxy)androstane-6-(E)-ylideneacetaldehyde (0.18 g, 55%). $^1$H-NMR (300 MHz, acetone-$d_6$, ppm from TMS): δ 9.98 (dd, 1H), 5.46 (d, 1H), 3.91-3.70 (m, 8H), 3.35 (dd, 1H), 2.31-0.91 (m, 19H), 0.75 (s, 3H), 0.64 (s, 3H).

To a stirred suspension of 3,3:17,17-bis(ethylendioxy)androstane-6-(E)-ylideneacetaldehyde (110 mg) in MeOH (2.5 mL) at 0° C., $NaBH_4$ (5 mg) was added and the mixture was stirred for 1 h. Acetone (100 µL) was added and the mixture evaporated. The residue was treated with $H_2O$ and extracted with EtOAc. The combined organic extracts were washed with brine, dried over $Na_2SO_4$ and evaporated to dryness to give 3,3:17,17-bis(ethylendioxy)-6-(E)-(2-hydroxyethylidene)androstane (100 mg, 90%). $^1$H-NMR (300 MHz, acetone-$d_6$, ppm from TMS): δ 5.07 (m, 1H), 4.11 (m, 2H), 3.95-3.75 (m, 8H), 3.41 (d, 1H), 2.67 (m, 1H), 2.14-0.84 (m, 18H), 0.80 (s, 3H), 0.69 (s, 3H).

The title compound II-bh was prepared in 60% yield from 3,3:17,17-bis(ethylendioxy)-6-(E)-(2-hydroxyethylidene)androstane by the procedure described above for the preparation of 6α-cyanoandrostane-3,17-dione (II-ac, Prepn. 3). The combined organic extracts were washed with $H_2O$, dried over $Na_2SO_4$ and evaporated to dryness. The residue was purified by flash chromatography ($SiO_2$, n-hexane/acetone 70/30). $^1$H-NMR (300 MHz, acetone-$d_6$, ppm from TMS): δ 5.14 (m, 1H), 4.17 (m, 2H), 3.53 (t, 1H), 2.84 (dd, 1H), 2.65-1.01 (m, 20H), 0.97 (s, 3H), 0.85 (s, 3H).

Preparation 34

Methyl (3,17-dioxoandrostane-6(E)-ylidene)acetate (II-bi)

To a stirred solution of trimethylphosphonoacetate (5.17 mL) in DME (5.75 mL) at 0° C. under $N_2$ a 1.5 M solution of tert-butyllithium in n-pentane (18.5 mL) was added dropwise. After stirring 15 min at the same temperature a solution of 3,3:17,17-bis(ethylendioxy)androstane-6-one (1.00 g) in DME (15 mL) was added dropwise. The mixture was heated at 110° C. for 8 h and, after cooling, quenched by addition of $H_2O$ and extracted with EtOAc (3×). The combined organic extracts were dried over $Na_2SO_4$ and evaporated to dryness. The residue was purified by flash chromatography ($SiO_2$, n-hexane/$CH_2Cl_2$/acetone 80/10/10) to give [3,3:17,17-bis(ethylendioxy)androstane-6(E)-ylidene]acetic acid methyl ester (400 mg, 35%). $^1$H-NMR (300 MHz, acetone-$d_6$, ppm from TMS): δ 5.34 (s, 1H), 4.05-3.75 (m, 9H), 3.62 (s, 3H), 2.28 (m, 1H), 2.00-0.97 (m, 18H), 0.82 (s, 3H), 0.72 (s, 3H).

The title compound II-bi was prepared in 70% yield from [3,3:17,17-bis(ethylendioxy)androstane-6(E)-ylidene]acetic acid methyl ester by the procedure described above for the preparation of 6α-cyanoandrostane-3,17-dione (II-ac, Prepn. 3). The combined organic extracts were washed with $H_2O$, dried over $Na_2SO_4$ and evaporated to dryness. The residue was purified by flash chromatography (n-hexane/$CH_2Cl_2$/acetone 75/15/15). $^1$H-NMR (300 MHz, acetone-$d_6$, ppm from TMS): δ 5.42 (bs, 1H), 4.16 (dd, 1H), 3.66 (s, 3H), 2.73-1.16 (m, 19H), 0.99 (s, 3H), 0.87 (s, 3H).

Preparation 35

6-(Spirocyclopropane)androstane-3,17-dione (II-bj)

To a stirred solution of 3,3:17,17-bis(ethylendioxy)-6-methyleneandrostane (Prepn. 8, 200 mg) in dry toluene (10 mL) under $N_2$, 1 M $Et_2Zn$ in n-hexane (2.5 mL) was added. After heating at 60° C., $CH_2I_2$ (0.42 mL) was added in portions over 15 min. After 26 h the mixture was cooled and quenched by careful addition of 1N HCl. The suspension was extracted with $Et_2O$. The combined organic extracts were washed with 5% aqueous $NaHCO_3$ solution, brine, dried over $Na_2SO_4$ and evaporated to dryness. The crude product was dissolved in acetone (20 mL) and pTSA.$H_2O$ (39 mg) was added and the solution stirred at room temperature for 1 h. The solution was neutralized by addition of 5% aqueous $NaHCO_3$ and acetone was evaporated. The aqueous suspension was extracted with EtOAc. The combined organic extracts were washed with $H_2O$, dried over $Na_2SO_4$ and evaporated to dryness. The residue was purified by flash chromatography ($SiO_2$, n-hexane/$CH_2Cl_2$/EtOAc 90/5/5) to give the title compound II-bj (78 mg, 48%). $^1$H-NMR (300 MHz, acetone-$d_6$, ppm from TMS: δ 2.51-0.83 (m, 20H), 1.17 (s, 3H), 0.88 (s, 3H), 0.60 (m, 1H), 0.41 (m, 1H), 0.34 (m, 1H), −0.08 (m, 1H).

Preparation 36

6α-Acetamidomethylandrostane-6,17-dione (II-bk)

3,3:17,17-Bis(ethylendioxy)androstane-6α-carbaldehyde-(E,Z)-oxime (Prepn. 13, 1.94 g) was dissolved in dry THF (60 mL), and, at 0° C., $LiAlH_4$ (1.23 g) was rapidly added. After stirring at reflux for 2 hrs, the slurry was cooled to 0° C. and water (1.25 mL), NaOH 30% (1.25 mL) and water (3.75 mL) were subsequently added. The mixture was extracted with THF. The organic layers were washed with brine, dried over $Na_2SO_4$ to give, after evaporation to dryness, 3,3:17,17-bis(ethylendioxy)-6α-aminomethyl-androstane (1.87 g, 100%). $^1$H-NMR (300 MHz, DMSO, ppm from TMS): δ 3.90-3.68 (8H, m), 2.67 (1H, dd), 2.54 (1H, dd), 1.92-0.49 (23H, m), 0.76 (3H, s), 0.55 (3H, s).

3,3:17,17-Bis(ethylendioxy)-6α-aminomethylandrostane (250 mg) was dissolved in dry pyridine (1.25 mL) and acetic anhydride (0.12 mL) was added at 0° C. After stirring at room temperature for 2 hrs, the solvent was evaporated and the residue was diluted with EtOAc. The organic layer was washed with water, dried over $Na_2SO_4$ and evaporated to dryness to give 3,3:17,17-bis(ethylendioxy)-6α-acetamidomethylandrostane (215 mg, 78%) as an off-white solid, used as such in the next step. $^1$H-NMR (300 MHz, DMSO, ppm from TMS): δ 7.59 (1H, t), 3.90-3.67 (8H, m), 3.03-2.79 (2H, m), 1.92-0.48 (21H, m), 1.77 (3H, s), 0.75 (6H, s).

The title compound II-bk was prepared in 100% yield from 3,3:17,17-bis(ethylendioxy)-6α-acetamidomethylandrostane (210 mg) by the procedure described above for the preparation of 6α-cyanoandrostane-3,17-dione (II-ac, Prepn. 3). $^1$H-NMR (300 MHz, DMSO, ppm from TMS): δ 7.67 (1H, t), 3.10 (1H, m), 2.78 (1H, dd), 2.60-1.00 (21H, m), 1.78 (3H, s), 0.97 (3H, s) 0.79 (3H, s)

Preparation 37

6α-Formamidomethylandrostane-3,17-dione (II-bl)

To a solution of DCC (203 mg) in CHCl$_3$ (0.7 mL), 2 M HCOOH in CHCl$_3$ (1.3 mL) was added at 0° C. After 5 minutes at this temperature 3,3:17,17-bis(ethylendioxy)-6α-aminomethylandrostane (Prepn. 36, 200 mg) in pyridine (1.5 mL) was added dropwise. After 1 h the solvent was evaporated, the precipitate filtered off and the filtrate evaporated to dryness to give 3,3:17,17-bis(ethylendioxy)-6α-formamidomethylandrostane (194 mg, 92%). $^1$H-NMR (300 MHz, DMSO, ppm from TMS): δ 7.97 (1H, d), 7.87 (1H, m), 3.78 (8H, m), 2.97 (2H, m), 1.94-0.51 (21H, m), 0.76 (3H, s), 0.75 (3H, s).

The title compound II-bl was prepared in 92% yield from 3,3:17,17-bis(ethylendioxy)-6α-formamidomethylandrostane by the procedure described above for the preparation of 6α-cyanoandrostane-3,17-dione (II-ac, Prepn. 3). $^1$H-NMR (300 MHz, DMSO, ppm from TMS): δ 7.99 (0.9H, s), 7.94 (0.9H, m), 7.88 (0.1H, d), 7.67 (0.1H, m), 3.15 (1H, m), 2.87 (1H, m), 2.40-1.00 (21H, m), 0.98 (3H, s), 0.79 (3H, s).

Preparation 38

5α-Hydroxy-6-(E)-hydroxyiminoandrostan-3,17-dione (II-bm)

To a stirred solution of 3β-hydroxyandrost-5-en-17-one (0.81 g) in CH$_2$Cl$_2$ (7.4 mL) cooled at 0° C., a solution of mCPBA (0.77 mg) in CH$_2$Cl$_2$ (14 mL) was added dropwise. After 0.5 h at 0° C. and 0.5 h at room temperature, a 10% Na$_2$SO$_3$ aqueous solution was added. The mixture was neutralized by addition of 5% aqueous NaHCO$_3$ solution and extracted with CH$_2$Cl$_2$ (3×100 mL). The combined organic extracts were washed with H$_2$O, dried over Na$_2$SO$_4$, and evaporated to dryness to give 5α,6α-epoxyandrostan-17-one and 5β,6β-epoxyandrostan-17-one as a white foam (1/1 mixture; 1.24 g, 97%). $^1$H-NMR (300 MHz, acetone-d$_6$, ppm from TMS): 3β-hydroxy-5α,6α-epoxyandrostan-17-one δ 3.26 (d, 1H), 2.96 (d, 1H), 2.70-1.12 (m, 18H), 1.36 (s, 3H), 0.83 (s, 3H); 3β-hydroxy-5β,6β-epoxyandrostan-17-one: δ 2.98 (d, 1H), 2.93 (d, 1H), 2.71-1.13 (m, 18H), 1.06 (s, 3H), 0.84 (s, 3H).

To a solution of a 1/1 mixture of 3β-hydroxy-5α,6α-epoxyandrostan-17-one and 3β-hydroxy-5β,6β-epoxyandrostane-17-one (2.10 g, 6.90 mmol) in acetone (38 mL), Jones reagent (8.35 mL) was added dropwise, maintaining the temperature below 40° C. 5 min after completion of the addition, i-PrOH (10 mL) was added and, after further 10 min, the suspension was filtered and the filtrate evaporated to dryness. The residue was treated with H$_2$O (300 mL) and extracted with EtOAc (3×100 mL). The combined organic extracts were washed with H$_2$O (100 mL), 5% aqueous NaHCO$_3$ solution (100 mL), H$_2$O (100 mL), dried over Na$_2$SO$_4$ and evaporated to dryness to give 5α-hydroxyandrostane-3,6,17-trione as a white solid (1.65 g, 75%). $^1$H-NMR (300 MHz, acetone-d$_6$, ppm from TMS): δ 5.00 (s, 1H), 2.85 (m, 2H), 2.45-1.25 (m, 17H), 1.06 (s, 3H), 0.88 (s, 3H).

A solution of 5α-hydroxyandrostane-3,6,17-trione (2.23 g) and pTSA.H$_2$O (80 mg) in 2-methyl-2-ethyl-1,3-dioxolane (29 mL) was stirred at 40° C. for 6 h. The solution was neutralized by addition of 5% aqueous Na$_2$HPO$_4$ and extracted with EtOAc. The combined organic extracts were washed with brine, dried over Na$_2$SO$_4$ and evaporated to dryness. The residue was purified by flash chromatography (SiO$_2$, cyclohexane/acetone/CH$_2$Cl$_2$ 80/10/10) to give 3,3:17,17-bis(ethylendioxy)-5α-hydroxyandrostan-6-one (1.56 g, 55%). $^1$H-NMR (300 MHz, acetone-d$_6$, ppm from TMS: δ 4.36 (s, 1H), 4.07-3.74 (m, 8H), 2.64 (m, 1H), 2.10-1.17 (m, 18H), 0.82 (s, 3H), 0.78 (s, 3H).

3,3:17,17-Bis(ethylendioxy)-5α-hydroxy-6-(E)-hydroxyiminoandrostane was prepared in 85% yield from 3,3:17,17-bis(ethylendioxy)-5α-hydroxyandrostan-6-one by the procedure described above for the preparation of 6-(E)-hydroxyiminoandrostane-3,17-dione (II-at, Prepn. 20). The crude was purified by flash chromatography (SiO$_2$, cyclohexane/acetone/CH$_2$Cl$_2$ 70/15/15). $^1$H-NMR (300 MHz, DMSO-d$_6$, ppm from TMS: δ 10.45 (s, 1H), 4.33 (s, 1H), 3.96-3.69 (m, 8H), 2.96 (dd, 1H), 2.02-1.08 (m, 18H), 0.74 (s, 3H), 0.71 (s, 3H).

The title compound II-bm was prepared in 80% yield from 3,3:17,17-bis(ethylendioxy)-5α-hydroxy-6-(E)-hydroxyiminoandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. The residue was purified by flash chromatography (SiO$_2$, n-hexane/acetone/CH$_2$Cl$_2$ 60/20/20). $^1$H-NMR (300 MHz, acetone-d$_6$, ppm from TMS: δ 10.72 (s, 1H), 5.35 (s, 1H), 3.12 (dd, 1H), 2.85-1.09 (m, 18H), 0.94 (s, 3H), 0.78 (s, 3H).

Preparation 39

5α-Hydroxy-6-(E)-methoxyiminoandrostane-3,17-dione (II-bn)

3,3:17,17-Bis(ethylendioxy)-5α-hydroxy-6-(E)-methoxyiminoandrostane was prepared in 85% yield from 3,3:17,17-bis(ethylendioxy)-5α-hydroxyandrostan-6-one (Prepn. 38) by the procedure described above for the preparation of 6-(E)-hydroxyiminoandrostane-3,17-dione (II-at, Prepn. 20). The crude was purified by flash chromatography (SiO$_2$, cyclohexane/acetone/CH$_2$Cl$_2$ 70/15/15). $^1$H-NMR (300 MHz, acetone-d$_6$, ppm from TMS: δ 4.31 (s, 1H), 4.05-3.76 (m, 8H), 3.75 (s, 3H), 3.00 (dd, 1H), 2.15-1.15 (m, 18H), 0.82 (s, 6H).

The title compound II-bn was prepared in 80% yield from 3,3:17,17-bis(ethylendioxy)-5α-hydroxy-6-(E)-methoxyiminoandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. The residue was purified by flash chromatography (SiO$_2$, n-hexane/acetone/CH$_2$Cl$_2$ 60/20/20). $^1$H-NMR (300 MHz, DMSO-d$_6$, ppm from TMS: δ 5.47 (s, 1H), 3.75 (s, 3H), 3.02 (dd, 1H), 2.79 (d, 1H), 2.45-1.13 (m, 17H), 0.95 (s, 3H), 0.77 (s, 3H).

Preparation 40

5α-Hydroxy-6-methylenandrostan-3,17-dione (II-bo)

To a stirred suspension of methyltriphenylphosphonium bromide (14.1 g) in dry THF (240 mL) cooled at 0° C. under N$_2$, potassium tert-butoxide (4.31 g) was added. After stirring for 10 min, a solution of 3,3:17,17-bis(ethylendioxy)-5α-hydroxyandrostan-6-one (Prepn. 38, 4.00 g) in dry THF (77 mL) was added dropwise at room temperature over 0.5 h. After 2 h at room temperature, the mixture was quenched by addition of 5% NaH$_2$PO$_4$ aqueous solution and extracted with EtOAc (2×100 mL). The combined organic extracts were washed with 5% NaH$_2$PO$_4$ aqueous solution, brine, dried over Na$_2$SO$_4$ and evaporated to dryness. The residue was purified by flash chromatography (SiO$_2$, n-hexane/CH$_2$Cl$_2$/acetone 80/10/10) to give 3,3:17,17-bis(ethylendioxy)-5α-hydroxy-6-methyleneandrostane (2.40 g, 60%). $^1$H-NMR (300 MHz, DMSO-d$_6$, ppm from TMS): δ 4.69 (m, 1H), 4.51 (m, 1H), 4.10 (s, 1H), 3.83 (m, 8H), 2.18-1.05 (m, 19H), 0.73 (s, 3H), 0.72 (s, 3H).

The title compound II-bo was prepared in 78% yield from 3,3:17,17-bis(ethylendioxy)-5α-hydroxy-6-methyleneandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, DMSO-d$_6$, ppm from TMS): δ 4.93 (s, 1H), 4.83 (m, 1H), 4.60 (m, 1H), 2.83 (d, 1H), 2.90-1.10 (m, 18H), 0.95 (s, 3H), 0.77 (s, 3H).

Preparation 41

Androstane-3,7,17-trione (II-bp)

A mixture of 3β-acetoxyandrost-5-ene-7,17-dione (7.97 g) and 10% Pd/C (0.80 g) in EtOH (0.5 L) was stirred under H$_2$ at atm pressure for 2 h. The mixture was filtered through Celite and the filtrate evaporated to dryness. The crude product was crystallized from Et$_2$O to give 3β-acetoxyandrostane-7,17-dione (4.75 g, 60%). $^1$H-NMR (300 MHz, acetone-d$_6$, ppm from TMS): δ 4.57 (m, 1H), 2.66-0.96 (m, 20H), 1.96 (s, 3H), 1.05 (s, 3H), 0.77 (s, 3H).

To a solution of 3β-acetoxyandrostane-7,17-dione in MeOH (156 mL), 5N NaOH (54 mL) was added. After stirring at room temperature for 10 min, the solution was evaporated and the residue extracted with CH$_2$Cl$_2$ (2×). The combined organic extracts were washed with brine, dried over Na$_2$SO$_4$, filtered and evaporated to dryness to give 3β-hydroxyandrostane-7,17-dione (1.70 g, 95%). $^1$H-NMR (300 MHz, acetone-d$_6$, ppm from TMS): δ 4.56 (d, 1H), 3.35 (m, 1H), 2.66-0.87 (m, 20H), 1.02 (s, 3H), 0.76 (s, 3H).

To a stirred solution of 3β-hydroxyandrostane-7,17-dione (1.65 g), TPAP (0.100 g), NMNO (1.40 g) under N$_2$ in CH$_2$Cl$_2$ (90 mL), molecular sieve type 4 Å powder (2.6 g) was added. After 0.5 h the mixture was filtered and the filtrate was purified by flash chromatography (SiO$_2$, CH$_2$Cl$_2$) to give the title compound II-bp (1.32 g, 81%). $^1$H-NMR (300 MHz, acetone-d$_6$, ppm from TMS): δ 2.82-1.12 (m, 20H), 1.39 (s, 3H), 0.88 (s, 3H).

Preparation 42

7(E)-Hydroxyiminoandrostane-3,17-dione (II-bq)

3,3:17,17-Bis(ethylendioxy)androstane-7-one was prepared in 82% yield from 3,3:17,17-bis(ethylendioxy)-5-androsten-7-one by the procedure described above for the preparation of 3β-acetoxyandrostane-7,17-dione (Prepn. 41) using EtOAc instead of EtOH. The crude product was purified by flash chromatography (SiO$_2$, n-hexane/EtOAc 6/4). $^1$H-NMR (300 MHz, acetone-d$_6$, ppm from TMS): δ 3.96-3.75 (m, 8H), 2.54-1.10 (m, 20H), 1.13 (s, 3H), 0.83 (s, 3H).

3,3:17,17-Bis(ethylendioxy)-7(E)-hydroxyiminoandrostane was prepared in 95% yield from 3,3:17,17-bis(ethylendioxy)androstane-7-one by the procedure described above for the preparation of 3,3:17,17-bis(ethylendioxy)-6(E)-hydroxyiminoandrostane (Prepn. 20). The combined organic extracts were washed with H$_2$O, dried over Na$_2$SO$_4$ and evaporated to dryness. The crude product was purified by flash chromatography (SiO$_2$, CH$_2$Cl$_2$/MeOH 9/1). $^1$H-NMR (300 MHz, DMSO-d$_6$, ppm from TMS): δ 10.17 (s, 1H), 3.88-3.70 (m, 8H), 2.89 (m, 1H), 2.23-0.71 (m, 19H), 0.90 (s, 3H), 0.77 (s, 3H).

The title compound II-bq was prepared in 50% yield from 3,3:17,17-bis(ethylendioxy)-7(E)-hydroxyiminoandrostane by the procedure described above for the preparation of 6α-cyanoandrostane-3,17-dione (II-ac, Prepn. 3). The crude product was purified by flash chromatography (SiO$_2$, n-hexane/EtOAc 6/4). $^1$H-NMR (300 MHz, DMSO-d$_6$, ppm from TMS): δ 10.37 (s, 1H), 2.99 (m, 1H), 2.58-0.67 (m, 19H), 1.12 (s, 3H), 0.82 (s, 3H).

Preparation 43

7(E)-Methoxyiminoandrostane-3,17-dione (II-br)

3,3:17,17-Bis(ethylendioxy)-7(E)-methoxyiminoandrostane was prepared in 90% yield from 3,3:17,17-bis(ethylendioxy)androstane-7-one by the procedure described above for the preparation of 3,3:17,17-bis(ethylendioxy)-6(E)-hydroxyiminoandrostane (Prepn. 20). The crude product was purified by flash chromatography (SiO$_2$, CH$_2$Cl$_2$/MeOH 9/1). $^1$H-NMR (300 MHz, DMSO-d$_6$, ppm from TMS): δ 3.88-3.70 (m, 8H), 3.69 (s, 3H), 2.79 (m, 1H), 2.28-0.72 (m, 19H), 0.89 (s, 3H), 0.77 (s, 3H).

The title compound II-br was prepared in 55% yield from 3,3:17,17-bis(ethylendioxy)-7(E)-methoxyiminoandrostane by the procedure described above for the preparation of 6α-cyanoandrostane-3,17-dione (II-ac, Prepn. 3). The crude product was purified by flash chromatography (SiO$_2$, n-hexane/EtOAc 6/4). $^1$H-NMR (300 MHz, DMSO-d$_6$, ppm from TMS): δ 3.72 (s, 3H), 2.89 (m, 1H), 2.63-0.93 (m, 19H), 1.12 (s, 3H), 0.82 (s, 3H).

Preparation 44

7(E)-Allyloxyiminooandrostane-3,17-dione (II-bs)

3,3:17,17-Bis(ethylendioxy)-7-(E)-allyloxyiminoandrostane was prepared in 86% yield from 3,3:17,17-bis(ethylendioxy)androstane-7-one by the procedure described above for the preparation of 3,3:17,17-bis(ethylendioxy)-6-(E)-hydroxyiminoandrostane (Prepn. 20). The crude product was purified by flash chromatography (SiO$_2$, n-hexane/EtOAc 6/4). $^1$H-NMR (300 MHz, acetone-d$_6$, ppm from TMS): δ 5.98 (m, 1H), 5.23 (m, 1H), 5.12 (m, 1H), 4.48 (m, 2H), 3.84 (m, 8H), 2.98 (m, 1H), 2.39-0.89 (m, 19H), 1.00 (s, 3H), 0.84 (s, 3H).

The title compound II-bs was prepared in 76% yield from 3,3:17,17-bis(ethylendioxy)-7(E)-allyloxyiminoandrostane by the procedure described above for the preparation of 6α-cyanoandrostane-3,17-dione (II-ac, Prepn. 3). The crude product was purified by flash chromatography (SiO$_2$, n-hexane/EtOAc 8/2). $^1$H-NMR (300 MHz, acetone-d$_6$, ppm from TMS): δ 5.99 (m, 1H), 5.25 (m, 1H), 5.14 (m, 1H), 4.51 (m, 2H), 3.10 (m, 1H), 2.75-1.04 (m, 19H), 1.26 (s, 3H), 0.90 (s, 3H).

Preparation 45

7α-Hydroxyandrostane-3,17-dione (II-bt)

To a stirred solution of 3,3:17,17-bis(ethylendioxy)androstane-7-one (Prepn. 42, 762 mg) in dry THF (21 mL) at −78° C. under N$_2$, 1M lithium selectride in THF (2.34 mL) was added. After completing the addition, the mixture was stirred at −78° C. for 0.5 h. After warming to −50° C. H$_2$O (7.8 mL)

was cautiously added dropwise followed by 6N NaOH (18.7 mL) and 9.8 M H₂O₂ (3.0 mL). After stirring at room temperature for 1 h, brine (20 mL) was added. The mixture was extracted with CH₂Cl₂ (2×20 mL). The combined organic extracts were washed with brine, dried over Na₂SO₄, filtered and evaporated to dryness. The residue was purified by flash chromatography (SiO₂, n-hexane/EtOAc 60/40) to give 3,3:17,17-bis(ethylendioxy)-7α-hydroxyandrostane (578 mg, 75%). ¹H-NMR (300 MHz, DMSO-d₆, ppm from TMS): δ 4.17 (d, 1H), 3.79 (m, 8H), 3.59 (m, 1H), 1.95-1.01 (m, 20H), 0.72 (s, 6H).

The title compound (II-bt) was prepared in 89% yield from 3,3:17,17-bis(ethylendioxy)-7α-hydroxyandrostane by the procedure described above for the preparation of 6α-cyanoandrostane-3,17-dione (II-ac, Prepn. 3). The combined organic extracts were washed with H₂O, dried over Na₂SO₄ and evaporated to dryness. ¹H-NMR (300 MHz, DMSO-d₆, ppm from TMS): δ 4.34 (d, 1H), 3.75 (m, 1H), 2.50-1.00 (m, 20H), 0.96 (s, 3H), 0.78 (s, 6H).

Preparation 46

7α-Formamidoandrostane-3,17-dione (II-bu)

3,3:17,17-Bis(ethylendioxy)-7α-aminoandrostane was prepared from 3,3:17,17-bis(ethylendioxy)-7(E)-hydroxyiminoandrostane (Prepn. 42, 1.61 g) by the procedure described above for the preparation of 3,3:17,17-bis(ethylendioxy)-6α-aminomethylandrostane (Prepn. 36). The combined organic extracts were washed with H₂O, dried over Na₂SO₄ and evaporated to dryness. The crude product was purified by flash chromatography (SiO₂, CH₂Cl₂/MeOH/NH₄OH 90/10/1) to give a mixture of 3,3:17,17-bis(ethylendioxy)-7α-aminoandrostane and 3,3:17,17-bis(ethylendioxy)-7β-aminoandrostane (1.19 g, ratio 35/65).

To a stirred solution of a mixture of 3,3:17,17-bis(ethylendioxy)-7α-aminoandrostane and 3,3:17,17-bis(ethylendioxy)-7β-aminoandrostane (1.17 g, ratio 35/65) and Et₃N (1.67 mL) under N₂ in CH₂Cl₂ (35 mL) at 0° C., 9-fluorenylmethoxycarbonyl chloride (1.39 g) was added. After stirring overnight at room temperature, water was added and the mixture extracted with CH₂Cl₂. The organic phase was washed with 5% NaHCO₃ dried over Na₂SO₄ and evaporated to dryness. The residue was purified by flash chromatography (SiO₂; n-hexane/EtOAc 70/30) to give [3,3:17,17-bis(ethylendioxy)-androstane-7α-yl]carbamic acid 9H-fluoren-9-ylmethyl ester (505 mg, 28%) ¹H-NMR (300 MHz, DMSO-d₆, ppm from TMS): δ 7.90-6.90 (m, 9H), 4.46-4.10 (m, 3H), 3.90-3.60 (m, 9H), 1.90-1.00 (m, 20H), 0.75 (s, 6H).

To a stirred solution of [3,3:17,17-bis(ethylendioxy)androstane-7α-yl]carbamic acid 9H-fluoren-9-ylmethyl ester (464 mg) in dry THF (29 mL) at 0° C., 1M tetrabutylammonium fluoride in THF (1.13 mL) was added. After stirring at room temperature for 4 h, the solution was concentrated to small volume and purified by flash chromatography (SiO₂, CH₂Cl₂/MeOH/26% NH₄OH 92/8/0.8) to give 3,3:17,17-bis(ethylendioxy)-7α-aminoandrostane (247 mg, 84%) ¹H-NMR (300 MHz, DMSO-d₆, ppm from TMS): δ 3.77 (m, 8H), 2.84 (m, 1H), 1.90-1.05 (m, 22H), 0.74 (s, 6H).

3,3:17,17-Bis(ethylendioxy)-7α-formamidoandrostane was prepared in 92% yield from 3,3:17,17-bis(ethylendioxy)-7α-aminoandrostane by the procedure described above for the preparation of 3,3:17,17-bis(ethylendioxy)-6α-formamidoandrostane (II-bc, Prepn. 28). ¹H-NMR (300 MHz, DMSO-d₆, ppm from TMS): δ 8.23 (dd, 1H), 7.97 (d, 1H), 4.00-3.70 (m, 8H), 1.85-1.05 (m, 20H), 0.76 (s, 3H), 0.74 (s, 3H).

The title compound II-bu was prepared in 97% yield from 3,3:17,17-bis(ethylendioxy)-7α-formamidoandrostane by the procedure described above for the preparation of 6α-cyanoandrostane-3,17-dione (II-ac, Prepn. 3). The crude product was purified by flash chromatography (SiO₂, n-hexane/acetone 70/30). ¹H-NMR (300 MHz, DMSO-d₆, ppm from TMS): δ 8.18 (dd, 1H), 7.97 (d, 1H), 4.13 (m, 1H), 2.90-0.95 (m, 20H), 1.00 (s, 3H), 0.79 (s, 3H).

Preparation 47

7-Methyleneandrostane-3,17-dione (II-bv)

3,3:17,17-Bis(ethylendioxy)-7-methyleneandrostane was prepared in 85% yield from 3,3:17,17-bis(ethylendioxy)androstane-7-one (Prepn. 42) by the procedure described above for the preparation of 3,3:17,17-bis(ethylendioxy)-6-methyleneandrostane (Prepn. 8). The combined organic extracts were washed with H₂O, dried over Na₂SO₄ and evaporated to dryness. ¹H-NMR (300 MHz, acetone-d₆, ppm from TMS): δ 4.67 (m, 1H), 4.60 (m, 1H), 3.86 (m, 8H), 2.12-0.75 (m, 20H), 0.97 (s, 3H), 0.86 (s, 3H).

The title compound II-bv was prepared in 87% yield from 3,3:17,17-bis(ethylendioxy)-6-methyleneandrostane by the procedure described above for the preparation of 6α-cyanoandrostane-3,17-dione (II-ac, Prepn. 3). The combined organic extracts were washed with H₂O, dried over Na₂SO₄ and evaporated to dryness. ¹H-NMR (300 MHz, acetone-d₆, ppm from TMS): δ 4.78 (m, 1H), 4.76 (m, 1H), 2.53-0.88 (m, 20H), 1.23 (s, 3H), 0.91 (s, 3H).

Preparation 48

7β-Methylandrostane-3,17-dione (II-bw)

A mixture of 3,3:17,17-bis(ethylendioxy)-7-methyleneandrostane (II-bw, Prepn. 47) (520 mg) and (1,5-cyclooctadiene)(pyridine)(tricyclohexylphosphine)iridium(1)-hexafluorophosphate (Crabtree catalyst) (75 mg) in CH₂Cl₂ (52 mL) was stirred under H₂ at atm pressure for 4 h. The mixture was evaporated to dryness and purified by flash chromatography (SiO₂, n-hexane/EtOAc 85/15) to give 3,3:17,17-bis(ethylendioxy)-7β-methylandrostane (287 mg, 55%). ¹H-NMR (300 MHz, acetone-d₆, ppm from TMS): δ 3.48 (m, 8H), 1.95-0.65 (m, 21H), 0.97 (d, 3H), 0.84 (s, 3H), 0.81 (s, 3H).

The title compound II-bw was prepared in 90% yield from 3,3:17,17-bis(ethylendioxy)-7β-methylandrostane by the procedure described above for the preparation of 6α-cyanoandrostane-3,17-dione (II-ac, Prepn. 3). The combined organic extracts were washed with H₂O, dried over Na₂SO₄ and evaporated to dryness. ¹H-NMR (300 MHz, acetone-d₆, ppm from TMS): δ 2.50-0.82 (m, 21H), 1.07 (d, 3H), 1.06 (s, 3H), 0.88 (s, 3H).

Preparation 49

7α-Hydroxymethylandrostane-3,17-dione (II-bx) and 7β-hydroxymethylandrostane-3,17-dione (II-by)

3,3:17,17-Bis(ethylendioxy)-7β-hydroxymethylandrostane and 3,3:17,17-bis(ethylendioxy)-7α-hydroxymethylandrostane were prepared in 10% and 70% yield, respectively, from 3,3:17,17-bis(ethylendioxy)-7-methyleneandrostane (Prepn. 48) by the procedure described above for the preparation of 3,3:17,17-bis(ethylendioxy)-6β-hydroxymethylandrostane (Prepn. 9). The residue was purified by flash chromatography (SiO₂, n-hexane/EtOAc 60/40). 3,3:17,17-Bis (ethylendioxy)-7β-hydroxymethylandrostane: $^1$H-NMR (300 MHz, acetone-d$_6$, ppm from TMS): δ 3.84 (m, 8H), 3.58 (m, 2H), 3.32 (t, 1H), 1.94-0.68 (m, 21H), 0.85 (s, 3H), 0.81 (s, 3H). 3,3:17,17-Bis(ethylendioxy)-7α-hydroxymethylandrostane: $^1$H-NMR (300 MHz, acetone-d$_6$, ppm from TMS): δ 3.83 (m, 8H), 3.67 (m, 2H), 3.34 (t, 1H), 1.97-0.91 (m, 21H), 0.87 (s, 3H), 0.81 (s, 3H).

7α-Hydroxymethylandrostane-3,17-dione (II-bx) was prepared in 85% yield from 3,3:17,17-bis(ethylendioxy)-7α-hydroxymethylandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, DMSO-d$_6$, ppm from TMS): δ 4.30 (t, 1H), 3.48 (m, 2H), 2.46-0.95 (m, 21H), 1.00 (s, 3H), 0.78 (s, 3H)

7β-Hydroxymethylandrostane-3,17-dione (II-by) was prepared in 85% yield from 3,3:17,17-bis(ethylendioxy)-7β-hydroxymethylandrostane by the procedure described above for the preparation of 6α-cyanoandrostane-3,17-dione (II-ac, Prepn. 3). The combined organic extracts were washed with H$_2$O, dried over Na$_2$SO$_4$ and evaporated to dryness. $^1$H-NMR (300 MHz, acetone-d$_6$, ppm from TMS): δ 3.66 (m, 2H), 3.64 (t, 1H), 2.51-0.80 (m, 21H), 1.07 (s, 3H), 0.89 (s, 3H)

Preparation 50

7-(Spirocyclopropane)androstane-3,17-dione (II-bz)

7-(Spirocyclopropane)androstane-3,17-dione (II-bz) was prepared in 45% yield from 3,3:17,17-bis(ethylendioxy)-7-methyleneandrostane (Prepn. 47) by the procedure described above for the preparation of 6-(spirocyclopropane)androstane-3,17-dione (II-bj, Prepn. 35) The residue was purified by flash chromatography (SiO$_2$, n-hexane/EtOAc/acetone 10/1/1). $^1$H-NMR (300 MHz, acetone-d$_6$, ppm from TMS: δ 2.52-0.03 (m, 24H), 1.15 (s, 3H), 0.87 (s, 3H).

Preparation 51

6-(Z)-Hydroxyimino-7α-hydroxyandrostane-3,17-dione (II-ca)

A solution of chlorotrimethylsilane (3.7 mL) and LDA (15.6 mL, 1.5M in THF) in dry THF (15 mL) at −78° C. under nitrogen was added dropwise, in 30 minutes, to a solution of 3,3:17,17-bis(ethylendioxy)androstan-6-one (1.43 g) in THF (15 mL) at −78° C. After 2 h at the same temperature, TEA (7.3 mL) was added followed, after 30 min, by addition of solid NaHCO$_3$ and finally by extraction with EtOAc (3×). The combined organic extracts were washed with brine (3×), dried over Na$_2$SO$_4$ and evaporated to dryness. The residue was purified by flash chromatography (SiO$_2$, cyclohexane/EtOAc 90/10) to give 3,3:17,17-bis(ethylendioxy)-6-trimethylsililoxyandrost-6-ene (1.35 g, 80%). $^1$H-NMR (300 MHz, acetone-d$_6$, ppm from TMS): δ 4.67 (1H, m), 3.94-3.76 (8H, m), 2.31 (1H, m), 2.00-0.90 (17H, m), 0.86 (3H, s), 0.83 (3H, s), 0.17 (9H, s).

To a stirred solution of 3,3:17,17-bis(ethylendioxy)-6-trimethylsililoxyandrost-6-ene (940 mg) in CH$_2$Cl$_2$ (50 mL) at −15° C., solid NaHCO$_3$ (683 mg) was added followed by the addition of mCPBA (550 mg, 70%). After 1 h TBAF (2.56 g) was added and the mixture was warmed to room temperature. After 1 h the mixture was quenched with brine and extracted with CH$_2$Cl$_2$. The combined organic extracts were washed with H$_2$O, dried over Na$_2$SO$_4$ and evaporated to dryness. The residue was purified by flash chromatography (SiO$_2$, n-hexane/EtOAc 60/40) to give 3,3:17,17-bis(ethylendioxy)-7α-hydroxyandrostane-6-one (660 mg, 80%). $^1$H-NMR (300 MHz, dmso-d$_6$, ppm from TMS): δ 5.63 (1H, d), 3.90-3.70 (8H, m), 3.53 (1H, m), 3.13 (1H, m), 2.00-1.00 (17H, m), 0.74 (3H, s), 0.62 (3H, s).

3,3:17,17-Bis(ethylendioxy)-6-(Z)-hydroxyiminoandrostane-7α-ol was obtained (628 mg, 92%) from 3,3:17,17-bis(ethylendioxy)-7α-hydroxyandrostane-6-one (660 mg) by the procedure described for the preparation of 3,3:17,17-bis(ethylendioxy)-6-(E)-hydroxyiminoandrostane (Prepn. 20). The combined organic extracts were washed with H$_2$O, dried over Na$_2$SO$_4$ and evaporated to dryness. The residue was used without purification in the next step. $^1$H-NMR (300 MHz, DMSO-d$_6$, ppm from TMS): δ 10.42 (1H, s), 4.90 (1H, d), 4.80 (1H, m), 3.90-3.75 (8H, m), 2.75 (1H, m), 1.90-1.00 (17H, m), 0.73 (3H, s), 0.61 (3H, s).

The title compound II-ca was prepared (500 mg, 60%) from 3,3:17,17-bis(ethylendioxy)-6-(Z)-hydroxyimino-7α-hydroxyandrostane-6-one (628 mg) by the procedure described above for the preparation of 6-(E)-hydroxyiminoandrostane-3,17-dione (II-h, Prepn. 18). The combined organic extracts were washed with brine, dried over Na$_2$SO$_4$ and evaporated to dryness. The residue was purified by flash chromatography (SiO$_2$, n-hexane/acetone/CH$_2$Cl$_2$ 40/30/30). $^1$H-NMR (300 MHz, DMSO-d$_6$, ppm from TMS): δ 10.76 (1H, s), 5.14 (1H, d), 5.02 (1H, m), 2.84 (1H, m), 2.70-1.10 (17H, m), 0.85 (3H, s), 0.78 (3H, s).

Preparation 52

6α-Hydroxymethylandrostane-3,7,17-trione (II-cb)

3,3:17,17-Bis(ethylendioxy)-7-trimethylsililoxyandrost-6-ene was prepared (1.82 g, 84%) from 3,3:17,17-bis(ethylendioxy)androstane-7-one (1.86 g) by the procedure described above for the preparation of 3,3:17,17-bis(ethylendioxy)-6-trimethylsililoxyandrost-6-ene (Prepn. 51). The combined organic extracts were washed with H$_2$O, dried over Na$_2$SO$_4$ and evaporated to dryness. The residue was purified by flash chromatography (SiO$_2$, n-hexane/EtOAc 92/8). $^1$H-NMR (300 MHz, DMSO-d$_6$, ppm from TMS): δ 4.35 (1H, m), 3.90-3.70 (8H, m), 2.20-2.05 (1H, m), 1.90-0.90 (17H, m), 0.79 (3H, s), 0.69 (3H, s), 0.15 (9H, s).

To a solution of 2,6-diphenylphenol (3.8 g) in DCM (50 mL), trimethylaluminium (4 mL, 2M in hexanes) was added. After 1 h the temperature was brought to 0° C. and a solution of trioxane (231 mg) in DCM (1 mL) was added. After 1 h the mixture was cooled to −78° C. and a solution of 3,3:17,17-bis(ethylendioxy)-7-trimethylsililoxy-androst-6-ene (1.21 g) in DCM (15 mL) was added. After stirring overnight at −20° C., the reaction was quenched by addition of NaHCO$_3$ saturated aqueous solution. The mixture was filtered on a celite pad and washed with DCM. The filtrate was washed with water, dried over Na$_2$SO$_4$ and evaporated to small volume. TBAF (2.8 mL, 1M in THF) was added and the mixture stirred at room temperature for 1.5 h. The solution was washed with water, dried over Na$_2$SO$_4$ and evaporated to dryness. The residue was purified by flash chromatography (SiO$_2$, n-hexane/EtOAc 30/70) to give 3,3:17,17-bis(ethylendioxy)-6α-hydroxymethylandrostane-7-one (783 mg, 72%). $^1$H-NMR (300 MHz, DMSO-d$_6$, ppm from TMS): δ 4.05 (1H, t), 3.90-3.70 (8H, m), 3.50 (2H, m), 2.45-2.28 (2H, m), 2.10-1.95 (1H, m), 1.90-1.10 (16H, m), 1.05 (3H, s), 0.75 (3H, s).

The title compound II-cb was prepared (570 mg, 92%) from 3,3:17,17-bis(ethylendioxy)-6α-hydroxymethylandrostane-7-one (780 mg) by the procedure described for 6α-cyanoandrostane-3,17-dione (II-ac, Prepn. 3). The combined organic extracts were washed with brine, dried over Na$_2$SO$_4$ and evaporated to dryness. The residue was used without purification in the next step. $^1$H-NMR (300 MHz, DMSO-d$_6$, ppm from TMS): δ 4.25 (1H, t), 3.55 (2H, m), 2.51 (2H, m), 2.10 (1H, m), 1.90-1.10 (16H, m), 0.95 (3H, s), 0.80 (3H, s).

Preparation 53

3-N-Methylaminoethoxyamine dihydrochloride (III-a)

To a suspension of potassium hydroxide (19.7 g) in DMSO (200 mL), under vigorous stirring, benzophenone oxime (20.2 g) was added. A solution of N-methyl-2-chloroethylamine hydrochloride (5.2 g) in DMSO (40 mL) was added dropwise. After 2.5 hrs at room temperature the reaction was poured into ice/water (400 mL), acidified with 37% HCl to pH 2.5 and washed with Et$_2$O. The aqueous layer was treated with powdered KOH to pH 10 and extracted three times with Et$_2$O; the combined organic layers were washed with water, brine, dried over Na$_2$SO$_4$ and the solvent evaporated to dryness. Purification by flash chromatography (SiO$_2$, CHCl$_3$:MeOH:AcOH from 9:1:0.1 to 7:3:0.3) gave benzophenone O-(2-N-methylaminoethyl)oxime (4.65 g, 62%) as a viscous oil. $^1$H-NMR (300 MHz, DMSO-d$_6$, ppm from TMS): δ 7.51-7.25 (10H, m), 4.13 (2H, t), 2.72 (2H, t), 2.26 (3H, s), 1.60 (1H, bb).

Benzophenone O-(2-N-methylaminoethyl)oxime (4.65 g) was suspended in 6N HCl (24 mL) and the mixture refluxed for 2 hrs. The reaction was cooled and extracted with Et$_2$O. The aqueous layer was evaporated to dryness to give the title compound III-a (1.78 g, 80%) as a hygroscopic white solid. $^1$H-NMR (300 MHz, DMSO-d$_6$, ppm from TMS): δ 10.5 (5H, bb), 4.26 (2H, t), 3.22 (2H, t), 2.55 (3H, s).

Preparation 54

3-N-Methylaminopropoxyamine dihydrochloride (III-b)

Benzophenone O-(3-N-methylaminopropyl)oxime was prepared in 62% yield from benzophenone oxime and N-methyl-3-chloropropylamine hydrochloride by the procedure described above for the preparation of benzophenone O-(2-N-methylaminoethyl)oxime (Prep. 53). $^1$H-NMR (300 MHz, DMSO-d$_6$, ppm from TMS): δ 9.20 (2H, bb), 7.37 (10H, m), 4.14 (2H, t), 2.70 (2H, t), 2.36 (3H, s), 1.87 (2H, m), 1.83 (3H, s).

The title compound III-b was prepared in 80% yield from benzophenone O-(3-N-methylaminopropyl)oxime by the procedure described above for the preparation 2-N-methylaminoethoxyamine dihydrochloride (III-a, Prepn. 53). $^1$H-NMR (300 MHz, DMSO-d$_6$, ppm from TMS): δ 11.08 (3H, bb), 9.10 (2H, bb), 4.10 (2H, t), 2.91 (2H, m), 2.50 (3H, s), 1.96 (2H, m).

Preparation 55 cis-4-Aminocyclohexyloxyamine dihydrochloride (III-c)

To a solution of trans-4-aminocyclohexanol hydrochloride (2.00 g) and triethylamine (3.90 mL) in MeOH (20 mL), cooled at 0° C., di-tert-butyl dicarbonate (3.12 g) was added. After stirring at room temperature for 6 h, the solvent was evaporated to dryness. The residue was dissolved with CH$_2$Cl$_2$, washed with water and the organic phase evaporated to dryness. The crude trans-4-(tert-butoxycarbonyl)aminocyclohexanol (2.51 g, 90%) was used as such in the next step. $^1$H-NMR (300 MHz, DMSO-d$_6$, ppm from TMS): δ 6.64 (1H, d), 4.47 (1H, d), 3.28 (1H, m), 3.12 (1H, m), 1.73 (4H, m), 1.35 (9H, s), 1.13 (4H, m).

To a solution of trans-4-(tert-butoxycarbonyl)aminocyclohexanol (2.50 g), triphenyl phosphine (6.55 g) and N-hydroxyphthalimide (1.63 g) in THF (130 mL) cooled at 0° C., diisopropyl azodicarboxylate (5.4 mL) was added dropwise. After stirring for 6 h, the solvent was evaporated and the crude product was purified by flash chromatography (SiO$_2$, hexane:EtOAc 7:3) to tert-butyl cis-4-[(1,3-dioxo-1,3-dihydro-2H-isoindol-2-yl)oxy]cyclohexylcarbamate (2.00 g, 50%). $^1$H-NMR (300 MHz, DMSO-d$_6$, ppm from TMS): δ 7.84 (4H, m), 6.88 (1H, d), 4.25 (1H, m), 3.31 (1H, m), 1.40-2.00 (8H, m), 1.36 (9H, s).

A suspension of tert-butyl cis-4-[(1,3-dioxo-1,3-dihydro-2H-isoindol-2-yl)oxy]-cyclohexylcarbamate (2.00 g) in MeOH (23 mL), hydrazine (26% in water, 1.1 mL) was added. After stirring at room temperature for 30 min, the mixture was filtered. The filtrate was evaporated to dryness and purified by flash chromatography (SiO$_2$, CH$_2$Cl$_2$:MeOH 9:1) to give cis-4-(tert-butoxycarbonyl)aminocyclohexyloxyamine (0.80 g, 63%). $^1$H-NMR (300 MHz, DMSO-d$_6$, ppm from TMS): δ 6.73 (1H, d), 5.75 (2H, bb), 3.45 (1H, m), 3.21 (1H, m), 1.30-1.90 (8H, m), 1.36 (9H, s).

cis-4-(tert-Butoxycarbonyl)aminocyclohexyloxyamine (0.80 g) was dissolved in a 5M HCl solution in EtOAc (20 mL). After 1 h the solvent was removed under reduced pressure to give the title compound III-c (0.64 g, 99%) as a white solid. $^1$H-NMR (300 MHz, DMSO-d$_6$, ppm from TMS): δ 11.03 (3H, bb), 8.08 (3H, bb), 4.26 (1H, m), 3.02 (1H, m), 1.50-2.10 (8H, m).

Preparation 56 cis-2-Aminocyclopentyl-1-oxyamine dihydrochloride (III-d)

Following the procedure described in Prepn. 55 and starting from trans-2-aminocyclopentan-1-ol hydrochloride (3.00 g), trans-2-(tert-butoxycarbonyl)aminocyclopentan-1-ol was obtained (9.20 g, 97%) and used in the next step without purification. $^1$H-NMR (300 MHz, DMSO-d$_6$, ppm from TMS): δ 6.70 (1H, d), 4.59 (1H, d), 3.75 (1H, m), 3.47 (1H, m), 1.36 (9H, s), 1.20-1.90 (6H, m).

Following the procedure described in Prepn. 55 and starting from trans-2-(tert-butoxycarbonyl)aminocyclopentan-1-ol (2.50 g), tert-butyl cis-4-[(1,3-dioxo-1,3-dihydro-2H-isoindol-2-yl)oxy]cyclopentylcarbamate (3.50 g, 83%) was obtained after flash chromatography (SiO$_2$, CH$_2$Cl$_2$, then CH$_2$Cl$_2$:EtOAc from 99:1 to 98:2). $^1$H-NMR (300 MHz, DMSO-d$_6$, ppm from TMS): δ 7.85 (4H, m), 6.66 (1H, d), 4.63 (1H, m), 3.78 (1H, m), 1.31 (9H, s), 1.30-2.00 (6H, m).

Following the procedure described in Prepn. 55 and starting from tert-butyl cis-4-[(1,3-dioxo-1,3-dihydro-2H-isoindol-2-yl)oxy]cyclopentylcarbamate (2.50 g), cis-2-(tert-butoxycarbonyl)amino-1-cyclopentyloxyamine was obtained (1.36 g, 63%) after flash chromatography (SiO$_2$, CH$_2$Cl$_2$:EtOAc 95:5). $^1$H-NMR (300 MHz, DMSO-d$_6$, ppm from TMS): δ 6.49 (1H, d), 5.92 (2H, bb), 3.80 (1H, m), 3.69 (1H, m), 1.37 (9H, s), 1.30-1.80 (6H, m).

Following the procedure described in Prepn. 55 and starting from cis-2-(tert-butoxycarbonyl)amino-1-cyclopentyloxyamine (1.36 g), the title compound III-d was obtained (1.10 g, 92%) as a white solid. $^1$H-NMR (300 MHz, DMSO-d$_6$, ppm from TMS): δ 9.00-12.00 (6H, bb), 4.59 (1H, m), 3.63 (1H, m), 1.50-2.00 (6H, m).

Preparation 57 trans-2-Aminocyclopentyloxyamine dihydrochloride
(III-e)

To a solution of trans-2-(tert-butoxycarbonyl)aminocyclopentan-1-ol (Prepn. 47, 3.00 g) triphenyl phosphine (5.90 g) and 4-nitrobenzoic acid (2.50 g) in THF (90 mL) was added, at 0° C., diisopropyl azodicarboxylate (4.50 mL). After stirring for 4 h, the solvent was evaporated and the crude product was purified by flash chromatography (SiO$_2$, CH$_2$Cl$_2$:acetone 99:1) to give cis-2-(tert-butoxycarbonyl)amino-1-(4-nitrobenzoyloxy)cyclopentane (3.70 g, 70%). $^1$H-NMR (300 MHz, DMSO-d$_6$, ppm from TMS): δ 8.33 (2H, d), 8.23 (2H, d), 7.08 (1H, d), 5.25 (1H, m), 3.92 (1H, m), 1.40-2.10 (6H, m), 1.28 (9H, s).

To a solution of cis-2-(tert-butoxycarbonyl)amino-1-(4-nitrobenzoyloxy)cyclopentane (3.70 g) in a mixture methanol/water 1:1 (20 mL) at room temperature, potassium carbonate (2.37 g) was added and stirred overnight. Water was added and the mixture extracted with diethyl ether. The combined organic layers were separated, dried over Na$_2$SO$_4$ and evaporated to dryness to give cis-2-(tert-butoxycarbonyl) aminocyclopentan-1-ol (1.94 g, 91%). $^1$H-NMR (300 MHz, DMSO-d$_6$, ppm from TMS): δ 6.09 (1H, d), 4.54 (1H, bb), 3.86 (1H, m), 3.53 (1H, m), 1.30-1.80 (6H, m), 1.37 (9H, s).

Following the procedure described in Prepn. 55 and starting from cis-2-(tert-butoxycarbonyl)aminocyclopentan-1-ol (0.97 g), tert-butyl trans-4-[(1,3-dioxo-1,3-dihydro-2H-isoindol-2-yl)oxy]cyclopentylcarbamate was obtained (1.30 g, 78%) after flash chromatography (SiO$_2$, CH$_2$Cl$_2$:acetone 99:1). $^1$H-NMR (300 MHz, DMSO-d$_6$, ppm from TMS): δ 7.84 (4H, m), 6.95 (1H, d), 4.59 (1H, m), 3.93 (1H, m), 1.30-2.10 (6H, m), 1.17 (9H, s).

Following the procedure described in Prepn. 55 and starting from tert-butyl trans-4-[(1,3-dioxo-1,3-dihydro-2H-isoindol-2-yl)oxy]cyclopentylcarbamate (1.30 g) trans-2-(tert-butoxycarbonyl)amino-1-cyclopentyloxyamine was obtained (0.75 mg, 100%) after flash chromatography (SiO$_2$, CH$_2$Cl$_2$:methanol 99:1). $^1$H-NMR (300 MHz, DMSO-d$_6$, ppm from TMS): δ 6.86 (1H, d), 4.25 (1H, m), 3.73 (1H, m), 1.30-1.90 (6H, m), 1.77 (3H, s), 1.73 (3H, s), 1.36 (9H, s).

Following the procedure described in Prepn. 55 and starting from trans-2-(tert-butoxycarbonyl)amino-1-cyclopentyloxyamine (745 mg), the title compound III-e (0.51 g, 90%) was obtained, after purification by flash chromatography (SiO$_2$, CH$_2$Cl$_2$:MeOH:NH$_3$ 9:1:0.1). $^1$H-NMR (300 MHz, DMSO-d$_6$, ppm from TMS): δ 11.00 (3H, bb), 8.48 (3H, bb), 4.66 (1H, m), 3.60 (1H, m), 1.50-2.10 (6H, m).

Preparation 58

3β-(5-Aminopentyl)androstane-6,17-dione
hydrochloride

Following the procedure described in EP 0825197 A2 and starting from androstane-3,6,17-trione (3.90 g), 3β-formylandrostane-6,17-dione (2.40 g, 62%) and of 3α-formylandrostane-6,17-dione (0.78 g, 20%) were obtained after separation by flash chromatography (SiO$_2$; CH$_2$Cl$_2$:EtOAc 9:1). $^1$H-NMR (300 MHz, DMSO-d$_6$, ppm from TMS): β-isomer: δ 9.57 (1H, d), 2.45-1.10 (21H, m), 0.78 (3H, s), 0.63 (3H, s); α-isomer: δ 9.56 (1H, bs), 2.60-0.95 (21H, m), 0.76 (3H, s), 0.60 (3H, s).

Potassium hydride (20% in mineral oil, 245 mg) was carefully washed with Et$_2$O, under nitrogen atmosphere. At −78° C. anhydrous THF (4 mL), 1,1,1,3,3,3-hexamethyldisilazane (200 mg) and (4-azidobutyl)triphenylphosphonium bromide (537 mg) were added. After complete dissolution, 3β-formylandrostane-6,17-dione (350 mg) in THF (8 mL) was added and the reaction mixture was allowed to raise from −78° C. to room temperature over 5 hrs. The mixture was poured into 5% aqueous NaHCO$_3$ and extracted with EtOAc. The combined organic layers were dried, evaporated to dryness, and after purification by flash chromatography (SiO$_2$; hexane:CH$_2$Cl$_2$: acetone 70:15:15) gave (Z) 3β-(5-azidopent-1-enyl)androstane-6,17-dione (215 mg, 50%). $^1$H-NMR (300 MHz, DMSO-d$_6$, ppm from TMS): δ 5.31 (2H, m), 3.34 (2H, t), 2.50-1.15 (25H, m), 0.87 (3H, s), 0.76 (3H, s).

A suspension of (Z) 3β-(5-azidopent-1-enyl)androstane-6,17-dione (160 mg) and 5% Pd/C (10 mg) in absolute EtOH (10 mL) and 1N hydrochloric acid (0.4 mL) was stirred, at room temperature under 1 atmosphere of hydrogen, for 1 h. The mixture was filtered on celite, and the filtrate evaporated to dryness. The crude residue was purified by washing with EtOAc and Et$_2$O to give 120 mg (75%) of 3β-(5-aminopentyl) androstane-6,17-dione hydrochloride as a white solid. $^1$H-NMR (300 MHz, DMSO-d$_6$, ppm from TMS): δ 7.68 (2H, bb), 2.73 (2H, m), 2.50-0.85 (29H, m), 0.77 (3H, s), 0.63 (3H, s).

Preparation 59

(Z) 3β-(5-Aminopent-1-enyl)androstane-6,17-dione
hydrochloride

To a solution of (Z) 3β-(5-azidopent-1-enyl)androstane-6, 17-dione (Prepn. 58, 145 mg), in THF (7 mL), triphenylphosphine (100 mg) and water (11 μL) were added and stirred at room temperature for 2 days. The crude product obtained after evaporation was purified by flash chromatography (SiO$_2$; CH$_2$Cl$_2$:MeOH 9:1 then CH$_2$Cl$_2$:MeOH:NH$_3$ 7:3:0.3). The solvent evaporated to reduced volume to remove ammonia, then 1N hydrochloric acid was added: a precipitate was obtained and filtered to give (Z) 3β-(5-aminopent-1-enyl)androstane-6,17-dione hydrochloride (115 mg, 85%). $^1$H-NMR (300 MHz, DMSO-d$_6$, ppm from TMS): δ 7.78 (3H, bb), 5.25 (2H, m), 2.73 (2H, m), 2.55-1.05 (25H, m), 0.78 (3H, s), 0.67 (3H, s).

Preparation 60

3β-(4-Aminobutyl)androstane-6,17-dione
hydrochloride

Following the procedure described in Prepn. 58 and starting from (3-azidopropyl)triphenylphosphonium bromide (520 mg), (Z) 3β-(4-azidobut-1-enyl)androstane-6,17-dione was obtained (292 mg, 72%), after purification by flash chromatography (SiO$_2$; n-hexane:CH$_2$Cl$_2$:acetone 70:15:15). $^1$H-NMR (300 MHz, acetone-d$_6$, ppm from TMS): δ 5.36 (2H, m), 3.33 (2H, t), 2.50-1.20 (23H, m), 0.87 (3H, s), 0.76 (3H, s).

Following the procedure described in Prepn. 58 and starting from (Z) 3β-(4-azidobut-1-enyl)androstane-6,17-dione (290 mg), 3β-(4-aminobutyl)androstane-6,17-dione hydrochloride was obtained (228 mg, 74%) as a white solid. $^1$H-NMR (300 MHz, DMSO-d$_6$, ppm from TMS): δ 7.76 (3H, bb), 2.74 (2H, m), 2.50-0.85 (27H, m), 0.77 (3H, s), 0.63 (3H, s).

Preparation 61

(Z) 3β-(4-Aminobut-1-enyl)androstane-6,17-dione hydrochloride

The procedure described in Prepn. 59 was followed, starting from (Z) 3β-(4-azidobut-1-enyl)androstane-6,17-dione (Prepn. 60, 415 mg). After evaporation of the solvent, the crude was purified by flash chromatography (SiO$_2$; CH$_2$Cl$_2$: MeOH 9:1, then CH$_2$Cl$_2$:MeOH:NH$_3$ 6:4:0.4). The solvent was evaporated to reduced volume and 1N HCl was added. The precipitate was filtered to give the title compound (300 mg, 71%). 1H-NMR (300 MHz, DMSO-d$_6$, ppm from TMS): δ 7.80 (3H, bb), 5.38 (1H, m), 5.23 (1H, m), 2.75 (2H, m), 2.55-1.10 (23H, m), 0.78 (3H, s), 0.67 (3H, s).

Preparation 62

3α-(5-Aminopentyl)androstane-6,17-dione hydrochloride

To a solution of (4-azidobutyl)triphenylphosphonium bromide (750 mg) in THF (5 mL), lithium bis(trimethylsilyl) amide (1M in THF, 1.7 mL) was added at −5° C. and the reaction mixture was stirred to complete dissolution. 3α-Formylandrostane-6,17-dione (Prepn. 46, 490 mg) was added and the reaction mixture allowed to rise from −78° C. to room temperature in 5 hrs. The mixture was poured into 5% aqueous NaHCO$_3$ and extracted with EtOAc. The combined organic layers were dried over Na$_2$SO$_4$ and evaporated to dryness. The residue was purified by flash chromatography (SiO$_2$; hexane:CH$_2$Cl$_2$:acetone 70:15:15) to give (Z) 3α-(5-azidopent-1-enyl)androstane-6,17-dione (265 mg, 43%). $^1$H-NMR (300 MHz, acetone-d$_6$, ppm from TMS): δ 5.79 (1H, m), 5.34 (1H, m), 3.35 (2H, t), 2.85 (1H, m), 2.60-1.20 (24H, m), 0.87 (3H, s), 0.79 (3H, s).

Following the procedure described in Prepn. 58 and starting from (Z) 3α-(5-azidopent-1-enyl)androstane-6,17-dione (60 mg), the title compound was obtained (45 mg, 75%) as a white solid. $^1$H-NMR (300 MHz, DMSO-d$_6$, ppm from TMS): δ 7.70 (3H, bb), 2.73 (2H, m), 2.50-1.10 (29H, m), 0.77 (3H, s), 0.67 (3H, s).

Preparation 63

(Z) 3α-(5-Aminopent-1-enyl)androstane-6,17-dione

Following the procedure described in Prepn. 59 and starting from (Z) 3α-(5-azidopent-1-enyl)androstane-6,17-dione (Prepn. 62, 250 mg), the title compound was obtained (220 mg, 86%) as a white solid. $^1$H-NMR (300 MHz, DMSO-d$_6$, ppm from TMS): δ 7.87 (3H, bb), 5.74 (1H, m), 5.26 (1H, m), 2.74 (3H, m), 2.55-1.10 (24H, m), 0.78 (3H, s), 0.69 (3H, s).

Preparation 64

3α-(4-Aminobutyl)androstane-6,17-dione hydrochloride

Following the procedure described in Prepn. 58 and starting from (3-azidopropyl)triphenylphosphonium bromide (713 mg), (Z) 3α-(4-azidobut-1-enyl)androstane-6,17-dione was obtained (350 mg, 60%), after purification by flash chromatography (SiO$_2$, n-hexane:CH$_2$Cl$_2$:acetone 70:15:15), as a solid. $^1$H-NMR (300 MHz, acetone-d$_6$, ppm from TMS): δ 5.88 (1H, m), 5.38 (1H, m), 3.35 (2H, t), 2.98 (1H, m), 2.60-1.20 (22H, m), 0.87 (3H, s), 0.79 (3H, s).

Following the procedure described in Prepn. 58 and starting from (Z) 3α-(4-azidobut-1-enyl)androstane-6,17-dione (35 mg), 3α-(4-aminobutyl)androstane-6,17-dione hydrochloride was obtained (32 mg, 89%) as a white solid. $^1$H-NMR (300 MHz, DMSO-d$_6$, ppm from TMS): δ 7.79 (3H, bb), 2.74 (2H, m), 2.50-1.15 (27H, m), 0.77 (3H, s), 0.67 (3H, s).

Preparation 65

(Z) 3α-(4-Aminobut-1-enyl)androstane-6,17-dione hydrochloride

Following the procedure described in Prepn. 59 and starting from (Z) 3α-(4-azidobut-1-enyl)androstane-6,17-dione (Prepn. 64, 60 mg), the title compound was obtained (50 mg, 80%) as a white solid. $^1$H-NMR (300 MHz, DMSO-d$_6$, ppm from TMS): δ 7.77 (3H, bb), 5.84 (1H, m), 5.28 (1H, m), 2.74 (3H, m), 2.55-1.10 (22H, m), 0.78 (3H, s), 0.70 (3H, s).

Preparation 66

(Z) 3α-(6-Aminohex-1-enyl)androstane-6,17-dione hydrochloride

Following the procedure described in Prepn. 58 and starting from (3-azidopentyl)triphenylphosphonium bromide (600 mg), (Z) 3α-(4-azidohex-1-enyl)androstane-6,17-dione was obtained (240 mg, 40%), after purification by flash chromatography (SiO$_2$, hexane:CH$_2$Cl$_2$:acetone 70:15:15), as a solid. $^1$H-NMR (300 MHz, acetone-d$_6$, ppm from TMS): δ 5.75 (1H, m), 5.34 (1H, m), 3.34 (2H, t), 2.92-1.21 (27H, m), 0.87 (3H, s), 0.79 (3H, s).

The title compound was obtained following the procedure described in Prepn. 58 and starting from (Z) 3α-(6-azidohex-1-enyl)androstane-6,17-dione (133 mg). The crude product was purified by flash chromatography (SiO$_2$, CH$_2$Cl$_2$:MeOH:NH$_3$ 92:8:0.8); the eluate was concentrated to small volume, acidified with 1N HCl, and evaporated the solvent to dryness. (Z) 3α-(6-Aminohex-1-enyl)androstane-6,17-dione hydrochloride was obtained (60 mg, 44%) as a white powder. $^1$H-NMR (300 MHz, DMSO-d$_6$, ppm from TMS): δ 7.73 (3H, bb), 5.71 (1H, m), 5.26 (1H, m), 2.74 (3H, m), 2.56-1.12 (26H, m), 0.78 (3H, s), 0.69 (3H, s).

Preparation 67

5-(5α-Hydroxy-17-keto-androstane-3α-yl)pent-4-(Z)-en-1-yl carbamic acid 9H-fluoren-9-yl methyl ester Following the procedures described for the preparation of 5α-hydroxyandrostane-3,17-dione (II-ad, Prepn. 4), starting from 17,17-(ethylendioxy)-5-androsten-3β-ol after epoxidation with mCPBA, reduction with LAH, and oxidation with IBX, 17,17-(ethylendioxy)-5α-hydroxyandrostane-3-one was obtained in 55% yield. $^1$H-NMR (300 MHz, DMSO-d$_6$, ppm from TMS): δ4.29 (s, 1H), 3.78 (m, 4H), 2.69-1.10 (m, 21H), 1.07 (s, 3H), 0.76 (s, 3H).

Following the procedure described above for the preparation 3,3:17,17-bis(ethylendioxy)-6-methyleneandrostane (Prepn. 8) and starting from 17,17-(ethylendioxy)-5α-hydroxyandrostane-3-one, 17,17-(ethylendioxy)-3-methyleneandrostane-5α-ol was obtained in 98% yield. $^1$H-NMR (300 MHz, DMSO-d$_6$, ppm from TMS): δ 4.62 (m, 1H), 4.50 (m, 1H), 3.78 (m, 4H), 3.42 (s, 1H), 2.36-1.03 (m, 21H), 0.93 (s, 3H), 0.75 (s, 3H).

Following the procedure described for the preparation of 3,3:17,17-bis(ethylendioxy)-6β-hydroxymethylandrostane (Prepn. 9) and starting from 17,17-(ethylendioxy)-3-methylenandrostane-5α-ol, 17,17-(ethylendioxy)-3α-hydroxymethylandrostane-5α-ol was obtained in 98% yield. $^1$H-NMR (300 MHz, DMSO-$d_6$, ppm from TMS): δ 4.44 (t, 1H), 3.81 (s, 1H), 3.76 (m, 4H), 3.58 (m, 1H), 3.39 (m, 1H), 1.91-0.97 (m, 22H), 0.87 (s, 3H), 0.74 (s, 3H).

A solution of 17,17-(ethylendioxy)-3α-hydroxymethylandrostane-5α-ol (1.04 g) and IBX (1.20 g) in DMSO (14.3 mL) was stirred at room temperature for 1 h and then quenched at room temperature by addition of $H_2O$ (250 mL). After stirring for 15 min, the mixture was filtered and the cake was washed with $H_2O$ (3×50 mL) and then acetone/MeOH 1/1. The aqueous phase was extracted with $Et_2O$/EtOAc 70/30 (3×50 mL). The combined organic extracts were dried over $Na_2SO_4$ and evaporated to dryness. The residue was purified by flash chromatography ($SiO_2$, n-hexane/$CH_2Cl_2$/acetone 80/10/10) to give 17,17-(ethylendioxy)-5α-hydroxyandrostane-3α-carbaldehyde hemiacetal (0.90 g, 88%). $^1$H-NMR (300 MHz, DMSO-$d_6$, ppm from TMS): δ 5.87 (d, 1H), 4.96 (d, 1H), 3.77 (m, 4H), 1.98-1.01 (m, 22H), 0.84 (s, 3H), 0.73 (s, 3H).

Prepared by following the procedure described for the preparation 6-methyleneandrostane-3,17-dione (II-ah, Prepn. 8) and starting from 17,17-(ethylendioxy)-5α-hydroxyandrostane-3α-carbaldehyde hemiacetal and triphenyl 3-cyanopropylphosphonium bromide. The crude product was purified by flash chromatography ($SiO_2$, n-hexane/$CH_2Cl_2$/acetone 80/10/10) to give 17,17-(ethylendioxy)-3α-(4-cyanobut-1-(Z)-enyl)androstane-5α-ol and 17,17-(ethylendioxy)-3α-(4-cyanobut-1-(E)-enyl)androstane-5α-ol (85/15 mixture) in 73% yield. $^1$H-NMR (300 MHz, DMSO-$d_6$, ppm from TMS): δ 6.21 (m, 1H), 5.07 (m, 1H), 3.78 (m, 4H), 3.47 (s, 1H), 2.73-1.00 (m, 26H), 0.88 (s, 3H), 0.74 (s, 3H).

To a stirred solution of 17,17-(ethylendioxy)-3α-(4-cyanobutyl-1-(Z)-enyl)androstane-5α-ol and 17,17-(ethylendioxy)-3α-(4-cyanobutyl-1-(E)-enyl)androstane-5α-ol (85/15 mixture, 1.00 g) in abs. EtOH at reflux (100 mL), Na (5.56 g) was added in small pieces over 2.45 h. The mixture was refluxed for further 3 h. After cooling to 0° C., the mixture was quenched by careful addition of 5% $NaH_2PO_4$ aqueous solution, followed by 1N HCl to bring the pH to 8. The mixture was extracted with $CH_2Cl_2$ (2×300 mL). The combined organic extracts were washed with brine, dried, filtered and evaporated to dryness to give 17,17-(ethylendioxy)-3α-(5-aminopent-1-(Z)-enyl)androstane-5α-ol and 17,17-(ethylendioxy)-3α-(5-aminopent-1-(E)-enyl)androstane-5α-ol (85/15 mixture, 0.93 g, 92%). $^1$H-NMR (300 MHz, DMSO-$d_6$, ppm from TMS): δ 6.05 (m, 1H), 5.08 (m, 1H), 3.77 (m, 4H), 3.44 (s, 1H), 2.73-0.99 (m, 30H), 0.87 (s, 3H), 0.74 (s, 3H).

Prepared by following the procedure described for the preparation [3,3:17,17-bis(ethylendioxy)androstane-7α-yl] carbamic acid 9H-fluoren-9-ylmethyl ester (Prepn. 46) and starting from 17,17-(ethylendioxy)-3α-(5-aminopent-1-(Z)-enyl)androstane-5α-ol and 17,17-(ethylendioxy)-3α-(5-aminopent-1-(E)-enyl)androstane-5α-ol (85/15 mixture). The crude product was purified by flash chromatography ($SiO_2$, n-hexane/EtOAc 80/20) to give 5-[17,17-(ethylendioxy)-5α-hydroxyandrostane-3α-yl]pent-4-(Z)-en-1-yl carbamic acid 9H-fluoren-9-ylmethyl ester in 69% yield. $^1$H-NMR (300 MHz, DMSO-$d_6$, ppm from TMS): δ 7.92-7.22 (m, 9H), 6.05 (m, 1H), 5.05 (m, 1H), 4.22 (m, 3H), 3.76 (m, 4H), 3.42 (s, 1H), 3.03-0.97 (m, 28H), 0.83 (s, 3H), 0.74 (s, 3H).

Prepared by following the procedure described for the preparation of 6α-cyanoandrostane-3,17-dione (II-ac, Prepn. 3) and starting from 5-[17,17-(ethylendioxy)-5α-hydroxyandrostane-3α-yl]pent-4-(Z)-en-1-yl carbamic acid 9H-fluoren-9-ylmethyl ester. The combined organic extracts were washed with brine, dried over $Na_2SO_4$, filtered and evaporated to dryness to give 5-(5α-hydroxy-17-keto-androstane-3α-yl)pent-4-(Z)-en-1-yl carbamic acid 9H-fluoren-9-ylmethyl ester in 87% yield. $^1$H-NMR (300 MHz, DMSO-$d_6$, ppm from TMS): δ 8.00-7.20 (m, 9H), 6.05 (m, 1H), 5.05 (m, 1H), 4.23 (m, 3H), 3.48 (s, 1H), 3.02-1.00 (m, 28H), 0.86 (s, 3H), 0.75 (s, 3H).

Preparation 68

3β-(2-Aminoacetoxy)androstane-6,17-dione fumarate

To a stirred suspension of 3β-tert-butyldimethylsilyloxyandrostane-6α,17β-diol (EP 0825197 A2, 6.21 g) in DMSO (160 mL) IBX (16.45 g) was added at room temperature. After 1.5 h the mixture was quenched at room temperature by addition of $H_2O$ (300 mL). After 15 min the mixture was filtered and the cake was washed with $H_2O$. The cake was extracted with $Et_2O$ (4×). The combined organic extracts were dried over $Na_2SO_4$ and evaporated to dryness to give 3β-tert-butyldimethylsilyloxy-androstane-6,17-dione (0.36 g, 75%). $^1$H-NMR (300 MHz, DMSO-$d_6$, ppm from TMS: δ 3.54 (m, 1H), 2.47-1.08 (m, 20H), 0.84 (s, 9H), 0.77 (s, 3H), 0.66 (s, 1H), 0.01 (s, 6H).

To a stirred suspension of 3β-tert-butyldimethylsilyloxyandrostane-6,17-dione (2.00 g) in EtOH (20 mL), 37% HCl (40 µL) was added. After 3 h the solution was quenched with 5% aqueous $NaHCO_3$ to pH 7. The organic solvent was evaporated and the aqueous phase was extracted with $CH_2Cl_2$ (4×350 mL). The combined organic extracts were washed with saturated aqueous $NH_4Cl$, brine, $H_2O$, dried over $Na_2SO_4$ and evaporated to dryness. The residue was purified by flash chromatography ($SiO_2$, cyclohexane/EtOAc 90/10) to give 3β-hydroxyandrostane-6,17-dione (1.25 g, 86%). $^1$H-NMR (300 MHz, DMSO-$d_6$, ppm from TMS): δ 4.56 (d, 1H), 3.31 (m, 1H), 2.45-1.15 (m, 20H), 0.77 (s, 3H), 0.65 (s, 3H).

To a solution of 3β-hydroxyandrostane-6,17-dione (0.40 g) in THF (8 mL), N-(9-fluorenylmethoxycarbonyl)glycine (0.43 g), N,N'-dicyclohexylcarbodiimide (0.32 g) and 4-dimethylaminopyridine (16 mg) were added and the reaction mixture was stirred at room temperature for 1 h. After evaporation to dryness, the residue was purified by flash chromatography ($SiO_2$; EtOAc:n-hexane 6:4) to give 3β-{2-[N-(9-fluorenylmethoxycarbonyl)]aminoacetoxy}androstane-6,17-dione (0.73 mg, 95%). $^1$H-NMR (300 MHz, acetone, ppm from TMS): δ 7.93-7.30 (8H, m), 6.86 (1H, t), 4.71 (1H, m), 4.40-4.20 (3H, m), 3.91 (2H, d), 2.55-1.25 (20H, m), 0.87 (3H, s), 0.78 (3H, s).

A solution of 3β-{2-[N-(9-fluorenylmethoxycarbonyl)] aminoacetoxy}androstane-6,17-dione (690 mg) in THF (5 mL), was added to 1M solution of tetrabutylammonium fluoride in THF (2.3 mL), and stirred for 45 minutes. The solvent was evaporated and the crude purified by flash chromatography ($SiO_2$, $CH_2Cl_2$:MeOH:$NH_3$ 9:1:0.1). The collected fractions were evaporated and the residue was dissolved in EtOAc and treated with fumaric acid to give, after filtration, 3β-(2-aminoacetoxy)androstane-6,17-dione fumarate (366 mg, 65%). $^1$H-NMR (300 MHz, DMSO, ppm from TMS): δ 8.00 (4H, bb), 6.40 (2H, s), 4.66 (1H, m), 3.49 (2H, s), 2.55-1.15 (20H, m), 0.78 (3H, s), 0.69 (3H, s).

Preparation 69

3β-(3-Aminopropionyloxy)androstane-6,17-dione fumarate

Following the procedure described in Prepn. 68, and starting from N-(9-fluorenylmethoxycarbonyl)-β-alanine (0.45 g), 3β-{3-[N-(9-fluorenylmethoxycarbonyl)]-aminopropionyloxy}androstane-6,17-dione was obtained (0.77 mg, 98%). $^1$H-NMR (300 MHz, acetone, ppm from TMS): δ 7.90-7.25 (8H, m), 6.56 (1H, t), 4.67 (1H, m), 4.38-4.16 (3H, m), 3.42 (2H, m), 2.55-1.00 (22H, m), 0.87 (3H, s), 0.80 (3H, s).

Following the procedure described in Prepn. 68 and starting from 3β-{3-[N-(9-fluorenylmethoxycarbonyl)]aminopropionyloxy}androstane-6,17-dione (770 mg), the title compound was obtained (420 mg, 67%). $^1$H-NMR (300 MHz, DMSO, ppm from TMS): δ 8.00 (4H, bb), 6.42 (2H, s), 4.61 (1H, m), 2.95 (2H, t), 2.59 (2H, t), 2.55-1.15 (20H, m), 0.78 (3H, s), 0.69 (3H, s).

Preparation 70

3β-(4-Aminobutyryloxy)androstane-6,17-dione hydrochloride

Following the procedure described in Prepn. 68 and starting from 4-(tert-butoxycarbonylamino)butyric acid (147 mg), 3β-[4-(N-tert-butoxycarbonyl)aminobutyryloxy]androstane-6,17-dione was obtained (230 mg, 73%), after purification by flash chromatography (SiO$_2$; CH$_2$Cl$_2$:MeOH 99:1). $^1$H-NMR (300 MHz, DMSO, ppm from TMS): δ 6.82 (1H, t), 4.56 (1H, m), 2.90 (2H, m), 2.50-1.15 (24H, m), 1.35 (9H, s), 0.77 (3H, s), 0.68 (3H, s).

A solution of 3β-[4-(N-tert-butoxycarbonyl)aminobutyryloxy]-androstane-6,17-dione (230 mg) in THF (8 mL) was treated with a solution of 5M HCl in EtOAc (0.3 mL) and stirred at 0° C. for 1.5 hrs. The solid was filtered off, to give the title compound (200 mg, 94%). $^1$H-NMR (300 MHz, DMSO, ppm from TMS): δ 7.93 (3H, bb), 4.89 (1H, m), 2.78 (2H, t), 2.50-1.15 (24H, m), 0.78 (3H, s), 0.69 (3H, s).

Preparation 71

3β-(3R,S-Aminobutyryloxy)androstane-6,17-dione hydrochloride

A solution of 3β-hydroxyandrostane-6,17-dione (Prepn. 68, 60.15 mg), EDAC (75.7 mg), 3R,S-(N-tert-butoxycarbonyl)aminobutyric acid (50.7 mg), DMAP (1.2 mg) in THF (1.9 mL) and H$_2$O (100 μL) was stirred overnight at room temperature. The mixture was diluted with THF, dried over Na$_2$SO$_4$ and evaporated to dryness. The residue was purified by flash chromatography (SiO$_2$, cyclohexane/EtOAc 10/90) to give 3β-(3R,S-(N-tert-butoxycarbonyl)aminobutyryloxy)androstane-6,17-dione (49 mg, 55%). $^1$H-NMR (300 MHz, DMSO-d$_6$, ppm from TMS): δ 6.95 (d, 1H), 4.64 (m, 1H), 3.30-1.12 (m, 23H), 1.35 (s, 9H), 1.21 (d, 3H), 0.78 (s, 3H), 0.69 (s, 3H).

Following the procedure described in Prepn. 70 and starting from 3β-(3R,S-(N-tert-butoxycarbonyl)aminobutyryloxy)androstane-6,17-dione the title compound was obtained in 55% yield. 1H-NMR (300 MHz, DMSO-d$_6$, ppm from TMS): δ 8.00 (bb, 3H) 4.63 (m, 1H), 3.47 (m, 1H), 2.78-1.12 (m, 22H), 1.21 (d, 3H), 0.78 (s, 3H), 0.70 (s, 3H).

Preparation 72

3β-(2R,S-Methyl-3-aminopropionyloxy)androstane-6,17-dione hydrochloride (I-cv)

Following the procedure described in Prepn. 68, 3β-(2R,S-methyl-3-(N-tert-butoxycarbonyl)aminopropionyloxy)androstane-6,17-dione was prepared in 63% yield starting from 3β-hydroxyandrostane-6,17-dione (Prepn. 68) and 2R,S-methyl-3-(N-tert-butoxycarbonyl)aminopropionic acid. $^1$H-NMR (300 MHz, DMSO-d$_6$, ppm from TMS): δ 6.86 (t, 1H), 4.62 (m, 1H), 3.15-1.05 (m, 23H), 1.35 (s, 9H), 1.15 (d, 3H), 0.78 (s, 3H), 0.70 (s, 3H).

Following the procedure described in Prepn. 70 and starting from 3β-(2R,S-methyl-3-(N-tert-butoxycarbonyl)aminopropionyloxy)androstane-6,17-dione the title compound was obtained in 63% yield. 1H-NMR (300 MHz, DMSO-d$_6$, ppm from TMS): δ 7.98 (bb, 3H) 4.61 (m, 1H), 3.26-1.03 (m, 23H), 1.15 (d, 1.5H), 1.14 (d, 1.5H), 0.78 (s, 3H), 0.70 (s, 3H).

Preparation 73

3β-[N-(2-Aminoethyl)carbamoyloxy]androstane-6,17-dione

To a solution of 3β-hydroxyandrostane-6,17-dione (Prepn. 68, 300 mg) in THF (8 mL) 1,1'-carbonyldiimidazole (340 mg) was added and the resulting mixture was stirred at reflux for 4 hr. After cooling, the solvent was evaporated. The residue was dissolved in CH$_2$Cl$_2$ and washed with water. The organic layer was dried over Na$_2$SO$_4$ and evaporated to dryness to give 3β-(1-imidazolylcarbonyloxy)androstane-6,17-dione (360 mg, 90%). $^1$H-NMR (300 MHz, CDCl$_3$, ppm from TMS): δ 8.24 (1H, bs), 7.45 (1H, bs), 7.12 (1H, bs), 4.94 (1H, m), 2.60-1.25 (23H, m), 0.90 (3H, s), 0.87 (3H, s).

N-(tert-Butoxycarbonyl)ethylendiamine (0.20 mL) was added to a solution of 3β-(1-imidazolylcarbonyloxy)androstane-6,17-dione (200 mg) in CH$_2$Cl$_2$ (10 mL) and 2-propanol (1 mL). After heating under reflux for 9 hr, the mixture was cooled to room temperature and water was added. The organic layer was separated, dried over Na$_2$SO$_4$ and evaporated to dryness. The residue was purified by flash chromatography (SiO$_2$; CH$_2$Cl$_2$:EtOAc 1:1) to give 3β-[N-(2-tert-butoxycarbonylaminoethyl)-carbamoyloxy]androstane-6,17-dione (184 mg, 76%). $^1$H-NMR (300 MHz, CDCl$_3$, ppm from TMS): δ 5.02 (1H, bb), 4.84 (1H, bb), 4.56 (1H, m), 3.27 (4H, m), 2.50-1.20 (20H, m), 1.45 (9H, s), 0.87 (3H, s), 0.80 (3H, s).

Following the procedure described in Prepn. 70 and starting from 3β-[N-(2-tert-butoxycarbonylaminoethyl)carbamoyloxy]androstane-6,17-dione (260 mg), 3β-[N-(2-aminoethyl)carbamoyloxy]androstane-6,17-dione was obtained (158 mg, 70%), as a yellow solid. $^1$H-NMR (300 MHz, DMSO-d$_6$, ppm from TMS): δ 7.57 (3H, bb), 7.20 (1H, t), 4.42 (1H, m), 3.17 (2H, m), 2.78 (2H, t), 2.50-1.15 (20H, m), 0.78 (3H, s), 0.68 (3H, s).

Preparation 74

3β-(4-Aminobutyramido)androstane-6,17-dione hydrochloride

Following the procedure described in Example 4 and starting from 6α-hydroxyandrostane-3,17-dione (5.00 g) and hydroxylamine hydrochloride (5.80 g), (E,Z) 3-hydroxyimino-6α-hydroxyandrostan-17-one was obtained (3.93 g, 75%) after filtration from THF. $^1$H-NMR (300 MHz, DMSO-d$_6$, ppm from TMS): δ 10.10 (0.5H, s), 10.07 (0.5H, s), 4.47 (0.5H, d), 4.44 (0.5H, d), 3.47 (0.5H, m), 3.24 (1H, m), 3.03 (0.5H, m), 2.60-0.60 (19H, m), 0.85 (3H, s), 0.77 (3H, s).

A solution of (E,Z) 3-hydroxyimino-6α-hydroxyandrostan-17-one (3.10 g) in CHCl$_3$ (23 mL) and MeOH (355 mL) was hydrogenated in a Parr shaker over PtO$_2$ hydrate (2.3 g) at 3.5 atm at room temperature. After 24 hr, the mixture was filtered, the cake washed with CHCl$_3$ and water. The organic layer was separated, dried and evaporated to dryness. The residue was purified by flash chromatography (SiO$_2$; CH$_2$Cl$_2$: MeOH:NH$_3$ 8:2:0.2). Two groups of fractions were collected and evaporated to dryness. After dissolution in MeOH of the residue (1.00 g) of the first group, addition of the theoretical amount of fumaric acid and evaporation to dryness 3α-aminoandrostane-6α,17β-diol fumarate (1.39 g, 34% yield) was obtained. Repeating the same procedure to the residue (1.5 g) of the second fraction, 3β-aminoandrostane-6α,17β-diol fumarate (2.05 g, 50%) was obtained. $^1$H-NMR (300 MHz, DMSO-d$_6$, ppm from TMS): 3α-isomer: δ 7.97 (4H, bb), 6.40 (2H, s), 4.45 (2H, bb), 3.50-3.10 (3H, m), 2.05-0.55 (20H, m), 0.72 (3H, s), 0.60 (3H, s); 3β-isomer: δ 7.88 (4H, m), 6.40 (2H, s), 4.43 (2H, bb), 3.50-2.75 (3H, m), 2.20-0.55 (20H, m), 0.73 (3H, s), 0.40 (3H, s).

IBX (2.00 g) was added to a solution of 3β-aminoandrostane-6α,17β-diol fumarate (1.50 g) in dimethylsulfoxide (10 mL) and trifluoroacetic acid (0.54 mL). After stirring overnight at room temperature, water was added and the mixture extracted with CH$_2$Cl$_2$. The organic layer was washed with brine, dried over Na$_2$SO$_4$ and evaporated to dryness. The residue was purified by flash chromatography (SiO$_2$; CHCl$_3$: MeOH:NH$_3$ 9:1:0.1): the fractions were evaporated and treated 5M HCl in EtOAc to give 3β-aminoandrostane-6,17-dione hydrochloride (780 mg, 65%). $^1$H-NMR (300 MHz, DMSO-d$_6$, ppm from TMS): δ 8.04 (3H, bb), 2.94 (1H, m), 2.50-1.15 (20H, m), 0.78 (3H, s), 0.66 (3H, s).

A solution of 3β-aminoandrostane-6,17-dione hydrochloride (150 mg) in CH$_2$Cl$_2$ was treated with powdered KOH (25 mg) and stirred for 15 min. 4-(tert-Butoxycarbonylamino) butyric acid (98 mg), EDAC (168 mg) and 4-dimethylaminopyridine (8 mg) were added at 0° C. The reaction temperature was raised to room temperature and stirred for 24 hrs. The mixture was washed with water (2×10 mL) and 5% NaHCO$_3$ (10 mL). The organic layer was dried and evaporated to dryness. The residue was purified by flash chromatography (SiO$_2$; CH$_2$Cl$_2$:MeOH:NH$_3$ 9:1:0.1) to give 3β-[4-(tert-butoxycarbonylamino)butyramido]-androstane-6,17-dione (161 mg, 75%). $^1$H-NMR (300 MHz, DMSO-d$_6$, ppm from TMS): δ 7.68 (1H, d), 6.77 (1H, t), 3.46 (1H, m), 2.87 (2H, m), 2.45-1.10 (24H, m), 1.36 (9H, s), 0.78 (3H, s), 0.66 (3H, s).

Following the procedure described in Prepn. 70 and starting from 3β-[4-(tert-butoxycarbonylamino)butyramido]androstane-6,17-dione (110 mg), 3β-(4-aminobutyramido)androstane-6,17-dione hydrochloride was obtained (62 mg, 65%), as a white solid. $^1$H-NMR (300 MHz, DMSO-d$_6$, ppm from TMS): δ 7.85 (1H, d), 7.76 (3H, bb), 3.45 (1H, m), 2.76 (2H, m), 2.45-1.15 (24H, m), 0.78 (3H, s), 0.66 (3H, s).

Preparation 75

3β-(3-Aminopropionamido)androstane-6,17-dione hydrochloride

Using the same reaction conditions described in Prepn. 74 and starting from 3β-aminoandrostane-6,17-dione hydrochloride (180 mg) and N-(tert-butoxycarbonyl)-β-alanine (Prepn. 61, 110 mg), 3β-[3-(tert-butoxycarbonylamino)-N-propionamido]androstane-6,17-dione was obtained (138 mg, 55%), after purification by flash chromatography (SiO$_2$; CH$_2$Cl$_2$:MeOH 95:5). $^1$H-NMR (300 MHz, DMSO-d$_6$, ppm from TMS): δ 7.74 (1H, d), 6.72 (1H, t), 3.46 (1H, m), 3.08 (2H, m), 2.45-1.10 (22H, m), 1.36 (9H, s), 0.78 (3H, s), 0.66 (3H, s).

Following the procedure described in Prepn. 70 and starting from 3β-[3-(tert-butoxycarbonylamino)propionamido] androstane-6,17-dione (120 mg), 3β-(3-aminopropionamido)androstane-6,17-dione hydro-chloride was obtained (67 mg, 65%) as a white solid. $^1$H-NMR (300 MHz, DMSO-d$_6$, ppm from TMS): δ 8.01 (1H, d), 7.76 (3H, bb), 3.48 (1H, m), 2.96 (2H, m), 2.45-1.15 (22H, m), 0.78 (3H, s), 0.67 (3H, s).

Preparation 76

3β-[3-(N-tert-Butoxycarbonyl-N-methyl)aminopropoxy]-6-hydroxyiminoandrostane-17-(2-spiro-1,3-dioxolane)

To a solution of 3β-hydroxyandrost-5-en-17-one (10.00 g) in pyridine (66 mL), toluene-4-sulfonyl chloride (13.20 g) and DMAP (10 mg) were added at 0° C. under stirring. The reaction was allowed to warm to room temperature and stirred for 15 hr. After dilution with EtOAc (300 mL) the mixture was poured into iced water. The organic layer was separated, washed with 1N H$_2$SO$_4$, water and brine, dried and evaporated to dryness to give 3β-(p-toluensulfonyloxy)androst-5-en-17-one (14.70 g, 96%), as a white solid. $^1$H-NMR (300 MHz, acetone-d$_6$, ppm from TMS): δ 7.81 (2H, m), 7.48 (2H, m), 5.35 (1H, m), 4.26 (1H, m), 2.46 (3H, s), 2.54-0.93 (19H, m), 1.05 (3H, s), 0.85 (3H, s).

3β-(p-Toluensulfonyloxy)androst-5-en-17-one (12.00 g) was added to a suspension of propane-1,3-diol (61 mL) and PTSA (610 mg) at 95° C. After stirring for 40 minutes, the mixture was cooled to room temperature, and poured in water (800 mL), bringing the pH to 7 with 5% NaHCO$_3$. After 3 hrs the solid was filtered and dissolved in CH$_2$Cl$_2$. The solution was dried over Na$_2$SO$_4$ and evaporated to dryness under reduced pressure to give 3β-(3-hydroxypropoxy)androst-5-en-17-one (9.10 g, 97%), used without further purification. $^1$H-NMR (300 MHz, DMSO-d$_6$, ppm from TMS): δ 5.35 (1H, m), 4.34 (1H, t), 3.43 (4H, m), 3.06 (1H, m), 2.45-0.85 (21H, m), 0.96 (3H, s), 0.79 (3H, s).

Ethylene glycol (15.0 mL) and PTSA (470 mg) were added to a solution of 3β-(3-hydroxypropoxy)androst-5-en-17-one (9.10 g) in toluene (370 mL). The reaction mixture was stirred at reflux for 3 hr. After cooling to room temperature, water (200 mL) was added, 5% NaHCO$_3$ was added to bring pH to 7. The mixture was extracted with EtOAc (3×100 mL). The combined organic layers were dried and evaporated to dryness. The residue was purified by flash chromatography (SiO$_2$; n-hexane:EtOAc 55:45) to give of 3β-(3-hydroxypropoxy)androst-5-en-17-(2-spiro-1,3-dioxolane) (10.2 g, 100%). $^1$H-NMR (300 MHz, DMSO-d$_6$, ppm from TMS): δ 5.31 (1H, m), 4.34 (1H, t), 3.78 (4H, m), 3.43 (4H, m), 3.05 (1H, m), 2.35-0.80 (21H, m), 0.93 (3H, s), 0.77 (3H, s).

To a solution of 3β-(3-hydroxypropoxy)androst-5-en-17-(2-spiro-1,3-dioxolane) (2.00 g) and triethylamine (0.82 mL) in CH$_2$Cl$_2$ (30 mL), cooled at 0° C., methanesulfonyl chloride (0.41 mL) was added. After stirring for 3 h at room temperature, the mixture was poured in iced water and extracted with CH$_2$Cl$_2$. The organic phase was washed with 5% NaHCO$_3$, water, brine, dried and evaporated to give an oil which solidified on standing overnight in the refrigerator. The solid obtained was crystallized with Et$_2$O to give 3β-(3-methanesulfonyloxypropoxy)-17-(2-spiro-1,3-dioxolane)androst-5- ene (2.33 g, 97%), as a yellow solid. $^1$H-NMR (300 MHz, DMSO-d$_6$, ppm from TMS): δ 5.31 (1H, m), 4.22 (2H, t), 3.78 (4H, m), 3.48 (2H, t), 3.15 (3H, s), 3.09 (1H, m), 2.36-0.81 (21H, m), 0.94 (3H, s), 0.77 (3H, s).

3β-(3-Methanesulfonyloxypropoxy)-17-(2-spiro-1,3-dioxolane)androst-5-ene (1.90 g) was dissolved in a 2.23 M solution of methylamine in MeOH (53 mL) and the solution was heated at 120° C. in a steel bomb for 4 hr. After cooling to room temperature, CHCl$_3$ was added and the mixture washed with 5% NaHCO$_3$, water, brine. The organic layer was dried and evaporated to dryness to give 3β-(3-N-methylaminopropoxy)-17-(2-spiro-1,3-dioxolane)androst-5-ene (1.60 g, 100%) as a light green residue and used without purification in the next step. $^1$H-NMR (300 MHz, DMSO-d$_6$, ppm from TMS): δ 5.30 (1H, m), 3.78 (4H, m), 3.41 (2H, t), 3.05 (1H, m), 2.46 (2H, t), 2.23 (3H, s), 2.33-0.80 (22H, m), 0.93 (3H, s), 0.77 (3H, s).

Following the N-Boc protection procedure described in Prepn. 55 and starting from 3β-(3-N-methylaminopropoxy)-17-(2-spiro-1,3-dioxolane)androst-5-ene (1.60 g), 3β-(3-N-tert-butoxycarbonyl-N-methylaminopropoxy)-17-(2-spiro-1,3-dioxolane)androst-5-ene was obtained (1.60 g, 80%), after purification by flash chromatography (SiO$_2$, n-hexane:EtOAc 85:15). $^1$H-NMR (300 MHz, DMSO-d$_6$, ppm from TMS): δ 5.30 (1H, m), 3.78 (4H, m), 3.37 (2H, t), 3.18 (2H, t), 3.06 (1H, m), 2.74 (3H, s), 2.36-0.80 (21H, m), 1.37 (9H, s), 0.93 (3H, s), 0.77 (3H, s).

Following the hydroboration procedure described in Prepn. 9 and starting from 3β-(3-N-tert-butoxycarbonyl-N-methylaminopropoxy)-17-(2-spiro-1,3-dioxolane)androst-5-ene (1.50 g), 3β-[3-(N-tert-butoxycarbonyl-N-methyl)aminopropoxy]-17-(2-spiro-1,3-dioxolane)androstan-6β-ol was obtained (1.20 g, 76%) after purification by flash chromatography (SiO$_2$, hexane:EtOAc 1:1). $^1$H-NMR (300 MHz, DMSO-d$_6$, ppm from TMS): δ 4.30 (1H, d), 3.77 (4H, m), 3.45-3.00 (6H, m), 2.74 (3H, s), 2.27-0.50 (22H, m), 1.37 (9H, s), 0.74 (3H, s), 0.71 (3H, s).

Following the IBX oxidation procedure described in Prepn. 11 and starting from 3β-[3-(N-tert-butoxycarbonyl-N-methyl)aminopropoxy]-17-(2-spiro-1,3-dioxolane)androstan-6α-ol (180 mg), 3β-[3-(N-tert-butoxycarbonyl-N-methyl)aminopropoxy]-17-(2-spiro-1,3-dioxolane)-androstan-6-one was obtained (160 mg, 90%), after purification by flash chromatography (SiO$_2$; hexane:EtOAc 6:4). $^1$H-NMR (300 MHz, DMSO-d$_6$, ppm from TMS): δ 3.78 (4H, m), 3.42-3.05 (5H, m), 2.74 (3H, s), 2.33-1.07 (22H, m), 1.37 (9H, s), 0.75 (3H, s), 0.62 (3H, s).

Following the procedure described in Example 4 and starting from 3β-[3-(N-tert-butoxycarbonyl-N-methyl)aminopropoxy]-17-(2-spiro-1,3-dioxolane)androstan-6-one (120 mg), 3β-[3-(N-tert-butoxycarbonyl-N-methyl)aminopropoxy]-6-hydroxyimino-androstane-17-(2-spiro-1,3-dioxolane) was obtained (110 mg, 90%) and used as such for the next step. $^1$H-NMR (300 MHz, DMSO-d$_6$, ppm from TMS): δ 10.34 (1H, s), 3.78 (4H, m), 3.40-3.07 (6H, m), 2.74 (3H, s), 1.96-0.83 (21H, m), 1.37 (9H, s), 0.74 (3H, s), 0.62 (3H, s).

Preparation 77

3β-[3-(N-tert-Butoxycarbonyl-N-methyl)aminopropoxy]-6α-hydroxymethylandrostane-17-(2-spiro-1,3-dioxolane)

Following the procedure described in Prepn. 8 for the Wittig reaction, and starting from 3β-[3-(N-tert-butoxycarbonyl-N-methyl)aminopropoxy]-17-(2-spiro-1,3-dioxolane)androstan-6-one (Prepn. 66, 500 mg), 3β-[3-(N-tert-butoxycarbonyl-N-methyl)amino-propoxy]-6-methylene-androstane-17-(2-spiro-1,3-dioxolane) was obtained (470 mg, 94%), after purification by flash chromatography (SiO$_2$; n-hexane:EtOAc 75:25). $^1$H-NMR (300 MHz, DMSO-d$_6$, ppm from TMS): δ 4.69 (1H, m), 4.40 (1H, m), 3.78 (4H, m), 3.42-3.10 (5H, m), 2.74 (3H, s), 2.27-0.77 (22H, m), 0.73 (3H, s), 0.60 (3H, s).

Following the hydroboration procedure described in Prepn. 9 and starting from 3β-[3-(N-tert-butoxycarbonyl-N-methyl)aminopropoxy]-6-methylene-androstane-17-(2-spiro-1,3-dioxolane) (450 mg), 3β-[3-(N-tert-butoxycarbonyl-N-methyl)aminopropoxy]-6β-hydroxymethylandrostane-17-(2-spiro-1,3-dioxolane) was obtained (281 mg, 60%), after purification by flash chromatography (SiO$_2$; n-hexane:EtOAc 1:1). $^1$H-NMR (300 MHz, DMSO-d$_6$, ppm from TMS): δ 4.24 (1H, t), 3.78 (4H, m), 3.45-1.05 (7H, m), 2.74 (3H, s), 1.90-0.50 (23H, m), 1.37 (9H, s), 0.77 (3H, s), 0.68 (3H, s).

Following the IBX oxidation procedure described in Prepn. 11 and starting from 3β-[3-(N-tert-butoxycarbonyl-N-methyl)aminopropoxy]-6β-hydroxymethylandrostane-17-(2-spiro-1,3-dioxolane) (280 mg), 3β-[3-(N-tert-butoxycarbonyl-N-methyl)aminopropoxy]-6β-formylandrostane-17-(2-spiro-1,3-dioxolane) was obtained (274 mg, 100%), as a glassy solid. $^1$H-NMR (300 MHz, DMSO-d$_6$, ppm from TMS): δ 9.83 (1H, bs), 3.78 (4H, m), 3.45-3.10 (5H, m), 2.75 (3H, s), 2.40-0.60 (23H, m), 1.37 (9H, s), 0.73 (3H, s), 0.63 (3H, s).

Following the epimerization procedure described in Prepn. 11 and starting from 3β-[3-(N-tert-butoxycarbonyl-N-methyl)aminopropoxy]-6β-formylandrostane-17-(2-spiro-1,3-dioxolane) (220 mg), 3β-[3-(N-tert-butoxycarbonyl-N-methyl)aminopropoxy]-6α-formylandrostane-17-(2-spiro-1,3-dioxolane) was obtained (186 mg, 85%), as an oil. $^1$H-NMR (300 MHz, DMSO-d$_6$, ppm from TMS): δ 9.41 (1H, d), 3.78 (4H, m), 3.40-3.05 (5H, m), 2.73 (3H, s), 2.21-0.61 (23H, m), 1.37 (9H, s), 0.77 (3H, s), 0.75 (3H, s).

Following the NaBH$_4$ reduction procedure described in Prepn. 14 and starting from 3β-[3-(N-tert-butoxycarbonyl-N-methyl)aminopropoxy]-6α-formyl-androstane-17-(2-spiro-1,3-dioxolane) (180 mg), 3β-[3-(N-tert-butoxycarbonyl-N-methyl)aminopropoxy]-6β-hydroxymethylandrostane-17-(2-spiro-1,3-dioxolane) was obtained (110 mg, 65%), after purification by flash chromatography (SiO$_2$; n-hexane:EtOAc 55:45), as a glassy solid. $^1$H-NMR (300 MHz, DMSO-d$_6$, ppm from TMS): δ 4.20 (1H, t), 3.78 (4H, m), 3.41-3.00 (7H, m), 2.74 (3H, s), 1.97-0.48 (23H, m), 1.37 (9H, s), 0.75 (3H, s), 0.74 (3H, s).

Preparation 78

3α-(2-Trifluoroacetamidoethylthio)-6-(E)-hydroxyiminoandrostan-17-one

To a solution of triphenylphosphine (2.38 g) in THF (140 mL) cooled at 0° C., diisopropyl azodicarboxylate (1.79 mL) was added dropwise. After stirring for 30 minutes, thioacetic acid (0.65 mL) and androstane-3β,6α,17β-triol (2.00 g) were added. After 2 hrs at 0° C. and overnight at room temperature EtOAc was added. The mixture was washed with water and the organic layer evaporated to dryness. The crude product was purified by flash chromatography (SiO$_2$, cyclohexane:EtOAc 55:45) to give 3α-acetylthioandrostane-6α,17β-diol (1.60 g, 66%). $^1$H-NMR (300 MHz, DMSO-d$_6$, ppm from TMS): δ 4.42 (1H, bb), 4.28 (1H, bb), 3.91 (1H, bb), 3.42 (1H, m), 3.11 (1H, m), 2.28 (3H, s), 2.00-0.80 (20H, m), 0.74 (3H, s), 0.60 (3H, s).

To a stirred suspension of 3α-acetylthioandrostane-6α, 17β-diol (1.40 g) in CH$_2$Cl$_2$ (50 mL), NMNO (1.37 g), TPAP (68 mg) and powdered molecular sieves 4 Å (2.1 g) were added at room temperature. After 2 hrs NMNO (0.7 g), TPAP (34 mg) and molecular sieves 4 Å (1 g) were added again and the reaction was stirred for further 1.5 hrs. The crude product was purified by flash chromatography (SiO$_2$, cyclohexane:EtOAc 7:3) to give 3α-acetylthioandrostane-6,17-dione (1.07 g, 76%). $^1$H-NMR (300 MHz, acetone-d$_6$, ppm from TMS): δ 3.99 (1H, bb), 2.55-1.20 (23H, m), 0.86 (3H, s), 0.79 (3H, s).

To a suspension of 3α-acetylthioandrostane-6,17-dione (1.07 g) in MeOH (30 mL), sodium propanethiolate (0.28 g) was added and the reaction stirred for 20 minutes at room temperature. The mixture was neutralized with 1N HCl. Water was added and the mixture extracted with EtOAc. The organic layer was separated, washed with brine, and dried over Na$_2$SO$_4$ and evaporated to dryness to give 3α-mercaptoandrostane-6,17-dione (943 mg, 100%), used without further purification. $^1$H-NMR (300 MHz, DMSO-d$_6$, ppm from TMS): δ 3.54 (1H, m), 2.77 (1H, m), 2.54 (1H, d), 2.45-1.10 (19H, m), 0.78 (3H, s), 0.66 (3H, s).

To a stirred solution of 3α-mercaptoandrostane-6,17-dione (253 mg) in dry DMF (3 mL), NaH 60% in oil (32 mg) was added at 0° C. After 5 min. a solution of 2-N-methyltrifluoroacetamidoethylchloride (216 mg) in DMF (1 mL) was dropped in 30 min. at room temperature. After 2 hrs, a 5% NaH$_2$PO$_4$ solution was added. The phases were separated and the aqueous phase was extracted with EtOAc. The organic layers were washed with brine, dried over Na$_2$SO$_4$ and evaporated to dryness. The crude product was purified by flash chromatography (SiO$_2$, cyclohexane/EtOAc 65/35) to give 3α-(2-N-methyltrifluoroacetamidoethylthio)androstane-6,17-dione (265 mg, 68%). $^1$H-NMR (300 MHz, DMSO-d$_6$, ppm from TMS): δ 9.25 (1H, t), 3.29 (3H, m), 2.67 (1H, m), 2.60 (2H, t), 2.50-1.10 (20H, m), 0.77 (3H, s), 0.68 (3H, s).

Following the procedure described in Example 1 and starting from 3α-(2-N-methyltrifluoroacetamidoethylthio)androstane-6,17-dione (220 mg), 3α-(3-N-methyltrifluoroacetamidoethylthio)-6(E)-hydroxyiminoandrostan-17-one was obtained (186 mg, 85%) after flash chromatography (SiO$_2$, CH$_2$Cl$_2$/acetone/n-hexane 2/2/6), as an oil. $^1$H-NMR (300 MHz, DMSO-d$_6$, ppm from TMS): δ 10.30 (1H, s), 9.40 (1H, t), 3.23 (4H, m), 2.55-0.90 (21H, m), 0.76 (3H, s), 0.67 (3H, s).

Preparation 79

3α-(3-Trifluoroacetamidoproylthio)-6-(E)-hydroxyiminoandrostan-17-one

Following the same reaction conditions described in Prepn. 78 and starting from 3α-mercaptoandrostane-6,17-dione (Prepn. 65, 865 mg) and 3-N-trifluoroacetamidopropylbromide (695 mg), 3α-(3-trifluoroacetamidopropylthio)-androstane-6,17-dione was obtained (1.18 g, 93%), without any purification, as a white solid. $^1$H-NMR (300 MHz, DMSO-d$_6$, ppm from TMS): δ 9.42 (1H, t), 3.23 (3H, m), 2.70-1.17 (24H, m), 0.77 (3H, s), 0.68 (3H, s).

Following the procedure described in Example 1 and starting from 3α-(3-trifluoroacetamidopropylthio)androstane-6,17-dione (394 mg) and hydroxylamine hydrochloride (64 mg), 3α-(3-trifluoroacetamidopropylthio)-6-(E)-hydroxyiminoandrostane-17-one (203 mg, 50%) was obtained. $^1$H-NMR (300 MHz, DMSO-d$_6$, ppm from TMS): δ 10.39 (1H, s), 9.42 (1H, t), 3.23 (4H, m), 2.55-0.90 (23H, m), 0.76 (3H, s), 0.67 (3H, s).

Preparation 80

3α-(4-Trifluoroacetamidobutylthio)-6-(E)-hydroxyiminoandrostan-17-one

Using the same reaction conditions described in Prepn. 78 and starting from 3α-mercaptoandrostane-6,17-dione and 4-N-trifluoroacetamidobutylbromide, 3α-(4-trifluoroacetamidobutylthio)androstane-6,17-dione was obtained (0.68 g, 85%), without any purification, as a white solid. $^1$H-NMR (300 MHz, DMSO-d$_6$, ppm from TMS): δ 9.40 (1H, t), 3.20 (3H, m), 2.75-1.10 (26H, m), 0.77 (3H, s), 0.68 (3H, s).

Following the reaction conditions described in Example 1 and starting from 3α-(4-trifluoroacetamidobutylthio)androstane-6,17-dione and hydroxylamine hydrochloride, 3α-(4-trifluoroacetamidobutylthio)-6-(E)-hydroxyiminoandrostane-17-one (238 mg, 40%) was obtained. $^1$H-NMR (300 MHz, DMSO-d$_6$, ppm from TMS): δ 10.35 (1H, s), 9.40 (1H, t), 3.20 (4H, m), 2.55-0.90 (25H, m), 0.76 (3H, s), 0.67 (3H, s).

Preparation 81

3α-(3-N-Methylaminopropylthio)androstane-6,17-dione fumarate

By using the same reaction conditions described in Prepn. 78 and starting from 3α-mercaptoandrostane-6,17-dione (Prepn. 65, 253 mg) and 3-(N-methyl)trifluoro-acetamidopropylchloride (216 mg), 3α-(3-N-methyltrifluoroacetamido-propylthio)androstane-6,17-dione was obtained (265 g, 68%) as a white solid. $^1$H-NMR (300 MHz, DMSO-d$_6$, ppm from TMS): δ 3.43 (2H, m), 3.24 (1H, m), 3.07 (1.8H, q), 2.93 (1.2H, bs), 2.70-1.15 (24H, m), 0.77 (3H, s), 0.68 (3H, s).

Following the same reaction conditions described in Example 1 and starting from 3α-(3-N-methyltrifluoroacetamidopropylthio)androstane-6,17-dione (265 mg) and hydroxylamine hydrochloride (41 mg), 3α-(3-trifluoroacetamidopropylthio)-6-(E)-hydroxyiminoandrostane-17-one (116 mg, 43%) was obtained. $^1$H-NMR (300 MHz, DMSO-d$_6$, ppm from TMS): δ 10.39 (1H, s), 3.44 (2H, m), 3.26 (2H, m), 3.07 (1.8H, q), 2.94 (1.2H, bs), 2.56-0.93 (23H, m), 0.77 (3H, s), 0.68 (3H, s).

Preparation 82

3α-(3-Trifluoroacetamidopropylthio)-6-methyleneandrostane-17-one

To a stirred solution of 3α-acetylthioandrostane-6,17-dione (Prepn. 78, 600 mg) in THF (8 mL) cooled at −50° C., a solution of ylide prepared from methyltriphenylphosphonium bromide (1.47 g) in THF dry (8 mL) at −50° C. and potassium tert-butoxide (484 mg), was added. After 2 h the temperature was raised to room temperature. The mixture was quenched by addition of 5% NaH$_2$PO$_4$ aqueous solution and extracted with EtOAc (2×60 mL). The combined organic extracts were washed with 5% NaH$_2$PO$_4$ aqueous solution, brine, dried over Na$_2$SO$_4$, and evaporated to dryness. The residue was purified by flash chromatography (n-hexane/EtOAc 9/1) to give 3α-acetylthio-6-methyleneandrostan-17-one (210 mg, 35% yield) and 3α-mercapto-6-methyleneandrostan-17-one (208 mg, 35% yield). $^1$H-NMR (300 MHz, DMSO-d$_6$, ppm from TMS): 3α-acetylthio-6-methyleneandrostane-17-one: δ 4.73 (1H, m), 4.39 (1H, m), 3.96 (1H, m), 2.44-0.84 (20H, m), 2.29 (3H, s), 0.75 (3H, s), 0.66 (3H, s); 3α-mercapto-6-methyleneandrostane-17-one: δ 4.73 (1H, m), 4.38 (1H, m), 3.57 (1H, m), 2.52 (1H, d), 2.45-0.95 (20H, m), 0.76 (3H, s), 0.63 (3H, s).

To a solution of 3α-acetylthio-6-methyleneandrostane-17-one (210 mg) in MeOH (3 mL), 1N NaOH (0.6 mL) was added. After 1 h at room temperature 5% NaH$_2$PO$_4$ aqueous solution was added and the mixture extracted with Et$_2$O (2×20 mL). The combined organic extracts were washed with brine, dried over Na$_2$SO$_4$ and evaporated to dryness to give 3α-mercapto-6-methyleneandrostane-17-one (185 mg, 100%).

By using the same reaction conditions described in Prepn. 78 and starting from 3α-mercapto-6-methyleneandrostane-17-one (100 mg) and N-trifluoroacetamidopropylbromide (147 mg), 3α-(3-trifluoroacetamidopropylthio)-6-methyleneandrostane-17-one was obtained (104 mg, 70%) as a white solid, after purification by flash chromatography (SiO$_2$, n-hexane/EtOAc 75/25). $^1$H-NMR (300 MHz, DMSO-d$_6$, ppm from TMS): δ 9.43 (1H, bb), 4.72 (1H, m), 4.41 (1H, m), 3.24 (3H, m), 2.50-0.86 (24H, m), 0.75 (3H, s), 0.65 (3H, s).

Preparation 83

3α-(3-N-Methyltrifluoroacetamidopropylthio)-6-methyleneandrostane-17-one

By using the same reaction conditions described in Prepn. 78 and starting from 3α-mercapto-6-methyleneandrostane-17-one (Prepn. 69, 140 mg) and N-methyltrifluoroacetamidopropylbromide (178 mg), 3α-(3-N-methyltrifluoroacetamidopropylthio)-6-methyleneandrostane-17-one was obtained (105 mg, 60%) as a white solid, after purification by flash chromatography (SiO$_2$, n-hexane/EtOAc 75/25). $^1$H-NMR (300 MHz, DMSO-d$_6$, ppm from TMS): δ 4.73 (1H, m), 4.41 (1H, m), 3.44 (2H, m), 3.25 (1H, m), 3.07 (2.0H, br), 2.94 (1.0H, br), 2.50-0.89 (24H, m), 0.75 (3H, s), 0.65 (3H, s).

Preparation 84

3α-[(S)-3-Trifluoroacetamidopropylsulfinyl]-6-methyleneandrostane-17-one

To a solution of 3α-(3-trifluoroacetamidopropylthio)-6-methyleneandrostane-17-one (Prepn. 82, 286 mg) in dry CH$_3$CN (14 mL), NMO (213 mg) and molecular sieves (4 Å, 280 mg) were added followed by the addition of TPAP (10.6 mg). After 1 h at room temperature the mixture was evaporated to dryness. The residue was purified by flash chromatography (SiO$_2$, n-hexane/acetone 65/35) to give 3α-[(S)-3-trifluoroacetamidopropylsulfinyl]-6-methyleneandrostane-17-one (100 mg, 34% yield). $^1$H-NMR (300 MHz, DMSO-d$_6$, ppm from TMS): δ 9.43 (1H, bb), 4.72 (1H, m), 4.41 (1H, m), 3.24 (3H, m), 2.50-0.86 (24H, m), 0.75 (3H, s), 0.65 (3H, s).

Preparation 85

3α-[(R)-3-Trifluoroacetamidopropylsulfinyl]-6-methyleneandrostane-17-one

The title compound was obtained from a second fraction of the column described in Prepn. 84 (70 mg, 24% yield). $^1$H-NMR (300 MHz, DMSO-d$_6$, ppm from TMS): δ 9.43 (1H, bb), 4.70 (1H, m), 4.41 (1H, m), 3.24 (3H, m), 2.50-0.86 (24H, m), 0.75 (3H, s), 0.65 (3H, s).

Preparation 86

7α-Methoxymethylandrostane-3,17-dione

Following the procedure described in Prepn. 10 and starting from 3,3:17,17-bis(ethylendioxy)-7α-hydroxymethylandrostane (Prepn. 49) (2.00 g), the title compound was obtained in 70% yield. $^1$H-NMR (300 MHz, acetone-d$_6$, ppm from TMS): δ 3.30 (3H, s), 3.28 (2H, m), 2.53-0.75 (21H, m), 1.13 (3H, s), 0.90 (3H, s).

Preparation 87

7α-Methoxyandrostane-3,17-dione

Following the procedure described in Prepn. 10 and starting from 3,3:17,17-bis(ethylendioxy)-7α-hydroxyandrostane (Prepn. 45) (1.5 g), the title compound was obtained in 68% yield. $^1$H-NMR (300 MHz, acetone-d$_6$, ppm from TMS): δ 3.35 (3H, s), 2.58-1.00 (21H, m), 0.96 (3H, s), 0.78 (3H, s).

Preparation 88

3β-(2-Trifluoroacetamidoethylthio)-6-(E)-hydroxyiminoandrostane-17-one

To a solution of PPh$_3$ (15.0 g) and DIAD (9.0 mL) in THF (250 mL) at 0° C., androstane-3β,6α,17β-triol (5.0 g) and formic acid (2.1 mL) were added then the mixture stirred for 1 h. The solvent was evaporated to dryness and the crude purified by flash chromatography (SiO$_2$, n-hexane/EtOAc 1/1) to give 3α-formyloxyandrostane-6α,17β-diol in 50% yield as a white solid. $^1$H-NMR (300 MHz, DMSO-d$_6$, ppm from TMS): δ 8.20 (1H, s), 5.10 (1H, bs), 4.35 (1H, d), 4.24 (1H, d), 3.40 (1H, m), 3.15 (1H, m), 2.10-0.80 (20H, m), 0.74 (3H, s), 0.60 (3H, s).

To a stirred solution of 3α-formyloxyandrostane-6α,17β-diol (2.50 g) in CH$_2$Cl$_2$ (100 mL), NMO (2.7 g) and molecular sieves (4 Å, 3.8 g) were added followed by the addition of TPAP (270 mg). After stirring for 2 h at room temperature, the solvent was removed and the mixture purified by flash chromatography (SiO$_2$, n-hexane/EtOAc 65/35) to give 3α-formyloxyandrostane-6,17-dione in 90% yield as a white solid. $^1$H-NMR (300 MHz, acetone-d$_6$, ppm from TMS): δ 8.15 (1H, s), 5.12 (1H, bs), 2.40-0.90 (20H, m), 0.77 (3H, s), 0.66 (3H, s).

To a solution of 3α-formyloxyandrostane-6,17-dione (2.20 g) in MeOH (100 mL), K$_2$CO$_3$ (2.70 g) was added and the mixture stirred at room temperature for 10 minutes, then HCl 1N (20 mL) was added, the phases were separated and the aqueous one extracted with EtOAc (2×). The combined organic extracts were washed with H$_2$O, dried over Na$_2$SO$_4$ and evaporated to dryness to give 3α-hydroxyandrostane-6,17-dione (quantitative yield), which was used in the next step without purification. $^1$H-NMR (300 MHz, DMSO-d$_6$, ppm from TMS): δ 4.35 (1H, d), 3.40 (1H, m), 2.40-0.95 (20H, m), 0.80 (3H, s), 0.69 (3H, s).

3α-Methanesulfonyloxyandrostane-6,17-dione was obtained in quantitative yield following the procedure described in Prepn. 76. $^1$H-NMR (300 MHz, acetone-d$_6$, ppm from TMS): δ 5.05 (1H, m), 3.10 (3H, s), 2.70-1.30 (20H, m), 0.88 (3H, s), 0.79 (3H, s).

To a solution of 3α-methanesulfonyloxyandrostane-6,17-dione (2.00 g) in dry DMF (25 mL), thioacetic acid potassium salt (1.20 g) was added. The mixture was heated to 70° C. for 3 h. After cooling, 5% NaH$_2$PO$_4$ was added and extracted with EtOAc (3×). The organic extracts were washed with brine, dried over Na$_2$SO$_4$ and evaporated to dryness. The residue was purified by flash chromatography (SiO$_2$, n-hexane/EtOAc 8/2) to give 3β-acetylthioandrostane-6,17-dione in 55% yield as a yellow solid. $^1$H-NMR (300 MHz, acetone-d$_6$, ppm from TMS): δ 4.50 (1H, m), 3.10 (3H, s), 2.50-0.90 (20H, m), 0.88 (3H, s), 0.77 (3H, s).

Following the procedure described in Prepn. 78 and starting from 3β-acetylthioandrostane-6,17-dione, 3β-mercaptoandrostane-6,17-dione was obtained in 80% yield. $^1$H-NMR (300 MHz, DMSO-d$_6$, ppm from TMS): δ 2.70-1.00 (22H, m), 0.78 (3H, s), 0.67 (3H, s).

Following the procedure described in Prepn. 78 and starting from 3β-mercaptoandrostane-6,17-dione and 2-N-trifluoroacetamidoethylchloride, 3β-(2-N-trifluoroacetamidoethylthio)androstane-6,17-dione was obtained in 70% yield after purification by flash chromatography (SiO$_2$, n-hexane/EtOAc 7/3). $^1$H-NMR (300 MHz, DMSO-d$_6$, ppm from TMS): δ 9.25 (1H, t), 3.29 (3H, m), 2.67 (1H, m), 2.60 (2H, t), 2.50-1.10 (20H, m), 0.77 (3H, s), 0.68 (3H, s).

Following the procedure described in Example 1 and starting from 3β-(2-N-methyltrifluoroacetamidoethylthio)androstane-6,17-dione (220 mg), 3α-(2-N-trifluoroacetamidoethylthio)-6(E)-hydroxyiminoandrostane-17-one was obtained in 85% yield after flash chromatography (SiO$_2$, CH$_2$Cl$_2$/acetone/n-hexane 2/2/6). $^1$H-NMR (300 MHz, DMSO-d$_6$, ppm from TMS): δ 10.30 (1H, s), 9.40 (1H, t), 3.23 (4H, m), 2.55-0.90 (21H, m), 0.76 (3H, s), 0.67 (3H, s).

Preparation 89

3β-(3-Trifluoroacetamidopropylthio)-6-(E)-hydroxyiminoandrostane-17-one

Following the same reaction conditions described in Prepn. 78 and starting from 3β-mercaptoandrostane-6,17-dione (Prepn. 88, 870 mg) and 3-N-trifluoroacetamidopropylbromide (700 mg), 3β-(3-trifluoroacetamidopropylthio)androstane-6,17-dione was obtained (1.2 g, 93%) as a white solid. $^1$H-NMR (300 MHz, DMSO-d$_6$, ppm from TMS): δ 9.40 (1H, t), 3.23 (3H, m), 2.70-1.17 (24H, m), 0.77 (3H, s), 0.68 (3H, s).

Following the procedure described in Example 1 and starting from 3β-(3-trifluoroacetamidopropylthio)androstane-6,17-dione (395 mg) and hydroxylamine hydrochloride (65 mg), 3β-(3-trifluoroacetamidopropylthio)-6-(E)-hydroxyiminoandrostane-17-one (200 mg, 50%) was obtained. $^1$H-NMR (300 MHz, DMSO-d$_6$, ppm from TMS): δ 10.40 (1H, s), 9.42 (1H, t), 3.23 (4H, m), 2.55-0.90 (23H, m), 0.76 (3H, s), 0.67 (3H, s).

Preparation 90

3β-(4-Trifluoroacetamidobutylthio)-6-(E)-hydroxyiminoandrostan-17-one

Using the same reaction conditions described in Prepn. 78 and starting from 3β-mercaptoandrostane-6,17-dione and 4-N-trifluoroacetamidobutylbromide, 3β-(4-trifluoroacetamidobutylthio)androstane-6,17-dione was obtained (0.70 g, 85%) as a white solid. $^1$H-NMR (300 MHz, DMSO-d$_6$, ppm from TMS): δ 9.39 (1H, t), 3.20 (3H, m), 2.75-1.10 (26H, m), 0.77 (3H, s), 0.68 (3H, s).

Following the reaction conditions described in Example 1 and starting from 3β-(4-trifluoroacetamidobutylthio)androstane-6,17-dione and hydroxylamine hydrochloride, 3β-(4-trifluoroacetamidobutylthio)-6-(E)-hydroxyiminoandrostane-17-one (240 mg, 40%) was obtained. $^1$H-NMR (300 MHz, DMSO-d$_6$, ppm from TMS): δ 10.35 (1H, s), 9.40 (1H, t), 3.20 (4H, m), 2.55-0.90 (25H, m), 0.76 (3H, s), 0.67 (3H, s).

Preparation 91

6α-Hydroxymethyl-7α-hydroxyandrostane-3,17-dione

To a stirred solution of 3,3:17,17-bis(ethylendioxy)-6α-hydroxymethylandrostane-7-one (Prepn. 52) (2.00 g) in MeOH (100 mL) NaBH$_4$ (270 mg) was added at 0° C. The temperature was raised to rt. After 1 h the mixture was quenched by addition of 5% NaH$_2$PO$_4$ and extracted with CH$_2$Cl$_2$. The combined organic extracts were washed with brine, dried over Na$_2$SO$_4$ and evaporated to dryness. The residue was dissolved in dioxane (25 mL) and 1N HCl (8 mL) was added and the resulting mixture stirred at room temperature for 1 h. After evaporation to dryness, the residue was purified by flash chromatography (SiO$_2$, n-hexane/CH$_2$Cl$_2$/acetone 50/25/25) to give the title compound in 73% yield. $^1$H-NMR (300 MHz, DMSO-d$_6$, ppm from TMS): δ 4.36 (1H, t), 4.26 (1H, d), 3.86 (1H, m), 3.43 (2H, m), 2.40-1.10 (19H, m), 0.99 (3H, s), 0.79 (3H, s).

Preparation 92

(S)-2-Aminopropoxyamine dihydrochloride

To a solution of (S)-(+)-2-amino-1-propanol (2.00 g) and triethylamine (4.27 mL) in MeOH (20 mL) at 0° C., di-tert-butyl dicarbonate (6.42 g) was added. After stirring at room temperature for 12 h, the solvent was evaporated. The residue was diluted with CH$_2$Cl$_2$, washed with water and the organic phase was evaporated to dryness to give (S)-2-(tert-butoxycarbonyl)amino-1-propanol (4.6 g, 100%) which was used without further purification in the next step. $^1$H-NMR (300 MHz, DMSO-d$_6$, ppm from TMS): δ 6.40 (1H, d), 4.51 (1H, m), 3.64 (1H, m), 3.10 (1H, m), 3.34 (1H, m), 1.46 (9H, s), 1.02 (3H, d).

To a solution of (S)-2-(tert-butoxycarbonyl)amino-1-propanol (4.95 g), triphenyl phosphine (11.12 g) and N-hydroxyphthalimide (6.91 g) in THF (130 mL) at 0° C., diisopropyl azodicarboxylate (8.36 g) was added. After stirring at room temperature for 3 h, the solvent was evaporated and the crude product purified by flash chromatography (SiO$_2$, n-hexane:EtOAc 1:1) to give (S)-2-(tert-butoxycarbonyl)amino-1-phthalimidoxypropane (7.69 g, 85%). $^1$H-NMR (300 MHz, DMSO-d$_6$, ppm from TMS): δ 7.81 (4H, m), 4.40 (1H, m), 3.82 (1H, m), 3.61 (1H, m), 1.24 (9H, s), 1.10 (3H, d).

To a solution of S)-2-(tert-butoxycarbonyl)amino-1-phthalimidoxypropane (7.69 g) in MeOH (70 mL), hydrazine hydrate (3.5 mL) was added. After 1 h the white solid was filtered, the solvent evaporated and the crude product purified by flash chromatography (SiO$_2$, CH$_2$Cl$_2$:MeOH 95:5) to give (S)-2-(tert-butoxycarbonyl)aminopropoxyamine (3.40 g. 75%). $^1$H-NMR (300 MHz, DMSO-d$_6$, ppm from TMS): δ 6.65 (1H, bb), 5.96 (2H, bs), 3.71 (1H, m), 3.32 (2H, m), 1.32 (9H, s), 0.96 (3H, d).

To a solution of (S)-2-(tert-butoxycarbonyl)aminopropoxyamine (3.40 g) in EtOAc (30 mL) at 0° C., a 5.9 M HCl solution in EtOAc (10 mL) was added. After 30 min the white solid was filtered to give the title compound (2.40 g. 82%). $^1$H-NMR (300 MHz, DMSO-$d_6$, ppm from TMS): δ 11.12 (2H, bs), 8.48 (2H, bs), 4.08 (2H, m), 3.52 (1H, m), 1.25 (3H, m).

Preparation 93

(R)-2-Aminopropoxyamine dihydrochloride

Following the procedure described in Prepn. 92 and starting from (R)-(−)-2-amino-1-propanol (2.02 g), (R)-2-(tert-butoxycarbonyl)-aminopropanol was obtained (4.24 g, 90%) and used without purification in the next step. $^1$H-NMR (300 MHz, DMSO-$d_6$, ppm from TMS): δ 6.40 (1H, d), 4.51 (1H, m), 3.64 (1H, m), 3.10 (1H, m), 3.34 (1H, m), 1.46 (9H, s), 1.02 (3H, d).

Following the procedure described in Prepn. 92 and starting from (R)-2-(tert-butoxycarbonyl)aminopropanol (4.12 g), (R)-2-(tert-butoxycarbonyl)amino-1-phthalimidoxypropane (6.10 g, 81%) was obtained after purification by flash chromatography (SiO$_2$, n-hexane:CH$_2$Cl$_2$:acetone 6:3:1). $^1$H-NMR (300 MHz, DMSO-$d_6$, ppm from TMS): δ 7.81 (4H, m), 4.40 (1H, m), 3.82 (1H, m), 3.61 (1H, m), 1.24 (9H, s), 1.10 (3H, d).

Following the procedure described in Prepn. 92 and starting from (R)-2-(tert-butoxycarbonyl)amino-1-phthalimidoxypropane (6.00 g) in MeOH (40 mL), (R)-2-(tert-butoxycarbonyl)aminopropoxyamine was obtained as a green oil (1.80 g, 51.5%), after purification by flash chromatography (SiO$_2$, CH$_2$Cl$_2$:MeOH 97.5:2.5). $^1$H-NMR (300 MHz, DMSO-$d_6$, ppm from TMS): δ 6.65 (1H, bb), 5.96 (2H, bs), 3.71 (1H, m), 3.32 (2H, m), 1.32 (9H, s), 0.96 (3H, d).

Following the procedure described in Prepn. 92 and starting from (R)-2-(tert-butoxycarbonyl)aminopropoxyamine (1.80 g), (R)-2-aminopropoxyamine dihydrochloride was obtained (1.20 g, 80%) as a white solid. $^1$H-NMR (300 MHz, DMSO-$d_6$, ppm from TMS): δ 11.12 (2H, bs), 8.48 (2H, bs), 4.08 (2H, m), 3.52 (1H, m), 1.25 (3H, m).

Preparation 94

3-Amino-2-methyl-1-propoxyamine dihydrochloride

To a solution of potassium tert-butoxide (2.78 g) in dry DMSO (40 mL), tert-butyl-N-hydroxycarbamate (3.00 g) was added. After 5 minutes methyl 2-bromoisobutyrate (2.97 g) in DMSO (50 mL) was added dropwise, maintaining the temperature below 30° C. After 0.5 hrs at room temperature the reaction was poured into ice/water (120 mL) and extracted three times with EtOAc. The combined organic layers were washed with water, brine, dried over Na$_2$SO$_4$ and the solvent evaporated to dryness to give methyl 2-(tert-butyl-N-hydroxycarbamoyl)isobutyrate (5.04 g, 96%) which was used without purification in the next step. $^1$H-NMR (300 MHz, DMSO-$d_6$, ppm from TMS): δ 9.53 (1H, s), 3.66 (3H, s), 1.40 (9H, s), 1.33 (6H, s).

To a stirred solution of methyl 2-(tert-butyl-N-hydroxycarbamoyl)-isobutyrate (2.00 g) in dry CH$_2$Cl$_2$ (20 mL) at −78° C. under N$_2$, 1M DIBAH in CH$_2$Cl$_2$ (17.14 mL) was added dropwise. The mixture was stirred at −78° C. for 3 hours and quenched by careful addition of MeOH (28 mL), Et$_2$O (30 mL) and saturated aqueous solution of sodium potassium tartrate (30 mL). After 1 h the mixture was extracted three times with Et$_2$O. The combined organic layers were washed with water, brine, dried over Na$_2$SO$_4$ and the solvent evaporated to dryness to give 2-(tert-butyl-N-hydroxycarbamoyl)-isobutyraldehyde (1.23 g, 71%). $^1$H-NMR (300 MHz, DMSO-$d_6$, ppm from TMS): δ 10.02 (1H, s), 9.58 (1H, s), 1.38 (9H, s), 1.17 (6H, s).

To a solution of 2-(tert-butyl-N-hydroxycarbamoyl)isobutyraldehyde (1.20 g) in MeOH (15 mL) under N$_2$, 4 Å molecular sieves (120 mg) and 4-methoxybenzylamine (0.846 mL) were added. After 1 h sodium cyanoborohydride (650 mg) was added and the resulting mixture was stirred for 1 h at room temperature. The molecular sieves were filtered and the solvent evaporated to dryness. The crude product was dissolved in 5% aqueous NaHCO$_3$ solution, extracted with Et$_2$O (3×) and washed with a saturated aqueous solution of NaCl. The organic layer was dried over Na$_2$SO$_4$ and evaporated to dryness. The crude product was purified by flash chromatography (SiO$_2$, CH$_2$Cl$_2$/MeOH/26% NH$_4$OH 94/6/0.6) to give 1-(tert-butyl-N-hydroxycarbamoyl)-2-methyl-[N-(4-methoxybenzyl)]-2-propanamine (627 mg, 32%) $^1$H-NMR (300 MHz, DMSO-$d_6$, ppm from TMS): δ 9.85 (1H, bs), 7.21 (2H, m), 6.84 (2H, m), 3.71 (2H, s), 3.57 (2H, m), 2.38 (2H, s), 1.38 (9H, s), 1.09 (6H, s).

A mixture of 1-(tert-butyl-N-hydroxycarbamoyl)-2-methyl-[N-(4-methoxybenzyl)]-2-propanamine (334 mg) and 20% Pd(OH)$_2$/C (83 mg) in MeOH (4.66 mL) and acetic acid (0.117 mL) was stirred under H$_2$ at 55 psi pressure for 5 h. The mixture was filtered through Celite and the filtrate evaporated to dryness. The crude residue was dissolved in 2 N HCl in Et$_2$O (30 mL), stirred overnight and concentrated. The crude product was filtered, washed with EtOH/Et$_2$O 1/9 and triturated overnight with EtOAc to give title compound (0.110 g, 60%). $^1$H-NMR (300 MHz, DMSO-$d_6$, ppm from TMS): δ 7.90 (4H, bs), 3.03 (2H, s), 6.84 (2H, m), 1.23 (6H, s).

Preparation 95

3-Amino-2-methyl-2-propoxyamine hydrochloride

To a solution of 2-methyl-2-propen-1-ol (0.856 g) triphenyl phosphine (4.67 g) and N-hydroxyphthalimide (2.90 g) in THF (90 mL), at 0° C., diisopropyl azodicarboxylate (3.51 mL) was added. After stirring for 2 hours, the solvent was evaporated and the crude product was purified by flash chromatography (SiO$_2$, cyclohexane/EtOAc 85/15) to give 2-(2-methylallyloxy)isoindole-1,3-dione (2.13 g, 83%). $^1$H-NMR (300 MHz, DMSO-$d_6$, ppm from TMS): δ 7.80 (4H, bs), 5.02 (2H, d), 4.54 (2H, s), 1.83 (3H, s).

To a solution of 2-(2-methylallyloxy)isoindole-1,3-dione (0.705 g) chloroacetonitrile (0.61 mL) in CH$_3$COOH (0.56 mL) at 0° C., 98% H$_2$SO$_4$ (3.5 mL) was added. After 1.5 h the mixture was quenched by careful addition of ice and 5% aqueous NaHCO$_3$ solution to pH 7 and extracted with CH$_2$Cl$_2$ (3×). The combined organic extracts were washed with H$_2$O, dried over Na$_2$SO$_4$, and evaporated to dryness to give 2-chloro-N-[2-(1,3-dioxo-1,3-dihydroisoindol-2-yloxy)-1,1-dimethylethyl]acetamide (0.93 g, 92%) which was used as such in the next step. $^1$H-NMR (300 MHz, DMSO-$d_6$, ppm from TMS): δ 7.75 (4H, bb), 4.32 (2H, s), 3.87 (2H, s), 1.35 (6H, s).

A solution of 2-chloro-N-[2-(1,3-dioxo-1,3-dihydroisoindol-2-yloxy)-1,1-dimethylethyl]acetamide (0.49 g) in 6 N HCl (10 mL) was refluxed for 1.5 hrs and then concentrated. The crude product was dissolved in water and washed with Et$_2$O. The aqueous solution was evaporated to dryness and the crude product was triturated overnight with EtOH to give the title compound. $^1$H-NMR (300 MHz, DMSO-$d_6$, ppm from TMS): δ 11.02 (2H, bs), 8.31 (2H, bs), 4.05 (2H, s), 1.23 (6H, s).

Preparation 96

7-Difluoromethyleneandrostane-3,17-dione

Using the same reaction conditions described in Prepn. 31 and starting from 3,3:17,17-bis(ethylendioxy)androstane-7-one (Prepn. 42, 353 mg), 3,3:17,17-bis(ethylendioxy)-7-difluoromethyleneandrostane was obtained after flash chromatography (SiO$_2$; cyclohexane:CH$_2$Cl$_2$:acetone 8:1:1) (115 mg, 30%). $^1$H-NMR (300 MHz, acetone-d$_6$, ppm from TMS): δ 3.85 (8H, m), 2.10-0.9 (20H, m), 0.96 (3H, s), 0.83 (3H, s).

Following the reaction conditions described in Prepn. 31 and starting from 3,3:17,17-bis(ethylendioxy)-7-difluoromethyleneandrostane (135 mg) the title compound was obtained (96 mg, 90%) after purification by flash chromatography (SiO$_2$, n-hexane/Et$_2$O 1/1). $^1$H-NMR (300 MHz, DMSO-d$_6$, ppm from TMS): δ 2.61-1.10 (m, 20H), 1.22 (s, 3H), 0.89 (s, 3H).

Preparation 97

3β-[3-(N-Carbobenzyloxy-N-methylamino)propionyloxy]-6-(E)-hydroxyiminoandrostan-17-one Following the procedure described in Prepn. 68 and starting from 3β-hydroxyandrostane-6,17-dione (Prepn. 68, 0.50 g) and N-carbobenzyloxy-N-methyl-3-aminopropionic acid (0.39 g), after purification by flash chromatography (SiO$_2$; EtOAc:n-hexane 6:4) 3β-(N-carbobenzyloxy-N-methyl-3-aminopropionyloxy)androstane-6,17-dione (0.79 g, 90%) was obtained. $^1$H-NMR (300 MHz, DMSO-d$_6$, ppm from TMS): δ 7.32 (5H, m), 5.05 (2H, s), 4.56 (1H, m), 3.50-0.90 (27H, m), 0.77 (3H, s), 0.67 (3H, s).

The procedure described in Prepn. 20 was followed starting from 3β-(N-carbobenzyloxy-N-methyl-3-aminopropionyloxy)androstane-6,17-dione (0.70 g) and hydroxylamine hydrochloride. The residue was purified by flash chromatography (SiO$_2$, n-hexane/acetone 60/40) to give the title compound (0.43 g, 60%). $^1$H-NMR (300 MHz, DMSO-d$_6$, ppm from TMS): δ 10.31 (1H, s), 7.30 (5H, m), 5.05 (2H, s), 4.56 (1H, m), 3.50-0.87 (27H, m), 0.78 (3H, s), 0.68 (3H, s).

Preparation 98

3β-[(2,2-Dimethyl)-3-(carbobenzyloxyamino)propionyloxy]-6-(E)-hydroxyiminoandrostane-17-one Following the procedure described in Prepn. 68 and starting from 3β-hydroxyandrostane-6,17-dione (Prepn. 68, 0.50 g) and 3-(benzyloxycarbonylamino)-2,2-dimethylpropanoic acid (0.41 g), after purification by flash chromatography (SiO$_2$; EtOAc:n-hexane 6:4) to give 3β-[(2,2-dimethyl)-3-(carbobenzyloxyamino)propionyloxy]-androstane-6,17-dione (0.81 g, 90%) was obtained. $^1$H-NMR (300 MHz, DMSO-d$_6$, ppm from TMS): δ 7.34 (5H, m), 5.07 (2H, s), 7.01 (1H, m), 4.57 (1H, m), 2.50-1.10 (22H, m), 1.10 (6H, s), 0.78 (3H, s), 0.70 (3H, s).

Following the procedure described in Preparation 20 and starting from 3β-[(2,2-dimethyl)-3-N-carbobenzoxyamino-propionyloxy]androstane-6,17-dione (0.80 g), after purification by flash chromatography (SiO$_2$, n-hexane/acetone 60/40) the title compound (0.49 g, 60%) was obtained. $^1$H-NMR (300 MHz, DMSO-d$_6$, ppm from TMS): δ 10.34 (1H, s), 7.34 (5H, m), 5.07 (2H, s), 7.01 (1H, m), 4.57 (1H, m), 3.00-1.10 (22H, m), 1.10 (6H, s), 0.78 (3H, s), 0.72 (3H, s).

Biological Results

To test the inhibition of the enzymatic activity of the Na$^+$, K$^+$-ATPase, the Na$^+$, K$^+$-ATPase was purified according to Jorghensen (Jorghensen P., BBA, 1974, 356, 36) and Erdmann (Erdmann E. et al., Arzneim. Forsh., 1984, 34, 1314) and the inhibition was measured as % of hydrolysis of $^{32}$P-ATP in presence and in absence of the tested compound (Mall F. et al., Biochem. Pharmacol., 1984, 33, 47; see Table 1).

TABLE 1

Dog Kidney Na$^+$, K$^+$-ATPase Inhibition

| Example n° | Na$^+$, K$^+$-ATPase Inhibition IC$_{50}$, μM | Example n° | Na$^+$, K$^+$-ATPase Inhibition IC$_{50}$, μM |
|---|---|---|---|
| I-aa | 0.33 | I-ab | 2.9 |
| I-ac | 1.1 | I-ad | 0.54 |
| I-ae | 11 | I-af | 0.62 |
| I-ag | 5.4 | I-ah | 0.042 |
| I-ai | 0.084 | I-aj | 1.6 |
| I-ak | 3.0 | I-al | 0.53 |
| I-am | 0.32 | I-an | 0.39 |
| I-ao | 0.18 | I-ap | 3.0 |
| I-aq | 0.50 | I-ar | 16 |
| I-as | 0.63 | I-at | 0.63 |
| I-au | 0.41 | I-av | 0.024 |
| I-aw | 0.017 | I-ax | 1.7 |
| I-ay | 43 | I-az | 6.0 |
| I-ba | 0.30 | I-bb | 0.87 |
| I-bc | 0.91 | I-bd | 0.20 |
| I-be | 0.16 | I-bf | 45 |
| I-bg | 1.1 | I-bh | 0.19 |
| I-bi | 1.7 | I-bj | 0.77 |
| I-bk | 64 | I-bl | 0.85 |
| I-bm | 3.6 | I-bn | 5.1 |
| I-bo | 0.079 | I-bp | 0.040 |
| I-bq | 0.099 | I-br | 0.21 |
| I-bs | 0.13 | I-bt | 12 |
| I-bu | 3.8 | I-bv | 0.52 |
| I-bw | 6.0 | I-bx | 0.40 |
| I-by | 0.64 | I-bz | 1.1 |
| I-ca | 0.91 | I-cb | 0.13 |
| I-cc | 2.1 | I-cd | 0.012 |
| I-ce | 0.65 | I-cf | 1.3 |
| I-cg | 2.6 | I-ch | 0.20 |
| I-ci | 0.33 | I-cj | 0.38 |
| I-ck | 0.57 | I-cl | 0.69 |
| I-cm | 4.0 | I-cn | 1.9 |
| I-co | 1.1 | I-cp | 1.3 |
| I-cq | 1.2 | I-cr | 0.43 |
| I-cs | 1.1 | I-ct | 1.4 |
| I-cu | 0.39 | I-cv | 0.74 |
| I-cw | 2.3 | I-cx | 0.61 |
| I-cy | 85 | I-cz | 1.1 |
| I-da | 1.0 | I-db | 2.9 |
| I-dc | 1.1 | I-dd | 1.1 |
| I-de | 1.2 | I-df | 2.0 |
| I-dg | 0.39 | I-dh | 1.1 |
| I-di | 0.25 | I-dj | 1.3 |
| I-dk | 0.69 | I-dl | 90 |
| I-dm | 0.47 | I-dn | 6.0 |
| I-do | 0.95 | I-dp | 1.1 |
| I-dq | 6.2 | I-dr | 85 |
| I-ds | 70 | I-dt | 1.1 |
| I-du | 1.1 | I-dv | 40 |
| I-dw | 0.85 | I-dx | 3.5 |
| I-dy | 1.7 | I-dz | 1.5 |
| I-ea | 2.8 | I-eb | 7.2 |
| I-ec | 80 | I-ed | 38 |
| I-ee | 14 | I-ef | 20 |
| I-eg | 1.5 | I-eh | 3.5 |
| I-ei | 0.044 | I-ej | 0.022 |
| I-ek | 0.32 | I-el | 0.33 |
| I-em | 0.30 | I-en | 25 |
| I-eo | 0.020 | I-ep | 0.087 |
| I-eq | 1.8 | I-er | 30 |
| digoxin | 0.40 | compd 22b | 0.33 |

Moreover the compounds of the present invention possess positive inotropic features, as shown by slow intravenous infusion in anesthetized guinea pig according to Cerri (Cerri A. et al., J. Med. Chem. 2000, 43, 2332) and have a low toxicity, i.e. a better therapeutic ratio, when compared with standard cardiotonic steroids, e.g. digoxin.

The compounds of the present invention possess a higher efficacy and/or a better therapeutic ratio and/or a longer duration of action compared to compound 22b ((EZ) 3-(2-aminoethoxyimino)androstane-6,17-dione hydrochloride) reported by S. De Munari et al. in J. Med. Chem. 2003, 64, 3644-3654. The activity of some compounds of general formula (I) on the above mentioned tests was determined and the results are shown in the following Table 2. The inotropic activity is shown as maximum increase in contractile force ($E_{max}$ measured as $+dP/dT_{max}$), dose inducing maximum positive inotropic effect ($ED_{max}$), inotropic potency ($ED_{80}$, dose increasing $+dP/dT_{max}$ by 80%); the toxicity as the ratio between lethal dose and inotropic potency, or safety ratio, (calculated in the died animals); the maximum dose infused in the survived animals; the duration of the inotropic effect as the decrease of the effect from the $ED_{max}$ measured 20 minutes after the end of the infusion.

(from Sprague Dawley, males, weights in the range 285-295 grams; viability 80-90%; concentration: 2590000-3084000 hepatocytes/ml; test item nominal concentration: 45 µM) are reported in comparison with compd 22b which is almost completely metabolized within 60 minutes.

TABLE 3

Metabolism in rat hepatocytes

| Example N° | % of compound metabolized after 60 minutes |
|---|---|
| I-ai | 27 |
| I-be | 16 |
| I-bp | 32 |
| I-bs | 15 |
| I-ci | 41 |
| I-dk | 12 |
| I-dm | 71 |
| I-ee | 22 |
| I-ej | 5 |
| Compound 22b | 95 |

The compounds of the present invention possess also antihypertensive activity, as taught by P. Ferrari et al., in *Cardio-*

TABLE 2

Inotropic Effect and Lethal Dose in Anesthetized Guinea-pig.

Slow intravenous infusion (over 90 minutes) in anesthetized guinea-pig

| Example N° | $E_{max}$ % increase in $+dP/dT_{max}$ | $ED_{max}$ µmol/kg | $ED_{80}$ umol/kg | Dead/treated | Lethal dose/$ED_{80}$ (safety ratio) | Maximum dose infused µmol/kg | % decrease from $E_{max}$ after 20 min from the end of the infusion |
|---|---|---|---|---|---|---|---|
| I-ad | 202 | 22.5 | 5.14 | 0/3 | nd | 50.1 | 100 |
| I-ai | 235 | 2.99 | 1.20 | 0/5 | nd | 3.2 | 100 |
| I-am | 238 | 17.2 | 2.50 | 2/3 | 22.7 | 50.5 | 17 |
| I-ao | 166 | 7.37 | 1.80 | 0/3 | nd | 12.6 | 100 |
| I-aw | 183 | 5.77 | 2.35 | 0/5 | nd | 12.7 | 100 |
| I-ba | 203 | 5.78 | 3.09 | 0/3 | nd | 6.3 | 100 |
| I-bd | 163 | 9.89 | 4.59 | 0/3 | nd | 12.8 | 16 |
| I-be | 174 | 27.4 | 1.99 | 1/5 | 32.8 | 50.4 | 37 |
| I-bo | 214 | 4.86 | 1.30 | 0/3 | nd | 12.5 | 82 |
| I-bq | 173 | 15.7 | 5.87 | 0/3 | nd | 25.3 | 10 |
| I-br | 264 | 13.5 | 1.62 | 2/5 | 32.4 | 50.4 | 100 |
| I-cl | 263 | 8.95 | 1.54 | 2/2 | 27.6 | 42.5 | — |
| I-co | 177 | 2.79 | 0.93 | 2/2 | 47.4 | 44.1 | — |
| I-cr | 180 | 11.8 | 1.21 | 1/4 | 52.9 | 50.4 | 47 |
| I-dg | 105 | 11.4 | 8.62 | 0/3 | nd | 12.9 | 29 |
| I-ej | 258 | 7.55 | 0.34 | 3/3 | 50 | 25.0 | — |
| digoxin | 158 | 0.65 | 0.29 | 10/10 | 4.0 | 1.16 | — |
| compd 22b | 182 | 5.74 | 1.82 | 7/8 | 22.6 | 32.1 | 100 |

As reported in Table 2, the compounds show positive inotropic effects with higher safety ratios than those displayed by digoxin and compd 22b. In fact the lethal dose/$ED_{80}$ ratios were either higher or even not determinable, when no animals died; noteworthy, for some compounds a lower percentage of animals died in comparison to digoxin and compd 22b. Further, some compounds showed a prolonged action, as shown by the persistence of the inotropic effect after stopping the infusion (% decrease from $E_{max}$ after 20 min from the end of the infusion). When no animal died, higher doses were not tested since the maximum increases in contractile force were comparable or higher to those displayed by digoxin and compd 22b.

Further data on the longer duration of action of the compounds of the present invention were originated and the results are shown in Table 3, where the results of the metabolism of the compounds in fresh rat hepatocytes are reported

*vascular Drug Reviews*, 1999, 17, 39-57, who demonstrated that compounds affecting $Na^+$, $K^+$-ATPase can lower blood pressure in models of hypertension.

The ability of these compounds to lower blood pressure was tested by using an animal model with induced hypertension, in particular, rats made hypertensive by chronic infusion of ouabain, according to Ferrari P., et al. J. Pharm. Exp. Ther. 1998, 285, 83-94.

The procedure adopted to test the antihypertensive activity of the compounds on the above mentioned model was the following: systolic blood pressure (SBP) and heart rate (HR) were measured by an indirect tail-cuff method. The blood pressure lowering effect was measured in hypertensive ouabain-sensitive rats. The compound, suspended in Methocel 0.5% (w/v), was administered daily at the dose of 10 µg/kg/day by mouth for four weeks. SBP and HR were measured weekly 6 hours after the treatment. The comparison are ouabain sensitive rats (OS rats) and non hypertensive rats (control), both treated only with Methocel 0.5% (w/v). As shown in the following Table 4, treatment with a compound of the present invention lowers the blood pressure of OS rats (170 mm Hg) to almost the level of control rats (150 mm Hg).

TABLE 4

Systolic blood pressure fall in hypertensive ouabain-sensitive rats (os rats)

| EXAMPLE n° | RATS | SBP mm Hg | SBP - mm Hg | SBP - % | HR beats/ min. | HR % beats/ min |
|---|---|---|---|---|---|---|
| Comp. I-bt | 8 | 155.8 | 14.2 | 8.3 | 368 | 0 |
| Comp. I-ee | 8 | 151.0 | 19.0 | 11.0 | 381 | +5.1 |
| OS rats | 8 | 170.0 | — | — | 368 | — |
| Control | 8 | 150.0 | — | — | 376 | — |

The invention claimed is:

1. Compounds of formula (I)

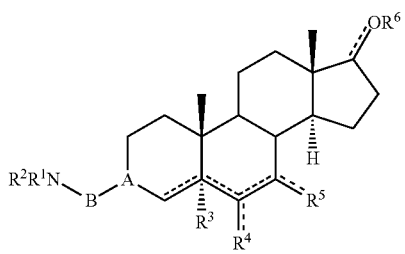

wherein:

A is C=N—O, $CR^7$—CH=CH—, wherein the left end carbon atom in any of these groups is at position 3 of the androstane skeleton;

$R^7$ is hydrogen or hydroxy;

B is a $C_1$-$C_6$ straight or branched alkylene or a $C_3$-$C_6$ cycloalkylene, optionally containing a phenyl ring;

$R^1$ and $R^2$, which can be the same or different, are H, $C_1$-$C_6$ alkyl, phenyl-$C_1$-$C_4$ alkyl or when $R^1$ is hydrogen, $R^2$ can also be C(=$NR^{10}$)$NHR^{11}$ or $R^1$ and $R^2$ can be taken together with the nitrogen atom to form an unsubstituted or substituted saturated or unsaturated mono heterocyclic 4-, 5- or 6-membered ring optionally containing another heteroatom selected from the group consisting of oxygen, sulphur or nitrogen, and $R^1$ and $R^2$ can be optionally substituted by one or more hydroxy, methoxy, ethoxy groups;

$R^{10}$ and $R^{11}$, which can be the same or different, are H, $C_1$-$C_6$ alkyl, or $R^{10}$ and $R^{11}$ can be taken together with the nitrogen atoms and the guanidinic carbon atom to form an unsubstituted or substituted saturated or unsaturated mono heterocyclic 5- or 6-membered ring optionally containing another heteroatom selected from the group consisting of oxygen, sulphur or nitrogen;

$R^3$ is H, $C_1$-$C_6$ alkyl, $ONO_2$, $OR^{12}$;

$R^{12}$ is H, $C_1$-$C_6$ alkyl, optionally substituted by one or more hydroxy, methoxy, ethoxy; or $R^{12}$ is allyl or propargyl;

when the bond === linking the carbon atom in position 6 of the androstane skeleton with $R^4$ is a double bond, $R^4$ is N—$OR^{13}$ or $CR^{14}R^{15}$;

when the bond === linking the carbon atom in position 7 of the androstane skeleton with $R^5$ is a double bond, $R^5$ is O, with the meaning of a keto group, or N—$OR^{13}$ or $CR^{14}R^{15}$;

$R^{13}$ is H, $C_1$-$C_6$ alkyl, optionally substituted by one or more hydroxy, methoxy, ethoxy; or $R^{13}$ is allyl or propargyl;

$R^{14}$ and $R^{15}$, which can be the same or different, are H, $C_1$-$C_6$ alkyl group, optionally substituted by one or more hydroxy, methoxy, ethoxy; or $R^{14}$ and $R^{15}$, which can be the same or different, are allyl, propargyl, F, $COOR^{16}$, CN, $CONR^{17}R^{18}$, or $R^{14}$ and $R^{15}$ taken together form a cycloalkylene substituent;

$R^{16}$ is H, $C_1$-$C_6$ alkyl group optionally substituted by one or more hydroxy, methoxy, ethoxy;

$R^{17}$ and $R^{18}$, which can be the same or different, are H, $C_1$-$C_6$ alkyl groups or $R^{17}$ and $R^{18}$ canoptionally be taken together with the nitrogen atom to form a heterocyclic group, when the bond === linking the carbon atom in position 6 of the androstane skeleton with $R^4$ is a single bond, $R^4$ is H, $C_1$-$C_6$ alkyl group, vinyl, ethynyl, $COOR^{16}$, CN, $CONR^{17}R^{18}$, $ONO_2$, NHCHO, $NHCOCH_3$, CH=N—OH, spirocyclopropane, spirooxirane, where the alkyl group can be optionally substituted by one or more hydroxy, methoxy, ethoxy;

when the bond === linking the carbon atom in position 7 of the androstane skeleton with $R^5$ is a single bond, $R^5$ is H, $C_1$-$C_6$ alkyl group, vinyl, ethynyl, $COOR^{16}$, CN, $CONR^{17}R^{18}$, $OR^{19}$, $ONO_2$, NHCHO, $NHCOCH_3$, CH=N—OH, spirocyclopropane, spirooxirane, where the alkyl group can be optionally substituted by one or more hydroxy, methoxy, ethoxy;

$R^{16}$, $R^{17}$, and $R^{18}$ are as above defined;

$R^{19}$ is H, $C_1$-$C_6$ alkyl group optionally substituted by one or more hydroxy, methoxy, ethoxy;

$R^6$ is not present and the bond === in position 17 is a double bond with the meaning of a keto group;

$R^{16}$, $R^{17}$, and $R^{18}$, when present in the same compound in different positions, can be the same or different;

the symbol — represents an α or β single bond or an E or Z diastereoisomer when it is linked to a double bond;

the symbol === in positions 6 and 7 represents, independently, a single or double bond, and when it is a single exocyclic bond in positions 6 or 7 it can be an α or β single bond;

the symbol === in positions 4 and 5 represents a single bond with the following provisos:

that $R^3$, $R^4$ and $R^5$ are not hydrogen at the same time, their tautomers, stereoisomers, Z and E isomers, optical isomers and their mixtures, and the pharmaceutically acceptable salts.

2. Compounds according to claim 1, wherein the symbols $R^3$ and $R^5$ represent H, $R^1R^2N$ and B are as defined above, and the symbol A is C=N—O or $CR^7$—CH=CH—, wherein $R^4$ is methylene, difluoromethylene, hydroxyimino, methoxyimino or ethoxyimino when the symbol === in position 6 linking $R^4$ represents a double bond, or $R^4$ is α-methyl, β-methyl, α-carbamoyl, α-methoxycarbonyl, α-hydroxymethyl, α-methoxymethyl, α-nitroxy, α-formylamino, α-ethynyl, α-CN, α-CHO, spirodioxolyl, spirooxiranyl or spirocyclopropyl when the symbol === in position 6 represents a single bond; and $R^7$ and $R^8$ are as defined above, their tautomers, stereoisomers, Z and E isomers, optical isomers and their mixtures, and the pharmaceutically acceptable salts.

3. Compounds according to claim 1, wherein the symbol $R^3$ represents hydroxy, the symbol $R^5$ represents H and $R^4$ represents methylene, hydroxyimino or methoxyimino, when the symbol === in position 6 linking $R^4$ represents a double bond, or $R^4$ represents H when the symbol === in position 6 linking $R^4$ represents a single bond, their tautomers, stereoisomers, Z and E isomers, optical isomers and their mixtures, and the pharmaceutically acceptable salts.

4. Compounds according to claim 1, wherein the symbols $R^3$ and $R^4$ represent H, the symbol $R^5$ represents O with the meaning of keto, methylene, difluoromethylene, hydroxyimino or methoxyimino, when the symbol === in position 7 linking $R^4$ represents a double bond, or the symbol $R^5$ represents
   α-methyl, α-carbamoyl, α-methoxycarbonyl, α-hydroxy, α-hydroxymethyl,
   α-methoxymethyl, α-nitroxy, α-formylamino, α-ethynyl, β-methyl,
   β-carbamoyl, β-methoxycarbonyl, β-hydroxymethyl, β-methoxymethyl,
   β-nitroxy, β-formylamino, β-ethynyl or spirocyclopropyl when the symbol === in position 7 represents a single bond, their tautomers, stereoisomers, Z and E isomers, optical isomers and their mixtures, and the pharmaceutically acceptable salts.

5. A Compound according to claim 1, wherein A is selected from the group consisting of 2-aminoethoxyimino, 3-aminopropoxyimino, 2-(N-methylamino)ethoxyimino, 3-(N-methylamino)propoxyimino, 3-(2-aminocyclopentyloxyimino), 3-(2-aminocyclopentyloxyimino), 3α-(5-aminopent-1-Z-enyl), 3α-(4-aminobut-1-Z-enyl), their tautomers, stereoisomers, optical isomers and their mixtures, and the pharmaceutically acceptable salts.

6. Compounds according to claim 1, selected from the group consisting of:
   EZ 3-(2-aminoethoxyimino)-6-methyleneandrostan-17-one,
   EZ 3-(3-aminopropoxyimino)-6-methyleneandrostan-17-one,
   EZ 3-(2-(N-methylamino)ethoxyimino)-6-methyleneandrostan-17-one,
   EZ 3-(3-(N-methylamino)propoxyimino)-6-methyleneandrostan-17-one,
   EZ 3-(2-aminocyclopentoxyimino)-6-methyleneandrostan-17-one,
   3α-(5-aminopent-1Z-enyl)-6-methyleneandrostan-17-one,
   3α-(4-aminobut-1Z-enyl)-6-methyleneandrostan-17-one,
   and the corresponding 6-hydroxyimino and 6-methoxyimino derivatives;
   EZ 3-(2-aminoethoxyimino)-6α-methylandrostan-17-one,
   EZ 3-(3-aminopropoxyimino)-6α-methylandrostan-17-one,
   EZ 3-(2-(N-methylamino)ethoxyimino)-6α-methylandrostan-17-one,
   EZ 3-(3-(N-methylamino)propoxyimino)-6α-methylandrostan-17-one,
   EZ 3-(2-aminocyclopentoxyimino)-6α-methylandrostan-17-one,
   3α-(5-aminopent-1Z-enyl)-6α-methylandrostan-17-one,
   3α-(4-aminobut-1Z-enyl)-6α-methylandrostan-17-one,
   and the corresponding 6α-carbamoyl, 6α-methoxycarbonyl, 6α-hydroxymethyl, 6α-methoxymethyl, 6α-nitroxy, 6α-formylamino, α-ethynyl derivatives;
   EZ 3-(2-aminoethoxyimino)-5α-hydroxy-6α-methylandrostan-17-one,
   EZ 3-(3-aminopropoxyimino)-5α-hydroxy-6α-methylandrostan-17-one,
   EZ 3-(2-(N-methylamino)ethoxyimino)-5α-hydroxy-6α-methylandrostan-17-one,
   EZ 3-(3-(N-methylamino)propoxyimino)-5α-hydroxy-6α-methylandrostan-17-one,
   EZ 3-(2-aminocyclopentoxyimino)-5α-hydroxy-6α-methylandrostan-17-one,
   3α-(5-aminopent-1Z-enyl)-5α-hydroxy-6α-methylandrostan-17-one,
   3α-(4-aminobut-1Z-enyl)-5α-hydroxy-6α-methylandrostan-17-one,
   and the corresponding 6α-carbamoyl, 6α-methoxycarbonyl, 6α-hydroxymethyl, 6α-methoxymethyl, 6α-nitroxy, 6α-formylamino, α-ethynyl derivatives;
   EZ 3-(2-aminoethoxyimino)-7-methyleneandrostan-17-one,
   EZ 3-(3-aminopropoxyimino)-7-methyleneandrostan-17-one,
   EZ 3-(2-(N-methylamino)ethoxyimino)-7-methyleneandrostan-17-one,
   EZ 3-(3-(N-methylamino)propoxyimino)-7-methyleneandrostan-17-one,
   EZ 3-(2-aminocyclopentoxyimino)-7-methyleneandrostan-17-one,
   3α-(5-aminopent-1Z-enyl)-7-methyleneandrostan-17-one,
   3α-(4-aminobut-1Z-enyl)-7-methyleneandrostan-17-one,
   and the corresponding 7-hydroxyimino and 7-methoxyimino derivatives;
   EZ 3-(2-aminoethoxyimino)-7α-methylandrostan-17-one,
   EZ 3-(3-aminopropoxyimino)-7α-methylandrostan-17-one,
   EZ 3-(2-(N-methylamino)ethoxyimino)-7α-methylandrostan-17-one,
   EZ 3-(3-(N-methylamino)propoxyimino)-7α-methylandrostan-17-one,
   EZ 3-(2-aminocyclopentoxyimino)-7α-methylandrostan-17-one,
   3α-(5-aminopent-1Z-enyl)-7α-methylandrostan-17-one,
   3α-(4-aminobut-1Z-enyl)-7α-methylandrostan-17-one,
   and the corresponding 7α-carbamoyl, 7α-methoxycarbonyl, 7α-hydroxymethyl, 7α-methoxymethyl, 7α-nitroxy, 7α-formylamino, α-ethynyl derivatives and the corresponding 7β-methyl, 7β-carbamoyl, 7β-methoxycarbonyl, 7β-hydroxymethyl, 7β-methoxymethyl, 7β-nitroxy, 7β-formylamino, β-ethynyl derivatives;
   EZ 3-(2-aminoethoxyimino)-5α-hydroxy-6-methyleneandrostan-17-one,
   EZ 3-(3-aminopropoxyimino)-5α-hydroxy-6-methyleneandrostan-17-one,
   EZ 3-(2-(N-methylamino)ethoxyimino)-5α-hydroxy-6-methyleneandrostan-17-one,
   EZ 3-(3-(N-methylamino)propoxyimino)-5α-hydroxy-6-methyleneandrostan-17-one,
   EZ 3-(2-aminocyclopentoxyimino)-5α-hydroxy-6-methyleneandrostan-17-one,
   3α-(5-aminopent-1Z-enyl)-5α-hydroxy-6-methyleneandrostan-17-one,
   3α-(4-aminobut-1Z-enyl)-5α-hydroxy-6-methyleneandrostan-17-one,
   and the corresponding 6-hydroxyimino and 6-methoxyimino derivatives;
   EZ 3-(2-aminoethoxyimino)-5α-hydroxy-7-methyleneandrostan-17-one,
   EZ 3-(3-aminopropoxyimino)-5α-hydroxy-7-methyleneandrostan-17-one,
   EZ 3-(2-(N-methylamino)ethoxyimino)-5α-hydroxy-7-methyleneandrostan-17-one, EZ 3-(3-(N-methylamino)propoxyimino)-5α-hydroxy-7-methyleneandrostan-17-one,
EZ 3-(2-aminocyclopentoxyimino)-5α-hydroxy-7-methyleneandrostan-17-one,
3α-(5-aminopent-1Z-enyl)-5α-hydroxy-7-methyleneandrostan-17-one,
3α-(4-aminobut-1Z-enyl)-5α-hydroxy-7-methyleneandrostan-17-one,
and the corresponding 7-hydroxyimino and 7-methoxyimino derivatives;
EZ 3-(2-aminoethoxyimino)-5α-hydroxy-6α-methylandrostan-17-one,
EZ 3-(3-aminopropoxyimino)-5α-hydroxy-6α-methylandrostan-17-one,
EZ 3-(2-(N-methylamino)ethoxyimino)-5α-hydroxy-6α-methylandrostan-17-one,
EZ 3-(3-(N-methylamino)propoxyimino)-5α-hydroxy-6α-methylandrostan-17-one,
EZ 3-(2-aminocyclopentoxyimino)-5α-hydroxy-6α-methylandrostan-17-one,
3α-(5-aminopent-1Z-enyl)-5α-hydroxy-6α-methylandrostan-17-one,
3α-(4-aminobut-1Z-enyl)-5α-hydroxy-6α-methylandrostan-17-one,
and the corresponding 6α-carbamoyl, 6α-methoxycarbonyl, 6α-hydroxymethyl, 6α-methoxymethyl, 6α-nitroxy, 6α-formylamino, α-ethynyl derivatives;
EZ 3-(2-aminoethoxyimino)-5α-hydroxy-7α-methylandrostan-17-one,
EZ 3-(3-aminopropoxyimino)-5α-hydroxy-7α-methylandrostan-17-one,
EZ 3-(2-(N-methylamino)ethoxyimino)-5α-hydroxy-7α-methylandrostan-17-one,
EZ 3-(3-(N-methylamino)propoxyimino)-5α-hydroxy-7α-methylandrostan-17-one,
EZ 3-(2-aminocyclopentoxyimino)-5α-hydroxy-7α-methylandrostan-17-one,
3α-(5-aminopent-1Z-enyl)-5α-hydroxy-7α-methylandrostan-17-one,
3α-(4-aminobut-1Z-enyl)-5α-hydroxy-7α-methylandrostan-17-one,
and the corresponding 7α-carbamoyl, 7α-methoxycarbonyl, 7α-hydroxymethyl, 7α-methoxymethyl, 7α-nitroxy, 7α-formylamino, 7α-ethynyl derivatives and the corresponding 7β-methyl, 7β-carbamoyl, 7β-methoxycarbonyl, 7β-hydroxymethyl, 7β-methoxymethyl, 7β-nitroxy, 7β-formylamino, 7α-ethynyl derivatives;
EZ 3-(2-aminoethoxyimino)-5α-hydroxyandrostan-17-one,
EZ 3-(3-aminopropoxyimino)-5α-hydroxyandrostan-17-one,
EZ 3-(2-(N-methylamino)ethoxyimino)-5α-hydroxyandrostan-17-one,
EZ 3-(3-(N-methylamino)propoxyimino)-5α-hydroxyandrostan-17-one,
EZ 3-(2-aminocyclopentoxyimino)-5α-hydroxyandrostan-17-one,
3α-(5-aminopent-1Z-enyl)-5α-hydroxyandrostan-17-one,
3α-(4-aminobut-1Z-enyl)-5α-hydroxyandrostan-17-one;
their tautomers, stereoisomers, Z and E isomers, optical isomers and their mixtures, and the pharmaceutically acceptable salts.

7. A process for the preparation of compounds of claim 1, where A is C=N—O, comprising reacting a compound of general formula (II)

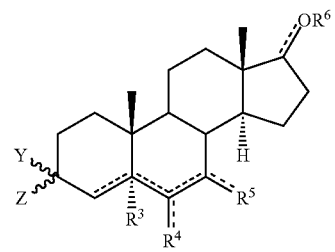

where the symbols $R^3$, $R^4$, $R^5$, $R^6$, and ═══ are as defined in claim 1 and Y and Z represent together a keto group (=O)
with a compound of general formula (III),

$$R^2R^1N-B-ONH_2 \quad (III)$$

where $R^2$, $R^1$, and B are as defined in claim 1.

8. A process for the preparation of compounds of claim 1, wherein $R^4$ and $R^5$ being the same or different, are N—$OR^{13}$ with the meaning of oxime, comprising reacting a compound of general formula (I), as specified in claim 1, wherein $R^4$ and $R^5$, being $R^4$ and $R^5$ the same or different, are O with the meaning of a keto group in case such a group is to be transformed into an oxime, with a compound of general formula $H_2NOR^{13}$ where $R^{13}$ has the meanings defined in claim 1.

9. A process for the preparation of compounds of claim 1, wherein $R^4$ or $R^5$ are $C_1$-$C_6$ alkyl groups substituted with a hydroxy group, comprising the following steps:

a): reacting a compound of general formula (XI),

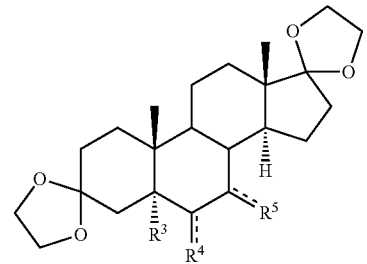

wherein $R^3$ is as defined in claim 1, one of $R^4$ and $R^5$ is $CR^{14}R^{15}$ with the meaning of alkene, the other being hydrogen, and $R^{14}$ and $R^{15}$ are hydrogens
with a hydroborating agent selected from the group consisting of diborane, disiamylborane or 9-boracyclo[3.3.1]nonane, in a solvent such as tetrahydrofuran at about room temperature, followed by peroxide oxidation using hydrogen peroxide in the presence of sodium hydroxide;

b): reacting the above-obtained intermediate (from step a) with a compound of general formula (III),

$$R^2R^1N-B-ONH_2 \quad (III)$$

where $R^2$, $R^1$, and B are as defined in claim 1.

10. A process for the preparation of compounds of claim 1, wherein $R^4$ is $C_1$-$C_6$ alkyl group substituted with a hydroxy group comprising a): reacting a compound of general formula (XII)

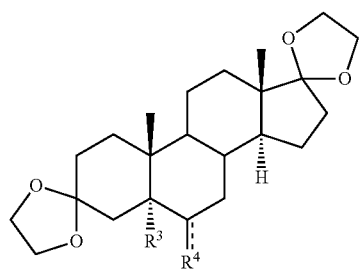 XII where $R^4$ is vinyl, and $R^3$ is as defined in claim 1, with a hydroborating agent selected from the group consisting of diborane, disiamylborane or 9-boracyclo[3.3.1]nonane, in a solvent such as tetrahydrofuran at about room temperature, followed by peroxide oxidation using hydrogen peroxide in the presence of sodium hydroxide; and b): reacting the above-obtained intermediate (from step a) with a compound of general formula (III),

 (III)

where $R^2$, $R^1$, and B are as defined in claim 1.

11. Pharmaceutical composition comprising a compound of claim 1 in admixture with at least one pharmaceutically acceptable vehicle and/or excipient.

12. A method of inhibiting of the enzymatic activity of the $Na^+$, $K^+$-ATPase in mammals, comprising administering an effective amount of a compound of claim 1 to a mammal in need thereof.

* * * * *

UNITED STATES PATENT AND TRADEMARK OFFICE
CERTIFICATE OF CORRECTION

PATENT NO. : 8,609,644 B2  
APPLICATION NO. : 12/295497  
DATED : December 17, 2013  
INVENTOR(S) : Cerri et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1354 days.

Signed and Sealed this  
Twenty-second Day of September, 2015

Michelle K. Lee  
*Director of the United States Patent and Trademark Office*